(12) United States Patent
Grabowsky et al.

(10) Patent No.: US 12,263,192 B2
(45) Date of Patent: Apr. 1, 2025

(54) COMPOSITIONS FOR MANAGEMENT OF DISORDERS OF THE GASTROINTESTINAL TRACT

(71) Applicant: PanTheryx, Inc., Phoenix, AZ (US)

(72) Inventors: Mark Grabowsky, New York, NY (US); Raymond J. Playford, Cobham (GB); Timothy W. Starzl, Boulder, CO (US); Tania Marchbank, Epsom (GB); Paul Kelly, Phoenix, AZ (US); Naheed Choudhry, Phoenix, AZ (US)

(73) Assignee: PanTheryx, Inc., Phoenix, AZ (US)

( * ) Notice: Subject to any disclaimer, the term of this patent is extended or adjusted under 35 U.S.C. 154(b) by 643 days.

(21) Appl. No.: 17/433,723

(22) PCT Filed: Feb. 26, 2020

(86) PCT No.: PCT/US2020/019923
§ 371 (c)(1),
(2) Date: Aug. 25, 2021

(87) PCT Pub. No.: WO2020/176637
PCT Pub. Date: Sep. 3, 2020

(65) Prior Publication Data
US 2022/0047646 A1 Feb. 17, 2022

Related U.S. Application Data

(60) Provisional application No. 62/978,104, filed on Feb. 18, 2020, provisional application No. 62/940,133, filed on Nov. 25, 2019, provisional application No. 62/896,429, filed on Sep. 5, 2019, provisional application No. 62/810,637, filed on Feb. 26, 2019.

(51) Int. Cl.

| | |
|---|---|
| A61K 35/57 | (2015.01) |
| A61K 31/07 | (2006.01) |
| A61K 31/355 | (2006.01) |
| A61K 31/4415 | (2006.01) |
| A61K 31/51 | (2006.01) |
| A61K 31/593 | (2006.01) |
| A61K 31/714 | (2006.01) |
| A61K 33/04 | (2006.01) |
| A61K 33/18 | (2006.01) |
| A61K 33/34 | (2006.01) |
| A61K 33/42 | (2006.01) |
| A61K 35/20 | (2006.01) |
| A61K 39/00 | (2006.01) |
| A61K 39/395 | (2006.01) |
| A61K 39/40 | (2006.01) |
| A61K 39/42 | (2006.01) |
| A61P 1/00 | (2006.01) |

(52) U.S. Cl.
CPC .......... *A61K 35/57* (2013.01); *A61K 31/07* (2013.01); *A61K 31/355* (2013.01); *A61K 31/4415* (2013.01); *A61K 31/51* (2013.01); *A61K 31/593* (2013.01); *A61K 31/714* (2013.01); *A61K 33/04* (2013.01); *A61K 33/18* (2013.01); *A61K 33/34* (2013.01); *A61K 33/42* (2013.01); *A61K 35/20* (2013.01); *A61K 39/39583* (2013.01); *A61K 39/40* (2013.01); *A61K 39/42* (2013.01); *A61P 1/00* (2018.01); *A61K 2039/55* (2013.01)

(58) Field of Classification Search
None
See application file for complete search history.

(56) References Cited

U.S. PATENT DOCUMENTS

| | | |
|---|---|---|
| 4,091,116 A | 5/1978 | Edwards et al. |
| 4,341,763 A | 7/1982 | Zygraich |
| 4,376,110 A | 3/1983 | David et al. |
| 4,377,569 A | 3/1983 | Plymate |
| 4,497,836 A | 2/1985 | Marquardt et al. |
| 4,550,019 A | 10/1985 | Polson |
| 4,668,771 A | 5/1987 | Kawakami et al. |
| 4,689,151 A | 8/1987 | Kosikowski et al. |
| 4,748,018 A | 5/1988 | Stolle et al. |
| 4,816,563 A | 3/1989 | Wilson et al. |
| 4,816,567 A | 3/1989 | Cabilly et al. |
| 4,861,597 A | 8/1989 | Kida et al. |
| 4,997,914 A | 3/1991 | Kawakami et al. |
| 5,017,372 A | 5/1991 | Hastings |
| 5,080,895 A | 1/1992 | Tokoro |
| 5,122,594 A | 6/1992 | Yoshida et al. |
| 5,126,322 A | 6/1992 | Collins et al. |
| 5,149,647 A | 9/1992 | Burling |
| 5,198,213 A | 3/1993 | Stott et al. |

(Continued)

FOREIGN PATENT DOCUMENTS

| | | |
|---|---|---|
| CN | 1037276 A | 11/1989 |
| CN | 1642561 A | 7/2005 |

(Continued)

OTHER PUBLICATIONS

Declaration of Timothy A. Hall under 37 CFR 1.132 and attachments, dated Nov. 19, 2015, 19 pages total.

(Continued)

*Primary Examiner* — Brian Gangle
(74) *Attorney, Agent, or Firm* — DLA Piper LLP (US)

(57) ABSTRACT

Effective and economical compositions and methods are disclosed for the treatment, and prevention of diseases and disorders associated with inflammation and/or damage to the gastrointestinal tract, including environmental enteric dysfunction. Compositions are provided comprising a synergistic combination of colostrum, immune egg, and optionally one or more additional active agents.

23 Claims, 40 Drawing Sheets

(56) References Cited

U.S. PATENT DOCUMENTS

| | | |
|---|---|---|
| 5,260,057 A | 11/1993 | Cordle et al. |
| 5,290,685 A | 3/1994 | Koide et al. |
| 5,367,054 A | 11/1994 | Lee |
| 5,470,835 A | 11/1995 | Kirkpatrick et al. |
| 5,554,372 A | 9/1996 | Hunter |
| 5,585,098 A | 12/1996 | Coleman |
| 5,719,267 A | 2/1998 | Carroll et al. |
| 5,753,228 A | 5/1998 | Sterling et al. |
| 5,762,934 A | 6/1998 | Williams et al. |
| 5,840,700 A | 11/1998 | Kirkpatrick et al. |
| 5,846,569 A | 12/1998 | Anderson et al. |
| 5,876,735 A | 3/1999 | Reed |
| 6,010,698 A | 1/2000 | Kussendrager et al. |
| 6,037,375 A | 3/2000 | Sakamoto et al. |
| 6,096,870 A | 8/2000 | Mozaffar et al. |
| 6,139,746 A | 10/2000 | Kopf |
| 6,316,008 B1 | 11/2001 | Godfrey |
| 6,346,284 B1 | 2/2002 | Briend et al. |
| 6,348,223 B1 | 2/2002 | Claycamp et al. |
| 6,348,230 B1 | 2/2002 | Campbell et al. |
| 6,410,058 B2 | 6/2002 | Gohlke et al. |
| 6,419,926 B2 | 7/2002 | Kodama et al. |
| 6,468,534 B1 | 10/2002 | Hennen et al. |
| 6,475,511 B2 | 11/2002 | Gohlke et al. |
| 6,521,277 B1 | 2/2003 | Mortensen |
| 6,537,550 B1 | 3/2003 | Larsson et al. |
| 6,569,447 B2 | 5/2003 | Kisic et al. |
| 6,740,447 B1 | 5/2004 | Keshishian |
| 6,793,921 B2 | 9/2004 | Kodama et al. |
| 6,852,700 B1 | 2/2005 | Janusz et al. |
| 6,866,868 B1 | 3/2005 | Lisonbee et al. |
| 6,903,068 B1 | 6/2005 | Stanton et al. |
| 6,939,954 B2 | 9/2005 | Yoder et al. |
| 7,426,440 B2 | 9/2008 | Playford |
| 7,431,942 B2 | 10/2008 | Shimizu et al. |
| 7,445,782 B2 | 11/2008 | Fairbrother et al. |
| 7,538,198 B2 | 5/2009 | Randolph et al. |
| 7,541,028 B2 | 6/2009 | Sung et al. |
| 7,547,770 B2 | 6/2009 | Keech et al. |
| 7,575,698 B2 | 8/2009 | Abe et al. |
| 7,713,527 B2 | 5/2010 | Pradip et al. |
| 7,727,531 B2 | 6/2010 | Fairbrother et al. |
| 7,815,943 B2 | 10/2010 | Hennen |
| 7,862,799 B2 | 1/2011 | Tay et al. |
| 7,935,334 B2 | 5/2011 | Lin |
| 8,657,075 B2 | 2/2014 | Sanz Gamboa |
| 8,946,147 B2 | 2/2015 | DiMarchi et al. |
| 9,452,141 B1 | 9/2016 | Chang et al. |
| 9,701,735 B2 | 7/2017 | Starzl |
| 10,611,828 B2 | 4/2020 | Starzl |
| 2001/0009668 A1 | 7/2001 | Richardson |
| 2001/0021384 A1 | 9/2001 | Jourdier et al. |
| 2002/0044942 A1 | 4/2002 | Dopson |
| 2002/0127279 A1 | 9/2002 | Matthews |
| 2002/0143157 A1 | 10/2002 | Yoder et al. |
| 2003/0021778 A1 | 1/2003 | Simon |
| 2003/0103989 A1 | 6/2003 | Hodgkinson et al. |
| 2003/0185856 A1 | 10/2003 | Lee et al. |
| 2003/0203042 A1 | 10/2003 | Cook |
| 2004/0182785 A1 | 9/2004 | Lee et al. |
| 2004/0266681 A1 | 12/2004 | Boldogh et al. |
| 2005/0058716 A1 | 3/2005 | Lisonbee et al. |
| 2005/0092684 A1 | 5/2005 | Keech et al. |
| 2006/0068022 A1 | 3/2006 | Playford |
| 2006/0134101 A1 | 6/2006 | Arson et al. |
| 2006/0198900 A1 | 9/2006 | Playford |
| 2006/0233781 A1 | 10/2006 | Pedersen et al. |
| 2007/0053917 A1 | 3/2007 | Robins-Browne et al. |
| 2007/0053919 A1 | 3/2007 | Lisonbee et al. |
| 2007/0264264 A1 | 11/2007 | Evans et al. |
| 2007/0274983 A1 | 11/2007 | Kluijtmans et al. |
| 2008/0069813 A1 | 3/2008 | Yoder et al. |
| 2008/0081076 A1 | 4/2008 | Lisonbee et al. |
| 2008/0124321 A1 | 5/2008 | Yoder et al. |
| 2008/0138435 A1 | 6/2008 | Van Den Berg et al. |
| 2008/0206233 A1 | 8/2008 | Frenken et al. |
| 2008/0274945 A1 | 11/2008 | Van Laere et al. |
| 2009/0053197 A1 | 2/2009 | Ramaekers |
| 2009/0092621 A1 | 4/2009 | Fairbrother et al. |
| 2009/0142377 A1 | 6/2009 | Gebbink et al. |
| 2009/0226418 A1 | 9/2009 | Frenken et al. |
| 2009/0246207 A1 | 10/2009 | Rahmani |
| 2009/0311333 A1 | 12/2009 | Elfstrand et al. |
| 2009/0317421 A1 | 12/2009 | Missiakas et al. |
| 2009/0324723 A1 | 12/2009 | Rawlin et al. |
| 2010/0040711 A1 | 2/2010 | Playford et al. |
| 2010/0183627 A1 | 7/2010 | Fairbrother et al. |
| 2010/0183632 A1 | 7/2010 | Fox |
| 2010/0233162 A1 | 9/2010 | Larsson et al. |
| 2010/0266607 A1 | 10/2010 | Fox |
| 2010/0297140 A1 | 11/2010 | Scammell |
| 2011/0129479 A1 | 6/2011 | Tobin |
| 2011/0200610 A1 | 8/2011 | Ilan et al. |
| 2012/0141458 A1 | 6/2012 | Starzl |
| 2012/0283185 A1 | 11/2012 | Whyte |
| 2014/0037603 A1 | 2/2014 | Bolster et al. |
| 2016/0206733 A1 | 7/2016 | Makino et al. |
| 2019/0282637 A1 | 9/2019 | Simon |
| 2020/0299360 A1 | 9/2020 | Starzl |
| 2020/0323954 A1 | 10/2020 | Playford |
| 2022/0362303 A1 | 11/2022 | Playford et al. |

FOREIGN PATENT DOCUMENTS

| | | |
|---|---|---|
| EP | 0074240 A2 | 3/1983 |
| EP | 0152270 A2 | 8/1985 |
| EP | 0352089 B1 | 2/1994 |
| EP | 0267692 B1 | 9/1994 |
| EP | 0914831 A2 | 5/1999 |
| EP | 0930316 A1 | 7/1999 |
| JP | S60123428 A | 2/1985 |
| JP | H10265393 A | 10/1998 |
| WO | 1988003171 A1 | 5/1988 |
| WO | 1989010139 A1 | 11/1989 |
| WO | 1990000615 A1 | 1/1990 |
| WO | 1998014209 A1 | 4/1998 |
| WO | 1998014473 A1 | 4/1998 |
| WO | 1999002188 A1 | 1/1999 |
| WO | 1999004804 A1 | 2/1999 |
| WO | 2000075173 A2 | 12/2000 |
| WO | 2003080082 A1 | 10/2003 |
| WO | 2004078209 A1 | 9/2004 |
| WO | 2005041680 A2 | 12/2005 |
| WO | 2009127519 A1 | 10/2009 |
| WO | 2010044095 A2 | 4/2010 |
| WO | 2010125565 A2 | 11/2010 |
| WO | 2011017483 A2 | 2/2011 |
| WO | 2012071346 A1 | 5/2012 |
| WO | 2017021795 A1 | 2/2017 |
| WO | 2019106147 A1 | 6/2019 |
| WO | 2020132296 A1 | 6/2020 |
| WO | 2020176637 A1 | 9/2020 |
| WO | 2020210491 A1 | 10/2020 |
| WO | 2022183012 A1 | 9/2022 |

OTHER PUBLICATIONS

Definition of "hyperimmunization" 2012; Dorland's Illustrated Medical Dictionary 32.sup.nd Edition, Elsevier Saunders, Philadelphia, PA; p. 890.

Dewey and Adu-Afarwuah "Systematic review of the efficacy and effectiveness of complementary feeding interventions in developing countries" 2008, Maternal & Child Nutrition 4:24-85.

Dhanapala et al. "Hypoallergenic Variant of the Major Egg White Allergen Gal d 1 Produced by Disruption of Cysteine Bridges" 2017 Nutrients 9:171.

Dignass et al. "Trefoil Peptides Promote Epithelial Migration through a Transforming Growth Factor β-independent Pathway" 1994, J. Clin. Invest. 94:376-383.

DiPietro "Soybean Protease Inhibitors in Foods" May 1989, J Food Sci, 54(3) 606-609.

(56) References Cited

OTHER PUBLICATIONS

Dukowicz et al. "SHO is Frequently Implicated as a Cause of Chronic Diarrhea and Malabsorption" 2007, Gastroent. & Hepatol. 3(2):112-122.
Egger et al. "Characterisation of acute murine dextran sodium sulphate colitis: cytokine profile and dose dependency" 2000, Digestion 62(4):240-248.
Enos et al. "Probiotics and nutrients for the first 1000 days of life in the developing world" Mar. 1, 2013, Beneficial Microbes 4(1):3-16.
Erlanger et al. "The preparation and properties of two new chromogenic substrates of trypsin" 1961, Archives of Biochemistry and Biophysics 95(2):271-278.
Eurasian Office Action for RU 201307127.28 mailed Apr. 9, 2015. (with English Translation).
Extended European Search Report for Application No. 18183215.5 dated Dec. 6, 2018.
Farthing "Treatment Options for the Eradication of Intestinal Protozoa" 2006, Nature Clinical Practice 3(8):436-445.
Fayer et al. "Immunotherapeutic efficacy of bovine colostral immunoglobulins from a hyperimmunized cow against cryptosporidiosis in neonatal mice" 1990, Infection and Immunity 58(9):2962-2965.
Feeney et al. "The specificities of chicken ovomucoid and ovoinhibitor" Apr. 1963, J Biol Chem. 238(4):1415-1418.
Feng et al. "BAM Chapter 4A: Diarrheagenic Escherichia coli" Feb. 2011, Bacteriological Analytical Manual, Chapter 4A, Fda.gov/food/BAM: Diarrhegenic *Escherichia coli*.
Filipescu et al. "Preventive effects of bovine colostrum supplementation in TNBS-induced colitis in mice"2018. PLoS ONE13:e202929.
Fiske et al. "ERBBs in the gastrointestinal tract: recent progress and new perspectives" Feb. 15, 2009, Exp. Cell. Res. 315(4):583-601.
Fitzgerald et al. Synergistic effects of systemic trefoil factor family 1 (TFF1) peptide and epidermal growth factor in a rat model of colitis 2004, Peptides 25(5):793-801.
Fogh et al. "One hundred and twenty-seven cultured human tumor cell lines producing tumors in nude mice" Jul. 1977, J. Natl. Cancer Inst. 59:221-226.
Freeman et al. "Dairy proteins and the response to pneumovax in senior citizens: A randomized, double-blind, placebo-controlled pilot study" Mar. 2010, Annals New York Academy of Sciences 1190:97-103.
Freeman et al. "Pancreatic secretory trypsin inhibitor in gastrointestinal mucosa and gastric juice" 1990, Gut 31:1318-1323.
Fricker "Children in the Tropics, Putting an End to Diarrheal Diseases" 1993, 204-1-166.
Gaensbauer et al. "Efficacy of a bovine colostrum and eggbased intervention in acute childhood andomiz in Guatemala: a andomized, double-blind, placebo-controlled trial" 2017, BMJ Glob. Health 2:e000452.
Gaffey et al. "Dietary management of childhood diarrhea in low- and middle-income countries: a systematic review" 2013, BMC Public Health 13(Suppl 3):S17:1-16.
Ghoshal et al. "Post-infectious IBS, tropical sprue and small intestinal bacterial overgrowth: the missing link" 2017, Nat. Rev. Gastroenterol. Hepatol. 14(7):435-441.
Ghoshal et al. "Small Intestinal Bacterial Overgrowth and Irritable Bowel Syndrome: A Bridge between Functional Organic Dichotomy" 2017. Gut Liver. 11:196-208.
Godat et al. "Swiss IBD Cohort Study Group. Frequency and type of drug-related side effects necessitating treatment discontinuation in the Swiss Inflammatory Bowel Disease Cohort" 2018, Eur J Gastroenterol Hepatol. 30:612-620.
Godden et al. "Colostrum Management for Dairy Calves" 2019, Veterinary Clinics of North America: Food Animal Practice 35:535-556.
Gonzalez et al. "Animal models of ischemia-reperfusion-induced intestinal injury: progress and promise for translational iarrhea" 2015, Am. J. Physiol. Gastrointest. Liver Physiol. 308:G63-G75.
Guarino et al. "The management of acute diarrhea in children in developed and developing areas: from evidence base to clinical practice" Jan. 2012, Expert Opinion on Pharmacotherapy 13(1):17-26.
Guarner et al. "Gut flora in health and disease" Feb. 8, 2003, Lancet 361:512-519.
Guindi et al. "Indeterminate colitis" 2004, J. Clin. Path. 57:1233-1244.
Ha et al. "Enhancement of Gastric Ulcer Healing and Angiogenesis by Hepatocyte Growth Factor Gene Mediated by Attenuated *Salmonella* in Rats" 2017, J Korean Med Sci., 32:186-194.
Haboubi et al. "Duodenal mucosal morphometry of elderly patients with small intestinal bacterial overgrowth: response to antibiotic treatment" 1991. Age Ageing. 20:29-32.
Hajos et al. "Biological Effects and Survival of Trypsin Inhibitors and the Agglutinin from Soybean in the Small Intestine of the Rat" 1995, J. Agric Food Chem 43:165-170.
Hamal et al. "Maternal Antibody Transfer from Dams to Their Egg Yolks, Egg Whites, and Chicks in Meat Lines of Chickens" 2006, Poultry Science Association, Inc., pp. 1364-1372.
Hamley "PEG—Peptide Conjugates" 2014, Biomacromolecules 15:1543-1559.
Hare et al. "Fat in colostrum: the cream of the crop" May 6, 2020, Progressive Dairy, pp. 1-4.
Harper et al. "Environmental enteric dysfunction pathwaysand child stunting: A systematic review" 2018 PLoS Neg. Trop Dis. 12(1):e0006205.
Hassl et al. "Purification of egg yolk immunoglobulins A two-step procedure using hydrophobic interaction chromatography and gel filtration" Jan. 18, 1988, Journal of Immunological Methods 110:225-228.
Hassoun et al. "Post-Injury Multiple Organ Failure: The Role of the Gut" Jan. 2001, Shock 15(1):1-10.
Hatta et al. "A Novel Isolation Method for Hen Egg Yolk Antibody, "IgY"" Feb. 5, 1990, gric. Biol. Chem. 54(10):2531-2535.
Hau et al. "Refinement of Polyclonal Antibody Production by Combining Oral Immunization of Chickens with Harvest of Antibodies from the Egg Yolk" 2005, ILAR Journal 46(3):294-299.
Hilpert et al. "Use of bovine milk concentrate containing antibody to rotavirus to treat rotavirus gastroenteritis in infants" Jul. 1987, The Journal of Infectious Diseases 156(1):158-166.
Huang et al. "Studies on phosphatidylcholine vesicles. Formation and physical characteristics " Jan. 1969; Biochemistry 8:344-352.
Hung et al. "Betel quid chewing damaged gastric mucosa: protective effects of cimetidine and sodium bicarbonate" 1994, Chin J Physiol. 37:213-218.
Huppertz et al. "Bovine colostrum ameliorates diarrhea in infection with diarrheagenic *Escherichia coli*, shiga toxin-producing *E. coli*, and *E. coli* expressing intimin and hemolysin" Oct. 1999, J. Pediatr. Gastroenterol. Nutr. 29(4):452-456.
Hurley et al. "Perspectives on Immunoglobulins in Colostrum and Milk" 2011, Nutrients 3:442-474.
Ianotti et al. "Eggs early in complementary feeding increase choline pathway biomarkers and DHA: a randomized controlled trial in Ecuador" 2017, Am. J. Clin. Nutr. 1106:1482-1489.
Barati "Egg Yolk Antibodies for Disease Prevention" Dec. 7, 2016, J. Bacteriology & Mycology: Open Access 3 (2) (entire document).
Leventogiannis et al. "Effect of a Preparation of Four Probiotics on Symptoms of Patients with Irritable Bowel Syndrome: Association with Intestinal Bacterial Overgrowth" Jun. 2019, Probiotics and Antimicrobian Proteins 11(2):627-634.
Soubieres et al. "Emerging Role of Novel Biomarkers in the Diagnosis of Inflammatory Bowel Disease" 2016, World J. Gastrointest Pharmacol. Ther. 7(1):41-50.
Ikemori "Passive protection of neonatal calves against bovine coronavirus-induced diarrhea by administration of egg yolk or colostrum antibody powder" (Nov) May 14, 1997, Veterinary Microbiology 58:105-111.
International Preliminary Report and Written Opinion for PCT/US2019/067574 dated Jun. 16, 2021.
International Search Report and Written Opinion for PCT/US2004/036566 mailed Oct. 20, 2005.

(56) References Cited

OTHER PUBLICATIONS

International Search Report and Written Opinion for PCT/US2019/067574 mailed Mar. 11, 2020.
International Search Report and Written Opinion for PCT/US2020/019923 mailed Sep. 3, 2020.
International Search Report and Written Opinion for PCT/US2020/027469 dated Sep. 4, 2020.
International Search Report and Written Opinion from PCT/US2011/061708 mailed Mar. 29, 2012.
Janusz et al. "Chemical and Physical Characterization of a Proline-Rich Polypeptide from Sheep Colostrum" 1981, Biochem. J. 199:9-15.
Japanese Office Action mailed Sep. 29, 2105 for corresponding patent application JP 2013-540999 (with English Translation).
Jensenius et al. "Eggs: conveniently packaged antibodies. Methods for purification of yolk IgG" 1981, J. Immunol. Methods 46:63-68 (abstract only).
Jeppesen "Clinical Significance of GLP-2 in Short-Bowel Syndrome" Nov. 2003, The Journal of Nutrition 133(11):3721-37244.
Jin et al. "Effect of anti-RV immunoglobulin therapy on infants with rotavirus enteritis" Dec. 2004, Pediatric Emergency Medicine 11(6):366-368, English language abstract provided, listed as a "Y" reference in English language translation of Search Report mailed Jan. 10, 2017 in corresponding Taiwan Application No. 105114213.
Karge et al. "Pilot Study on the Effect of Hyperimmune Egg Protein on Elevated Cholesterol Levels and Cardiovascular Risk Factors" 1999, Journal of Medicinal Food 2(2):51-63.
Karhausen et al. "Epithelial hypoxia-inducible factor-1 is protective in murine experimental colitis" Oct. 2004, J. Clin. Investig. 114(8):1098-1106.
Kato et al. "Chicken ovomucoid: determination of its amino acid sequence, determination of the trypsin reactive site, and preparation of all three of its domains" 1987, Biochemistry 26:193-201.
Keech "Colostrum" 2009, Peptide Immunotherapy, 2nd Ed. AKS Publishing, China, Chapter 6, pp. 67-97.
Khan et al. "Bactericidal action of egg yolk phosvitin against *Escherichia coli* under thermal stress" Apr. 25, 2000: J. Agric. Food Chem. 48(5):1503-1506.
Khan et al. "Use of the "nutriceutical", bovine colostrum, for the treatment of distal colitis: Results from an initial study" 2002, Alimentary Pharmacology and Therapeutics 16(11):1917-1922.
Kirkpatrick "Structural Nature and Functions of Transfer Factors" 1993, Ann N.Y. Acad. Sci. 685:362-368.
Knipping et al. "An Evaluation of the Inhibitory Effects Against Rotavirus Infection of Edible Plant Extracts" Jul. 2012, Virology J. 9:137-144.
Kohler et al. "Continuous cultures of fused cells secreting antibody of predefined specificity" 1975, Nature 256:495-497.
Kollberg et al. "Oral Administration of Specific Yolk Antibodies (IgY) May Prevent Pseudomonas aeruginosa Infections In Patients with Cystic Fibrosis: A Phase I Feasibility Study" 2003, Pediatric Pulmonology 35(6):433-440.
Korpe et al. "Environmental Enteropathy: Critical Implications of a Poorly Understood Condition" 2012, Trends Mol. Med. 18(6):328-336.
Kosek et al. "Fecal markers of intestinal inflammation and permeability associated with the subsequent acquisition of inear growth deficits in infants" 2013, Am. J. Trop. Med. Hyg. 88(2):390-396.
Kovacs-Nolan et al. "Advances in the value of eggs and egg components for human health." 2005, J. Agric. Food Chem. 53:8421-8431.
Kuijper "Clostridium difficile Ribotype 027, Toxinotype III, the Netherlands" May 2006, Emerging Infectious Diseases 12(5):827-830.
Kuroki et al. "Field evaluation of chicken egg yolk immunoglobulins specific for bovine rotavirus in neonatal calves" 1997, Arch Virol. 142:843-851.
Kuroki et al. "Passive protection against bovine rotavirus in calves by specific immunoglobulins from chicken egg yolk" 1994, Arch Virol. 138:143-148.
Kuroki et al. "Passive protection against bovine rotavirus-induced diarrhea in murine model by specific immunoglobulins for chicken egg yolk" 1993; Veterinary Microbiology 37:135-146.
Lakhashe et al. "No. Acquisition: A New Ambition for HIV Vaccine Development?" 2011, Curr. Opn. Virology 1:246-253.
Lamberti et al. "Oral zinc supplementation for the treatment of acute diarrhea in children: a systematic review and meta-analysis" Nov. 2013, Nutrients 5(11):4715-4740.
Larson et al. "Immunoglobulin production and transport by the mammary gland" 1980, J Dairy Sci. 63(4):665-671.
Larsson et al. "Oral immunotherapy with yolk antibodies to prevent infections in humans and animals" 2003, Upsala J. MedSci. 108:129-140.
Lee and Paik "Anticancer and immunomodulatory activity of egg proteins and peptides: a review" 2019, Poultry Sci. 98(1):6505-6515.
Levi et al. "Non-steroidal anti-inflammatory drugs: how do they damage the gut?" 1993, Br. J. Rheumatol. 33:605-612.
Li et al. "Chitosan-alginate Microcapsules for Oral Delivery of Egg Yolk Immunoglobulin (IgY)" 2007, Agric. Food Chem. 55(88):2911-2917.
Lineweaver at al. "Identification of the trypsin inhibitor of egg white with ovomucoid" Dec. 1947, Biochem. 171(2):565-581.
Liou et al. "Production of Egg Yolk Immunoglobulin Against *Escherichia coli* From White Leghorn and Lohmann Chickens" 2011, Journal of Animal and Veterinary Advances 10(18):2349-2356.
Liu "Soybean Trypsin Inhibitor Assay: Further Improvement of the Standard Method Approved and Reapproved by American Oil Chemists' Society and American Association of Cereal Chemists International" 2019, J Am Chem Soc. 96:635-645.
Liu et al. "Global, regional, and national causes of child mortality: an updated systematic analysis for 2010 with time trends since 2000" Jun. 9, 2000, Lancet 379(9832):2151-2161.
Lloyd et al. "The role of IgA immunoglobulins in the passive transfer of protection to Taenia taeniaeformis in the mouse" 1978, Immunology 34:939-945.
Losonsky et al., "Oral Administration of Human Serum Immunoglobulin in Immunodeficient Patients with Viral Gastroenteritis, A Pharmacokinetic and Functional Analysis" Dec. 1985, Journal of Clinical Investigation 76:2362-2367.
Louie "Treatment of Cryptosporidiosis with Oral Bovine Transfer Factor" Apr. 15, 1987, Clinical Immunology and Immunopathology 44:329-334.
Ludwiczek et al. "Imbalance between interleukin-1 agonists and antagonists: relationship to severity of inflammatory bowel disease" 2004, Clin. Exp. Immunol. 138:323-329.
Maffei et al. "Gastric pH and microflora of normal and diarrhoeic infants" 1975, Gut 16:719-726.
Mallick et al. "Ischemia-Reperfusion Injury of the Intestine and Protective Strategies Againsst Injury" Sep. 2004, Digestive DMallick et al. "Ischemia-Reperfusion Injury of the Intestine and Protective Strategies Againsst Injury" Sep. 2004, Digestive Diseases and Sciences 49(9):1359-1377iseases and Sciences 49(9):1359-1377.
Marchbank et al. "Pancreatic secretory trypsin inhibitor is a major motogenic and protective factor in human breast milk" 2009, Am. J. Physiol. Gastrointest. Liver Physiol. 296:G697-G703.
Marchbank et al. "Distribution and Expression of Pancreatic Secretory Trypsin Inhibitor and Its Possible Role in Epithelial Restitution" Mar. 1996, Am. J. Pathol. 148(3):715-722.
Marchbank et al. "Human Pancreatic Secretory Trypsin Inhibitor Stabilizes Intestinal Mucosa Against Noxious Agents" Nov. 2007, Am. J. Pathol. 171(5):1462-1473.
Marchbank et al. "Pancreatic Secretory Trypsin Inhibitor Causes Autocrine-mediated Migration and Invasion in Bladder Cancer and Phosphorylates in EGF Receptor, Akt2 and Akt3, and ERK1 and ERK2" 2013, Am. J. Physiol. Gastrointest. Liver Physiol. 305:F382-F389.
Marchbank et al. "Pancreatic Secretory Trypsin Inhibitor is a Major Motogenic and Protective Factor in Human Breast Milk" Apr. 2009, Am. J. Physiol. Gastrointest. Liver Physiol. 269:G697-G703.

(56) References Cited

OTHER PUBLICATIONS

Marcq et al. "Keep bacteria under control: Dietary modulation of gut microflora in farm animals by use of hen egg yolk antibodies" University of Liege, 1-6.
Martin et al. "Fractionation of livetin and the molecular weights of the alpha-and beta-components" 1957, Canada J. Biochem. Physiol. 35:241-250.
Martin et al. "Preparation and molecular weight of gamma-livetin from egg yolk" 1958, Canada J. Biochem. Physiol. 36:153-160.
McConnell et al. "A comparison of IgG and IgG1 activity in an early milk concentrate from non-immunised cows and a milk from hyperimmunised animals" 2001, Food Res. Int. 34:255-261.
McLead et al. "Orally Administered Bovine Colostral Anti-Cholera Toxin Antibodies: Results of Two Clinical Trials" Dec. 1988, Am. J. Med, 85(6):811-816.
Mine et al. "Chicken egg yolk antibodies as therapeutics in enteric infectious disease: a review" Fall 2002, Journal of Medicinal Food 5(3):159-169.
Moore et al. "The Postischemic Gut Serves as a Priming Bed for Circulating Neutrophils that Provoke Multiple Organ Failure" Dec. 1994, J. Trauma 37(6):881-887.
Morrison et al. "Chimeric human antibody molecules: Mouse antigen-binding domains with human constant region domains" Nov. 1994, Immunology, PNAS USA 81:6851-6855.
Mu et al. "Leaky Gut As a Danger Signal for Autoimmune Diseases" 2017, Frontiers in Immunol. 8:598.
Munson et al. "Ligand: a versatile computerized approach for characterization of ligand-binding systems" 1980, Anal. Biochem. 107:220-239.
Naylor et al. "Environmental Enteropathy, Oral Vaccine Failure and Growth Faltering in Infants in Bangladesh" 2015, EBioMedicine 2:1759-1766.
New Zealand First Examination Report dated Nov. 4, 2013 for corresponding New Zealand Patent Application 672299.
New Zealand Further Examination Report mailed Mar. 23, 2015 for corresponding New Zealand Patent Application 612299.
Newburg et al. "Role of human-milk lactadherin in protection against symptomatic rotavirus infection" Apr. 18, 1988, Lancet 351(9110):1160-1164.
Nicholls et al. "Cytokines in Stool's of Children with Inflammatory Bowel Disease or Infecctive Diarrhea" 1993, J. Clin. Pathol. 46:375-760.
Niinobu et al. "Identification and Characterization of Receptors Specific for Human Pancreatic Secretory Trypsin Inhibitor" Oct. 1990, J. Exp. Med. 172:1133-1142.
Numan et al. "Clostridium difficile-associated iarrhea: Bovine anti-Clostridium difficile whey protein to help aid the prevention of relapses" 2007, Gut 56(6): 888-889, doi:10.1136/gut.2006.119016., www.gutjnl.com.
O'Farrelly et al. "Oral Ingestion of Egg Yolk Immunoglobulin from Hens Immunized with an Enterotoxigenic *Escherichia coli* Strain Prevents Diarrhea in Rabbits Challenged with the Same Strain" Jul. 1992, Infection and Immunity 60(7):2593-2597.
O'Horo et al. "The role of immunoglobulin for the treatment of Clostridium difficile infection: a systematic review" 2009, International Society of Infectious Diseases 13:663-667.
OMIM Entry, 167790 Serine Protease Inhibitor, Kazal-Type, 1 SPINK1, http://omim.org/entry/167790, pp. 107, 2019.
Osuga et al. "Egg Proteins: In Food Constitute 42.4% of the Total Proteins in Egg Yolk" 1977, Food Proteins by J. R. Whitaker and S. R. Tannenbaum Eds. AVI Pub. Co., Westport, CT, Chapter 8, pp. 209-267.
Otto et al. "Randomized control trials using a table formulation of hyperimmune bovine colostrum to prevent diarrhea caused by enterotoxigenic *Escherichia coli* in volunteers" 2011, Scandinavian J. of Gastroenterology 14:862-868.
Papp et al. "Poster Presentations: Serum Myeloperoxidase Level is a Marker of Disease Activity in Patients with Inflammatory Bowel Disease" 2011, Clinical Diagnosis and Outsome-Abstract-European Crohn's and Colitis Organisation Congress Abstract P098.

Parreno et al. "Milk supplemented with immune colostrum: Protection against rotavirus diarrhea and modulatory effect on the systemic and mucosal antibody responses in calves experimentally challenged with bovine rotavirus" 2010, VeterinaryImmunology and Immunopathology 136:12-27.
Patel et al. "Pedimune in Recurrent Respiratory Infection and Diarrhoea—The Indian Experience—The PRIDE study" Jul. 2006, Indian Journal of Pediatrics 73:585-592.
Pauly et al. "IgY Technology: Extraction of Chicken Antibodies from Egg Yolk by Polyethylene Glycol (PEG) Precipitation" May 2011, JOVE 51:1-6, http://www.jove.com/video/3084/.
Pearson "Using the FASTA program to search protein and DNA sequence databases" 1994, Methods Mol. Biol. 24:307-331.
Pearson "An Introduction to Sequence Similarity ("Homology") Searching" Jun. 2013, Curr. Protoc. Bioinformatics, Author Manuscript Chapter 3(Unit3.1):doi:10.1002/0471250953.bi0301s42., pp. 1-9.
Pelligrini et al. "Proteolytic fragments of ovalbumin display antimicrobial activity" 2004, Biochim. Biophys. Acta 1672:76-85.
Phuka et al. "Complementary feeding with fortified spread and incidence of severe stunting in 6- to 18-month-old rural Malawians" 2008, Arch Pediatr Adolesc Med. 162(7)619-626.
Phuka et al. "Postintervention growth of Malawian children who received 12-mo dietary complementation with a lipid-based nutrient supplement or maize-soy flour" 2008, American Journal of Clinical Nutrition 89:382-390.
Pimentel et al. "Eradication of small intestinal bacterial overgrowth reduces symptoms of irritable bowel syndrome" 2000, Am J Gastroenterol. 95:3503-3506.
Platts-Mills et al. "Pathogen-specific burdens of community diarrhoea in developing countries: a multisite birth cohort study (MAL-ED)" 2015, The Lancet Global Health 3(9):e564-3575.
Playford "Effect of luminal growth factor preservation on intestinal growth" Apr. 3, 1993, Lancet 341(8849):843-848.
Playford "Peptide Therapy and the Gastroenterologist: Colostrum and Milk Derived Growth Factors" 2001; Clinical Nutrition 20(16)(Supp 1):101-106.
Playford et al. "Bovine colostrum is a health food supplement which prevents NSAID induced gut damage" 1999, Gut 44:653-658.
Playford et al. "Co-administration of the health food supplement, bovine colostrum, reduces the acute non-steroidal antiinflammatory drug-induced increase in intestinal permeability" 2001, Clin. Sci. (London) 100:627-633.
Playford et al. "Bovine Colostrum: Its Constituents and Uses" 2021, Nutrients 13(1):265.
Playford et al. "Colostrum and milk-derived peptide growth factors for the treatment of gastrointestinal disorders" 2000, Am. J. Clin. Nutr. 72(1):5-14.
Playford et al. "Epidermal growth factor is digested to smaller, less active forms in acidic gastric juice" 1995, Gastroenterology 108:92-101.
Playford et al. "Influence of Inflammatory Bowl Disease on the Distribution and Concentration of Pancreatic Secretory Tryypsin Inhibitor within the Colon" Feb. 1995, Am. J. Pathol. 146(2):310-316.
Playford et al. "Methods to improve efficacy of orally administered bioactive peptides using bovine colostrum as an exemplar" 2021, PLoS One 16(6): e0253422 (14 pages) https://doi.org/10.1371/journal.pone.0253422.
Playford et al "Marked variability in bioactivity between commercially available bovine colostrum for human use; Implications for clinical trials" 2020, PLoS One, e0234719 (16 pages).
Playford et al. "Pancreatic secretory trypsin inhibitor reduces multi-organ injury caused by gut ischemia/reperfusion in mice" 2020, PLoS One 15(1):0227059, 18 pages Cited in 801 by client IS AR X.
Playford et al. "Pasteurized Chicken Egg Powder Stimulates Proliferation and Migration of AGS, RIE1, and Caco-2 Cells and Reduces NSAID-Induced Injury in Mice and Colitis in Rats" 2020, The Journal of Nutrition 150:1434-1442.
Podolsky "Inflammatory bowel disease" 2002, N. Eng. J. Med. 347:417-429.

(56) References Cited

OTHER PUBLICATIONS

Polson et al. "Improvements in the isolation of IgY from the yolks of eggs laid by immunized hens" 1985, Immunol. Invest. 14:323-327.

Quezada-Tristan et al. "Biochemical parameters in the blood of Holstein calves given immunoglobulin Y-supplemented colostrums" 2014; BMC Veterinary Research 10:159.

Quigley "Passive Immunity in Newborn Calves" 2002; Adv Dairy Technol. 14:273-292.

Quigley et al. "Addition of Soybean Trypsin Inhibitor to Bovine Colostrum: Effects on Serum Immunoglobulin Concentrations In Jersey Calves" 1995, J Dairy Sci 78:886-892.

Quinhui et al. "Leaky Gut as a Danger Signal for Autoimmune Diseases" May 2017, Frontiers in Immunol. 8(598):1-10.

Rahman et al. "Randomized placebo-controlled clinical trial of immunoglobulin Y as adjunct to standard supportive therapy for rotavirus-associated diarrhea among pediatric patients" Jun. 29, 2012, Vaccine 30(31):4661-4669.

Ramakrishna et al. "Tropical malabsorption" Dec. 2006, Postgrad. Med. J. 82(974):779-787.

Rathe et al. "Bovine Colostrum Against Chemotherapy-Induced Gastrointestinal Toxicity in Children With Acute Lymphoblastic Leukemia: A Randomized, Double-Blind, Placebo-Controlled Trial" 2019, Journal of Parenteral and Enteral Nutrition 44 (2):337-347.

Rathe et al. "Clinical applications of bovine colostrum therapy: a systematic review" 2014, Nutritional Reviews 72(4):237-254.

Rehault-Godbert et al. "The Golden Egg: Nutritional Value, Bioactivities, and Emerging Benefits for Human Health_" Mar. 22, 2019, Nutrients 11(3):684.

Richard et al. "Diarrhea in early childhood: short-term association with weight and long-term association with length" Oct. 2013, Am J Epidemiol. 178(7):1129-1138.

Roda et al. "Cytokine Networks in Ulcerative Colitis" 2011, Ulcers (ID 391787) 5 pages.

Rossignol et al. "Effect of Nitazoxanide for Treatment of Severe Rotavirus Diarrhea: Randomized Double-blind Placebo Controlled Trial" 2006, Lancet 368:124-129.

Ruigomez et al. "Overall Mortality Among Patients Surviving an Episode of Peptic Ulcer Bleeding" 2000, J. Epidemiol. Community Health 54:130-133.

Rump et al. "Treatment of diarrhoea in human immunodeficiency virus-infected patients with immunoglobulins from bovine colostrum" Jul. 1992, Clinical Investigator 70(7):588-594.

Saif et al. "Passive Immunity to Bovine Rotavirus in Newborn Calves Fed Colostrum Supplements from Immunized or Nonimmunized Cows" Sep. 1983, Infection and Immunity 41(3):1118-1131.

Samal et al. "Incidence of Bacterial Enteropathogens Among Hospitalized Diarrhea Patients from Orissa, India" Sep. 2008, Japan J. Infect. Dis. 61(5):350-355.

Sarker et al. "Randomized, Placebo-Controlled, Clinical Trial of Hyperimmunized Chicken Egg Yolk Immunoglobulin in Children with Rotavirus Diarrhea" Jan. 2001, J. Pediatric Gastro. Nutri. 32:19-25.

Sarker et al. "Successful treatment of rotavirus diarrhea in children with immunoglobulin from immunized bovine colostrum" 1998, The Pediatric Infectious Disease Journal 17(12):1149-1154.

Sastry et al. "Mesenteric ischaemia following cardiac surgery: the influence of intraoperative perfusion parameters" 2014, Interactive CardioVascular and Thoracic Surgery 19:419-425.

Saturno et al. "Oral Immunoglobulin Therapy in a Child with Severe Clostridium Difficile Diarrhea" Feb. 2006, American Academy of Allergy, Asthma and Immunology, AAAAI 62.sup.hd Annual Meeting Mar. 3-Mar. 7, 2006, The Journal of Allergy and ClinicalImmunology 117(2) S284:1A Abstract #1096.

Satyaraj et al. "Supplementation of Diets with Bovine Colostrum Influences Immue Function in Dogs" 2013, British Journal of Nutrition 110:2216-2221.

Saxena et al. "Protein proteinase inhibitors from avian egg whites" 1997. CMLS, Cell. Mol. Life Sci. 53:13-23.

Schaefer et al. "Use of UV Treated Milk Powder to Increase Vaccine Efficacy in the Elderly" Oct. 17, 2018, Front Immunol. 9:2254.

Schenkels et al. "Biochemical Composition of Human Saliva in Relation to Other Mucosal Fluids" 1995, Crit. Rev. Oral Biol. Med. 6(2):161-175.

Scott et al. "Management of Persistent Rotaviral Diarrhea in Children with Cystic Fibrosis with Enteral Administration of Intravenous Immunoglobulin" Feb. 2004, American Academy of Allergy, Asthma and Immunology, AAAAI 60.sup.th Annual Meeting, SanFrancisco, CA, Mar. 19-Mar. 23, 2004, The Journal of Allergy and Clinical Immunology 113(2) S209 3A Abstract #734.

Selinger et al. "Resistance to Infection of the External Eye: The Role of Tears" Jul.-Aug. 1979, Survey of Ophthalmology, 24(1):33-38.

Shah et al. "Protection of salmon calcitonin breakdown with serine proteases by various ovomucoid species for oral drug delivery" 2004, J. Phar. Sci. 93:392-406.

Shing et al. "Purification of polypeptide growth factors from milk" 1987, Methods in Enzymology 146:42-48.

Sigma Product Information, Epidermal Growth Factor Human, Recombinant Expressed in *E.coli*, Catalog No. E9644, Sigma-aldrich, 1 page (downloded 2019).

Sigma Product Specification, Epidermal Growth Factor, Human, Animal Component Free, Product No. E5036, Sigma-Aldrich, 1 page (downloaded 2019).

Sinha et al. "Dysbiosis-Induced Secondary Bile Acid Deficiency Promotes Intestinal Inflammation" 2020, Cell Host & Microbe, https://doi.org/10.1016/j.chom.2020.01.021.

Slack et al. "A new method for making phospholipid vesicles and the partial reconstitution of the (Na+, K+)-activated ATPase" 1973, Biochem. Biophys. Acta 323:547-549.

Staroscik et al. "Immunologically active nonapeptide fragment of a proline-rich polypeptide from ovine colostrum: amino acid sequence and immunoregulatory properties" 1983, Molecular Immunology 20(12):1277-1282.

Stec et al. "Isolation and Purification of Poluclonal IgG Antibodies from Bovine Serum by High Performance Liquid Chromatography" 2004, Bull. Vet. Inst. Pulawy 48:321-327.

Stelwagen et al. "Immune components of bovine colostrum and milk" 2009, J Anim Sci. 87:3-9.

Stewart et al. "The effect of eggs on early child growth in rural Malawi: the Mazira Project randomized controlled trial" 2019, Am. J. Clin. Nutr. 110(4):1026-1033.

Strober et al. "Proinflammatory cytokines in the pathogenesis of inflammatory bowel diseases" May 2011, Gastroenterology 140(6):1756-1767.

Sullivan et al. "Epidermal growth factor in necrotizing enterocolitis" 1991, Lancet 338:53-54.

Sullivan et al., 2001, Clinical Environmental Health and tosix Exposures, 2nd Ed., Lippincott Williams & Wilkins, p. 1040.

Supplemental European Search Report and European Search Opinion for EP 11843171.7 mailed Jul. 2, 2015.

Suzuki et al. "Effect of dietary anti-Helicobacter pylori-urease immunoglobulin Y on Helicobacter pylori infection" 2004, Alimentary Pharmacology and Therapeutics 20(Supp 1):185-192.

Svanes et al. "Restitution of the Surface Epithelium of the In Vitro Frog Gastric Mucosa After Damage with Hyperosmolar Sodium Chloride" 1982, Gastroenterology 82:1409-1426.

Szoka et al. "Procedure for preparation of liposomes with large internal aqueous space and high capture by reverse-phase evaporation" Sep. 1, 1978, PNAS USA 75(9):4194-4198.

Tack et al. "Paradigm Shift: Functional Dyspepsia—A "Leaky Gut" Disorder?" Feb. 2021, The American Journal of Gastroenterology 116(2):274-275.

Taiwan Search Report mailed Jan. 9, 2017 in corresponding Taiwan Application No. 105114213 and English language translation thereof, 2 pages total.

Takayama et al. "Factors in Bovine Colostrum that Enhance the Migration of Human Fibroblasts in Type I Collagen Gels" 2001, Biosci. Biotech. Biochem. 65(12):2776-2779.

Takeuchi et al. "Hydroxyproline, a Serum Biomarker Candidate for Gastric Ulcer in Rats: A Comparison Study of Metabolic Analysis

(56) References Cited

OTHER PUBLICATIONS of Gastric Ulcer Models Induced by Ethanol, Stress, and Aspirin" 2014, Biomarker Insights 9:61-66.
Tawfeek "Efficacy of an infant formula containing anti-*Escherichia coli* colostral antibodies from hyperimmunized cows in preventing diarrhea in infants and children: a field trial" 2003, International Journal of Infectious Diseases7(2):120-128.
Tremaine "Diagnosis and Treatment of Indeterminate Colitis" Dec. 2011, Gastroenterology & Hepatology 7(12):826-828.
Tsay et al. "Enteric bacterial loads are associated with interleukin-6 levels in systemic inflammatory response syndrome patients" 2016, Formosan J. Surgery 49:208-216.
Tsou "Current status and prospective of passive immune-vaccinated egg antibody for controlling human and animal diseases" 2009, Biotechnology Bulletin 4:143-149, listed as an "A" reference in English language translation of SearchReport mailed Jan. 10, 2017 in corresponding Taiwan Application No. 105114213.
Tsuchida et al. "Expression of REG Family Genes in Human Inflammatory Bowel Diseases and Its Regulation" 2017, Biochem. Biophysics Reports 12:198-205.
UNICEF/WHO Joint Statement Integrated Community Case Management (ICCM), Jun. 2012, pp. 7.
UNICEF/WHO, Diarrhea: Why children are still dying and what can be done, 68 pages (2009).
UNICEF/WHO, Joint statement, "Clinical management of acute diarrhea", New York and Geneva: United Nations Children's Fund and the World Health Organization; pp. 8 (May 2004).
United States Pharmacopeia National Formulary USP XXII, 1990, pp. 1696-1697.
Uruakpa et al. "Colostrum and its benefits: a review" 2002, Nutrition Research 22:755-767.
Ushijima et al. "Bacteriostatic Activity of Bovine Colostrum" 1991, Journal of Japanese Association for Infectious Diseases 65(1):54-60, with English translation.
Vaishnavi et al. "Speciation of Fecal Candida Isolates in Antibiotic-Associated Diarrhea in NON-HIV Patients" 2008, Japan J. Infect. Dis. 61:1-4.
Van Dissel et al. "Bovine antibody-enriched whey to aid in the prevention of a relapse of Clostridium difficile-associated diarrhoea: Preclinical and preliminary clinical data" 2005, J. of Med. Microbiology 54:197-205.
Van Regenmortel, "Eggs as protein and antibody factories" 1993, Proceedings of the European Symposium on the quality of Poultry Meat, Tours, France: INRA pp. 257-263.
Vara et al. "Altered levels of cytokines in patients with irritable bowel syndrome are not correlated with fatigue" 2018, Int. J. Gen. Medicine 11:285-291.
Vega et al. "Egg yolk IgY: Protection against rotavirus induced diarrhea and modulatory effect on the systemic and mucosal antibody responses in newborn calves" 2011, Veterinary Immunology and Immunopathology 142:156-169.
Vega et al. "IgY antibodies protect against human Rotavirus induced diarrhea in the neonatal gnotobiotic piglet disease model" Aug. 2012, PLoS One 7(8):e42788.
Wang et al. "Clinical efficacy of low-level laser therapy in plantar fasciitis: A systematic review and meta-analysis" 2019, Medicine (Baltimore) 98(3)::e14088.
Weiner et al. "Passive immunity against human pathogens using bovine antibodies" 1999, Clin Exp. Immunol. 116:193-205.
Wergifosse et al. "Comparison of the pathogenic treponemes of human and animal origin" May 1989, Infection and Immunity 57(5):1629-1631.
Williams et al. "Enhanced Survival and Mucosal Repair After Dextran Sodium Sulfate-Induced Colitis in Transgenic Mice That Overexpress Growth Hormone" 2001, Gastroenterology 120:925-937.
World Health Organization, "Global Health Estimates (GHE): Global Burden of Disease Daly's 2000-2011". Available at www.who.int/healthinfor/global.sub.--burden.sub.-disease/en. Accessed Apr. 15, 2014. (PDF found atwww.who.int/healthinfo/statistics/GlobalDALYmethods.sub.--2000.sub.-2011-.pdf).
World Health Organization, Geneva, "Global networks for surveillance of rotavirus gastroenteritis, 2001-2008," Weekly epidemiological record, 47:421-428 (83.sup.rd Year, Nov. 21, 2008).
Xie et al. "Therapeutic effect of probiotics and oral IgY as supplementary drugs in the treatment of pediatric rotavirus enteritis: a comparative study" Nov. 2013, Zhongguo dang dai er ke za zhi = Chinese Journal of Contemporary Pediatrics 15(11):1000-1005 (Chinese With English Abstract).
Yang et al. "Crystalline monoclonal antibodies for subcutaneous delivery" Jun. 10, 2003, PNAS 100(12):6934-6939.
Ylitalo et al. "Antibodies in the treatment of acute rotaviral gastroenteritis" Mar. 1998, Acta Paediatrica 87(3):264-267.
Yokoyama et al. "Passive Protective Effect of Chicken Egg Yolk Immunoglobulins against Experimental Enterotoxigenic *Escherichia coli* Infection in Neonatal Piglets" Mar. 1992, Infection and Immunity 60(3):998-1007.
Yolken et al. "Antibodies to rotaviruses in chickens' eggs: a potential source of antiviral immunoglobulins suitable for human consumption" Feb. 1988, Pediatrics 81(2):291-295.
Zeitlin et al. "Preventing infectious disease with passive immunization" 2000, Microbes and Infection 2:701-708.
Zierenberg et al. "Intestinal absorption of polyenephosphatidylcholine in man" 1982, J. Lipid Res. 23:1136-1142.
Zhao et al. "Murine model of gastrointestinal ischemia associated with complement-dependent injury" 2002, J. Appl. Physioil. 93:338-345.
Zhou et al. "Kinetics of trypsin inhibition by its specific inhibitors" 1989. Biochemistr. 28:1070-1076.
"APS 45-18F1 Instantized Whole Colostrum Powder", APS BioGroup, dated Apr. 10, 2010, 13 pages total.
Adu-Afarwuah et al. "Randomized comparison of 3 types of micronutrient supplements for home fortification of complementary foods in Ghana: effects on growth and motor development" 2007, American Journal of Clinical Nutrition 86:412-420.
Aksoy et al. "Can serum progranulin levels be a biomarker following gastric ulcer therapy?" 2018, Gastroenterol. Review 13(4):313-321.
Alder et al. "Diversity and Function of Adaptive Immune Receptors in a Jawless Vertebrate" Dec. 23, 2005, Science 310:1970-1973.
Anderson et al. "Compositional changes in trypsin inhibitors, phytic acid, saponins and isoflavones related to soybean processing" 1995, J. Nutr. 125:581S-588S (abstract only).
Aydin et al. "Is the Platelet to Lymphocyte Ratio a Potential Biomarker for Predicting Mortality in Peptic Ulcer Perforation?" Feb. 8, 2019, Surgical Infections, https://doi.org/10.1089/sur.2018.288.
Bade et al. "Rapid method of extraction of antibodies from hen egg yolk" 1984, J. Immunol. Methods 72:421-426.
Bahl et al. "Efficacy of zinc-fortified oral rehydration solution in 6- to 35-month-old children with acute diarrhea" Nov. 2002, The Journal of Pediatrics 141(5):677-682.
Bangham et al. "Diffusion of univalent ions across the lamellae of swollen phospholipids" 1965, J. Mol. Biol. 13:238-252.
Barranco et al. "Establishment and characterization of an in vitro model system for human adenocarcinoma of the stomach" 1983, Cancer Res. 43:1703-1709.
Batzri et al. "Single bilayer liposomes prepared without sonication" 1973, Biochem. Biophys. Acta 298:1015-1019.
Berge et al. "Evaluation of the effects of oral colostrum supplementation during the first fourteen days on the health and performance of preweaned calves" 2009, Journal of Dairy Science 92:286-295.
Bhutta et al. "Therapeutic effects of oral zinc in acute and persistent diarrhea in children in developing countries: pooled analysis of randomized controlled trials" 2000, The American Journal of Clinical Nutrition 72:1516-1522.
Bjarnason "Non-Steroid Anti-Inflammatory drug Induced Small Intestinal inflammation in man" 1988, Recent Advances In Gastroenterology, vol. 7, Chapter 2, pp. 23-46, Church Livingstone Press, London.

(56) References Cited

OTHER PUBLICATIONS

Black et al. "Maternal and child undernutrition: global and regional exposures and health consequences" 2008, The Lancet 371(9608):243-260.
Blay et al. Characterization of an epithelioid cell line derived from rat small intestine: demonstration of cytokeratin filaments 1984, Cell Biol. Int. Rep. 8:551-560.
Bodammer et al. "Prophylactic application of bovine colostrum ameliorates murine colitis via induction of Immunoregulatory" 2011, J Nutr. 141:1056-1061.
Bradley et al. "Measurement of cutaneous inflammation: estimation of neutrophil content with an enzyme marker" 1982, J. Invest. Dermatol. 78:206-209.
Brandtzaeg "Induction of secretory immunity and memory at mucosal surfaces" 2007, Vaccine 25:5467-5484.
Brandtzaeg "Mucosal immunity in infectious disease and allergy" Aug. 25, 2003, International Congress Series 1257:11-20.
Brandtzaeg "Mucosal immunity in the female genital tract" Sep. 2, 1997, Journal of Reproductive Immunology 36:23-50.
Bratton et al. "Prevalence of and Risk for Gastrointestinal Bleeding and Peptic Ulcerative Disorders in a Cohort of HIV Patients From a U.S. Healthcare Claims Database" Jun. 30, 2007, PLOS One 12(6):e0180612 (13 pages).
Brussow et al. "Bovine Milk Immunoglobulins for Passive Immunity to Infantile Rotavirus Gastroenteritis" Jun. 1987, J Clin Microbiol. 25(6):982-986.
Casswall et al. "Treatment of enterotoxigenic and enteropathogenic *Escherichia coil*-induced iarrhea in children with bovine immunoglobulin milk concentrate from hyperimmunized cows: a double-blind, placebo-controlled, clinical trial" Jul. 2000, ScandinavianJournal of Gastroenterology 35(7):711-718.
Cechova "Trypsin inhibitor from cow colostrum" 1976, Methods Enzymology 45:806-813.
Certificate of Analysis, APS 45-18F1 Instantized Whole Colostrum Powder, 2011, four pages total.
Cesarone et al. "Prevention of influenza episodes with colostrum compared with vaccination in healthy and high-risk cardiovascular subjects" 2007, The epidemiologic study in San Valentino. Clin. Appl. Thromb. Hemost. 13:130-136.
Chandak et al. "Mutations in the pancreatic secretory trypsin inhibitor gene (PSTI/SPINK1) rather than the cationic trypsinogen gene (PRSS1) are significantly associated with tropical calcific pancreatitis" 2002, J. Med. Genet. 39:347-351.
Chaparro et al. "Use of lipid-based nutrient supplements (LNS) to improve the nutrient adequacy of general food distribution rations for vulnerable sub-groups in emergency settings" 2010, Maternal and Child Nutr. 6(suppl):1-69.
Chen et al. "Mutational analysis of the human pancreatic iarrhea trypsin inhibitor (PSTI) gene in hereditary and sporadic chronic pancreatitis" 2000, J. Med. Genet. 37:67-69.

Chey et al. "Irritable Bowel Syndrome" 2015 JAMA 313(9):982, https://www.niddk.nih.gov/health-information/digestive-diseases/irritable-bowel-syndrome/definition-facts.
Chilean Examination Report dated Oct. 13, 2014 for related Chilean Patent Application Serial No. 1469-2013.
Chinese Office Action and Search Report dated Jun. 16, 2017 for related Chinese Patent Application 201510309672.5; English Translation.
Chinese Office and Search Report dated May 7, 2014 for related Chinese Patent Application Serial No. 201180065699.4; English Translation.
Choi et al. "Beneficial roles of probiotics on the modulation of gut microbiota and immune response in pigs" 2019, PLOSone 14(8):e217194.
Church et al. "Exploring the relationship between environmental enteric dysfunction and oral vaccine responses" 2018, Future Microbiol. 13(9):1055-1070.
Clackson et al. "Making antibody fragments using phage display libraries," Aug. 15, 1991, Nature 352:624-628.
Cleveland et al. "Bacteriocins: safe, natural antimicrobials for food preservation" 2001, Int. J. Food Microbiol. 71:1-50.
Cochran "Necrotizing Enterocolitis" Oct. 2018, Merck Manual Professional Version, pp. 1-5, https://www.merckmanuals.cm/en-ca/professional/pediatrics/gastrointestinal-disorders-inj neonates I infants.
Columbian Office Action dated Sep. 12, 2014 for related Columbian Patent Application Serial No. 13-148.236. English Translation.
Cooke et al. "Biomarkers of Helicobacter pylori-associated gastric cancer" 2013, Gut Microbes 4(6):532-540.
Cooper et al. "Clinicopathologic study of dextrin sulfate sodium experimental murine colitis." 1993, Lab Invest. 69:238-249.
Crabb "Antibody-based Immunotherapy of Cryptosporidiosis" 1988, Advances in Parasitology 40:122-149.
Crane et al. "Environmental Enteric Dysfunction: an Overview" 2015, Food Nutr. Bull. 36(1-suppl):S76-S78.
Cummins et al. "The Hydroxylase Inhibitor Dimethyloxalyglycine is Protective in a Muring Model of Colitis" Jan. 2008, Gastroenterology 134(1):156-165.
Da Silva et al. "IgY: A promising antibody for use in immunodiagnostic and in immunotherapy" 2010, Veterinary Immunol. Immunopath. 135:173-180.
Davidson et al. "Passive iarrhea ion of children with bovine colostrum containing antibodies to human rotavirus" Sep. 23, 1989, The Lancet 2(8665):709-712.
Davison et al. "Zinc camosine works with bovine colotrum in truncating heavy exercise-induced increase I gut permeability in healthy volunteers" 2016, Am. J. Clin. Nutr. 104:526-536.
Deamer et al. "Large vol. Liposomes by an Ether Vaporization Method" 1976, Biochem. Biophys. Acta 443(3):629-634.
Dean "Hyperimmune Eggs Capture Natural Immune Support" Jun. 2000, Alternative & Complementary Therapies, pp. 118-124.
International Search Report and Written Opinion for PCT/US2022/017937 dated May 23, 2022.

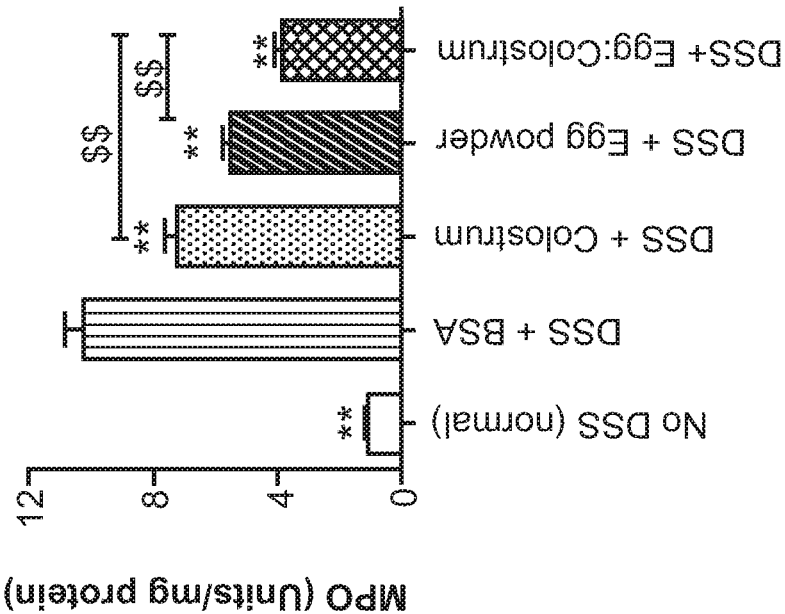
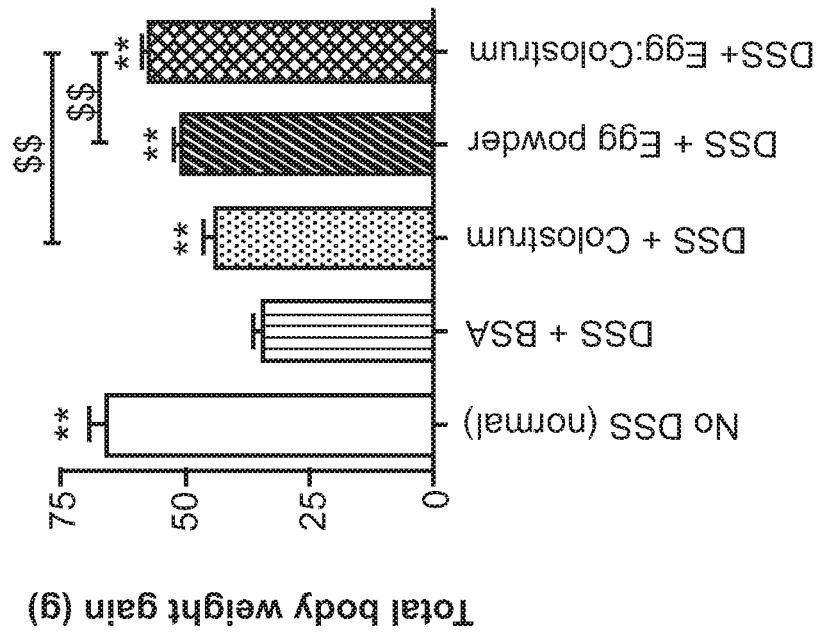
FIG. 13B
FIG. 13A

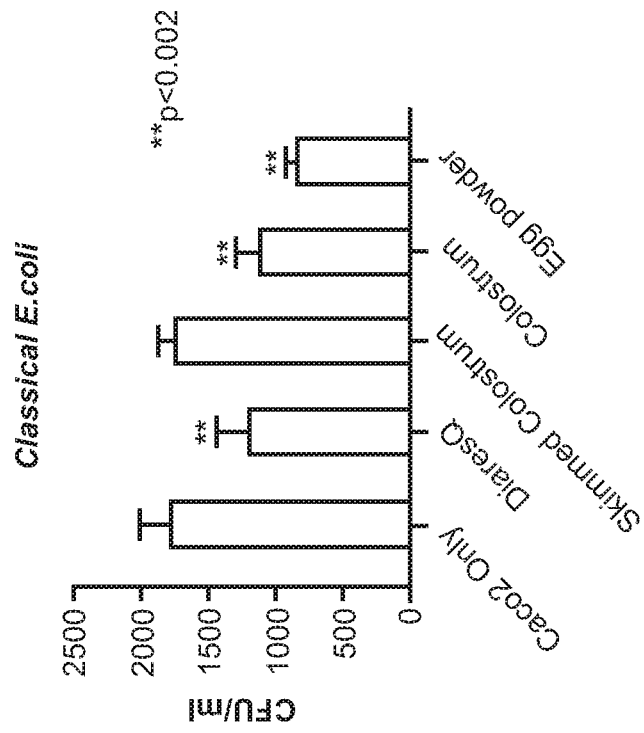
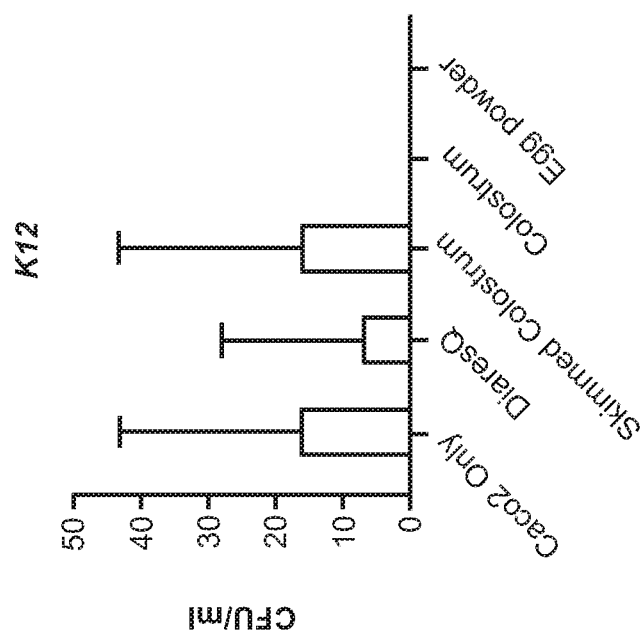
FIG. 21B
FIG. 21A

COMPOSITIONS FOR MANAGEMENT OF DISORDERS OF THE GASTROINTESTINAL TRACT

CROSS-REFERENCE TO RELATED APPLICATIONS

This application is a national stage entry of PCT International Patent Application No. PCT/US2020/019923, filed Feb. 26, 2020, which claims the benefit of U.S. Patent Application Ser. No. 62/810,637, filed on Feb. 26, 2019, U.S. Patent Application Ser. No. 62/896,429, filed on Sep. 5, 2019, U.S. Patent Application Ser. No. 62/940,133, filed on Nov. 25, 2019, and U.S. Patent Application Ser. No. 62/978,104, filed on Feb. 18, 2020, the disclosure of each of which is incorporated herein by reference in its entirety.

BACKGROUND OF THE DISCLOSURE

Field of the Disclosure

Compositions and methods are provided herein for the treatment, prevention and/or dietary management of diseases, disorders and conditions associated with inflammation or damage of the gastrointestinal tract, including environmental enteric dysfunction, inflammatory bowel disease, mucositis, chemotherapy-induced diarrhea, non-steroidal antiinflammatory drug-induced gastrointestinal damage, malabsorption syndrome, or severe acute malnutrition. Compositions comprising a synergistic combination of colostrum, specific immune egg, and one or more additional active agents are provided.

DESCRIPTION OF THE RELATED ART

Environmental enteropathy (also called environmental enteric dysfunction or tropical enteropathy) is a subclinical condition which may be caused by constant fecal-oral contamination and the resulting in blunting of intestinal villi and intestinal inflammation. The failure of nutritional interventions and oral vaccines in the developing world may be attributed to environmental enteropathy, as the intestinal absorptive and immunologic functions are significantly deranged.

Environmental Enteric Dysfunction (EED) is a common condition afflicting children in low- and middle-income countries (LMIC's) with an estimated 80% prevalence by 12 weeks of age. Naylor et al. EBioMedicine. 2015. EED is an asymptomatic inflammation of the gastrointestinal tract associated with living in poor sanitary conditions. EED consists of chronic, subclinical intestinal inflammation and is thought result from continuous asymptomatic pathogen carriage and recurrent enteric infection. Korpe P S, Petri Jr W A. Environmental enteropathy: Critical implications of a poorly understood condition. Trends Mol Med. 2012; 18(6): 328-336. These stimuli are plentiful in LMIC's with diarrhea being common and children harboring greater than 2 pathogens per non-diarrheal stool. Platts-Mills et al. The Lancet Global Health. 2015; 3(9):e564-e575. EED has been shown to be associated with malignant effects on nutrition and growth, cognitive development, and oral vaccine efficacy and thus is a major cause of childhood morbidity in impoverished settings. Kosek et al. Am J Trop Med Hyg. 2013; 88(2):390-396, Lin et al. Am J Trop Med Hyg. 2013; 89(1):130-137. One in four children under 5 are stunted according to WHO Global Database on Child Growth and Malnutrition 2013 update. Stunted is defined as height-for-age Z score (HAZ)<−2. A stunted child is 60% more likely to die by his $5^{th}$ birthday.

The histologic changes associated with EED include blunting of the intestinal villi and intestinal inflammatory infiltrate. However, since assessment of histology is often impractical, there has recently been a push in the field of international child health to discover non-invasive EED biomarkers. A few promising candidates include fecal Reg 1B, fecal myeloperoxidase (MPO), serum C-reactive protein (CRP), serum soluble CD-14 (sCD14), urinary Lactulose: Mannitol test (LM), and glucose-hydrogen breath testing.

Growth stunting and associated pathologic changes in the intestinal mucosa have been found in infants as young as 3 months. Models depicting the use of known interventions—including vitamin A and zinc supplementation, balanced energy protein supplementation, complementary feeding, breastfeeding promotion, and micronutrient supplementation in pregnancy—showed that the use of these interventions in 99% of children worldwide would only decrease stunting by 33%. Korpe, P S and Petri, WA Trends in Molecular Medicine June 2012, Vol. 18, No. 6, pp. 328-336.

Currently there is no known effective treatment for EED. While implementation of adequate sanitation throughout the world remains an utmost priority, treatment of EED is also essential. The lack of effective therapy for EED remains an immense knowledge gap in the efforts to improve childhood health worldwide. Novel therapy directed at decreasing enteric inflammation and limiting pathogen carriage/infection is needed with the goal of targeted intervention at time points when morbidity is most severe.

Colostrum and milk-derived peptide growth factors derived from colostrum have been suggested to address other gastrointestinal disorders including inflammatory bowel disease, nonsteroidal antiinflammatory drug-induced gut injury, and chemotherapy-induced mucositis. Playford et al., 2000, Am J Clin Nutr, vol. 72, pp. 5-14.

There is a need for effective and economical compositions and methods for treatment, prevention, or dietary management of diseases, disorders and conditions associated with inflammation or damage of the gastrointestinal tract including infectious disease, gut dysregulation, and drug-induced injury. Combinations of active components have been designed to address both pathogen targeting and gut repair. Methods are provided for treatment and/or prevention of environmental enteric dysfunction, inflammatory bowel disease, mucositis, chemotherapy-induced diarrhea, gastritis, peptic ulcers including gastric ulcers, duodenal ulcers, and gastroduodenal ulcers, non-steroidal antiinflammatory drug-induced gastrointestinal damage, malabsorption syndrome, or severe acute malnutrition. Improved efficacy is provided by combining compositions for orally-administered compositions comprising colostrum and antibody product with additional active agents.

SUMMARY OF THE DISCLOSURE

Compositions are provided for treating or preventing a disease or disorder associated with inflammation or damage of the gastrointestinal tract in a subject in need thereof, the composition comprising bovine colostrum; and immune egg antibody product comprising specific avian antibodies, or antigen binding fragments thereof, wherein the antibodies or fragments are specific for binding to an antigenic region of a pathogenic organism, undesirable strain, toxin, or adhesin element. The composition may comprise one or more additional active agents in an effective amount.

Compositions and methods are provided for treating or preventing environmental enteropathy (EED), small intestinal bacterial overgrowth (SIBO), leaky gut syndrome, tropical sprue, severe acute malnutrition, inflammatory bowel disease, irritable bowel syndrome, non-steroidal antiinflammatory drug (NSAID) gastrointestinal disorder or gut damage, chemotherapy-induced mucositis, radiation-induced mucositis, pseudomembranous colitis, peptic ulcers including gastric ulcers, duodenal ulcers, and gastroduodenal ulcers, gastritis, and necrotizing entercolitis. The compositions of the disclosure have been shown to reduce bacterial translocation through an intestinal epithelial barrier and reduce pathogen-induced intestinal epithelial barrier dysregulation.

The immune egg antibody product may comprise whole immune egg. The colostrum may be whole bovine colostrum. The bovine colostrum may be hyperimmune bovine colostrum or non-hyperimmune bovine colostrum. In some embodiments, the colostrum is whole, non-hyperimmune bovine colostrum. The composition may comprise a weight ratio of colostrum to immune egg antibody product, on a dry weight equivalent basis of from about 10:1 to about 1:10, or about 5:1 to 1:5, or about 3:1 to 1:3. The composition may comprise a non-neonate human effective amount of from 3 g to 50 g, 4 g to 30 g, 5 g to 20 g, or 6 g to 15 g of combined weight of the immune egg antibody product and the colostrum on a dry weight equivalent basis per dose. In some embodiments, the immune egg is whole immune egg comprising IgY specific for rotavirus, coronavirus and *E. coli*. In some embodiments, the immune egg is whole immune egg comprising IgY specific for enterotoxigenic *E. coli* spp., *E. coli* K99 pili adherence factor, *Clostridium perfringens* toxoid, *Salmonella typhimurium*, rotavirus, and coronavirus.

In some embodiments, the subject is a non-neonate human subject.

In some embodiments, the disease or disorder is associated with inflammation or damage of the gastrointestinal tract. The disease or disorder may be an infective or non-infective disease or disorder of the gastrointestinal tract. The disease or disorder may be selected from the group consisting of environmental enteric disorder (EED), tropical sprue, severe acute malnutrition, inflammatory bowel disease, irritable bowel syndrome, non-steroidal antiinflammatory drug (NSAID) gastrointestinal disorder or gut damage, chemotherapy-induced mucositis, radiation-induced mucositis, pseudomembranous colitis, SIBO, leaky gut syndrome, peptic ulcers including gastric ulcers, duodenal ulcers, and gastroduodenal ulcers, gastritis, and necrotizing entercolitis. The inflammatory bowel disease may be selected from ulcerative colitis, Crohn's disease, or indeterminate colitis. In some embodiments, the compositions of the disclosure may be used for treatment or prevention of environmental enteric disorder (EED). In some embodiments, the compositions of the disclosure may be used for treatment or prevention of tropical sprue. In some embodiments, the compositions of the disclosure may be used for treatment or prevention of severe acute malnutrition. In some embodiments, the compositions of the disclosure may be used for treatment or prevention of an inflammatory bowel disease. In some embodiments, the compositions of the disclosure may be used for treatment or prevention of ulcerative colitis. In some embodiments, the compositions of the disclosure may be used for treatment or prevention of indeterminate colitis. In some embodiments, the compositions of the disclosure may be used for treatment or prevention of indeterminate colitis. In some embodiments, the compositions of the disclosure may be used for treatment or prevention of Crohn's disease. In some embodiments, the compositions of the disclosure may be used for treatment or prevention of irritable bowel syndrome. In some embodiments, the compositions of the disclosure may be used for treatment or prevention of non-steroidal antiinflammatory drug (NSAID) gastrointestinal disorder or gut damage. In some embodiments, the compositions of the disclosure may be used for treatment or prevention of chemotherapy-induced mucositis. In some embodiments, the compositions of the disclosure may be used for treatment or prevention of radiation-induced mucositis. In some embodiments, the compositions of the disclosure may be used for treatment or prevention of pseudomembranous colitis. In some embodiments, the compositions of the disclosure may be used for treatment or prevention of peptic ulcers including gastric ulcers, duodenal ulcers, and gastroduodenal ulcers. In some embodiments, the compositions of the disclosure may be used for treatment or prevention of gastritis. In some embodiments, the compositions of the disclosure may be used for treatment or prevention of necrotizing entercolitis. In some embodiments, the compositions of the disclosure may be used for gastrointestinal flora management of a subject, such as for treating or preventing small intestinal bacterial overgrowth (SIBO). In some embodiments, the compositions of the disclosure may be used for treating or preventing small intestinal bacterial overgrowth (SIBO). In some embodiments, the compositions of the disclosure may be used for treating or preventing small intestinal bacterial overgrowth leaky gut syndrome. In some embodiments, the compositions of the disclosure may be used for treating, preventing, or preventing relapse of infectious diarrhea or enteric infection.

In some embodiments, the immune egg antibody product may include antibodies, or antigen-binding fragments thereof that are specific for an antigenic region derived from a pathogenic organism, undesirable strain, pathogen related toxin, or pathogen related adhesin element. The pathogen may be a human or veterinary, enteric or gastrointestinal, pathogen causing gastroenteritis. The pathogenic organism, undesirable strain, toxin, or adhesin may be selected from or derived from the group consisting of rotavirus, norovirus, calicivirus, enteric adenovirus, coronavirus, parvovirus, cytomegalovirus, astrovirus, herpes zoster virus, *Clostridium* spp., *Clostridium perfringens*, *Clostridium perfringens* type C toxoid, *Clostridium difficile*, *Clostridium perfringens* enterotoxin, perfringolysin O produced by *Clostridium perfringens* type C or type B, enteropathogenic *E. coli* (EPEC) strains, typical EPEC strains, atypical EPEC (aEPEC) strains, enterotoxigenic *E. coli* (ETEC) strains, enteroinvasive *E. coli* (EIEC) strains, enterohemorrhagic *E. coli* (EHEC) strains, Shiga toxin-producing *E. coli* (STEC) strains, enteroaggregative *E. coli* (EAEC) strains, diffusely adherent *E. coli* (DAEC) strains, *E. coli* K99 pili adherence factor, *E. coli* K88 pili adherence factor, *E. coli* 987P pili adherence factor, *E. coli* F41 pili adherence factor, *E. coli* F41 pili adherence factor, *E. coli* endotoxin, *Campylobacter* spp., *Shigella* spp., *Salmonella* spp., *Salmonella typhimurium*, *Salmonella enterica* serovar *Typhi*, endotoxin derived from gram negative bacteria (LPS, lipopolysaccharides), *Plesiomonas shigelloides Vibrio cholera*, *Vibrio cholerae* O1, *Vibrio* O139, Non-O1 Vibrios, *Vibrio parahaemolyticus*, *Aeromonas hydrophila*, *Candida* spp., enterohepatic *Helicobacter* (including *Helicobacter pylori*), *Staphylococcus aureus*, *Klebsiella*, Cholera toxin, Staphylococcal Enterotoxin B, *Yersinia enterocolitica*, *Shigella dysenteriae*, Shiga toxin, *Campylobacter jejuni*, *Campylobacter jejuni* enterotoxin, *E. coli* heat stable enterotoxins LT and LT-II, alpha-toxin (CPA), beta-toxin (CPB), epsilon-toxin (ETX), enterotoxin, beta2-toxin (CPB2), lipooligosaccharides (LOS), *Bacillus thuringiensis Bacillus thuringiensis* delta endotoxin, *Fusarium* spp., *Fusarium* mycotoxin, Trichothecenes, Zearalenone, *Aspergillus* spp., *Aspergillus* mycotoxin, Aflatoxins, Ochtatoxin A, Patulin, *Gibberella* spp., *Gibberella* mycotoxins, Fumonisins, Fusarin C, *Penicillium* spp., *Penicillium* mycotoxins, Patulin, Citrinin, Ochratoxin A, Cyclopiazonic acid, *Byssochlamys* spp., *Byssochlamys* mycotoxins, Patulin, *Claviceps* spp., *Claviceps* mycotoxins, Ergot alkaloids, *Alternaria, Alternaria* mycotoxins, Alternariol, Tenuazonic acid, *Gardnerella* spp., *Listeria monocytogenes, Neisseria gonorrhoeae, Chlamydiaceae trachomatis, Mycoplasma* spp., *Trichomonas vaginalis*, herpes virus type 1, herpes virus type 2, *Candida albicans, Candida glabrata, Candida tropicalis, Candida parapsilosis, Candida krusei*, Group A *Streptococcus* spp., *Giardia* spp., *Entamoeba* spp., *Acanthamoeba* spp., *Cryptosporidium* spp., *Cyclospora* spp, *Taenia* spp., *Taenia saginata, Taenia solium, Ancylostoma duodenale, Necator americanus, Ancylostoma caninum*, and *Ascaris lumbricoides*. The immune egg antibody product may include specific avian antibodies, or antigen binding fragments thereof, that are specific for a pathogen, a pathogen related toxin, or a pathogen related adhesin element, derived from one, two, three, four, five, six, seven, or eight, or more, different pathogenic organisms. The pathogen related toxin may be an endotoxin or exotoxin. The pathogen related adhesin element may be an adhesin, cadherin, cilia, fimbrillae, viral adhesin structure, or a combination thereof.

In some embodiments, the composition further comprises an additional active agent. In some embodiments, the additional active agent is selected from one or more of an antibiotic drug, antifungal drug, antimicrobial drug, antiparasitic drug, antiprotozoal drug, antiviral drug, bacteriocin, micronutrient, oral rehydration salt, antidiarrheal adsorbent, anticholinergic, antimotility drug, isolated egg bioactive molecule, additional non-immunoglobulin colostrum component, n-3 LC-PUFA, probiotic, secondary bile acid, or antisecretory agent.

In some embodiments, the composition further comprises a antibiotic. In some embodiments, the antibiotic may be selected from the group consisting of ampicillin, clindamycin, fluoroquinolone, cephalosporin, prulifloxacin, ulifloxacin, fidaxomicin, minocyclin, metronidazole, sulfamethoxazole, trimethoprim, ofloxacin, norfloxacin, tinidazole, norfloxacin, ofloxacin, ornidazole, levofloxacin, nalidixic acid, ceftriaxone, azithromycin, cefixime, ceftriaxone, cefalexin, ceftriaxone, rifaximin, ciprofloxacin, norfloxacin, ofloxacin, levofloxacin, gatifloxacin, gemifloxacin, prufloxacin, ulifloxacin, and moxifloxacin, or a combination thereof.

In some embodiments, the composition further comprises an antifungal drug. In some embodiments, the antifungal drug may be selected from nystatin, amphotericin B, flucytosine, ketoconazole, posaconazole, clotrimazole, voriconazole, griseofulvin, miconazole nitrate, and fluconazole, or a combination thereof.

In some embodiments, the composition further comprises an anti-microbial drug. In some embodiments, the antimicrobial drug may be selected from the group consisting of metronidazole, tinidazole, nitazoxanide, satranidazole, ornidazole, ofloxocin, diloxanide furoate, tetracycline, trimethoprim, sulfamethoxazole, albendazole, rifampicin, secnidazole, paromomycin, ciprofloxacin, diloxanide furoate, and fumagillin, or a combination thereof.

In some embodiments, the composition further comprises a micronutrient. In some embodiments, the micronutrient may be selected from the group consisting of vitamin A, vitamin D, vitamin E, vitamin $B_{12}$, vitamin B6, riboflavin, niacin, pantothenic acid, thiamine, choline, folic acid, biotin, vitamin K, vitamin C, cobalt, copper, iron, manganese, iodine, calcium, magnesium, phosphorus, a zinc supplement, and selenium, or any combination thereof.

In some embodiments, the micronutrient comprises vitamin A, vitamin C, folic acid, iron, and zinc. In some embodiments, the micronutrient comprises vitamin A, 100 to 1000 µg; vitamin C, 15 to 60 mg; folic acid, 80 to 600 µg; iron, 0.5 to 18 mg; and zinc, 1 to 50 mg. In some embodiments, the micronutrient comprises vitamin A, 200 to 400 µg; vitamin C, 20 to 40 mg; folic acid, 140 to 180 µg; iron, 5 to 15 mg; and zinc, 5 to 20 mg.

In some embodiments, the micronutrient comprises Vitamin A, 300 µg; Vitamin D, 5 µg; Vitamin E, 6 mg; Vitamin C, 30 mg; Thiamin, 0.5 mg; Riboflavin, 0.5 mg; Vitamin B-6, 0.5 mg; Vitamin B-12, 0.5 µg; Niacin, 6 mg; Folic acid, 160 µg; Iron, 10 mg; Zinc, 10 mg; Copper, 0.5 mg; Selenium, 20 µg; Iodine, 90 µg; Calcium, 100 mg; Magnesium, 20 mg; Phosphorus, 100 mg; Manganese, 0.6 mg; Vitamin K, 20 µg; Pantothenic acid, 1.8 mg; and Biotin, 6 µg.

In some embodiments, the micronutrient comprises Vitamin A, 100 to 1000 µg; Vitamin D, 2 to 25 µg; Vitamin E, 3 to 15 mg; Vitamin C, 15 to 60 mg; Thiamin, 0.2 to 1.5 mg; Riboflavin, 0.2 to 1.3 mg; Vitamin B-6, 0.2 to 2 mg; Vitamin B-12, 0.2 to 5 µg; Niacin, 3 to 16 mg; Folic acid, 80 to 600 µg; Iron, 0.5 to 18 mg; Zinc, 1 to 50 mg; Copper, 0.2 to 1.6 mg; Selenium, 10 to 80 µg; Iodine, 45 to 290 µg; Calcium, 50 to 1300 mg; Magnesium, 10 to 420 mg; Phosphorus, 50 to 1250 mg; Manganese, 0.3 to 2.6 mg; Vitamin K, 2 to 120 µg; Pantothenic acid, 0.9 to 7 mg; and Biotin, 3 to 35 µg.

In some embodiments, the micronutrient comprises Vitamin A, 300 µg; Vitamin D, 5 µg; Vitamin E, 6 mg; Vitamin C, 30 mg; Thiamin, 0.5 mg; Riboflavin, 0.5 mg; Vitamin B-6, 0.5 mg; Vitamin B-12, 0.5 µg; Niacin, 6 mg; Folic acid, 160 µg; Iron, 10 mg; Zinc, 10 mg; Copper, 0.5 mg; Selenium, 20 µg; Iodine, 90 µg; Calcium, 100 mg; Magnesium, 20 mg; Phosphorus, 100 mg; Manganese, 0.6 mg; Vitamin K, 20 µg; Pantothenic acid, 1.8 mg; and Biotin, 6 µg.

In some embodiments, the micronutrient may comprise zinc in the form of a zinc supplement selected from an inorganic zinc salts and/or organic zinc salts. The inorganic zinc salts may be zinc sulfate or zinc oxide. The organic zinc salts may be zinc carnosine, zinc acetate, zinc gluconate, zinc monomethionine, zinc picolinate, or zinc glycinate. In a specific aspect the zinc supplement may be zinc L-carnosine. The zinc supplement may be zinc sulfate, zinc oxide, zinc carnosine, zinc acetate, zinc gluconate, zinc monomethionine, zinc picolinate, and zinc glycinate.

In some embodiments, composition may further comprise an oral rehydration salt. The oral rehydration salt may be selected from the group consisting of sodium chloride, potassium citrate, potassium chloride, and sodium citrate, or a combination thereof.

In some embodiments, the composition further comprises a antidiarrheal adsorbent. The antidiarrheal absorbent may be selected from the group consisting of bismuth subsalicylate, kaolin, attapulgite and pectin, or a combination thereof.

In some embodiments, the composition further comprises a anticholinergic drug. The anticholinergic drug may be selected from the group consisting of a *belladonna* alkaloid, atropine and hyoscyamine, or a combination thereof.

In some embodiments, the composition further comprises a antisecretory agent selected from the group consisting of Racecadotril, Crofelemer, iOWH032, albumin tannate, Sulfasalazine, Mesalazine, Olsalazine, and Octreotide, or a combination thereof.

In some embodiments, the composition further comprises a antimotility drug selected from the group consisting of loperamide and diphenoxylate, or a combination thereof.

In some embodiments, the composition further comprises an additional colostrum component selected from the group consisting of a free secretory component, lactoferrin, epidermal growth factor (EGF), insulin-like growth factor I (IGF-I), IGF-II, transforming growth factor (TGF) alpha, TGF beta, platelet-derived growth factor (PDGF), vascular endothelial growth factor (VEGF), lysozyme, lactoperoxidase, growth factor, lactalbumin, beta-lactoglobulin, proline-rich polypeptides (PRPs), kappa-caseino glycomacropeptide, clusterin, orotic acid, fats, cytokines, phospholipase, defensins, opsonins, components of the complement system, beta-lysin, transferrin, interleukins, chemokines, interferons, TNF-alpha, fibronectin, leukocytes, phagocytes, mast cells, eosinophils, basophils, natural killer (NK) cells, lymphokine activated killer (LAK) cells, defensins, proteolytic enzymes including elastase, cathepsin G, myeloperoxidase, and NADPH oxidase, or a combination thereof.

In some embodiments, the additional active agent may be a probiotic. The probiotic may be selected from *Saccharomyces* spp., *Bifidobacterium* spp., Ruminococcaceae, *Lactobacillus* spp., optionally wherein the probiotic is selected from the group consisting of *Saccharomyces boulardii*, *Bifidobacterium lactis*, Ruminococcaceae, *Lactobacillus acidophilus*, *Lactobacillus plantarum*, and *Lactobacillus casei*.

In some embodiments, the probiotic may be a SBA producing bacteria. The SBA producing bacteria may be a Ruminococcaceae, optionally a Ruminococcus spp., such as Ruminococcus *albus*, Ruminococcus callidis, Ruminococcus bromii. The additional active agent may be a secondary bile acid (SBA). The SBA may be, for example, deoxycholic acid (DCA) or lithocholic acid (LCA).

In some embodiments, the composition further comprises an agent selected from the group consisting of Nitazoxanide orone, *Nelumbo nucifera* Gaertn., *Aspalathus linearis* (Burm. f.) R. Dahlgren, *Urtica dioica* L., *Glycyrrhiza glabra* L., *Olea europaea* L; luteolin, vitexin, and apigenin 7-O-glucoside.

In some embodiments, the composition is in the form of a powder, capsule, tablet, paste, bar, troche, soft chew, or liquid.

In some embodiments, a method is provided for preparing a composition of the disclosure, comprising: (a) obtaining a colostrum; (b) obtaining an immune egg antibody product comprising at least one specific antibody, or antigen binding fragment thereof, that specifically binds to an antigenic region of a diarrhea-causing pathogenic organism, a pathogen related toxin, a pathogen related adhesin element, or an undesirable strain; (c) optionally obtaining an additional active agent; and (d) combining an effective amount of the antibody product, an effective amount of the colostrum, and optionally the effective amount of the additional active agent with an excipient and/or a carrier to provide the composition of the disclosure. The method may 3 further comprise (e) packaging the composition in a powder, capsule, tablet, paste, bar, troche, soft chew, or a liquid form.

In some embodiments, the composition comprises a pharmaceutically acceptable carrier and/or excipient.

In some embodiments, the composition comprises a nutritionally acceptable carrier and/or excipient. The nutritionally acceptable carrier and/or excipient may be a macronutrient.

In some embodiments, the composition further comprises a carrier selected from the group consisting of a lipid-rich substance, vegetable fat, powdered protein product, additional carbohydrate, and lipid-based nutrient supplement.

In some embodiments, the disclosure provides a method of treating or preventing a disease or disorder associated with inflammation or damage of the gastrointestinal tract in a subject in need thereof, the method comprising administering a non-neonate human effective amount of a composition comprising: (a) an immune egg antibody product comprising at least one specific avian antibody, or antigen binding fragment thereof, that specifically binds to an antigenic region of a pathogenic organism, a pathogen related toxin, a pathogen related adhesion, or an undesirable strain; and (b) a bovine colostrum. In some embodiments, the method further comprises coadministering an effective amount of additional active agent. In some embodiments, the method comprises administering a composition that further comprises an additional active agent.

In some embodiments, the disclosure provides a composition for manufacture of a medicament for use in treating or preventing a disease or disorder associated with inflammation or damage of the gastrointestinal tract in a subject in need thereof; the composition comprising a non-neonate human effective amount of a composition comprising: (a) an immune egg antibody product comprising at least one specific avian antibody, or antigen binding fragment thereof, that specifically binds to an antigenic region of a pathogenic organism, a pathogen related toxin, a pathogen related adhesion, or an undesirable strain; and (b) a bovine colostrum. In some embodiments, the composition further comprises an effective amount of additional active agent. In some embodiments, the method comprises administering a composition that further comprises an additional active agent.

In some embodiments, a method is provided for treatment or prevention of a disease or disorder selected from the group consisting of environmental enteric disorder (EED), tropical sprue, severe acute malnutrition, inflammatory bowel disease, irritable bowel syndrome, non-steroidal anti-inflammatory drug (NSAID) gastrointestinal disorder, chemotherapy-induced mucositis, radiation-induced mucositis, pseudomembranous colitis, peptic ulcers, gastritis, and necrotizing entercolitis. The inflammatory bowel disease may be ulcerative colitis, Crohn's disease, or indeterminate colitis.

In some embodiments, a composition is provided for use in the treatment or prevention of a disease or disorder selected from the group consisting of environmental enteric disorder (EED), tropical sprue, severe acute malnutrition, inflammatory bowel disease, irritable bowel syndrome, non-steroidal antiinflammatory drug (NSAID) gastrointestinal disorder, chemotherapy-induced mucositis, radiation-induced mucositis, pseudomembranous colitis, peptic ulcers, gastritis, and necrotizing entercolitis. The inflammatory bowel disease may be ulcerative colitis, Crohn's disease, or indeterminate colitis.

In some embodiments, the subject is a non-neonate human.

In some embodiments, the non-neonate human effective amount of the composition comprises from 3 g to 50 g, 4 g to 30 g, 5 g to 20 g, or 6 g to 15 g of combined weight of the immune egg antibody product and the colostrum on a dry weight equivalent basis per dose.

In some embodiments, the non-neonate human effective amount of the composition alleviates one or more symptoms, or signs, and/or improves one or more biomarkers in the subject associated with a disease, disorder or condition related to inflammation or damage of the gastrointestinal tract. In some embodiments, the symptom, sign, or biomarker of the disease, disorder or condition related to inflammation or damage of the gastrointestinal tract in a subject, is selected from one or more enteric inflammation, change in intestinal microbiome, blunting of intestinal villi, intestinal integrity, ulceration, leakage of intestinal contents, systemic inflammation, weight-for-age (WAZ) z-score<−1 SD, weight-for-age (WAZ) z-score<−2 SD, height-for-age (HAZ) z-score<−1 SD, weight-for-height z-score (WHZ) <−1 SD, mid-upper arm circumference (MUAC), antigen-specific antibody titer, diarrhea volume, diarrhea duration, abdominal pain, abdominal cramping, abdominal discomfort, flatulence, diarrhea, constipation, fatigue, nausea, loss of bowel control or urgency of diarrhea symptoms, physician-assessed well-being of the subject, abnormal flattening of villi in small intestine, inflammation of the lining of small intestine, for example, as observed during an endoscopic procedure, presence of inflammatory cells (e.g., lymphocytes) in biopsy of small intestine tissue, loss of appetite (anorexia), night blindness, weight loss, loss of strength or energy (asthenia), nutrient malabsorption, anemia, low levels of vitamins A, $B_{12}$, E, D, or K, low serum albumin, low serum calcium, low serum folate, excess fat in feces (steatorrhea), thickened small bowel folds seen on imaging, and fibromyalgia. In some embodiments, the effective amount of the composition results in a significant average improvement in a symptom, sign, or biomarker in the subject. In some embodiments, the symptom, sign, or biomarker is a significant improvement of an anthropometry score selected from HAZ, WHZ, WAZ, or MUAC in the subject.

In some embodiments, the compositions of the disclosure exhibit significant improvement compared to control in one or more in vivo or in vitro assays selected from restitution/cell migration assay in vitro, cell proliferation assays in vitro, intestinal permeability model in humans in vivo, chemotherapy-induced mucositis animal model in vivo, DSS-induced colitis animal model in vivo, NSAID-induced animal model of small intestine damage in vivo, NSAID-induced animal model of gastric damage in vivo, LPS-induced diarrhea animal model, or repair and protection factor scoring method for bioactive agents. The repair and protection scoring method may be performed according to the method of Playford disclosed in U.S. Pat. No. 7,426,440, which is incorporated herein by reference.

Compositions are provided comprising dried bovine colostrum and dried egg. The compositions may be useful as nutritional compositions or pharmaceutical compositions. The egg may include immune egg and/or non-hyperimmune egg. The bovine colostrum may include non-hyperimmune colostrum and/or hyperimmune colostrum. In one embodiment, the composition includes immune egg and non-hyperimmune colostrum. In one embodiment, the composition includes dried immune egg and dried non-hyperimmune colostrum. In one embodiment, the composition includes dried non-hyperimmune egg and dried hyperimmune bovine colostrum. In one embodiment, the composition includes dried non-hyperimmune egg and dried non-hyperimmune bovine colostrum. The dried egg may be dried chicken egg. The dried egg may include dried whole egg, dried egg yolk, and/or dried egg white. The dried egg may be dried whole egg. The dried egg may be dried egg yolk alone. The dried egg may be dried egg white alone. The dried egg may be dried pasteurized egg. The dried pasteurized egg may include dried pasteurized whole egg. The dried egg may be dried pasteurized raw whole egg. The dried egg may be fractionated dried pasteurized raw whole egg. The fractionated dried egg may be whole egg separated into separate fractions of, for example, >30 kDa, 10-30 kDa, 5-10 kDa and <5 kDa, by any suitable means. In some embodiments, the dried egg is not dried cooked egg. The dried egg may be, for example, spray dried egg, lyophilized egg, and/or freeze dried egg. The dried egg may be dried powdered egg.

The dried colostrum may be dried bovine colostrum. The dried bovine colostrum may include non-hyperimmune colostrum; hyperimmune colostrum; whole, non-defatted colostrum; defatted colostrum; fractionated colostrum; immune milk; whole milk; fractionated milk; milk; whole hyperimmune colostrum, whole non-hyperimmune colostrum; non-defatted hyperimmune colostrum; or non-defatted non-hyperimmune colostrum. The dried bovine colostrum may be dried whole bovine colostrum. The dried colostrum may be dried whole bovine colostrum powder. The dried colostrum may include, for example, spray dried colostrum, lyophilized colostrum, and/or freeze dried colostrum. The dried bovine colostrum powder may be instantized and/or agglomerated. The dried bovine colostrum powder may be instantized and/or agglomerated dried whole colostrum powder.

The composition may include dried egg and dried colostrum and optionally one or more additional active components as provided herein.

Compositions are provided that are suitable for nutritional support in a subject having or at risk of a disease or disorder associated with inflammation or damage of the gastrointestinal tract, stunting, or failure to grow. The disease or disorder may be environmental enteric disorder (EED), tropical sprue, severe acute malnutrition, inflammatory bowel disease, irritable bowel syndrome, non-steroidal anti-inflammatory drug (NSAID) gastrointestinal disorder, chemotherapy-induced mucositis, radiation-induced mucositis, pseudomembranous colitis, gastritis, peptic ulcers, and necrotizing enterocolitis.

In some embodiments, a kit is provided for the treatment or prevention of a pathogenic infection or undesirable strain of microorganisms in a subject in need thereof; the kit comprising one or a multiplicity of first single dose packets, and one or a multiplicity of second single-dose packets, the first single dose packets comprising: (a) an effective amount of an antibody product comprising at least one specific avian antibody, or active binding fragment thereof, that specifically binds to an antigenic region of a diarrhea-causing pathogenic organism, a pathogen related toxin, a pathogen related adhesion, or an undesirable strain; (b) an effective amount of bovine colostrum; and the second single dose packets comprising (c) an effective amount of an additional active agent. In some embodiments, the second single dose packets comprise an additional active agent selected from the group consisting of an antibiotic drug, antifungal drug, antimicrobial drug, antiparasitic drug, antiprotozoal drug, antiviral drug, bacteriocin, micronutrient, oral rehydration salt, antidiarrheal adsorbant, anticholinergic, antimotility drug, additional non-immunoglobulin colostrum component, or antisecretory agent.

BRIEF DESCRIPTION OF THE DRAWINGS

FIG. 11A shows in vitro proliferation for cells incubated in 0.25-4 mg/ml of egg (■), bovine colostrum (●), or 40:60 combination (▲) of egg and colostrum. Changes in proliferation assessed using a cell viability reagent (ALAMARBLUE™). Results expressed as % response compared to effect caused by adding 1 μg/ml EGF (positive control, defined as 100%). Results expressed as means+/−SEM of 4 wells.

FIG. 11B shows comparison of fresh vs. powdered whole egg, egg yolk, egg white and boiled whole egg and effect of heating on proliferation. Cells incubated in 1 mg/ml of test products. ** indicates $p<0.01$ of fresh versus heated equivalent. Cells exposed to fresh or powdered whole egg, egg yolk, or egg white each exhibited significantly greater % proliferation than either fresh or powdered boiled whole egg.

FIG. 11C shows effect on proliferation of egg powder with or without an EGFR-inhibitor (Tyrphostin), TGFβ neutralising antibody, ovomucoid antibody, or ovalbumin antibody, respectively. * and ** indicates p<0.02 and <0.01, respectively versus egg powder alone. Cells exposed to egg powder alone exhibited significantly greater % proliferation compared to cells exposed to egg powder and EGFR-inhibitor Tyrphostin, egg powder and ovomucoid antibody, and egg powder and ovalbumin antibody.

FIG. 11D shows effect on cell migration of egg powder with or without an EGFR-inhibitor (Tyrphostin), TGFβ neutralising antibody, ovomucoid antibody, or ovalbumin antibody, respectively. * and ** indicates p<0.02 and <0.01, respectively versus egg powder alone. Cells exposed to egg powder alone exhibited significantly greater % migration in leading edge in 24 hours compared to cells exposed to egg powder and EGFR-inhibitor Tyrphostin, egg powder, TGFβ antibody, egg powder and ovomucoid antibody, and egg powder and ovalbumin antibody.

FIG. 12A shows a photomicrograph showing morphology of microdissected normal duodenal villi.

FIG. 12B shows a photomicrograph showing morphology of microdissected villi following exposure to NSAID indomethacin. Compared to normal villi (FIG. 12A), NSAID caused shortening of villus length with some bulbous expansion.

FIG. 12C shows a photomicrograph showing morphology of microdissected villi following exposure to egg alone and NSAID indomethacin. The degree of injury appeared less severe in animals that received egg alone with NSAID, when compared to FIG. 12B. Similar appearance was seen in animals given colostrum alone (not shown).

FIG. 12D shows a photomicrograph showing morphology of microdissected villi following exposure to NSAID indomethacin with 40:60 wt powdered pasteurized whole egg/colostrum. The greatest protection was seen in animals that received the 40:60 combination of powdered pasteurized whole egg and colostrum.

FIG. 12E shows a photomicrograph showing morphology of microdissected villi following exposure to NSAID indomethacin with cooked whole egg powder. Cooked whole egg powder had no effect on NSAID-induced injury.

FIG. 12F shows a bar graph of average villus height (mm) with no NSAID, NSAID alone, NSAID+colostrum, NSAID+powdered whole pasteurized egg, NSAID+40:60 egg/colostrum, and NSAID+cooked egg. NSAID induced damage (shortening) was significantly reduced by 29% in animals given colostrum, by 51% in animal given egg, and by 68% when the 40:60 combination was used (P<0.01 vs egg or colostrum given alone). ** signifies p<0.01 vs NSAID alone group. $$ indicates p<0.01 versus egg or colostrum alone.

FIGS. 13A-B show effects of egg and/or colostrum in a rat DSS-induced colitis model. Rats received 20 mg/kg/day of BSA (negative control), powdered pasteurized whole egg, powdered whole colostrum, or 40:60 egg:colostrum combination for 9 days. The rats also received DSS (4%, w/v) in drinking water for the final 7 days.

FIG. 13A shows a bar graph of cumulative total body weight gain (g) in rat DSS-induced colitis model over 9 days. Data shown as mean±SEM of 8 per group. **p<0.01, compared to DSS alone. $$ indicates p<0.01 versus egg or colostrum alone. Rats receiving DSS+egg, DSS+colostrum, or DSS+egg:colostrum each exhibited significantly greater total body weight gain than rats receiving DSS alone. Rats receiving the combination of egg:colostrum exhibited significantly more weight gain than rats receiving either egg or colostrum alone.

FIG. 13B shows a bar graph of colonic tissue MPO levels in rat DSS-induced colitis model over 9 days. Data shown as mean±SEM of 8 per group. **p<0.01, compared to DSS alone. $$ indicates p<0.01 versus egg or colostrum alone. Rats receiving DSS+egg, DSS+colostrum, or DSS+egg:colostrum each exhibited significantly less colonic MPO than rats receiving DSS alone. Rats receiving the combination of egg:colostrum exhibited significantly less colonic MPO than rats receiving either egg or colostrum alone.

FIG. 14A shows a photomicrograph of representative normal morphology in a normal rat (no DSS).

FIG. 14B shows a photomicrograph in a rat receiving DSS alone. Morphology showed DSS alone caused marked loss of overlying epithelium and diminished numbers of crypts, with the remaining ones often showing cystic dilatation compared to FIG. 14A.

FIG. 14C shows a photomicrograph in a rat receiving DSS+colostrum. The morphological changes appeared reduced in animals receiving DSS that had also received colostrum compared to DSS alone (FIG. 14B).

FIG. 14D shows a photomicrograph in a rat receiving DSS+powdered pasteurized whole egg. The morphological changes appeared reduced in animals receiving DSS that had also received egg compared to DSS alone (FIG. 14B).

FIG. 14E shows a photomicrograph in a rat receiving DSS+40:60 powdered pasteurized whole egg:colostrum combination. The 40:60 egg and colostrum combination group exhibited nearly normal morphology.

FIG. 14F shows a bar graph of total colitis score per colon in rats based on histological appearance. **p<0.01, compared to DSS alone. $$ indicates p<0.01 versus egg or colostrum alone. Rats receiving DSS+egg, DSS+colostrum, or DSS+egg:colostrum each exhibited significantly lower average colitis score than rats receiving DSS alone. A 74% reduction in injury was exhibited in egg:colostrum combination group compared to DSS alone, P<0.01 vs using either egg or colostrum alone.

FIG. 20A shows TER (Ohms cm2) for Caco2 cells only, DiaResQ®, skimmed colostrum, whole colostrum, or egg powder when no infection was present (open bars), or with K12-*E. coli* infection (filled bars).

FIG. 20B shows TER (Ohms cm2) for Caco2 cells only, DiaResQ®, skimmed colostrum, whole colostrum, or egg powder when no infection was present (open bars), or with *E. coli* infection (filled bars). DiaResQ®, whole colostrum, or egg powder each significantly reversed pathogen-induced barrier dysfunction. Skimmed colostrum did not significantly reduce pathogen-induced barrier dysfunction.

FIG. 20C shows TER (Ohms cm2) for Caco2 cells only, DiaResQ®, skimmed colostrum, whole colostrum, or egg powder when no infection was present (open bars), or with EPEC infection (filled bars). DiaResQ®, whole colostrum, or egg powder each significantly reversed pathogen-induced barrier dysfunction. Skimmed colostrum did not significantly reduce pathogen-induced barrier dysfunction.

FIG. 20D shows TER (Ohms cm2) for Caco2 cells only, DiaResQ®, skimmed colostrum, whole colostrum, or egg powder when no infection was present (open bars), or with *Salmonella enteriditis* infection (filled bars). DiaResQ®, whole colostrum, or egg powder each significantly reversed pathogen-induced barrier dysfunction. Skimmed colostrum did not significantly reduce pathogen-induced barrier dysfunction.

FIG. 20E shows TER (Ohms cm2) for Caco2 cells only, DiaResQ®, skimmed colostrum, whole colostrum, or egg powder when no infection was present (open bars), or with Klebsiellapneumoniae infection (filled bars). Egg powder significantly reversed pathogen-induced barrier dysfunction.

FIG. 20F shows TER (Ohms cm2) for Caco2 cells only, DiaResQ®, skimmed colostrum, whole colostrum, or egg powder when no infection was present (open bars), or with *Klebsiella*+K12 *E. coli* infection (filled bars). DiaResQ significantly reversed pathogen-induced barrier dysfunction. Skimmed colostrum, whole colostrum, or egg powder did not significantly reduce pathogen-induced barrier dysfunction.

FIG. 20G shows TER (Ohms cm2) for Caco2 cells only, DiaResQ®, skimmed colostrum, whole colostrum, or egg powder when no infection was present (open bars), or with Staphyloccocus *aureus* infection (filled bars). Egg powder significantly reversed pathogen-induced barrier dysfunction.

FIG. 20H shows TER (Ohms cm2) for Caco2 cells only, DiaResQ®, skimmed colostrum, whole colostrum, or egg powder when no infection was present (open bars), or with *Staphylococcus*+K12 *E. coli* infection (filled bars). DiaResQ significantly reversed pathogen-induced barrier dysfunction. Skimmed colostrum, whole colostrum, or egg powder did not significantly reduce pathogen-induced barrier dysfunction.

FIG. 20I shows TER (Ohms cm2) for Caco2 cells only, DiaResQ®, skimmed colostrum, whole colostrum, or egg powder when no infection was present (open bars), or with *Streptococcus pneumonia* infection (filled bars). DiaResQ® or egg powder both significantly reversed pathogen-induced barrier dysfunction.

FIG. 20J shows TER (Ohms cm2) for Caco2 cells only, DiaResQ®, skimmed colostrum, whole colostrum, or egg powder when no infection was present (open bars), or with *Enterrococcus faecalis* infection (filled bars).

FIG. 20K shows TER (Ohms cm2) for Caco2 cells only, DiaResQ®, skimmed colostrum, whole colostrum, or egg powder when no infection was present (open bars), or with *Proteus mirabilis* infection (filled bars).

FIG. 21A-K show bar graphs of an in vitro model of bacterial translocation (BT) across intestinal monolayer. Bacteria isolated and cultured from the basolateral compartment of the Transwell chamber, signified bacterial translocation (BT) had occurred across the epithelium. (**p<0.002; *p<0.05).

FIG. 21A shows very little to no bacterial translocation (cfu/ml) of K12-*E. coli* across intestinal monolayer for Caco2 cells only at 24 h incubation.

FIG. 21B shows bacterial translocation (cfu/ml) of classical *E. coli* across intestinal monolayer for Caco2 cells only, or with DiaResQ®, skimmed colostrum, whole colostrum, or egg powder. DiaResQ®, whole colostrum, or egg powder each significantly reduced BT during incubation of *E. coli* in the in vitro model at 24 h incubation. (**p<0.002). Skimmed colostrum did not significantly reduce BT.

FIG. 21C shows bacterial translocation (cfu/ml) of EPEC across intestinal monolayer for Caco2 cells only, or with DiaResQ®, skimmed colostrum, whole colostrum, or egg powder. DiaResQ®, whole colostrum, or egg powder each significantly reduced BT during incubation of EPEC in the in vitro model at 24 h incubation. (**p<0.002). Skimmed colostrum also significantly reduced BT. (*p<0.05).

FIG. 21D shows bacterial translocation (cfu/ml) of *Salmonella* enteridis across intestinal monolayer for Caco2 cells only, or with DiaResQ®, skimmed colostrum, whole colostrum, or egg powder. DiaResQ®, whole colostrum, or egg powder each significantly reduced BT during incubation of *Salmonella* enteridis in the in vitro model at 24 h incubation. Skimmed colostrum did not significantly reduce BT.

FIG. 21E shows bacterial translocation (cfu/ml) of *Klebsiella pneumoniae* across intestinal monolayer for Caco2 cells only, or with DiaResQ®, skimmed colostrum, whole colostrum, or egg powder. Egg powder significantly reduced BT during incubation of *Klebsiella pneumoniae* in the in vitro model at 24 h incubation. (**p<0.002).

FIG. 21F shows bacterial translocation (cfu/ml) of a combination of *Klebsiella pneumoniae*+K12 *E. coli* across intestinal monolayer for Caco2 cells only, or with DiaResQ®, skimmed colostrum, whole colostrum, or egg powder. DiaResQ®, whole colostrum, or egg powder each significantly reduced BT during incubation of the combination of *Klebsiella pneumoniae*+K12 *E. coli* in the in vitro model at 24 h incubation. (**p<0.002). Skimmed colostrum did not significantly reduce BT.

FIG. 21G shows some bacterial translocation (cfu/ml) of *Enterococcus faecalis* across intestinal monolayer for Caco2 cells only, or with DiaResQ®, skimmed colostrum, whole colostrum, or egg powder. Whole colostrum significantly reduced BT during incubation of *Enterococcus faecalis* in the in vitro model at 24 h incubation. (**p<0.05).

FIG. 21H shows bacterial translocation (cfu/ml) of a combination of *Proteus mirabilis* across intestinal monolayer for Caco2 cells only, or with DiaResQ®, skimmed colostrum, whole colostrum, or egg powder. DiaResQ®, whole colostrum, or egg powder each significantly reduced BT during incubation of the combination of *Proteus mirabilis* in the in vitro model at 24 h incubation. (**p<0.05). Skimmed colostrum did not significantly reduce BT.

FIG. 21I shows very little to no bacterial translocation (cfu/ml) of *Streptococcus pneumonia* across intestinal monolayer for Caco2 cells only at 24 h incubation.

FIG. 21J shows very little to no bacterial translocation (cfu/ml) of *Staphylococcus aureus* across intestinal monolayer for Caco2 cells only at 24 h incubation.

FIG. 21K shows little bacterial translocation (cfu/ml) of *Staphylococcus aureus*+K12 *E. coli* across intestinal monolayer for Caco2 cells only at 24 h incubation.

DETAILED DESCRIPTION

Figure 1:
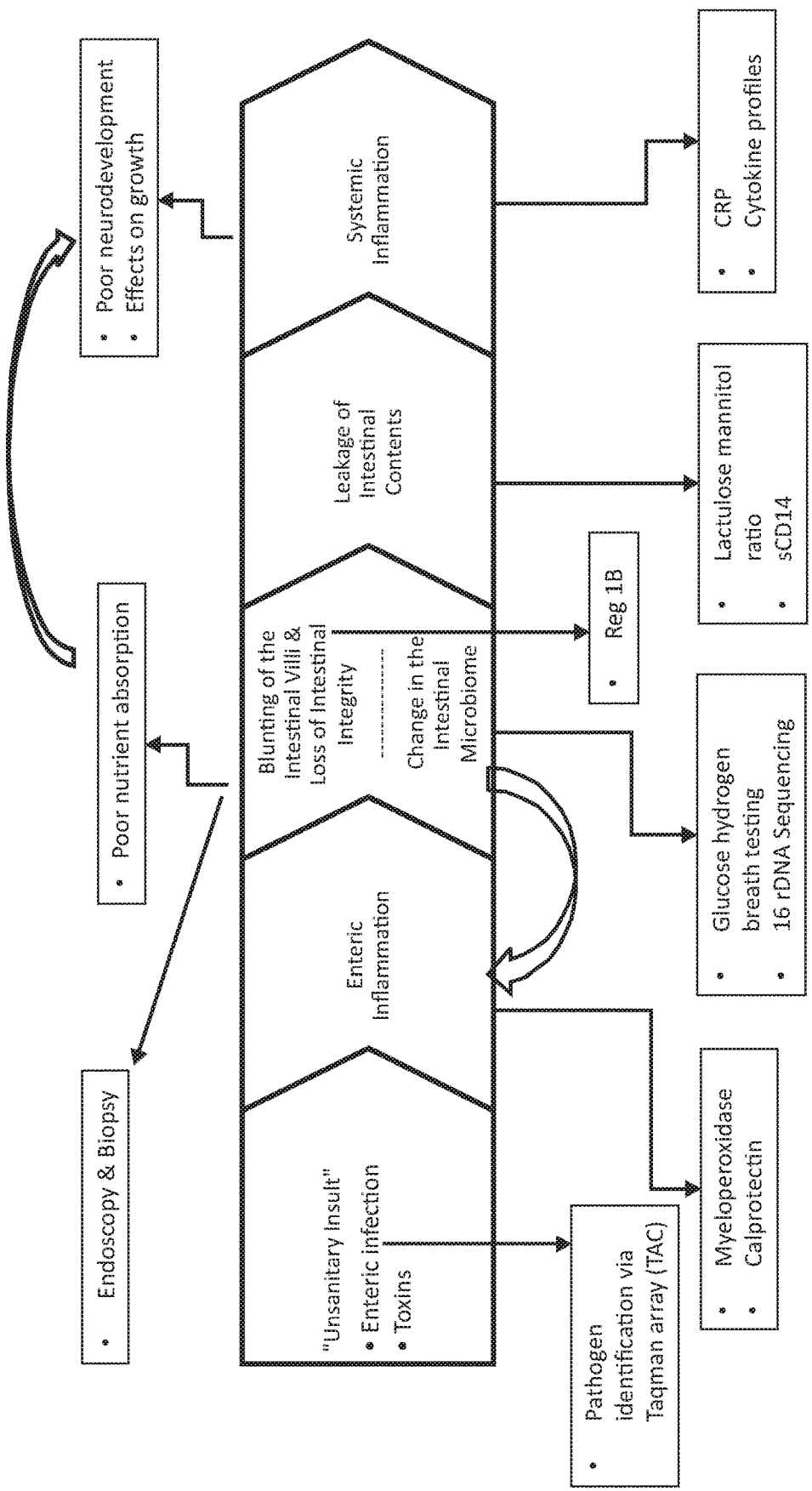
FIG. 1 shows a schematic of Environmental Enteric Dysfunction (EED) pathogenesis and biomarkers and analyses used during a 30 day study in 6 to 9 month old malnourished children.

The disclosure provides compositions and methods for effective management of infective and/or non-infective gastrointestinal tract conditions. Non-infective conditions may include, for example, NSAID injury or inflammatory bowel disease. Infective conditions may include, for example, subclinical infection or diarrhea due to a pathogenic infection or presence of an undesirable strain. The compositions may include, for example, i) colostrum present in an effective amount, ii) immune egg antibody product comprising specific antibodies; and optionally iii) an additional active agent. The additional active agent may be selected from among accepted standard of care protocols.

The colostrum in the compositions may be whole colostrum, wherein, without being bound by theory, the lipid components of the colostrum provide some degree of protection to the antibodies from degradation in the gastrointestinal tract. In some embodiments, whole colostrum is used in an amount effective to provide protection of the antibodies from denaturation due to temperature, acid hydrolysis and enzymatic degradation in the gastrointestinal environment. In some embodiments, the colostrum is whole bovine colostrum.

The immune egg antibody product may comprise specific antibodies that are specific for an antigenic region of a diarrhea-causing pathogenic organism, toxin, or adhesion. In some embodiments, the specific antibodies are avian antibodies selected from one or more of an IgY, IgA, or IgM. The immune egg antibody product may be whole immune egg, pasteurized whole immune egg, pasteurized immune egg yolk, pasteurized immune egg white, pasteurized raw whole immune egg, pasteurized raw whole immune egg powder, dried pasteurized raw whole immune egg, or dried powdered pasteurized raw whole immune egg.

The additional active agent may be selected from one or more agents known to be useful in the treatment of diseases or conditions associate with inflammation or damage of the gastrointestinal tract. In some embodiments, the additional active agent is selected from one or more of an antibiotic, antifungal, antiviral, antimicrobial, bacteriocin, micronutrient, oral rehydration salt, antidiarrheal adsorbant, anticholinergic, antisecretory agent, antimotility drug, isolated egg bioactive molecule, or additional colostrum component, or a combination thereof.

Definitions

The terms "prevention", "prevent", "preventing", "prophylaxis" and as used herein refer to a course of action (such as administering a compound or pharmaceutical composition of the present disclosure) initiated prior to the onset of a clinical manifestation of a disease state or condition so as to prevent or reduce such clinical manifestation of the disease state or condition. Such preventing and suppressing need not be absolute to be useful.

The terms "treatment", "treat" and "treating" as used herein refers a course of action (such as administering a compound or pharmaceutical composition) initiated after the onset of a clinical manifestation of a disease state or condition so as to eliminate or reduce such clinical manifestation, such as one or more symptoms, of the disease state or condition. Such treating need not be absolute to be useful.

The term "in need of treatment" or "in need thereof" as used herein refers to a judgment made by a caregiver that a patient or subject requires or will benefit from treatment. This judgment is made based on a variety of factors that are in the realm of a caregiver's expertise, but that includes the knowledge that the subject or patient is ill, or will be ill, as the result of a condition that is treatable by a method, compound or pharmaceutical composition of the disclosure.

The term "in need of prevention" as used herein refers to a judgment made by a caregiver that a patient or subject requires or will benefit from prevention. This judgment is made based on a variety of factors that are in the realm of a caregiver's expertise, but that includes the knowledge that the patient will be ill or may become ill, as the result of a condition that is preventable by a method, compound or pharmaceutical composition of the disclosure.

The term "individual", "subject" or "patient" as used herein refers to any animal, including mammals, such as humans, other primates, dogs, cats, swine, cattle, sheep, goat, horses, rabbits, mice, rats, cotton rats, gerbils, cavies, hamsters, other rodents, or or birds such as chickens, turkeys, ducks, swan, pheasant, geese, guinea fowl, ratite, ostrich, emu, quail, chukkar, pheasant, grouse, Cornish hens, and partridge, or exotic animal or zoo animal. In some embodiments, the subject is selected from a yak, elephant, tiger, lion, cougar, reindeer, elk, camel, fox, deer, raccoon, seal, otter, beaver, seabird, gull, pelican, albatross. The term may specify male or female or both, or exclude male or female. In some embodiments, the subject is a mammal. In some embodiments, the subject is a production animal. In some embodiments, the subject is an avian subject. Production animals refer to animals raised for consumption, food-producers, or fur, feather, or wool producers. In some embodiments the subject is selected from poultry and game birds. Chicken refers to meat-bearing chicken, which encompass chickens which are raised for slaughter, which are also called broilers, and egg-producing chickens, which are those that are used to produce eggs for human consumption. In some embodiments, the subject is a companion animal. In some embodiments, the companion animal is selected from a dog, cat, ferret, guinea pig, horse, donkey, or mule. In some embodiments, the subject is a puppy, kitten or foal. In some embodiments, the subject may be a human.

The human subject may be an adult human, a non-neonate human, a human toddler, child, or adolescent.

The term "child" refers to a human below the age of 18 years.

The non-neonate human may be a child greater than 6 months of age, from 6 months to 18 years, 6 months to 12 years, 6 months to 6 years, or 6 months to 2 years of age.

The term "neonate", or newborn, refers to an infant in the first 28 days after birth. The term "non-neonate" refers to an animal older than 28 days of age.

The term "effective amount" as used herein refers to an amount of an agent, either alone, or as a part of a pharmaceutical composition or nutritional composition, that is capable of having any detectable, positive effect on any symptom, aspect, or characteristics of a disease state or condition following administration to a subject. Such effect need not be absolute to be beneficial. In some embodiments the composition comprises an immune egg antibody product comprising an antibody, or antigen binding fragment thereof, a colostrum, and optionally an additional active agent selected from an antibiotic, antifungal, antimicrobial, micronutrient, oral rehydration salt, antidiarrheal adsorbant, anticholinergic, antisecretory agent, antimotility drug, or immunologically active colostrum component.

The non-neonate human effective amount of the composition in the subject may improve or alleviate a symptom, sign of a disease, disorder or condition related to inflammation or damage of the gastrointestinal tract, wherein the sign or symptom is selected from the group consisting of decreased enteric inflammation, change in intestinal microbiome, decreased blunting of intestinal villi, increased intestinal integrity, decreased ulceration, decreased leakage of intestinal contents, decreased systemic inflammation, increased weight-for-age (WAZ) z-score, increased height-for-age (HAZ) z-score, increased weight-for-height z-score (WHZ), increased mid-upper arm circumference (MUAC), change in antigen-specific antibody titer in the subject, reduction of diarrhea volume, reduction of diarrhea duration, reduction of abdominal pain, reduction of nausea, reduction of cramping, reduction of loss of bowel control or urgency of diarrhea symptoms; increase in physician-assessed well-being of the subject, decreased abnormal flattening of villi and inflammation of the lining of small intestine, for example, as observed during an endoscopic procedure, decreased presence of inflammatory cells (e.g., lymphocytes) in biopsy of small intestine tissue; alleviation of loss of appetite (anorexia), night blindness, weight loss, loss of strength or energy (asthenia), nutrient malabsorption, anemia, low levels of vitamins A, B12, E, D, and K, low serum albumin, low serum calcium, low serum folate, anemia, excess fat in feces (steatorrhea), thickened small bowel folds seen on imaging, abdominal cramping, abdominal pain, abdominal discomfort, flatulence, diarrhea, constipation, fatigue, and fibromyalgia. In some embodiments, the subject is a non-neonate human child and the symptom, sign, or biomarker is a measurable improvement of a anthropometry score selected from HAZ, WHZ, WAZ, or MUAC in the subject. For example, improvement of a anthropometry score may be an increased height-for-age z-score (HAZ) of >−2 SD, or >−1 SD; increased weight-for-height z-score (WHZ) of >−3 SD, >−2 SD, or >−1 SD; increased weight-for-age z-score (WAZ) of >−2 SD, or >−1 SD; or increased mid-upper arm circumference (MUAC) >115 mm, in the subject over time.

The non-neonate human effective amount of the composition in the subject may improve one or more biomarkers selected from the group consisting of fecal Reg 1, fecal MPO, serum sCD14, serum CRP, urine lactulose:mannitol (L:M) ratio, plasma IL-6, fecal IL-6, plasma TNFalpha, fecal TNFalpha, plasma IL-1Ra, plasma IL-1sR1, and hydrogen breath testing for small intestinal bacterial overgrowth (SIBO) or malabsorption.

The alleviation or improvement of the sign or symptom or biomarker may occur following administering the composition of a period of time from 1 week to 2 years, 2 weeks to 18 months, 3 weeks to 12 months, 4 weeks to 9 months, 6 weeks to 6 months, or 8 weeks to 3 months, or 1, 2, 3, 4, 5, 6, 7, 8, 9, 10, 11, 12, 13, 14, 15, 16, 17, 18, 19, 20, 21, 22, 23, or 24 months after starting the administration.

An "effective amount" of colostrum may be further defined herein as an amount of colostrum effective to provide a desirable activity, or to improve or preserve the stability of an antibody, immunoglobulin or fragment of the composition by at least 10%, 20%, 30%, 50%, 70%, 100% or 2-fold, 3-fold, 4-fold, or greater, for example, in terms of binding activity, relative to the same antibody, immunoglobulin or fragment without the agent such as colostrum when exposed to the same conditions for the same period of time. The effective amount of colostrum is selected from 0.5 g to 100 g, 1 g to 75 g, 2 g to 50 g, 3 g to 20 g, or at least 1 gram, 2 grams, 3 grams, 4 grams, 5 grams, 6 grams, 7 grams, 8 grams, 9 grams, 10 grams of colostrum on a dry weight basis per daily therapeutic dose of composition. The colostrum may be in a dry, powdered, semi-solid, paste, or liquid form.

The term "chronic" when used in reference to a disease or disorder refers to a condition lasting 3 months or more.

The term "including" as used herein is non-limiting in scope, such that additional elements are contemplated as being possible in addition to those listed; this term may be read in any instance as "including, but not limited to."

The term "immunize", "actively immunize", "actively immunizing", and "active immunization" means to purposefully immunize an animal by exposing the animal to an antigen, for example, an antigen derived from a microorganism, such as but not limited to, a virus or a bacteria or a toxin derived therefrom; such exposure may be carried out by exposing the animal to an intact organism, an attenuated organism, a portion of the organism, one or more antigens present on the organism, a protein, adhesin, or toxin produced by the organism, or a combination of the foregoing.

The term "passively immunize", "passively immunizing", and "passive immunization" means to provide antibodies against an antigen, for example, an antigen derived from a microorganism, such as but not limited to, a virus or a bacteria, to a subject without necessarily eliciting an immune response to the organism in the subject. Passive immunization provides immediate protection but the subject does not develop memory cells as a result.

The term "passive immunity" as used herein refers to artificially acquired immunity achieved by the transfer of antibodies to the subject.

The terms "egg" or "egg product" each mean an avian sourced whole shell egg (conventional, immunized or otherwise) or any product or fraction derived therefrom. The avian is selected from a hen of one or more avian domestic species selected from chicken, duck, goose, turkey, guineafowl, pigeon, quail, emu, or ostrich.

The terms "immune egg" or "immune egg product" each mean whole egg or any product or fraction derived therefrom, such as egg yolk, egg white, de-lipidized egg yolk, or isolated IgY, IgA, and/or IgM obtained from an egg producing animal maintained in a immunized state beyond that required for health of the hen. The immune egg or fraction may be raw, pasteurized raw, in a dried form, powdered, spray dried, lyophilized, liquid, particle, or paste form. The immune egg may be immune egg antibody product. The immune egg antibody product may be in the form of, for example, whole immune egg, pasteurized whole immune egg, pasteurized immune egg yolk, pasteurized immune egg white, pasteurized raw whole immune egg, dried pasteurized raw whole immune egg, and dried powdered pasteurized raw whole immune egg.

In some embodiments, the immune egg is whole immune egg comprising IgY specific for rotavirus, coronavirus and *E. coli*. In some embodiments, the immune egg is powdered pasteurized raw whole immune egg comprising IgY specific for rotavirus, coronavirus and *E. coli*. In some embodiments, the immune egg is whole immune egg comprising IgY specific for enterotoxigenic *E. coli* spp., *E. coli* K99 pili adherence factor, *Clostridium perfringens* toxoid, *Salmonella typhimurium*, rotavirus, and coronavirus.

The term "antigen" refers to an entity or fragment thereof which can induce an immune response in an organism, particularly an animal. The term includes immunogens and regions thereof responsible for antigenicity or antigenic determinants.

The term "polyclonal antibody" refers to antibodies that are heterogeneous populations of antibody molecules derived from the sera of animals immunized with an antigen or an antigenic functional derivative thereof. For the production of polyclonal antibodies, various host animals may be immunized by injection with the antigen. Various adjuvants may be used to increase the immunological response, depending on the host species.

The term "monoclonal antibody" is well recognized in the art and refers to an antibody that is mass produced in the laboratory from a single clone and that recognizes only one antigen. Monoclonal antibodies are typically made by fusing a normally short-lived, antibody-producing B cell to a fast-growing cell, such as a cancer cell (sometimes referred to as an "immortal" cell). The resulting hybrid cell, or hybridoma, multiplies rapidly, creating a clone that produces large quantities of the antibody. "Monoclonal antibodies" are substantially homogenous populations of antibodies directed to a particular antigen or epitope. They may be obtained by any technique which provides for the production of antibody molecules by continuous cell lines in culture. Monoclonal antibodies may be obtained by methods known to those skilled in the art. See, for example, Kohler, et al., Nature 256:495-497, 1975, and U.S. Pat. No. 4,376,110.

The term "colostrum" also known as "first milk" refers to a fluid produced by the mammary glands in late pregnancy and the first few days after giving birth. Typically colostrum is considered as the milk produced in the first 48 hours after birth. Colostrum may be obtained from first milking, first 24 hours, or first 48 hours after giving birth. Colostrum is rich in immunoglobulins, antimicrobial peptides (e.g., lactoferrin, lactoperoxidase) and other bioactive molecules including growth factors. Newborns, or neonates, have developing digestive systems, and colostrum delivers a high concentration of nutrients, antibodies and growth factors in a concentrated, low-volume form. Colostrum as used herein may be non-hyperimmune colostrum; hyperimmune colostrum; whole colostrum also known as full-fat colostrum or non-defatted colostrum; defatted colostrum; size fractionated colostrum; or ion-exchange fractionated colostrum. The non-hyperimmune colostrum may be obtained from cows without special vaccination. In some embodiments, the fractionated colostrum may include two or more, three or more, four or more, five or more or six or more components of colostrum. In specific embodiments, the colostrum is selected from whole hyperimmune colostrum, whole non-hyperimmune colostrum; non-defatted hyperimmune colostrum; or non-defatted non-hyperimmune colostrum. In some embodiments, the colostrum may be derived from any mammalian species. The colostrum may be derived from any appropriate mammalian species, including but not limited to alpaca, banteng, bison, bovine, camel, cat, deer, dog, donkey, gayal, goat, guinea pig, horse, human, llama, mule, pig, rabbit, reindeer, sheep, water buffalo, or yak. In some embodiments, the colostrum is derived from bovine, human, caprine, ovine or porcine sources. In a specific embodiment, the colostrum is a bovine colostrum. The colostrum may be in any available form, such as a dried form, such as a spray dried form or lyophilized form, or a liquid, particle, or paste form. In a specific embodiment, the colostrum is bovine colostrum. The bovine colostrum may be non-hyperimmune bovine colostrum or hyperimmune bovine colostrum. The bovine colostrum may be whole bovine colostrum. The whole colostrum is not defatted. The whole colostrum may not be otherwise fractionated. In another embodiment, the colostrum may be defatted colostrum, size fractionated colostrum, or ion-exchange fractionated colostrum.

The term "undifferentiated diarrhea" means that the causative agent or agents of the diarrhea is undiagnosed. "Undifferentiated diarrhea" as used herein refers to diarrhea due to infection or overgrowth in the gastrointestinal tract of a subject with an undesirable strain, pathogenic organism, or toxin, or adhesin derived therefrom, or a combination thereof. In some embodiments, the diarrhea is due to infection or overgrowth in the gastrointestinal tract of a subject with an undesirable strain, pathogenic organism, or toxin, or adhesin or combination that is not identified. In some embodiments, the diarrhea due to infection or overgrowth in the gastrointestinal tract of a subject with a causative agent selected from an undesirable strain, pathogenic organism, or toxin, or adhesin derived therefrom, or combination that is partially identified; for example, where one infectious strain or organism is identified, but the diarrhea is a result of infection with a combination of causative agents. Due to the wide variety of etiology, an effective, broad spectrum, economical and safe method of treating undifferentiated diarrhea is desired.

The term "antibody fragment" encompasses any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("scFv proteins"), and minimal recognition units consisting of the amino acid residues that mimic the hypervariable region. Antibody fragments include a portion of an antibody such as F(ab')2, F(ab)2, Fab', Fab, Fv, sFv and the like. Regardless of structure, an antibody active binding fragment binds with the same antigen that is recognized by the intact antibody.

The term "antibody product" is used to define a crude, or isolated, or purified polyclonal antibody preparation. For example, the antibody product may be immune egg containing specific avian polyclonal antibodies such as IgY, IgA and/or IgM. Antibody product may include antibodies or antigen-specific antigen-binding fragments thereof, derived from avian immune egg, blood, or plasma prior to addition of colostrum or excipients. Antibody product may be selected from whole immune egg, immune egg yolk, defatted immune egg yolk, isolated or purified IgY, IgA, and/or IgM isolated therefrom. The antibody product may be in a liquid or solid form, such as a dried powdered form. In a specific embodiment, the antibody product is whole immue egg.

The term "transfer factor" refers to an immune molecule of approximately 5000 Daltons, made up of amino acids, that cause antigen-specific cell-mediated immunity, primarily delayed hypersensitivity and the production of lymphokines, as well as binding to the antigens themselves. (Kirkpatrick 1993, Structural nature and functions of transfer factors. Ann. N.Y. Acad. Sci. 685:362-368.)

The term "variable lymphocyte receptors" refers to lymphocyte-derived molecules discovered in jawless vertebrates such as the lamprey and hagfish. These animals possess a large array of variable lymphocyte receptors that are produced from only a small number of genes and that bind to pathogenic antigens in a similar way to antibodies, and with the same degree of specificity. (Alder et al., 2005, Diversity and function of adaptive immune receptors in a jawless vertebrate. Science, 310(5756):1970-1973).

The term "cell receptor" refers to the ligand binding moiety of the B-cell receptor; a membrane bound immunoglobulin molecule of one isotype (for example, IgD, IgM, IgE). With the exception of the presence of an integral membrane domain, these are identical to their secreted forms.

The term "specific binding" in the context of the characteristics of specific binding molecules, also known as specific targeted immune factors, such as an antibody, antibody fragment, variable lymphocyte receptor, or transfer factor, refers to the ability to preferentially bind to a particular antigen that is present in a mixture of different antigens. In certain embodiments, a specific binding interaction will discriminate between desirable and undesirable antigens (for example, "target" and "non-target" antigens) in a sample; in some embodiments by more than about 10 to 100-fold or more (for example, more than about 1000- or 10,000-fold). In some embodiments, the specific binding molecule may specifically bind to an epitope shared among different species or strains of a microorganism as compared to non-shared epitopes. In certain embodiments, the affinity between an antibody and antigen when they are specifically bound in an antibody-antigen complex is characterized by a $K_D$ (dissociation constant) of less than $10^{-6}$ M, less than $10^{-7}$ M, less than $10^{-8}$ M, less than $10^{-9}$ M, less than $10^{-10}$ M, less than $10^{-11}$ M, or less than about $10^{-12}$ M or less.

As used herein, the term "cross-reactivity" refers to an antibody or population of antibodies binding to epitopes on antigens other than to which they were elicited. This can be caused either by low avidity or specificity of the antibody or by multiple distinct antigens having identical or very similar epitopes of >95%, >97%, >98%, or >99% sequence identity. Cross reactivity is sometimes desirable when one wants general binding to a related group of antigens or when attempting cross-species labeling when the antigen epitope sequence is not highly conserved in evolution. In some embodiments, the specific antibodies exhibit cross-reactivity.

The term "innate immune system", or non-specific immune system, refers to the cells, molecular components and mechanisms that defend the host from infection by other organisms in a non-specific manner. The cells and molecular components of the innate immune system recognize and respond to pathogens in a generic way, but unlike the adaptive immune system, it does not confer long-lasting or protective immunity to the subject. Innate immune systems provide immediate defense against infection. Vertebrates possess a second layer of protection, the adaptive immune system, which is activated by the innate response.

The term "adaptive immune system" refers to highly specialized, systemic cells and processes that recognize and respond to an antigen, for example, to eliminate, neutralize or prevent pathogenic growth. The system is highly adaptable due to somatic hypermutation (a process of accelerated somatic mutation) and V(D)J recombination (an irreversible genetic recombination of antigen receptor gene segments). Adaptive immunity is also referred to as acquired immunity and creates an immunological memory. An adaptive immune response is pathogen and antigen specific and there is a lag time between exposure and maximal response. An adaptive immune response is based on the principle of clonal recognition, such that upon first exposure to an antigen, primed lymphocytes either differentiate into immune effector cells or form an expanded pool of memory cells that respond to secondary exposure to the same antigen by mounting an amplified and more rapid response.

The term "about" refers to a number or numerical range that is within +10% of the specified value or range unit.

The term "undesirable strain" refers to any strain of bacteria or yeast that can cause diarrhea or other gastrointestinal conditions or gastroenteric distress, although the strain may not be considered otherwise pathogenic. In some embodiments, the undesirable strain is an enteric pathogen or pathogenic organism. In some embodiments, the undesirable strain is a pathogenic organism selected from the group consisting of: *Campylobacter jejuni, Salmonella, Salmonella enterica* serovar *Typhi, Shigella* dystenteriae, *Plesiomonas shigelloides, Escherichia coli*, enteropathogenic *E. coli*, enterotoxigenic *E. coli*, enteroaggregative *E. coli*, enteroinvasive *E. coli*, haemorrhagic *E. coli*, diffuse adherent *E. coli, Clostridium dificile, Yersinia enterocolitica, Candida* spp., *Vibrio cholerae* 01, *Vibrio* 0139, Non-O1 Vibrios, *Vibrio parahaemolyticus, Aeromonas hydrophila, Clostridium perfringens*, enterohepatic *Helicobacter, Helicobacter pylori, Staphylococcus aureus, Klebsiella, Gardnerella* spp., *Listeria monocytogenes, Neisseria gonorrhoeae, Chlamydiaceae trachomatis, Mycoplasma* spp., *Campylobacter jejuni, Trichomonas vaginalis*, herpes virus type 1, herpes virus type 2, *Candida albicans, Candida glabrata, Candida tropicalis, Candida parapsilosis* and *Candida krusei*, Group A *Streptococcus* spp., rotavirus, coronavirus, norovirus, calicivirus, enteric adenovirus, cytomegalovirus, astrovirus, *S. pneumoniae, H. influenzae, Neisseria gonorrhoeae*, herpes zoster virus, *Fusarium* spp., and *Acanthamoeba* spp.

In some embodiments, the undesirable strain is selected from among gut bacteria present in a subject. In some embodiments, the undesirable strain is one or more species selected from the among the genera *Bacteroides, Clostridium, Fusobacterium, Eubacterium*, Ruminococcus, Peptococcus, *Peptostreptococcus, Bifidobacterium, Escherichia, Enterobacterium, Enterococcus, Klebsiella, Proteus*, and *Lactobacillus*.

For example, some undesirable strains include *E. coli* which is the predominant non-pathogenic flora of the human intestine, although several strains can cause disease in humans. In some embodiments, undesirable strains are selected from the group consisting of *Bacillus cereus, Bacteroides vulgatus, Bacteroides stercoris, Bacteroides fragilis, Bacteroides unformis, Clostridium ramosum, Clostridium difficile*, and *E. coli* strains. In some embodiments, the undesirable strain includes any enteric strain that causes diarrhea in the subject.

The term "additional active agent" refers to an agent useful either alone, administered simultaneously, administered sequentially, or in combination with one or more additional agents, in the treatment, prophylaxis or palliative care of a subject afflicted with a disease or disorder. The additional active agent may be selected from an antibiotic, antifungal, antiviral, antimicrobial, antiparasitic, micronutrient, oral rehydration salt, antidiarrheal adsorbant, anticholinergic drug, antisecretory agent, antimotility drug, or colostrum component, or a combination thereof.

The additional active agent is employed in compositions disclosed herein that further comprise colostrum and antibody product comprising specific antibodies derived from a different species than the colostrum. In some embodiments, the additional active agent is not an immunoglobulin or antibody.

In some embodiments, the additional active agent may be employed in the compositions in an amount previously employed alone as a "standard of care". In some embodiments, the additional active agent may be employed in the compositions in less than an amount previously employed alone as a "standard of care". In some embodiments, the additional active agent may be co-administered or employed in a composition of the disclosure in an amount effective to cause measurable reduction of a symptom or sign of a disease, disorder or condition related to inflammation or damage of the gastrointestinal tract, decreased enteric inflammation, change in intestinal microbiome, decreased blunting of intestinal villi, increased intestinal integrity, decreased ulceration, decreased leakage of intestinal contents, or decreased systemic inflammation, significant change in a biomarker, increased weight for age score, increased height for age score, change in antigen-specific antibody titer in the subject, reduction of diarrhea volume, reduction of diarrhea duration, reduction of abdominal pain, reduction of nausea, reduction of cramping, reduction of loss of bowel control or urgency of diarrhea symptoms; or in an amount to increase physician-assessed well-being of the subject; for example, as compared to the composition without the additional active agent.

As used herein, the term "pharmaceutically acceptable carrier or excipient" means a non-toxic, inert solid, semi-solid or liquid filler, carrier, diluent, excipient, vehicle, encapsulating material or formulation auxiliary of any type. Some examples of materials which can serve as pharmaceutically acceptable carriers are provided herein, for example, sugars such as lactose, glucose and sucrose; cyclodextrins such as alpha—(α), beta—(β) and gamma—(γ) cyclodextrins; starches such as corn starch, potato starch; cellulose and its derivatives such as sodium carboxymethyl cellulose, ethyl cellulose, cellulose acetate; powdered tragacanth; malt; gelatin; talc; excipients such as silicon dioxide, cocoa butter, suppository waxes; vegetable oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide, aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as solubilizing agents, coloring agents, releasing agents, coating agents, sweetening, flavoring, perfuming agents, preservatives and antioxidants can also be present in the composition, according to the judgment of the formulator.

All pronouns are intended to be given their broadest meaning. Unless stated otherwise, female pronouns encompass the male, male pronouns encompass the female, singular pronouns encompass the plural, and plural pronouns encompass the singular.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

MODES OF THE DISCLOSURE

The disclosure provides compositions and methods for the treatment or prevention of various inflammatory gastrointestinal conditions.

The present invention is based on the seminal discovery that the use bovine colostrum as a carrier matrix in conjunction with antibody product comprising specific avian antibodies can be used to transport and introduce an effective multi-parameter immunity to a subject in need thereof. An additional active agent may be added to enhance the efficacy and acceptability of the composition.

In some embodiments, the composition may comprise 1) colostrum, 2) immune egg antibody, and optionally 3) an additional active agent selected from an antibiotic, antifungal, antiviral, antimicrobial, micronutrient, oral rehydration salt, antidiarrheal adsorbant, anticholinergic, antisecretory agent, antimotility drug, or colostrum component, or a combination thereof.

In some specific embodiments, the composition comprises colostrum, antibody product comprising specific avian antibodies, and further comprises an additional active agent selected from one or more of an antibiotic, antimicrobial, micronutrient, or oral rehydration salt.

In some specific embodiments, the composition comprises bovine colostrum, antibody product comprising specific avian antibodies and a zinc supplement.

In some embodiments, the composition is useful in a method of treatment, prophylaxis or dietary management of a subject in need thereof.

One embodiment of the present invention is based on a method to create a targeted antibody-based formulation embedded or subsumed within colostrum, and comprising an additional active agent.

In some embodiments, the disclosure provides a composition effective for treating undifferentiated diarrhea in non-neonate humans. The composition takes advantage of an effective polyclonal antibody production strategy to generate high specificity antibodies targeted to several of the causes of diarrhea pathology.

In some embodiments, the compositions of the invention can be used for administering broad-spectrum passive immunity in treatment, prophylaxis, or prevention of relapse of a disease or disorder associated with a previous or subclinical pathogenic infection.

In one aspect, a low level of immunization of bovine animals can be sufficient to prepare a composition with an effective amount of anti-antigen specific binding molecule to result in an effective, broad-spectrum formulation when administered with an effective amount of colostrum as a carrier matrix.

In some embodiments, the disclosure provides an economical composition for the effective treatment of a disease or disorder associate with inflammation of the gastrointestinal tract. The composition may comprise an antibody product comprising a mixture of avian polyclonal antibodies, primarily IgY, but optionally containing IgA or IgM, specific for *E. coli, Salmonella* spp., rotavirus, gram negative bacteria, toxins produced by pathogens, and adhesins that enable pathogen attachment and colonization in the gastrointestinal tract.

In some embodiments, the antibodies use a controlled form of cross-reactivity to multiple clusters of related target antigens, and where the colostrum is present in an amount effective to enhance the stability and effect of the antibodies. The utility of such antibody/colostrum/additional active agent formulations includes providing broad-spectrum therapeutic interventions under conditions where the class of causative agent, but not the precise or specific causative agent, is known or suspected or under circumstances where multiple (mixed) causative agents are active.

In a preferred embodiment, the specific antibodies are polyclonal antibodies prepared from eggs of chickens inoculated with one or a mixture of pathogenic components.

Mixtures of antibodies may be designed to bind to several closely related epitopes that represent a structurally related cluster of antigens. These antigens may differ markedly in other respects, and may originate from diverse sources, organisms, or species.

One embodiment of the invention involves the method of treating a subject in need thereof with a composition comprising specific immunoglobulins (antibodies), with colostrum and an additional active agent, where the antibodies have specificity to a class of related antigens, and are specifically cross-reactive to different instances of members of that class; and further comprising an additional active agent.

There may exist a degree of structural similarity in related clusters of target antigens, without regard to the organism or pathogen that is the source of the antigen. Similarity in structure can result in a phenomenon known as "cross-reactivity" (the steric binding of a reactive molecule to an antigen other than the antigen intended). Cross-reactivity is often unintentional, and in most cases is considered a source of error and nonspecificity. However, in this embodiment the extent and degree of cross-reactivity may be controlled by various means to limit and channel its expression so as to provide desired characteristics.

This treatment is orally administered and confers passive immunity to patients. The nature of the treatment makes the associated risk factors comparable to that of eating food from the source where the antibodies were harvested (for example, risk factors would be similar to that of drinking a glass of milk). This is an effective treatment with less toxicity than the currently available alternative interventions.

In some embodiments, the disclosure provides a composition comprising: a) a non-neonate human effective amount of at least one specific antibody (immunoglobulin), or active binding fragment thereof, obtained from eggs of an immunized hen chicken, and that specifically binds to an antigen derived from a pathogenic microorganism; b) bovine colostrum in an amount effective to improve the stability of the antibody in the composition compared to the stability of the same antibody without the colostrum, and c) an additional active agent in an amount effective to improve the symptomology of the subject following administration of the composition.

The present invention provides compositions and methods for treatment of diarrhea in broad-spectrum, undifferentiated, or mixed clinical applications. In some specific embodiments, whole bovine colostrum can be administered orally in an effective amount in conjunction with specifically targeted avian antibodies, and an additional active agent to transport and introduce an effective multi-parameter therapeutic or prophylactic intervention to a subject in need thereof. Such compositions include various active components.

In some embodiments, antibodies created to react with specific targets associated with particular diseases or syndromes are embedded in colostrum such that the immune components within the colostrum and are activated by the interactions of the embedded specific antibodies, causing a cascade of immune system functions within the gastrointestinal tract.

The additional active agent may be selected from one or more of selected from one or more of an antibiotic, antifungal, antiviral, antimicrobial, micronutrient, oral rehydration salt, antidiarrheal adsorbant, anticholinergic, antisecretory agent, antimotility drug, or colostrum component, or a combination thereof is included to enhance the efficacy and acceptability of the compositions. In some embodiments, antibody product comprising specifically targeted avian antibodies and an additional active agent are embedded in colostrum, the complex of which is preconditioned, sensitized, or designed so as to be reactive with specific pathogens, toxins, or other targets related to the targeted disease state or syndrome, that will, in the presence of that targeted disease state or syndrome, activate a complex systems response within the matrix involving multiple components.

The disclosure includes methods comprising the use of specific antibodies and an additional active agent embedded within colostrum that contains numerous active components, where the in situ act of targeted antibody binding further causes additional events within the matrix that involves, uses or employs materials or substances within that matrix to create a sequence of events, cascade or progression similar to and consistent with a native immune system function.

In various embodiments, a composition is provided for use in the treatment or prevention of diseases or conditions associated with inflammation of the gastrointestinal tract. For example, the disease or condition may be selected from inflammatory bowel disease, irritable bowel syndrome, or environmental enteropathy. In a specific embodiment, a composition of the disclosure is provided for use in the treatment or prevention of environmental enteric dysfunction. A composition of the disclosure may be used in the manufacture of a medicament for treatment or prevention of environmental enteric dysfunction in non-neonate children. In a specific embodiment, the composition may be administered orally to non-neonate children for the treatment or prevention of environmental enteric dysfunction.

In a specific embodiment, a composition of the disclosure is provided for use in the treatment or prevention of an inflammatory bowel disease. A composition of the disclosure may be used in the manufacture of a medicament for treatment or prevention of inflammatory bowel disease in a non-neonate human. In a specific embodiment, the composition may be administered orally to non-neonate children for the treatment or prevention of an inflammatory bowel disease. The inflammatory bowel disease may be ulcerative colitis, Crohn's disease, or indeterminate colitis.

In a some embodiments, a composition of the disclosure may be employed for use in the treatment or prevention of other disorders associated with inflammation or damage of the gastrointerstinal tract including, for example, chemotherapy-induced mucositis, radiation-induced mucositis, chemotherapy-induced diarrhea, pseudomembranous colitis, necrotizing enterocolitis, NSAID-induced gastrointestinal disorders, peptic ulcers, gastritis, celiac disease, non-alcoholic fatty liver disease (NAFLD). A composition of the disclosure may be used in the manufacture of a medicament for treatment or prevention of other disorders associated with inflammation of the gastrointerstinal tract including, for example, chemotherapy-induced mucositis, radiation-induced mucositis, pseudomembranous colitis, necrotizing enterocolitis, NSAID-induced gastrointestinal disorders, celiac disease, non-alcoholic fatty liver disease (NAFLD).

In various embodiments, the compositions comprise bovine colostrum, an additional active agent, and an immune egg antibody product comprising at least one specific avian immunoglobulin, or an antigen-binding fragment thereof, that is specific for binding to an antigenic region of a diarrhea-causing pathogenic organism, or a pathogen related toxin, or adhesin originating therefrom, as described herein.

Nutritional Compositions

In some embodiments, the disclosure provides nutritional compositions for use in a method of dietary management comprising administering the composition to a subject in need thereof who is afflicted with a disease or disorder that creates special dietary needs such as Crohn's disease, cirrhosis, ulcerative colitis, indeterminate colitis, environmental enteric dysfunction, severe acute malnutrition, antibiotic-associated diarrhea, and HIV-associated diarrhea.

Compositions

Compositions and methods for treating or preventing diseases and conditions related to inflammation or damage of the gastrointestinal tract are provided. Compositions may include a specific binding molecule derived from or comprising immune egg, a protective reactive matrix comprising or derived from colostrum, and optionally an additional active component. The disease or condition may be selected from, for example, environmental enteric dysfunction, tropical sprue, SIBO, laky gut syndrome, inflammatory bowel disease, irritable bowel syndrome, environmental enteropathy, or acute severe malnutrition.

Environmental Enteric Dysfunction

Methods and compositions are provided herein for treatment or prevention of environmental enteropathy, also called Environmental Enteric Dysfunction (EED), or tropical enteropathy.

EED refers to an incompletely defined syndrome of inflammation, reduced absorptive capacity, and reduced barrier function in the small intestine. It is widespread in children and adults in low- and middle-income countries. EED is extablished during infancy and is associate with poor sanitation, certain gut infections, and micronutrient deficiencies. Crane et al., Food Nutr Bull 2015 March; 36 (10):S76-S87. Heliobacter *pylori* infection, small intestinal bacterial overgrowth (SIBO), abnormal gut microbiota, undernutrition, and toxins may all play a role. EED is typically assymptomatic, but is associated with stunting.

Diagnosis of EED may employ a dual sugar absorption test, although other biomarkers are emerging. A common dual sugar test is the lactulose:mannitol (L:M) test. Lactulose is a large sugar that is not normally absorbed by the small intestine. Mannitol is a smaller sugar that is absorbed by the small intestine in proportion to absorptive surface area. In the L:M test, after oral ingestion, both lactulose and mannitol are excreted intact in urine following minimal absorption. Urinary mannitol gives an index of absorptive capacity, while presence of lactulose in urine indicates impaired barrier function. Higher urinary L:M ratios reflect greater abnormalities of one or both functions. Measurement of lactulose and mannitol in urine may be performed by enzyme-linked immunosorbent assay (ELISA), anion exchange chromatography, or mass spectrometry.

New biomarkers of EED are being investigated. Some biomarkers are measured in feces. Including calprotectin, myeloperoxidase, neopterin, alpha-1-antitrypsin, mRNA, REG1b, and lactoferrin. Markers of gut permeability may be measured in blood such as zonulin, EndoCAb, soluble CD14, or citrulline, a marker of total enterocyte mass.

Currently there are limited effective treatments for EED. While implementation of adequate sanitation throughout the world remains an utmost priority, treatment of EED is also essential. The lack of effective therapy for EED remains an immense knowledge gap in the efforts to improve childhood health worldwide. Novel therapy directed at decreasing enteric inflammation and limiting pathogen carriage/infection is needed with the goal of targeted intervention at time points when morbidity is most severe.

The histologic changes associated with EED include blunting of the intestinal villi and intestinal inflammatory infiltrate. However, since assessment of histology is often impractical, there has recently been a push in the field of international child health to discover non-invasive EED biomarkers. The most promising candidates include fecal Reg 1B, fecal myeloperoxidase (MPO), serum C-reactive protein (CRP), serum soluble CD-14 (sCD14), urinary Lactulose: Mannitol test (L:M), and hydrogen breath testing (SIBO), such as glucose-hydrogen breath testing. Effective treatment of EED may be evaluated, for example, by measurement of one or more biomarkers, for example, selected from fecal Reg1B or fecal MPO. Another tool for assesment of EED is anthropometry, for example WAZ (weight-for-age z-score), WHZ (weight-for-height z-score), or HAZ ratios (height-for-age z-score). MUAC (mid-upper arm circumference) may be employed.

For example, improvement of very low WHZ (weight for height) of (<−3 z-scores for median WHO growth standards), low WHZ (weight for height) of (<−2 z-scores for median WHO growth standards), or MUAC (middle-upper-arm-circumference) of <115 mm in children 6-60 months of age, may be employed. https.//www.who.int/nutrition/topics/malnutrition/en/. See also WHO child growth standards and the identification of severe acute malnutrition in infants and children, a joint statement of the World Health Organization and the United Nations Children's Fund, 2009. The z-score is defined as number of standard deviations (SD) below or above the reference median value.

Several treatments of EED have been proposed including administration of vitamin A, *Lactobacillus*, alanyl-glutamine peptide, rifampicin, albendazole, secnidazole, n-3 LC-PUFAs (N-3 long chain polyunsaturated fatty acids such as eicosapentaenoic acid (EPA) or docosahexaenoic acid (DHA)), or zinc, exhibiting either no difference or mixed results.

Alternative effective and economical interventions for treatment or prevention of EED are desirable.

Infectious diarrhea, enteric infection, or small intestinal bacterial overgrowth may be a pre-condition or subclinical condition associated with inflammatory diseases and conditions of the gastrointestinal tract as provided herein.

In EED and other conditions associated with inflammation or damage of the gastrointestinal tract, biomarkers may be used to assess intestinal permeability, intestinal epithelial damage and repair, intestinal inflammation, microbial translocation and systemic immune activation. Biomarkers may be monitored before, during and/or after treatment to assess efficacy of the composition, dose, or dosing schedule. Biomarkers of intestinal permeability may include D-xylose, mannitol or rhamnose absorption, lactulose paracellular uptake, lactulose:mannitol ratio, AAT (alpha1-antitrypsin) leakage into gut lumen, or zonulin. Biomarkers of intestinal epithelial damage and repair may include I-FABP (intestinal fatty acid binding protein), plasma citrulline, and/or conversion of alanyl-glutamine to citrulline, lactose tolerance test (as a measure of brush border damage), fecal lipocalin, fecal REG1B (epithelial cell renewal). Biomarkers of intestinal damage may include stool calprotectin, MPO (myeloperoxidase), lactoferrin, neopterin. Biomarkers of microbial translocation and systemic immune activation may include plasma LPS (lipopolysaccharide) core antibody, LPS binding protein, circulating soluble CD14, KT ratio (kynurenine-tryptophan ratio), plasma cytokines, CRP (C-reactive protein). Hydrogen breath testing may be used as a measure of SIBO. Church et al., 2018, Future Microbiol 13(9), 1055-1070. Altered levels of cytokines may be exhibited by a subject having EED or another condition associated with inflammation or damage of the gastrointestinal tract. Therefore, additional biomarkers may be selected from the group consisting of REG1α, REG1β, MPO, TNF-α, CRP, sCD14, IL-1, IL-1p, IL-5, IL-6, IL-10, IL-12, IL-13, IL-17, IL-22, IL-23, IFN-γ, and IL-1sR1.

Loss of intestinal integrity may contribute to excessive inflammation following trauma or surgery. The correlation with gut barrier failure with IL-6 and bacterial translocation in ill patients is under investigation. For example, enteric bacterial loads were positively associated with interleukin-6 (IL-6) levels in systemic inflammatory response syndrome patients (SIRS). Tsay et al., 2016, Formosan J Surgery, 49, 208-216. IL-6 was measured by ELISA and enteric bacterial loads were measured through quantitative real-time polymerase chain reaction with primers for enteric bacteria.

Regenerating gene (REG) family proteins have been suggested to be involved in cellular proliferation of gastrointestinal cells. Concerning IBD, overexpression of REG1a and REG1b mRNA in resected colon tissue has been reported. Tsuchida et al., 2017, Expression of REG family genes in human inflammatory bowel diseases and its regulation. Biochem Biophysics Reports 12: 198-205. Reg1 is known to promote intestinal epithelial cell proliferation, regeneration and repair, and is up-regulated in a variety of enteric infections and inflammatory conditions. A decline in Reg1 correlates to a decline in intestinal tissue damage.

Myeloperoxidase (MPO) is a key component of the oxygen-dependent microbial activity of phagocytes but it also has been linked to tissue damage in acute or chronic inflammation. Papp et al., 2011, Poster presentations: Serum Myeloperoxidase level is a marker of disease activity in patients with inflammatory bowel disease, Clinical diagnosis and outcome-Abstract-European Crohn's and Colitis Organisation Congress Abstract-P098. Derived from polymorphonuclear leukocyte activity, myeloperoxidase (MPO) catalyzes the oxidation of substances through hydrogen peroxide ($H_2O_2$). The MPO $H_2O_2$-system has a toxic effect on many micro-organisms such as bacteria, fungi, viruses and *mycoplasma*. During inflammation in the intestinal mucosa, neutrophils migrate towards the gut mucosa and release myeloperoxidase from granulocytes which can be detected in stools and used as a marker of intestinal inflammation. A decline in MPO correlates with a decline in intestinal inflammation.

There is an increasing incidence of TNFalpha secreting cells in the mucosa in inflammatory bowel disease. Serum TNFalpha concentrations may raised in both ulcerative colitis and Crohn's disease.

C-reactive protein (CRP) and soluble CD-14 (sCD14) may be associated with systemic immune activation and microbial translocation or leakage of intestinal contents, respectively. Church et al., 2018, Future Microbiol 13(9), 1055-1070.

In some embodiments, a biomarker of the disease or disorder associated with inflammation or damage of the gastrointestinal tract is selected from D-xylose, mannitol absorption, rhamnose absorption, lactulose paracellular uptake, lactulose:mannitol ratio, AAT (alpha1-antitrypsin) leakage into gut lumen, zonulin, I-FABP (intestinal fatty acid binding protein), plasma citrulline, conversion of alanyl-glutamine to citrulline, lactose tolerance test (as a measure of brush border damage), fecal lipocalin, fecal REG1B (epithelial cell renewal), fecal calprotectin, fecal MPO (myeloperoxidase), fecal lactoferrin, fecal neopterin, plasma LPS (lipopolysaccharide) core antibody, LPS binding protein, circulating soluble CD14, KT ratio (kynurenine-tryptophan ratio), plasma cytokines, fecal cytokines, plasma IL-1Ra, plasma IL-1sR1, serum CRP (C-reactive protein), or hydrogen breath testing (as a measure of SIBO), REG1a, REG1β, MPO, TNF-α, CRP, sCD14, IL-1, IL-1p, IL-5, IL-6, IL-10, IL-12, IL-13, IL-17, IL-22, IL-23, IFN-γ, and/or IL-1sR1.

In some embodiments, the one or more biomarkers is selected from the group consisting of fecal Reg 1B, fecal MPO, serum sCD14, serum CRP, urine lactulose:mannitol (L:M) ratio, plasma IL-6, fecal IL-6, plasma TNFalpha, fecal TNFalpha, and hydrogen breath testing for small intestinal bacterial overgrowth (SIBO) or malabsorption. In some embodiments, the one or more biomarkers is selected from the group consisting of fecal Reg 1, and fecal MPO. In some embodiments, the biomarker is not sCD14. In some embodiments, the biomarker is not CRP.

Without being bound by theory, as illustrated in FIG. 1, it is hypothesized that an "unsanitary insult" such as an enteric infection, or presence of toxins, may lead to enteric inflammation. The enteric infection in the subject may be clinical or subclinical in which case pathogen identification may be performed by any suitable methods known in the art, for example, by Taqman array (TAC). The presence of enteric infection may be assessed, for example, by any suitable methods known in the art, for example, measurement of myeloperoxidase (MPO), or calprotectin in a subject. Enteric inflammation in the subject may lead to blunting of the intestinal villi and loss of intestinal integrity, leading to poor nutrient absorption and ultimately to poor neurodevelopment and negative effects on growth. Although endoscopy and biopsy may be performed to assess blunting of intestinal villi and loss of intestinal integrity, alternative methods are desirable, such as assessment of fecal Reg1B. The blunting of intestinal villi and loss of intestinal integrity may also result in a change in the intestinal microbiome. For example, small intestine bacterial overgrowth (SIBO) is defined as the presence of excessive bacteria in the small intestine. Dukowicz et al., 2007, Gastroenterology & Hepatology, 3 (2) 112-122. SIBO is frequently implicated as a cause pf chronic diarrhea and malabsorption. The change in intestinal microbiome may be determined, for example, by glucose hydrogen breath testing or 16 rDNA sequencing. Loss of intestinal integrity may lead to leakage of intestinal contents. Leakage of intestinal contents may be measured, for example, by a lactulose/mannitol ratio test oor measurement of serum soluble CD14. Ultimately, leakage of intestinal contents may cause systemic inflammation, which may also result in poor neurodevelopment and/or negative effects on growth. Systemic inflmmation may be measure, for example by CRP, and or cytokine profiles in the subject.

The compositions of the disclosure may also be evaluated in human models, animal models, cell restitution assays and/or cell proliferation asays. In some embodiments, the compositions of the disclosure exhibit significant improvement compared to control in one or more in vivo or in vitro assays selected from restitution/cell migration assay in vitro, cell proliferation assays in vitro, intestinal permeability model in humans in vivo, chemotherapy-induced mucositis animal model in vivo, DSS-induced colitis animal model in vivo, NSAID-induced animal model of small intestine damage in vivo, NSAID-induced animal model of gastric damage in vivo, LPS-induced diarrhea animal model, or repair and protection factor scoring method for bioactive agents. The repair and protection scoring method may be performed by any suitable method, for example, according to the method of Playford disclosed in U.S. Pat. No. 7,426,440, which is incorporated herein by reference.

Economical compositions and methods are provided herein for treatment or prevention of EED. Compositions are provided comprising specific antibodies directed to one or more, two or more, three or more, four or more, or five or more pathogenic microorganisms in combination with a protective reactive matrix to stabilize the antibodies in the gastrointestinal tract environment for oral administration, and to provide one or more, two or more, three or more growth factors that aid in restitution, repair, and/or proliferation of cells in the gastrointestinal tract. For example, a composition comprising from 4 g to 50 g, 5 g to 30 g, 7 g to 25 g, or 10 g to 20 g of a blend of immune egg and bovine colostrum, may be administered to a subject in need thereof on a daily basis. A composition comprising whole immune egg and whole bovine colostrum may be employed. The composition may comprise a weight ratio of colostrum to immune egg antibody product, on a dry weight equivalent basis of from about 10:1 to about 1:10, or about 5:1 to 1:5, or about 3:1 to 1:3. In one embodiment, a composition is provided herein comprising an effective amount of dried non-hyperimmune whole bovine colostrum and dried whole immune egg comprising specific binding activity to at least E. coli, rotavirus, and coronavirus (PTM202) for treatment or prevention of EED. In one specific embodiment, a composition is provided herein comprising 4 g dried non-hyperimmune whole bovine colostrum and 3 g dried whole immune egg comprising specific binding activity to at least E. coli, rotavirus, and coronavirus (PTM202) for treatment or prevention of EED. The composition may further include one or more micronutrients. The composition may alternatively be co-administered with micronutrients as provided herein for effective treatment of EED. The composition further comprise an additional active component. The composition may be administered one or more, two or more, three or more or four or more times daily. The composition may be administered over a period of one or more weeks, two or more weeks, three or more weeks, four or more weeks, five or more weeks, six or more weeks, seven or more weeks, 2 or more months, 3 or more months, 4 or more months, 5 or more months, 6 or more months, 9 or more months, 12 or more months, 18 or more months, 24 or more months for treating or preventing EED in a non-neonate human. The composition may be administered one or more, two or more, three or more, or four or more times daily.

Tropical Sprue

Methods and compositions are provided herein for treatment or prevention of tropical sprue. Tropical sprue is a malabsorption disease commonly found in tropical regions, associated with abnormal flattening of the villi and inflammation of the lining of the small intestine. It appears to be a severe form of environmental enteropathy. The cause of tropical sprue is not known. It may be caused by persistent bacterial, viral, amoebal, or parasitic infections. Folic acid deficiency, effects of malabsorbed fat on intestinal motility, and persistent small intestinal bacterial overgrowth may combine to cause the disorder. A link between small intestinal bacterial overgrowth (SIBO) and tropical sprue has also been proposed to be involved in the aetiology of post-infectious IBS. Tropical sprue may be associated with abnormal flattening of villi and inflammation of the lining of small intestine, for example, as observed during an endoscopic procedure, presence of inflammatory cells (e.g., lymphocytes) in the biosy of small intestine tissue, loss of appetite (anorexia), night blindness, weight loss, loss of strength or energy (asthenia), nutrient malabsorption, anemia, low levels of vitamins A, B12, E, D, and K, as well as serum albumin, calcium, and folate, by blood test, excess fat in feces (steatorrhea), thickened small bowel folds seen on imaging. Other conditions which can resemble tropical sprue may need to be differentiated. Coeliac disease (also known as coeliac sprue or gluten sensitive enteropathy), has similar symptoms to tropical sprue, with the flattening of the villi and small intestine inflammation and is caused by an autoimmune disorder in genetically susceptible individuals triggered by ingested gluten. Malabsorption can also be caused by protozoan infections, tuberculosis, HIV/AIDS, immunodeficiency, chronic pancreatitis and inflammatory bowel disease. Environmental enteropathy is a less severe, subclinical condition similar to tropical sprue. Ramakrishna et al. 2006, Postgrad Med J. 82 (974): 779-87.

Compositions and methods are provided for treatment or prevention of tropical sprue. A composition comprising from 4 g to 50 g, 5 g to 30 g, 7 g to 25 g, or 10 g to 20 g of a blend of immune egg and bovine colostrum, may be administered to a subject in need thereof on a daily basis. The composition may further include one or more micronutrients. The composition further comprise an additional active component. The composition may be administered one or more, two or more, three or more or four or more times daily. The composition may be administered over a period of one or more weeks, two or more weeks, three or more weeks, four or more weeks, five or more weeks, six or more weeks, seven or more weeks, 2 or more months, 3 or more months, 4 or more months, 5 or more months, 6 or more months, 9 or more months, 12 or more months, 18 or more months, 24 or more months for treating or preventing tropical sprue in a non-neonate human. The composition may be administered one or more, two or more, three or more, or four or more times daily.

Leaky Gut Syndrome

The disclosure provides methods and compositions for treatment or prevention of leaky gut syndrome (leaky gut). The intestinal epithelial lining, together with factors secreted from it, forms a barrier that separates the host from its environment. In pathologic conditions the permeability of the epithelial lining may be compromised allowing the passage of bacteria, toxins, antigens to enter the bloodstream causing a "leaky gut". Growing evidence suggests the gut microbiota is important in supporting the epithelial barrier.

Certain reports have suggested probiotics may have some benefit in reversing leaky gut by enhancing production of tight junction proteins; however, additional and longer term studies may be required. Conversely, pathogenic bacteria may facilitate a leaky gut. Mu, Qinghui et al., 2017 Frontiers in Immunology 8:598. doi: 10.3389/fimmu.2017.00598.

Colostrum and milk-derived peptide growth factors derived from colostrum have been suggested to address other gastrointestinal disorders including inflammatory bowel disease, nonsteroidal antiinflammatory drug-induced gut injury, and chemotherapy-induced mucositis. Playford et al., 2000, Am J Clin Nutr, vol. 72, pp. 5-14.

Compositions and methods are provided herein comprising colostrum and immune egg for treatment or prevention of SIBO, leaky gut, or tropical sprue.

Severe Acute Malnutrition

Methods and compositions are provided herein for treatment or prevention of Severe Acute Malnutrition (SAM). Compositions and methods provided herein may be effective for treatment of severe acute malnutrition. Severe acute malnutrition may include very low weight for height (<−3z scores for median WHO growth standards), visable severe wasting, presence of nutritional oedema, or MUAC (middle-upper-arm-circumference) of <115 mm in children 6-60 months of age. https.//www.who.int/nutrition/topics/malnutrition/en/. See also WHO child growth standards and the identification of severe acute malnutrition in infants and children, a joint statement of the World Health Organization and the United Nations Children's Fund, 2009. The z-score is defined as number of standard deviations (SD) below or above the reference median value.

Current nutritional supplements for treating SAM include lipid-based nutrient (LNS) supplements. For example, Chaparro et al., 2010, Maternal and Child Nutrition, 6 (suppl. 1), pp. 1-69, discloses use of a 20 g or 50 g per day of a lipid-based nutrient (LNS) supplement, for example, as characterized in Table 19 of Chaparro. Chaparro 2010 states LNS have been shown to improve linear growth of children (Adu-Afarwuah et al. 2007) and prevent severe stunting (Phuka et al. 2008, 2009), an effect that has not yet been demonstrated with micronutrients (MNPs) alone (Adu-Afarwuah et al. 2007; Dewey & Adu-Afarwuah 2008)." p. 10.

A composition comprising immune egg and whole standard bovine colostrum may be employed in the treatment of SAM. In some embodiments, a composition is provided comprising dried immune egg, dried full fat bovine colostrum, and a micronutrient which may optionally be formulated in a lipid-based nutrient supplement carrier formulation. Any known LNS supplement may be employed as a carrier, for example, as disclosed in U.S. Pat. No. 6,346,284, Briend, which is incorporated herein by reference.

One LNS is NUTRIBUTTER® (Nutriset), which is a complementary food supplement in the form of a paste comprising peanut, vegetable fat, dry skimmed milk powder, whey, maltodextrin, vitamin and mineral complex, and emulsifier: lecithin. For example, use of about 20 g sachet per day for a period of at least four months in children 6-24 months is recommended to prevent malnutrition. NUTRIBUTTER®, data sheet, Nutriset, 2011.

Another LNS is PLUMPY DOZ® (Nutriset), which is a ready-to-use soy-based nutrient supplement also defined as a lipid-based nutrient supplement medium quality (LNS-MQ) provided as a bulk paste product or in 50 g individual sachets that is a blend of vegetable oil, peanuts, sugar, nonfat milk powder, whey, maltodextrin, vitamins and minerals, cocoa and emulsifier for reducing cases of acute malnutrition in children ages 6 to 36 months.

Other lipid-based nutrient supplements may be employed as a carrier, for example, as disclosed in Chaparro et al., 2010, Table 19, which is incorporated herein by reference. The lipid-based nutrient supplement carrier formulation may include macronutrients including protein, carbohydrates and fats. The LNS carrier may include from 10-15 g protein, 30-40 g fat, and 90-140 g carbohydrate on a daily equivalent basis. For example the LNS carrier may include (i) at least one powdered protein product which provides proteins selected from skimmed milk powder, powdered yogurt, defatted soy flour, or whey; (ii) at least one product that supplies additional carbohydrates, for example, selected from sucrose, glucose, fructose, maltodextrin, skimmed milk, whey, or flour made from maize, wheat, millet, oats, rice, *quinoa*, cassava, or potato starch, and (iii) at least one product that supplies lipids, selected from the group consisting of vegetable fats and animal fats. The fats may include linoleic acid from 4-7 g daily, and alpha-linolenic acid at from 0.5 to 0.8 g daily. The composition may also comprise a lipid-rich substance derived from oleaginous seeds, for example, selected from peanuts, cocoa, beans, almonds, walnuts, hazelnuts, coconuts, and pistachio nuts. In one example, the LNS carrier may comprise skimmed milk powder, whey, maltodextrin, sucrose, micronutrient blend, peanut paste, and a plant-based fat.

In some embodiments, a composition is provided having a weight ratio of about 5-50 wt %, 10-40 wt %, or 20-35 wt % of a blend of immune egg and bovine colostrum on a dry weight basis, about 0.1 to 1 wt %, 0.2-0.8 wt %, or 0.4-0.7 wt % micronutrient (MNP), and about 50-95 wt %, 60-90 wt %, or about 65-80 wt % LNS base. This composition may be effective for treatment of EED, tropical sprue, or severe acute malnutrition.

Compositions and methods are provided for treatment or prevention of severe acute malnutrition. A composition comprising from 3 g to 50 g, 4 g to 30 g, 5 g to 20 g, or 6 g to 15 g of a blend of immune egg and bovine colostrum, may be administered to a subject in need thereof on a daily basis or a per dose basis on a dry weight equivalent basis. The composition may further include one or more micronutrients. The composition further comprise an additional active component. The composition may be administered one or more, two or more, three or more or four or more times daily. The composition may be administered over a period of one or more weeks, two or more weeks, three or more weeks, four or more weeks, five or more weeks, six or more weeks, seven or more weeks, 2 or more months, 3 or more months, 4 or more months, 5 or more months, 6 or more months, 9 or more months, 12 or more months, 18 or more months, 24 or more months for treating or preventing severe acute malnutrition in a non-neonate human. The composition may be administered one or more, two or more, three or more, or four or more times daily.

The compositions of the disclosure may be beneficial for treatment or prevention of other diseases or disorders associated with inflammation or damage of the gastrointestinal tract.

Chicken egg contains proteins possessing antimicrobial, immunoregulatory and growth factor activity. Its ability to influence gut defense and repair is investigated herein. Studies provided herein suggest that egg+/−colostrum may have therapeutic benefit for a wide variety of conditions. In addition to NSAID-induced gut injury and inflammatory bowel disease, a further area of potential interest is treating children with severe growth stunting in developing countries. This condition is often associated with environmental enteropathy, characterised by enteric infections, inflammation and villous blunting, preventing absorption of nutrients and creating a greater metabolic demand. Harper et al. (2018) PLoS Negl Trop Dis 12(1): e0006205.

As demonstrated herein, pasteurised raw egg powder contains bioactive compounds that stimulate protection and repair in a variety of in vitro and in vivo models of gut damage and that these reparative effects were synergistically enhanced if combined with bovine colostrum.

The findings of synergistic effects using egg and colostrum were seen in both the in vitro and in vivo models. Without being bound by theory, it is probable that multiple growth factors are involved in the protective/reparative effects seen in the present studies and that the protective matrix of the egg and colostrum, which includes protease inhibitors (Kovacs-Nolan et al., *J Agric Food Chem.* 2005; 53:8421-31) may facilitate increased survival of protective proteins/peptides within the gut lumen. Playford et al. *Lancet.* 1993; 341:843-848.

Well-validated in vivo and in vitro models were used herein to investigate the value of pasteurised egg powder to reduce gastrointestinal damage. Promigratory and proliferative activity was present in egg yolk and white and synergistic responses were seen when egg was combined with bovine colostrum. These synergistic effects were also seen in models of NSAID-small intestinal injury and DSS induced colitis. The effects were absent when the egg was heated to 100° C. for 8 minutes which represented cooked eggs.

One of the earliest stages of the repair process is surviving cells at the margin of the injured area migrate to re-establish a continuous epithelial layer, a process termed "epithelial restitution". This process starts within the first hour following damage to the stomach, small intestine or colon. Svanes et al. *Gastroenterology* 1982; 82:1409-26. Over the next 24-48 h, cellular proliferation increases in adjacent surviving glands to replenish lost cells. Our initial studies examined the effect of egg on these early repair processes. Three cell lines were used for the proliferation & migration studies; AGS (gastric) and Caco-2 (colonic) are of human origin and RIE1 cells derived from rat small intestine. Similar results were seen using all three cell lines, demonstrating our findings have applicability across the gastrointestinal tract and are not species dependent, although caution always must be shown when extrapolating from in vitro cancer cell lines to the human in vivo situation.

The disclosure provides methods and compositions comprising pasteurized spray dried egg for reducing gastrointestinal injury, for example, as caused by indomethacin or DSS, when given alone and in combination with bovine colostrum. Effects on proliferation (ALAMARBLUE™), and cell migration (wounded monolayers) were measured using Caco2, AGS and RIE cells. As demonstrated herein, fresh egg or whole egg powder (1 mg/ml) caused at least about a 3-fold increase in proliferation and migration in whereas cooked egg powder (8 min at 100° C.) had no effect. Bioactivity was equally distributed between yolk and white. Ovomucoid and ovalbumin antibodies reduced whole egg powder proliferative activity by 80% and 27% and migration by 69% and 10% respectively. Tyrphostin, an EGF receptor inhibitor reduced proliferative effect by 40% and promigratory effect by 18%. TGFβ neutralising antibody reduced migratory activity by 81%. Pretreatment with egg powder (20 mg/kg/day, 7 days, po) reduced NSAID-induced small intestinal injury (villus height) by 34% whereas heated egg had no effect. Pasteurised egg powder reduced DSS-induced colonic damage (myeloperoxidase and histological scoring) by 44-61%. Synergistic responses in proliferation, migration and in both in vivo models were seen when colostrum was co-administered. Ovomucoid and ovalbumin are major contributors to proliferation and migration. Uncooked egg powder+/−colostrum could provide a novel, inexpensive approach for prevention and treatment of gut injuries.

Having shown positive results in the in vitro models of repair, the effect of egg+/−colostrum was assessed in a mouse model of proximal small intestinal injury. This model has been employed to assess effects of other regulatory peptides (Playford et al. *Clin Sci (Lond).* 2001; 100:627-33) and gastrointestinal side effects of NSAID use continue to be a problem, despite acid suppressant therapy as they are ineffective against small intestinal injury. Bjarnason, Recent advances in gastroenterology. Vol 7, London: Churchill Livingstone Press, 1988:23-46. Indomethacin causes damage to the gastrointestinal tract by several mechanisms including reduction of mucosal prostaglandin levels, reduction of mucosal blood flow, stimulating neutrophil activation, and possibly also stimulating apoptosis. Levi et al. *Br. J. Rheumatol.* 1993; 33; 605-12. It is likely that many of these mechanisms will be influenced by the numerous growth factors present in the egg and colostrum preparation. In vivo protective effects were demonstrated using mouse indomethacin-induced small intestinal and rat DSS-induced colonic injury models.

Ulcerative colitis is a chronic relapsing disease where current therapies such as 5-aminosalisilic acid (5ASA) compounds have limited efficacy, and more powerful immunosuppressive therapies have serious side effects. Podolsky, *N Engl J Med* 2002; 347:417-29. There is, therefore, a need for new therapeutic approaches.

Several different models of colitis are available including genetically modified mice that result in aberrant immune responses (spontaneous models) and models that involve administration of noxious compounds either rectally or orally (inducible colitis models). Each model has its limitations when extrapolating to the clinical situation. The DSS model was selected as it is reproducible and has been used extensively by our group and others to test other biological potential therapeutic agents. It also allows the researcher to accurately decide on the temporal relationship between induction of colitis and administration of test products. The exact mechanism by which injury is sustained is unclear but is probably dependent on innate immune mechanisms with alteration in both Th1 and Th2 cytokine profiles occurring, although the Th1 response predominates. (Egger et al. 2000; Digestion 62:240-8). As in the proximal gut NSAID study, egg reduced the degree of injury, and synergistic responses were seen when added with colostrum. As excess immune activity is fundamental to the pathogenesis of DSS-induced injury, without being bound by theory, it may be likely that proteins/peptides that possess antioxidant and immune modulatory activity within egg such as ovalbumin, ovotransferrin and phosvitin, are as important as the "pro-reparative" growth factor activity. Pretreatment with egg powder (20 mg/kg per day for 7 days, po) reduced small intestinal injury (reduction in villus height) by 34% whereas cooked egg had no effect. Raw (pasteurized) egg powder reduced DSS-induced colonic damage (myeloperoxidase and histological scoring) by 44-61%. Synergistic responses in proliferation and migration were seen in both in vivo models when colostrum was co-administered. Uncooked (pasteurized) chicken egg powder, given alone, or in combination with colostrum could provide a novel, inexpensive approach for prevention and treatment of gut injuries such as inflammatory bowel disease and environmental enteropathy and may have advantages over cooked egg.

Bioactivity was roughly equivalent in raw and pasteurised powdered form. It was also evenly distributed between yolk and white suggesting potential clinical therapeutic molecules may be obtained from both sites. Previous studies examining eggs as a source of therapeutic agents have reported egg-derived proteins may be useful for blood pressure control (e.g. ovalbumin), antimicrobial activity (e.g. ovotransferrin, lysozyme) and anti-tumour activity (e.g. lysozyme and Ovomucin), (Réhault-Godbert et al Nutrients. 2019; 11:684; Kovacs-Nolan et al. J Agric Food Chem. 2005; 53:8421-31) although there has been limited translation to the clinical setting. Its potential value for gastrointestinal disease is however relatively unexplored.

Based on the present studies, it may be likely that more than one molecule may be involved in mediating the protective & reparative properties shown in the current studies, particularly as bioactivity was seen in both yolk and egg.

Ovomucoid is a 28 kDa protein with trypsin inhibitor activity, predominantly present in egg white (Kato et al. (1987) Biochemistry 26, 193-201.). Neutralising antibody studies herein showed that ovomucoid plays a major role in eliciting the proliferative and migratory effects of whole egg, accounting for about 80% of total activity. Its importance is also supported by the finding that the optimal dose of adding pure ovomucoid (50 µg/ml) is similar to the amount present in whole egg powder when added at 1 mg/ml (Lee, J. H., and Paik H-D. (2019) Poultry Science, pez381). It was previously shown that addition of soya bean trypsin inhibitor to these cell lines does not increase proliferation or migration (Marchbank et al. (1996) Am J Pathol. 148, 715-722), suggesting that the trypsin inhibitor activity of ovomucoid may not be important in mediating these effects. However, its trypsin inhibitor activity may have clinical value in other settings, as ovomucoid may be useful for enhancing oral delivery of therapeutic peptides and proteins which may be limited due to extensive proteolytic degradation in the gastrointestinal tract (Shah et al. (2004) J. Pharm. Sci. 93, 392-406).

Ovalbumin is a 42 kDa protein and is very abundant in egg white, accounting for about 50% of the total egg-white proteins (Réhault-Godbert et al. (2019) Nutrients. 11:684 doi:10.3390). The present studies dose-response curve showed addition of pure isolated ovalbumin at 400 mg/ml had a major stimulatory effect on proliferation and migration. This concentration was similar to that found in adding whole egg powder at 1 mg/ml (Lee et al. (2019) Poultry Science, pez381) and its relevance is also supported by the knock down effect on proliferation and migration seen when ovalbumin neutralising antibody was added in addition to egg powder. Ovalbumin has a variety of biological effects including anti-bacterial and immunomodulatory activity (Pellegrini et al. 2004, Biochim. Biophys. Acta 1672, 76-85).

Egg yolk is also a source of bioactive proteins. Apolipoprotein B, apovitellenin-1, vitellogenins, serum albumin, immunoglobulins, ovalbumin, and ovotransferrin are the most abundant proteins of egg yolk, representing more than 80% of total egg-yolk proteins (Réhault-Godbert et al. 2019, Nutrients. 11:684). For example, Phosvitin, a 45 kDa protein also present in egg yolk, possesses antibacterial and immunomodulatory activity (Khan et al. (2000) J. Agric. Food Chem. 48, 1503-1506).

Studies of the importance of the EGFR in mediating proliferative and migratory effects showed that the EGF receptor-inhibitor tyrphostin decreased proliferative activity of whole egg by about one third, and the migratory activity by 13%, suggesting this pathway is important in mediating these effects. The EGF receptor has multiple ligands (Fiske et al. (2009) Exp Cell Res. 315, 583-601), although neither ovomucoid nor ovalbumin are thought to be direct receptor ligands. Addition of TGFβ blocking antibody reduced pro-migratory effects of egg by over half, demonstrating the importance of this pathway. However, many growth factors, such as EGF and TGFα, as well as cytokines such as IL-1β and IFN-γ stimulate migration through increasing local production of TGF-β1 (Dignass et al. (1994) J Clin Invest. 94, 376-383). TGFβ may therefore be acting as an intermediary signalling molecule.

Having shown positive results in the in vitro models of repair, the effect of egg+/−colostrum was assessed in a mouse model of proximal small intestinal injury. This model was selected based on previous experience of using it to assess effects of other regulatory peptides (Playford et al. (1999) Gut. 44, 653-658) and gastrointestinal side effects of NSAID continue to be a problem, despite acid suppressant therapy which are ineffective against small intestinal injury (Bjarnason, I. (1988) Non-steroidal anti-inflammatory drug induced small intestinal inflammation in man. In: Pounder R, ed. Recent advances in gastroenterology. Vol London: Churchill Livingstone Press, pp 23-46.). Indomethacin causes damage to the gastrointestinal tract by several mechanisms including reduction of mucosal prostaglandin levels, reduction of mucosal blood flow, stimulating neutrophil activation, and possibly also stimulating apoptosis (Levi et al. (1993) Br. J. Rheumatol. 33, 605-12). It may be likely that many of these mechanisms will be influenced by the numerous growth factors present in the egg and colostrum preparation.

The present studies suggest that egg+/−colostrum may have therapeutic benefit for a wide variety of conditions. In addition to NSAID-induced gut injury and inflammatory bowel disease, a further area of potential interest is treating children with severe growth stunting in developing countries. This condition is often associated with environmental enteropathy, characterised by enteric infections, inflammation and villous blunting, preventing absorption of nutrients and creating a greater metabolic demand. A recent study from Ecuador found administering a (cooked) egg per day for six months enhanced growth of stunted children (Iannotti et al. (2017) Am J Clin Nutr. 106, 1482-1489). However, based on the results of the present studies of pre-heated vs pasteurised eggs, it seems likely that supplementation with pasteurised egg powder may provide additional benefit against the underlying enteropathy. Pasteurised egg powder may be more efficacious than cooked eggs, it may also have advantages over fresh eggs in terms of cost, shelf life, efficient storage, dosing and delivery.

The findings of synergistic effects using egg and colostrum were seen in both the in vitro and in vivo models. It may be that multiple growth factors are involved in the protective/reparative effects seen in the present studies, especially because synergistic responses are seen herein and by others when adding more than one peptide (FitzGerald et al. (2004) Peptides. 25, 793-801), and that the protective matrix of the egg and colostrum, which includes protease inhibitors such as ovomucoid may facilitate increased survival of other protective proteins/peptides within the gut lumen (Playford et al. (1993) Lancet. 341, 843-848).

Small Intestine Bacterial Overgrowth

Small intestine bacterial overgrowth (SIBO) is defined as the presence of excessive bacteria in the small intestine. Dukowicz et al., 2007, Gastroenterology & Hepatology, 3

(2) 112-122. It can cause a variety of symptoms and clinical manifestations which depend upon the type, density, and metabolic characteristics of colonizing bacteria and the response of the host.

SIBO can result in diarrhea, malabsorption syndromes resulting in weight loss, specific nutritional deficiencies and more generalized complications such as osteoporosis. Bloating, flatulence and abdominal discomfort are also common and can result in clinical features similar to those of the Irritable Bowel Syndrome (IBS). There is increasing recognition that SIBO is more common than previously thought and can occur in patients with normal gastrointestinal anatomy. It has been found to be a frequent cause of diarrhoea and malabsorption in elderly patients who have developed age related small bowel dysmotility.

Gastrointestinal surgery, in particular the formation of a "blind loop" such as that found in a Roux-en-Y reconstruction, has been widely appreciated as a cause of SIBO for many years. However, it is now evident that many conditions, particularly those that result in dysmotility are also associated with SIBO in the absence of surgery and with normal anatomy. Of particular interest is the recent observation that many patients with clinical features of IBS also have SIBO, it remains unclear if these patients have SIBO alone or both conditions exist in association.

SIBO is characterised by an increase in the density of bacteria commonly found as normal gut commensals and it is generally considered to be a result of a deficiency of the normal process which maintain homeostasis of resident enteric bacteria. Current research has identified disturbances in gut motility, immune function, anatomy and mucosal function as likely causes of SIBO. SIBO is frequently implicated as a cause of chronic diarrhea and malabsorption.

SIBO can be defined as a bacterial count in the small bowel of greater than $10^5$ colony forming units (CFUs)/mL, as compared to $10^3$ CFUs/ml which is considered to be the upper limit of normal. This increased bacterial count is often associated with inflammatory changes in the small bowel mucosa which include blunting of the villi, atrophy of mucosa and crypts and elevation of the intra-epithelial lymphocytes. The causal relationship being supported by the fact that these changes usually reverse after appropriate antibiotic therapy.

SIBO has overlapping symptoms with irritable bowel syndrome but the aetiology is distinct due to excess growth of bacteria in small intestine. A variety of microbes may be involved in SIBO including streptococci, *Escherichia coli*, staphylococci, and *klebsiella*.

Current treatment of SIBO is with non-absorbable antibiotic with or without probiotic with variable results and with a need to repeat in many patients. Alternative effective compositions and methods for the treatment or prevention of SIBO are desirable.

The disclosure provides methods and compositions for treatment or prevention of diseases and conditions of the gastrointestinal tract including small intestine bacterial overgrowth (SIBO), environmental enteropathy (EED), leaky gut syndrome, and tropical sprue. In some embodiments, the compositions are provided for gastrointestinal flora management, for example, in a method of dietary management to control overgrowth of undesirable microbial species, such as small intestinal bacterial overgrowth (SIBO). Unlike antibiotics or probiotics used to treat SIBO via direct attack on bacteria or competition (probiotics), the present invention may act predominantly via stabilizing the mucosa against the toxic effects of the pathogenic bacteria.

Under normal circumstances, the majority of resident bacteria in the small intestine are gram positive. However, in SIBO, gram negative organisms, enterococci and anaerobes which are more typical of colonic flora may become predominant and their pathological effects on intestinal function are considered to arise from their metabolic and immunogenic properties as well as their increased numbers.

Bacteria that deconjugate bile salts would tend to cause fat malabsorption whereas those that ferment carbohydrate might be expected to produce flatulence and bloating. Certain bacteria, particularly the gram negative population such as *Klebsiella*, produce substances that are toxic to the intestinal mucosa, leading to diarrhoea and malabsorption.

Aetiological Factors of SIBO

The incidence of SIBO is increased in certain disease states but is also present in a small number of apparently healthy control subjects. Conditions predisposing to small intestinal bacterial overgrowth in healthy subjects may include structural abnormalities, disorders of motility, mucosal damage/dysfunction, organ dysfunction, metabolic disorders, or certain drugs.

Structural abnormalities that may predispose an otherwise healthy subject to SIBO may include small intestinal diverticulitis, small intestinal strictures, Blind loops (Roux loops), resection of ileocaecal valve, gastrectomy, or coloenteric fistulation.

Disorders of motility that may predispose an otherwise healthy subject to SIBO may include intestinal myopathy, intestinal neuropathy, gastroparesis, pseudo-obstruction, drug induced intestinal stasis, age-related dysmotility, Parkinson's disease, or muscular dystrophy.

Mucosal damage or dysfunction that may predispose an otherwise healthy subject to SIBO may include Crohn's disease, Coeliac disease, or immunodeficiency.

Organ dysfunction that may predispose an otherwise healthy subject to SIBO may include cirrhosis, renal failure, hypchlorhydria, or pancreatitis.

Metabolic disorders that may predispose an otherwise healthy subject to SIBO may include diabetes.

Drugs that may predispose an otherwise healthy subject to SIBO may include those for acid suppression, or that cause intestinal stasis (i.e., opiates).

An abnormal luminal environment may predispose a subject to SIBO.

Hypochlorhydria

Reduced gastric acid production is often associated with conditions such as gastric atrophy, *Helicobacter pylori* infection and following vagotomy. Studies have found SIBO to be present in about 50% of patients taking standard doses of PPI and around 15% of those on H2 antagonists.

Pancreatic Exocrine Deficiency

Chronic pancreatitis is associated with a 30% incidence of SIBO, probably due to pancreatic exocrine insufficiency which leads to reduced levels of anti-bacterial proteolytic enzymes and maldigestion of food and luminal substances which facilitates the overgrowth of bacteria. Furthermore, the use of powerful analgesia to treat the symptoms of chronic pancreatitis often results in associated motility disturbances further increasing the likelihood of stasis and reduced bacterial clearance. This may in part explain the high incidence of SIBO in seen in patients with Cystic fibrosis (~50%) or pancreatic cancer.

Gastro-Intestinal Dysmotility

Under normal circumstances, regular sweeping peristaltic contractions generated by the intermittent ab-oral migratory motor complex limit the amount of food remaining in the small intestine between meals. Disturbances of motility which reduce the effectiveness of this process may result in the presence of excessive quantities of food debris in the lumen which can promote bacterial proliferation and overgrowth. Neuropathic and myopathic processes often underlie motility disturbances although are not commonly histologically characterised as this requires a full thickness intestinal biopsy. Systemic diseases such as diabetes, scleroderma and polymyositis may cause intestinal muscle damage, cirrhosis and renal failure have also been associated with disorders of peristalsis leading to stasis and SIBO.

Isolated gastroparesis may result in considerable gastric residue and bacterial overgrowth which may then provide the small intestine with excessive quantities of bacteria. This is often associated with diabetes and can also be caused by viral infections and certain medications.

Patients diagnosed with the irritable bowel syndrome have recently been reported to have evidence of SIBO in 30-80% of cases. As SIBO produces symptoms which are similar to those of IBS, many clinicians believe that these patients have SIBO as their primary diagnosis rather than IBS, others feel that SIBO has arisen because of dysmotilty caused by IBS.

Structural Abnormalities

Surgical procedures which result in regions of relative stasis are commonly associated with SIBO. The blind loop fashioned in the Billroth 11 and Roux-en-Y anastomoses following antral gastrectomy are good examples. Non-surgical anatomical disorders associated with stasis include diverticulae which can be large and sparse or small and numerous. Stasis also occurs proximal to strictures where the intestine may be dilated and these result from conditions such as Crohn's disease, scleroderma and following radiotherapy.

Mucosal Associated Immune Dysfunction

Bacterial populations in the intestine are also regulated by the mucosal immune system and its dysfunction can therefore result in SIBO. Studies have demonstrated SIBO in patients with isolated subgroup as well as more generalised immunoglobulin deficiency and T cell dysfunction. This is also seen in patients following intestinal transplantation who receive powerful immunosuppression and also have a degree of dysmotlity. A high incidence of SIBO has also been recorded in Chronic lymphocytic leukaemia (~50%) and lymphoma.

Disorders of the Intestinal Mucosa

Conditions which lead to damage and dysfunction of the mucosa such as coeliac disease, radiation enteritis and Crohn's disease are associated with SIBO. It is a common cause of ongoing diarrhoea in coeliac patients after treatment with a gluten free diet (~60%). It is likely that in addition to associated motility disturbances, a dysfunctional mucosa allows excessive proliferation of bacteria through impairment of innate and acquired immunity.

Age Associated SIBO

Studies in elderly populations have demonstrated an incidence of SIBO of between 15 and 30%. Immobility and comorbidity tend to be the main risk factor and although age related dysmotility has been widely suggested as the underlying cause.

Miscellaneous Conditions

Several studies have detected an association between Non-alcoholic steatohepatitis (NASH) and SIBO. A role for SIBO in the pathogenesis of NASH has been postulated and in some experimental models of NASH slow intestinal transit times have been found.

Patients with chronic alcoholism in the absence of cirrhosis have elevated levels of intestinal bacteria and this is believed to be a result of mucosal damage. Cirrhotic patients are immunocompromised with a high risk of infection. Gram negative bacteria are a frequent cause of enteric infections, as well as enterococci, *Vibrio* spp., *Aeromonas* spp., *Clostridium* spp., *Listeria monocytogenes, Plesiomonas shigelloides* and *Mycobacterium tuberculosis.*

Patients with Parkinson's disease are also more likely to have SIBO and this may be a neurological manifestation of the disorder or a consequence of drug therapy for the condition.

Clinical Features of SIBO

Clinical manifestations vary according to the metabolic and immunogenic properties of the bacteria and the response of the host. Abdominal bloating, discomfort or abdominal pain and flatulence with or without diarrhoea commonly occur and often closely overlap with the symptoms of IBS making differential difficult. When significant malabsorption is present, weight loss and steatorrhoea may occur and specific nutrient deficiencies can cause metabolic bone disease and hypocalcaemia (vitamin D), polyneuropathy and megaloblastic anaemia (vitamin B12), Iron deficiency anaemia and occasionally protein losing enteropathy. Night blindness from vitamin A deficiency and vitamin E deficiency causing neuropathy and T cell abnormalities have been reported. The main nutritional consequences of SIBO may include weight loss, fat malabsorption (steatorrhoea), vitamin and mineral deficiencies which may include fat soluble vitamins (vitamins D, E, A, K), vitamin B12, iron, magnesium, calcium, increased levels of, for example, folate or D-lactate, hypoproteinaemia, and/or hypoalbuminuria. In some cases, bacterial fermentation of sugars and easily fermentable polysaccharides produces D-Lactate for which there is no human metabolic pathway.

Diagnosis of SIBO

Methods for Diagnosis of SIBO may include bacterial culture and breath tests.

Bacterial culture may be used as a direct estimation of the quantity and nature of bacteria within the small intestinal lumen, and is generally considered to be the Gold standard for diagnosis of SIBO. However, the difficulties associated with collection and culture of bacteria have made this unpopular as a clinical tool. Molecular techniques to quantify intestinal bacteria have not yet been validated but offer a potential solution to the difficulties of culturing fastidious organisms. For example, composition of the intestinal microbiome may be assessed by analyzing samples from different gastrointestinal sites via 16S rRNA gene sequencing. Choi et al., 2019, PLoSONE 14 (8):e217194.

Breath Tests are less invasive indirect diagnostic techniques are more commonly used in clinical practice for diagnosis of SIBO. The Hydrogen breast test is the simplest example and is based on the premise that hydrogen is not produced by mammalian cells and therefore a significant rise in detectable hydrogen in the breath, following consumption of a fermentable substrate, can be assumed to be arising from bacterial fermentation of that substrate. In direct tests for diagnosis of SIBO are shown in Table 1.

TABLE 1

Indirect Tests for Detecting Bacterial Overgrowth of the Small Intestine

| Test | Measurement | End Point | Comment |
| --- | --- | --- | --- |
| Glucose 50 g oral Lactulose | Breath hydrogen/methane | Rise in [breath] of ≥20/≥12 ppm resp. | Measurement of both gases improves |

TABLE 1-continued

Indirect Tests for Detecting Bacterial Overgrowth of the Small Intestine

| Test | Measurement | End Point | Comment |
|---|---|---|---|
| 10 g oral $^{13}C/^{14}C$-D-Xylose oral | Breath $^{13}CO_2/^{14}CO_2$ | Individual laboratory normal ranges | accuracy Limited by expense and radioactivity |
| $^{13}C/^{14}C$-glycocholate oral | Breath $^{13}CO_2/^{14}CO_2$ | Individual laboratory normal ranges | Sensitivity lower as only detects de-conjugating bacteria |
| Bacterial metabolites in urine | Urine 4-hydroxyphenylacetic acid | Individual laboratory normal ranges | Useful in pediatric practice |
| Obermeyer Test | Urinary Indicans - an indole produced in urine when bacteria in GI tract act on Trp | Individual laboratory normal ranges | Sensitivity and specificity is lower than breath tests |
| Therapeutic trial of antibiotics | Clinical effect | Improvement of symptoms | May cause diagnostic confusion as other conditions can respond to antibiotics |

The substrates used in Breath Tests may include glucose, lactulose and xylose. Glucose is usually completely absorbed by the intestine and therefore will rarely give rise to hydrogen from fermentation by colonic bacteria. For this reason it is often preferred to lactulose which is poorly absorbed and produces a hydrogen peak from colonic bacteria which must be distinguished from an earlier peak if small bowel bacterial fermentation is present. This distinction can sometimes be difficult to determine, may lead to less diagnostic accuracy particularly if intestinal transit is rapid which is associated with lower sensitivity and specificity. However, the proximal absorption of glucose may result in failure to detect overgrowth of the distal intestine. Xylose is less easily absorbed and more reaches the distal small intestine which has the potential advantage of providing a better assessment of the entire small bowel. Unfortunately, incomplete absorption is more likely and the risk of confusion with colonic fermentation increased.

Breath methane is also an indicator of bacterial fermentation and a combination of both gas measurements is becoming more commonly used. This allows detection of those bacteria which produce either only hydrogen (~50%) or methane (~10-15%).

Breath hydrogen levels may be used to define bacterial overgrowth. A rise in hydrogen concentration of ≥20 parts per million (ppm) after a glucose challenge and ≥12 ppm after lactulose are usually taken to indicate bacterial overgrowth. Their diagnostic accuracy is reported to be approximately 70% and 50% respectively.

A further method of breath sample analysis using radio-isotope labelled substrates has been developed but is generally considered to be no more accurate that hydrogen and methane analysis. This employs $^{13}C$ and $^{14}C$-labelled xylose or glycocholic acid which when fermented produce isotope labelled $CO_2$ which is excreted and measured in breath samples. The use of isotopes is expensive and radio-isotopes can not be used in children and pregnancy. The glycocholic breath test only detects bacteria which are able to de-conjugate and these may be absent in up to 30% of cases of SIBO.

Treatment of SIBO

The aims of treatment can be divided into three areas, eradicating the overgrowth of bacteria, restoring any nutritional deficiencies, and resolving the underlying cause where possible. Current approaches to treatment of SIBO may include antibiotics, probiotics, nutritional support and treating the cause of bacterial overgrowth including surgical procedures to address structural abnormalities. In many cases the consequences of SIBO may be minor and the risks and inconvenience of treatments such as long term antibiotics or reconstructive surgery may be greater than the potential benefit. Patients may prefer symptomatic control with anti-diarrhoea agents for example.

Antibiotic Treatment

A mixed population of bacteria is present in bacterial overgrowth which may complicate selection of antibiotics and this is further compounded by the inability to culture more than about 20% of species present in the resident intestinal flora. Attempts to identify bacteria have found a mixture of aerobes (such as *Streptococcus, Escherichia coli, Staphylococcus* and *Klebsiella*) and anaerobes (such as *Bacteroides, Lactobacillus* and *Clostridium*). Broad spectrum antibiotics have therefore been used often in rotation to reduce the risk of developing colonisation with resistant organisms. Tetracycline has been extensively used in the past but the newer antibiotics including ciprofloxacin, amoxicillin/clavulante and doxycycline have been reported to have superior efficacy. Recent studies of the efficacy of metronidazole and rifaxamin have reported encouraging results with examples of long term remission, although most advocate repeated courses of 7-10 days or inclusion in a cyclical regime with other antibiotics. Long term studies suggest that, after a single course, there is a relapse rate of at least 50% at 9 months. Antibiotics and combinations thereof with supporting evidence of efficacy in SIBO include Rifaximin, Ciprofloxacin, Norfloxacin, Amoxicillin/clavulanate, Metronidazole+trimethoprin/sulfamethoxazole, and Metronidazole+cephalexin. Resistant cases may respond to the oral administration of antibiotics with poor oral bioavailability such as gentamicin but only anecdotal evidence of efficacy is available.

Probiotics

There have been few randomized controlled trails of probiotics as treatment for SIBO. A trial in pediatric patients with proton pump inhibitor induced SIBO failed to reveal any benefit from the combination of *Lactobacillus rhamnosus* and *Lactobacillus acidophilus*. However, a randomized double blind trial of *Lactobacillus casei* and *Lactobacillus* acidophillus significantly reduced diarrhea, whereas another randomized study did not find any benefit from *Lactobacillus fermentum*. One study showed symptomatic improvement in IBS patients with SIBO taking a probiotic capsule containing *Saccharomyces boulardii, Bifidobacterium lactis, Lactobacillus acidophilus,* and *Lactobacillus plantarum* (Lactolevure@) every 12 h for 30 days, when compared to IBS patients without SIBO. Leventogiannis et al., 2019, Probiotics and Antimicrobial Proteins (2019) 11:627-634.

Nutritional Support

The primary aim should be to replace any nutritional deficiencies and encourage normality of body weight. Particular attention should be given to replacement of likely deficiencies detailed above. Enhanced absorption of energy providing foods may be possible by dietary manipulation to encourage consumption of those foods which appear to be absorbed. Patients with marked steatorrhea may benefit from a diet richer in carbohydrates than fat and the opposite should be considered where bloating and flatulence are the main symptoms.

Treating the Cause of Bacterial Overgrowth

Structural abnormalities such as strictures and blind loops may be amenable to reconstructive surgery and large single small bowel diverticulum can sometimes be resected. Disorders of motility are equally difficult to treat, most neuropathies and myopathies do not respond adequately to medical treatment. Gastroparesis occasionally responds to prokinetic agents, and when associated with diabetes may improve with optimization of blood glucose control. The response to gastric pacemakers has generally been disappointing. When the result of a metabolic abnormality such as hypothyroidism or an electrolyte disturbance, pseudo-obstruction can often be treated but unfortunately in many cases are reversible cause can not be found. A careful review of all medications is important. Opiates are of particular concern but antidepressant with anti-cholinergic properties can also sometimes be implicated. Control of inflammatory conditions of the mucosa such as coeliac disease and Crohn's should be confirmed and optimized and in cases of immunodeficiency therapy such as immunoglobulin replacement must be adequate.

New Approaches to Dietary Management

In some embodiments, the disclosure provides a method for dietary management of one or more species of gut bacteria, or undesirable species, in a subject comprising administering a composition of the disclosure. In some embodiments, the disclosure provides a composition comprising colostrum and powdered immune egg for treating or preventing certain GI tract diseases or conditions. Compositions and methods are provided for treating or preventing small intestinal bacterial overgrowth (SIBO), leaky gut syndrome, environmental enteropathy and tropical sprue. The compositions of the disclosure have been shown to reduce bacterial translocation through an intestinal epithelial barrier and reduce pathogen-induced intestinal epithelial barrier dysregulation.

The compositions of the disclosure may be effective to reduce symptoms of SIBO, including reducing symptom severity and/or duration. The compositions of the disclosure may be used for gastrointestinal flora management in a subject, for example, to reduce or eliminate symptoms of SIBO in a subject in need thereof.

A method is provided for reducing pathogenic translocation through an intestinal epithelial barrier in a subject in need thereof, comprising administering an effective amount of a composition comprising a component selected from the group consisting of colostrum and egg product.

A method is provided for reducing pathogen-induced intestinal epithelial barrier dysregulation in a subject in need thereof, comprising administering an effective amount of a composition comprising colostrum and egg product.

A method of treating or preventing a disease or disorder in a subject in need thereof is provided, comprising administering an effective amount of a composition comprising colostrum and egg product. The disease or disorder may be caused by or exacerbated by a clinical or sub-clinical infection by one or more pathogens.

The disease or disorder may be associated with pathogenic translocation of harmful bacteria, bacterial products, or toxic luminal contents due to breakdown of the intestinal epithelial barrier and/or pathogen-induced intestinal epithelial barrier dysregulation.

The disease or disorder may be selected from the group consisting of environmental enteric disorder (EED), tropical sprue, small intestinal bacterial overgrowth (SIBO), and leaky gut syndrome.

The egg product may be selected from the group consisting of whole immune egg, dried whole egg, dried whole immune egg, pasteurized whole immune egg, pasteurized immune egg yolk, pasteurized immune egg white, pasteurized raw whole immune egg, dried pasteurized raw whole immune egg, and dried powdered pasteurized raw whole immune egg, optionally wherein the egg product is whole immune egg, preferably pasteurized raw dried whole immune egg powder.

The egg product may include immune egg. The immune egg may include polyclonal antibodies, or antigen binding fragments thereof, that are specific for a pathogen, a pathogen related toxin, or a pathogen related adhesin element, derived from one, two, three, four, five, six, seven, or eight, or more, of the pathogens.

The colostrum may be whole bovine colostrum, optionally non-hyperimmune whole bovine colostrum.

The weight ratio of colostrum to egg product, on a dry weight equivalent basis is selected from a weight ratio between about 10:1 to about 1:10, or about 5:1 to 1:5, or about 3:1 to 1:3.

The non-neonate human effective amount of the composition may include from 3 g to 50 g, 4 g to 30 g, 5 g to 20 g, or 6 g to 15 g of combined weight of the immune egg antibody product and the colostrum on a dry weight equivalent basis per dose.

The composition of the disclosure may be coadministered with an effective amount of additional active agent.

The composition may include an additional active agent. The additional active agent may be selected from the group consisting of an antibiotic drug, probiotic, antifungal drug, antimicrobial drug, antiparasitic drug, antiprotozoal drug, antiviral drug, bacteriocin, micronutrient, oral rehydration salt, antidiarrheal adsorbant, anticholinergic, antimotility drug, isolated egg bioactive molecule, additional non-immunoglobulin colostrum component, or antisecretory agent, as provided herein Inflammatory Bowel Disease Methods and compositions are provided herein for treatment or prevention of Inflammatory Bowel Disease (IBD). IBD is a serious, progressive condition involving inflammation of the gastrointestinal tract and that causes a significant decrease in the quality of life for those suffering from this disease. Inflammatory bowel diseases (IBD) includes ulcerative colitis, Crohn's disease, and indeterminate colitis. The symptoms of IBD may include malabsorption, diarrhea, abdominal pain, anemia, weight loss, and intestinal wall lesions. These diseases may also lead to fistula formation (deep ulcers of the intestine or rectum) and intestinal blockage. Crohn's disease can affect any part of the gastrointestinal (GI) tract, but ulcerative colitis affects only the colon and rectum.

Diagnosis and assessment of IBD may involve blood tests, e.g., for anemia, infection, or biomarkers, stool sample, e.g., for white blood cells or biomarkers, of infections due to bacteria or viruses or parasites, colonoscopy and biopsy, flexible sigmoidoscopy, x-ray to rule out complications such as perforated colon, computerized tomography (CT) scan of abdomen or pelvis, CT enterography, magnetic resonance (MR) enterography, e.g., to assess inflammation in small intestine or bowel.

Biomarkers of EED, IBD or other inflammatory gastrointestinal conditons may include regenerating gene (REG) family proteins that have been suggested to be involved in cellular proliferation of gastrointestinal cells. Concerning IBD, overexpression of REG1a and REG1b mRNA in resected colon tissue has been reported. Tsuchida et al., 2017, Expression of REG family genes in human inflammatory bowel diseases and its regulation. Biochem Biophysics Reports 12: 198-205. Reg1 is known to promote intestinal epithelial cell proliferation, regeneration and repair, and is up-regulated in a variety of enteric infections and inflammatory conditions. A decline in Reg 1 correlates to a decline in intestinal tissue damage.

In inflammatory bowel disease (IBD), enhanced inflammatory activity in the gut is thought to increase the risk of bacterial translocation and endotoxemia. Myeloperoxidase (MPO) is a key component of the oxygen-dependent microbial activity of phagocytes but it also has been linked to tissue damage in acute or chronic inflammation. Papp et al., 2011, Poster presentations: Serum Myeloperoxidase level is a marker of disease activity in pateints with inflammatory bowel dosease, Clinical diagnosis and outcome-Abstract-European Crohn's and Colitis Organisation Congress Abstract-P098. Derived from polymorphonuclear leukocyte activity, myeloperoxidase (MPO) catalyzes the oxidation of substances through hydrogen peroxide ($H_2O_2$). The MPO $H_2O_2$-system has a toxic effect on many micro-organisms such as bacteria, fungi, viruses and *mycoplasma*. During inflammation in the intestinal mucosa, neutrophils migrate towards the gut mucosa and release myeloperoxidase from granulocytes which can be detected in stools and used as a marker of intestinal inflammation. A decline in MPO correlates with a decline in intestinal inflammation.

Cytokines, small cell-signalling protein molecules secreted by various types of cells including immune cells and glia cells, may be major mediators of the mucosal lining in IBD. Ulcerative colitis may be characterized by a Th2 atypical immune response, since besides classic pro-inflammatory cytokines, such as IL-1, IL-6, and TNFalpha, in the pathogenesis of UC, the Th2 cytokines IL-10 and IL-13 may also play a role. Roda et al., 2011, Cytokine Networks in Ulcerative Colitis, Ulcers, vol. 2011, Article ID 391787, 5 pages. Plasma interleukin 1 receptor antagonist (IL-1Ra) levels may be higher in ulcerative colitis than in healthy subjects. Ludwiczek et al., Clin Exp Immunol 2004; 138: 323-329. Serum TNFalpha concentrations may raised in ulcerative colitis. Nicholls et al., 1993, Cytokines in stool's of children with inflammatory bowel disease or infective diarrhea. J Clin Pathol; 46:757-760. Blood based biomarkers of IBD may include C-reactive protein (CRP), CRP is produced by hepatocytes in response to inflammation, stimulated by certain cytokines. In the case of active IBD, these cytokines may include tumor necrosis factor-alpha (TNF-α), interleukin-6 (IL-6), and interleukin-Ibeta (IL-1β). Soubieres et al., 2016, Emerging role of novel biomarkers in the diagnosis of inflammatory bowel disease, World J Gastroinstesst Pharmacol Ther 7(1):41-50. Other biomarkers include erythrocyte sedimentation rate (ESR), antineutrophil cytoplasmic antibodies (ANCAs), ACSA, fecal calprotectin, fecal lactoferrin, fecal neopterin, fecal polymorphonuclear neutrophil(PMN)-elastase, S100A12, blood based anti-outer membrane protein C (anti-OmpC), blood based antibodies to flagellin, anti-I2 antibody, anti-carbohydrate antibodies, pancreatic antibodies, alpha-1 antitrypsinm (AAT), and granulocyte colony-stimulating factor (G-CSF).

ESR is a measure of systemic inflammation that is not entirely specific to IBD. Antineutrophil cytoplasmic antibodies (ANCAs) are antibodies against granules of neutrophil cytoplasm. They may be detected using indirect immunofluorescence (IIF) and show three main staining patterns: cytoplasmic(cANCA), speckled (sANCA), and perinuclear (pANCA). pANCA has been shown to increase significantly in UC. ASCA refers to antibodies for mannan in the cell wall of Sacchatomyces cerevisiae. In contrast to pANCA which is found in higher titres in UC, high ASCA levels are more specifc for CD. Fecal calprotectin is a zinc and calcium binding protein belonging to the S100 family that is derived mostly from neutrophils and monocytes, as well as activated macrophages. When the inflammatory process is triggered calprotectin is released due to degranulation or neutrophils, making it specific for gastrointestinal inflammation. Fecal lactoferrin is an iron-binding protein found on most mucosal surfaces. It is found within neutrophil granulocytes and becomes activated in acute inflammation. Levels of fecal lactoferrin have been found to be higher in active IBD, than in inactive IBD, IBS, and infectious bowel disease. There is an increasing incidence of TNFalpha secreting cells in the mucosa in inflammatory bowel disease. For example, serum TNF-α concentrations may raised in both ulcerative colitis and Crohn's disease. Anti-I2 antibody is specific for a fragment of bacterial DNA and shown to be associated with *Pseudomonas fluorescens*. Anti-I2 antibodies may be exhibited in CD or indeterminate colitis and ocassionally in UC. Other cytokines involved in the pathogenesis of IBD may include IL-1β, IL-6, IL-12, IL-17, IL-22, IL-23, and IFN-γ. Strober et al., 2011 Gastroenterology, 140(6):1756-1767.

Crohn's Disease

Crohn's disease is a type of inflammatory bowel disease (IBD). It causes inflammation of the gastrointestinal tract, which can lead to abdominal pain, severe diarrhea, fatigue, weight loss and malnutrition. Inflammation caused by Crohn's disease can involve different areas of the digestive tract in different people. Common areas affected by Crohn's disease are the last part of the small intestine and the colon. Ileocolic Crohn's disease includes both the ileum and the large intestine. Ileal Crohn's disease (Crohn's ileitis) affects only the last segment of the small intestine (ileum). Crohn's colitis is confined to the colon (part of the large intestine). Signs and symptoms of Crohn's disease can range from mild to severe. Symptoms may include diarrhea, fever, fatigue, abdominal pain, abdominal cramping, blood in the stool, mouth sores, reduced appetite, weight loss, malnutrition, pain or drainage near the anus due to inflammation from a fistula. Histologically, CD patients may exhibit granulomas, fissures, transmural inflammation, and/or mucosal inflammation. The exact cause of Crohn's disease is not known, but it is possible that a microorganism such as a virus or bacterium may trigger Crohn's disease. When the immune system tries to address the microorganism, an abnormal immune response may cause the immune system to attack the cells of the gastrointestinal tract. https://www.mayoclinic.org/diseases-conditions/crohns-disease/symptoms-causes/syc-20353304

Serum TNFalpha concentrations may raised in Crohn's disease. Plasma IL-6 may be raised in active Crohn's disease. Nicholls et al., 1993, Cytokines in stool's of children with inflammatory bowel disease or infective diarrhea. J Clin Pathol; 46:757-760. Plasma levels of IL-1sR1, an IL-1 soluble receptor, may be elevated in Crohn's disease. Ludwiczek et al., Clin Exp Immunol 2004; 138:323-329.

Ulcerative Colitis

Ulcerative colitis is a type of inflammatory bowel disease (IBD) that causes long-lasting inflammation and ulcers (sores) in the digestive tract. Ulcerative colitis affects the innermost lining of the large intestine (colon) and rectum. Ulcerative colitis is a chronic disease of the large intestine, also known as the colon, in which the lining of the colon becomes inflamed and develops tiny open sores, or ulcers, that produce pus and mucous. The combination of inflammation and ulceration can cause abdominal discomfort and frequent emptying of the colon. Signs and symptoms of ulcerative colitis may include: diarrhea, often with blood or pus, abdominal pain and cramping, rectal pain, rectal bleeding passing small amount of blood with stool, urgency to defecate, inability to defecate despite urgency, weight loss, fatigue, fever, and in children, failure to grow. https:// www.mayoclinic.org/diseases-conditions/ulcerative-colitis/ symptoms-causes/syc-20353326. Histologically, UC patients may exhibit transmural inflammation, and/or mucosal inflammation.

Prior art treatment of ulcerative colitis includes antiinflammatory drugs, e.g. 5-aminosalicylates sulfasalazine, mesalamine, balsalazide, or olsalazine, corticosteroids, e.g., prednisolone, hydrocortisone, and immune system suppressors, e.g., azathioprine, mercaptopurine, cyclosporine, infliximab, adalimumab, golimumab, or vedolizumab. However, each of these approaches are associated with undesirable side effects. For example, vedolizumab for intravenous infusion is a humanized IgG1 monoclonal antibody that binds to human alpha4beta7 (α4β7) integrin. Vedolizumab blocks interaction of a4p7 integrin with mucosal addressin cell adhesion molecule-1 (MAdCAM-1) and inhibits the migration of memory T-lymphocytes across the endothelium into inflamed gastrointestinal parachymal tissue. Side effects include risk of getting a serious infection, or liver problems. See ENTYVIO® prescribing information, Takeda Pharmaceuticals, 2018. Another approach to treatment of ulcerative colitis is use of a janus kinase (JAK) inhibitor, e.g., tofacitinib, however, this drug class may cause serius side effects such as lowering the ability of the patients immune system to fight infections, including tuberculosis, and infections caused by bacteria, fungi, or viruses. Some people taking JAK inhibitors may exhibit tears in stomach or intestine, most often in people taking NSAIDs, corticosteroids, or methotrexate. See XELJANZ® prescribing information, Pfizer, 2016. Management of ulcerative colitis may also include antibiotics, anti-diarrheal agents, iron supplements, and pain relievers, e.g., acetominophen, but not ibuprofen, naproxen sodium, or diclofenac sodium which may worsen symptoms. Treatment for ulcerative colitis may also involve administration of Firmicutes Ruminococcaceae such as Ruminococcus spp., or secondary bile acids such as deoxycholic acid (DCA) or lithocholic acid (LCA) to patients. Secondary bile acids (SBAs) are reduced in UC pouch patients, relative to familial adenomatous polyposis (FAP) control patients. Reduced Ruminococcaceae in UC pouches is associated with SBA deficiency. SBA supplementation ameliorates inflammation in animal models of colitis. It is said the protective effects of SBAs is in part dependent on TGR5 bile acid receptor. Sinha et al., 2020, Cell Host & Microbe, Dysbiosis-induced secondary bile acid deficiency promotes intestinal inflammation. https:// doi.org/10.1016/j.chom.2020.01.021. The disclosure provides a composition for treatment of ulcerative colitis comprising colostrum, egg product, and optionally one or more of aforementioned prior art additional active agents. For example, additional active agents may be SBA producing bacteria, such as Ruminococcaceae, e.g., *Ruminococcus* spp., such as *R. albus, R. callidis, R. bromii*, and/or secondary bile acids such as deoxycholic acid (DCA) or lithocholic acid (LCA).

Compositions and methods provided herein may also be used in the treatment or prevention of irritable bowel syndrome (IBS), pseudomembranous colitis, chemotherapy-induced mucositis, radiation-induced mucositis, nonsteroidal antiinflammatory drug (NSAID)-induced gut damage, infectious diarrhea, or for gastrointestinal flora management, for example, to reduce or eliminate small intestinal bacterial overgrowth (SIBO).

Indeterminate Colitis

Indeterminate colitis originally referred to those 10-15% of cases of inflammatory bowel disease (IBD) in which there was difficulty distinguishing between ulcerative colitis (UC) and Crohn's disease (CD) in the colectomy specimen. IC is associated with a form of fissuring ulceration, usually V-shaped clefts, in about 60% of IC cases. Guindi et al., 2004, J Clin Path 57:1233-1244. The term may be used to describe patients in whom a diagnosis of UC or CD cannot be made based on standard clinical testing, for example, colonoscopy, imaging, laboratory tests, and biopsy. A different term-inflammatory bowel disease—unclassified—has also been proposed to describe these patients. Serological biomarkers useful for diagnosing indeterminate colitis may include anti-*Saccharomyces cerevisiae* antibody (ASCA) and perinuclear antineutrophil cytoplasmic antibody (pANCA), also known as nuclear-specific antigen. Most patients with indeterminate colitis are negative for both biomarkers, while patients who have one or both will be more likely to manifest with CD or UC over time. Patients with indeterminate colitis are often managed the same as patients with ulcerative colitis. Tremaine, Gatroenterology & Hepatology, vol. 7, issue 12, 826-828.

Gastritis

Gastritis is a general term for a group of conditions that each involve inflammation of the lining of the stomach. The inflammation of gastritis may be a result of an infection by the same bacterium that causes most stomach ulcers—*H. pylori*. Gastritis may be acute or chronic. For example, *H. pylori* infection may lead to acute gastritis, then chronic gastritis, followed by atrophic gastritis, and may lead to peptic ulcer or gastric cancer. Signs and symptoms of gastritis include gnawing or burning ache or pain (indigestion) in the upper abdomen, nausea, vomiting, a feeling of fullness in upper abdomen after eating. Gastritis may be diagnosed via *H. pylori* blood, fecal, or breath test, endoscopy for signs of inflammation, biopsy, x-ray of upper digestive system using a contrast dye (e.g., containing barium). Biomarkers for gastritis may include one or more biomarkers, e.g., *H. pylori*-specific antibodies, pepsinogen, pepsinogen I, pepsinogen II, PGI/PGII ratio, and/or gastrin-17. Cooke et al., 2013, Gut microbes 4:6, 532-540. For example, a panel of biomarkers may be employed, e.g., GastroPanel® (Nordic Health Care Group), e.g., comprising pepsinogen I, pepsinogen II, amidated gastrin-17, and *H. pylori*-specific antibodies.

Prior art treatments may include antibiotic to kill *H. pylori* (e.g. clarithromycin, amoxicillin, metronidazole; proton pump inhibitors such as omeprazole, lansoprazole, rabeprazole, esomeprazole, dexlansoprazole, and pantoprazole); acid blockers also known as histamine blockers (e.g., including ranitidine, famotidine, cimetidine, and nizatidine), or antacids.

Peptic Ulcer

Peptic ulcer is alesion in the lining (mucosa) of the digestive tract, typically in the stomach or duodenum, caused by digestive action of pepsin and stomach acid. A common symptom of a peptic ulcer is stomach pain. Other symptoms include burning stomach pain, feeling of fullnes or bloating or belching, fatty food intolerance, heartburn, nausea, vomiting, vomiting blood, dark blood in stools, stools that are black or tarry, trouble breathing, feeling faint, unexplained weight loss, or appetite changes. Peptic ulcer disease is a major health problem and bleeding from peptic ulcer is a serious complication resulting in admission to a hospital with a case fatality rate of about 10%. Ruigomez et al., 2000, J Epidemiol Community Health 54: 130-133. Peptic ulcers may be associated with *H. pylori* infection, or long term use of aspirin or non-steroidal antiinflammatory drugs (NSAIDs), or other medications such as steroids, selective serotonin reuptake inhibitors (SSRIs), alendronate, or risedronate. Diagnosis of peptic ulcer may involve *H. pylori* blood, fecal, or breath test, endoscopy for signs of inflammation, biopsy, and/or x-ray of upper digestive system using a contrast dye (e.g., containing barium). Prior art treatment of gastric ulcer may include antibiotics to kill *H. pylori*, e.g., amoxicillin, clrithromycin, metronidazole, tinidazole, tetracycline, and lavofloxin; proton pump inhibitors, e.g., omeprazole, lansoprezole, rabeprazole, esomeprazole, and pantoprazole; acid blockers, also know as histamine (H2) blockers, e.g. ranitidine, famotidine, cimetidine, and nizatidine; antacids; and/or cytoprotective agents, e.g., sucralfate, misoprostol. Biomarkers for gastric ulcer may include serum progranulin, serum hydroxyproline, platelet to lymphocyte ratio (PLR), neutrophil to lymphocyte ration (NLR), and lymphocyte count values. Aksoy et al., 2018, Gastroenterol Review 13(4):313-321, Takeuchi et al., 2014, Biomarker Insights, 9:61-66, Aydin et al., Surgical Infections, 8 Feb. 2019, https://doi.org/10.1089/sur.2018.288.

Irritable Bowel Syndrome

Irritable bowel syndrome (IBS) is a group of symptoms-including abdominal pain and changes in the pattern of bowel movements without clear evidence of underlying damage. These symptoms may occur over a long time, often years. IBS has been classified into four main types depending on whether diarrhea is common, constipation is common, both are common, or neither occurs very often (IBS-D, IBS-C, IBS-M, or IBS-U respectively). IBS negatively affects quality of life and may result in missed school or work. Disorders such as anxiety, major depression, and chronic fatigue syndrome are common among people with IBS. Chey et al., 2015, JAMA 313(9) 982. https://www.niddk.nih.gov/health-information/digestive-diseases/irritable-bowel-syndrome/definition-facts. The causes of IBS are not clear. Theories include combinations of gut-brain axis problems, gut motility disorders, pain sensitivity, infections including small intestinal bacterial overgrowth, neurotransmitters. Symptoms of IBS may include abdominal pain, abdominal discomfort, flatulence, and altered bowel habits such as diarrhea, constipation, fatigue and/or fibromyalgia. A recent study reported serm levels of TL-5, TL-6, IL-10 and TNFalpha were significantly higher in patients with IBS compared to healthy controls. Vara et al., 2018, Int J Gen Medicine, 11, 285-291.

Some IBS cases may be triggered by an acute gastroenteritis infection. Genetic defects relating to the innate immune system and epithelial barrier as well as high stress and anxiety levels may increase the risk of developing post-infectious IBS. Post-infectious IBS may manifest itself as the diarrhea-predominant subtype. A link between small intestinal bacterial overgrowth and tropical sprue has been proposed to be involved in the cause of post-infectious IBS. Ghoshal et al. 2017. Nat Rev Gastroenterol Hepatol. 14 (7): 435-41.

Pseudomembranous Colitis

Pseudomembranous colitis refers to swelling or inflammation of the large intestine (colon) due to an overgrowth of *Clostridium difficile* (*C. difficile*) bacteria. This infection is a common cause of diarrhea after antibiotic use. The *C. difficile* bacteria normally lives in the intestine. However, too much of these bacteria may grow when antibiotics are administered. The bacteria give off a strong toxin that causes inflammation and bleeding in the lining of the colon. Any antibiotic can cause this condition. The drugs responsible for the problem may be ampicillin, clindamycin, fluoroquinolones, or cephalosporins. Pseudomembranous colitis is becoming more common in people who take antibiotics and are not in a hospital. https://medlineplus.gov/ency/article/000259.htm Mucositis Mucositis (sometimes called stomatitis) is inflammation and damage of the mucous membranes lining the mouth and other parts of the gastrointestinal (GI) tract. Mucositis is a common side effect of chemotherapy, radiation therapy, or bone-marrow transplants and can also be seen in individuals who receive bone-marrow transplants or radiation therapy. https://jamanetwork.com/journals/jamaoncology/fullarticle/2546658. Mucositis is associate with painful inflammation and ulceration of the mucous membranes lining the gastriintestinal tract. Musositis can occur anywhere in the gastrointestinal tract, but oral mucositis refers to inflammation and ulceration of the mouth. As a result of cell death in reaction to chemotherapy or radiation therapy the mucosal lining of the mouth becomes thin, may slough off and then become red, inflamed and ulcerated. Mucositis may be associate with change in taste perception, severe pain, burning sensation, trouble speaking or eating, or even opening the mouth.

The severity of oral mucositis can be evaluated using several different assessment tools. Two of the most commonly used are the World Health Organization (WHO) Oral Toxicity score and the National Cancer Institute Common Toxicity Criteria (NCI-CTC) for Oral Mucositis. Treatment may include oral hygeine, medicinal mouthwashes including chlorhexidene, lidocaine, keratinocyte growth factor (Palifermin) cryotherapy (ice chips), oral mucoadhesive oral protectants (e.g. MuGard), salt water, calcium-phosphate mouth rinse.

NSAID-Induced Gut Damage

Nonsteroidal antiinflammatory drugs (NSAIDs) are widely prescribed and are effective in the treatment of musculoskeletal injury and chronic arthritic conditions. Nevertheless, about 2% of subjects taking NSAIDs for one year suffer from gastrointestinal adverse effects, including bleeding, perforation, and stricture formation of the stomach and intestine. Acid suppressants and prostaglandin analogues have been shown to be effective in reducing gastric injury induced by NSAIDs but are less effective in preventing small intestinal injury. One prior art approach utilized a defatted colostrum preparation, said to be rich in the growth factors EGF, TGF-alpha, and TGF-beta, which reduced NSAID-induced gastric and intestinal injury in rats and mice, and was reported to reduce gastric erosions in human volunteers taking NSAIDs. NSAID use may be associated with gastritis or peptic ulcers. In one animal model, mice that received indomethacin alone exhibited markedly shortened villi with bulbous expansion of the tips. Mice that received indomethacin with defatted colostrum showed less marked changes to the villi. Playford et al., 2000, Am J Clin Nutr 72; 5-14.

Undifferentiated Diarrhea

Some embodiments of this disclosure include broad spectrum therapeutic or prophylactic compositions comprising an admixture of broad-spectrum neutralizing antibodies, colostrum in an amount effective to act as a protective/reactive matrix, and an additional active agent. The disclosure provides a method for treating, preventing or dietary management of a subject suffering from undifferentiated diarrhea, and can be administered across a wide range of unknown or undiagnosed conditions resulting in effective management of toxin, pathogen or adhesion-mediated diarrhea. Some embodiments of this invention provide a broad spectrum therapeutic or prophylactic anti-pathogen composition comprising colostrum in an amount effective to act as a protective/reactive matrix, an admixture of broad-spectrum anti-pathogen antibodies, and an additional active agent.

Some embodiments of this invention provide a broad spectrum therapeutic or prophylactic formulation comprising colostrum, an admixture of broad-spectrum antitoxin, anti-pathogen, and anti-adhesin antibodies, and an additional active agent.

Some embodiments of this invention provide a broad spectrum therapeutic or prophylactic anti-toxin composition comprising colostrum, an admixture of broad-spectrum antitoxin antibodies, and an additional active agent.

Some embodiments of this invention provide a broad spectrum therapeutic or prophylactic anti-pathogen composition comprising colostrum, an admixture of broad-spectrum anti-pathogen antibodies, and an additional active agent.

Some embodiments of this invention provide a broad spectrum therapeutic or prophylactic anti-adhesin composition comprising colostrum, an admixture of broad-spectrum anti-adhesin antibodies, and an additional active agent.

In some embodiments, the disclosure provides a method for treating a subject suffering from undifferentiated diarrhea, comprising administering a composition comprising colostrum, antibody product comprising antibodies, derived from a different species than the colostrum, specific for one or more antigen clusters, as described herein, and an additional active agent selected from antibiotics, antifungals, antimicrobials, antiparasitics, antiprotozoal drugs, antivirals, bacteriocins, micronutrients, oral rehydration salts, antidiarrheal adsorbants, anticholinergics, antisecretory agents, antimotility drugs, additional non-immunoglobulin colostrum components, micronutrients, or antisecretory agents. In some embodiments, the additional active agent is selected to allow the physician to conform to the current standard of care protocols known in the art. In some embodiments, the additional active agent is selected from an antibiotic, antimicrobial, micronutrient, or rehydration salt.

Antibodies, immunoglobulins, and other biological immune factors (referred to collectively as antibodies), both natural and their synthetic analogues, are known therapeutic agents in humans and animals.

In embodiments, the compositions of the disclosure are useful in the treatment or prevention of microbial infections caused by various pathogenic microorganisms such as bacteria, viruses, yeast, protozoa and parasites. In embodiments, the at least one specific avian antibody (immunoglobulin) specifically binds to a pathogen, a pathogen related toxin, a pathogen related adhesin element, or a combination thereof. In embodiments, the pathogen includes a human pathogen or a veterinary pathogen. In embodiments, the pathogen includes a human or veterinary, enteric or gastrointestinal, pathogen causing gastroenteritis.

In some embodiments, the specific antibodies are specific for binding an *E. coli* pathogenic strain, related toxin or adhesin element. Pathogenic strains of *E. coli* can be grouped into six categories: enteroaggregative (EAEC), enterohemorrhagic (EHEC), enteroinvasive (EIEC), enteropathogenic (EPEC), enterotoxigenic (ETEC), and diffuse adherent (DAEC) *E. coli*. Pathogenic *E. coli* are serotyped on the basis of their O (somatic), H (flagellar), and K(capsular) surface antigen profiles.

ETEC is recognized as the causative agent of travelers' diarrhea and illness is characterized by watery diarrhea with little or no fever. ETEC infections occur commonly in under-developed countries but, in the U.S., it has been implicated in sporadic waterborne outbreaks as well as due to the consumption of soft cheeses, Mexican-style foods and raw vegetables. Pathogenesis of ETEC is due to the production of any of several enterotoxins. ETEC produces heat labile toxin (LT) or a heat stable toxin (ST).

EIEC closely resemble *Shigella* and causes an invasive, dysenteric form of diarrhea in humans. Like *Shigella*, there are no known animal reservoirs; hence the primary source for EIEC appears to be infected humans. EIEC infection can result in mucoid, bloody stool.

EPEC causes a profuse watery diarrheal disease and it is a leading cause of infantile diarrhea in developing countries. EPEC outbreaks have been linked to the consumption of contaminated drinking water as well as some meat products. Pathogenesis of EPEC involves intimin protein (encoded by eae gene) that causes attachment and effacing lesions; but it also involves a plasmid-encoded protein referred to as EPEC adherence factor (EAF) that enables localized adherence of bacteria to intestinal cells.

EHEC are recognized as the primary cause of hemorrhagic colitis (HC) or bloody diarrhea, which can progress to the potentially fatal hemolytic uremic syndrome (HUS). EHEC are typified by the production of verotoxin or Shiga toxins (Stx).

Conventional methods for biochemical screening and identification of *E. coli* strains, and additional tests for each category, are described in Feng et al., 2011, Fda.gov/food/BAM: Diarrheagenic *Escherichia coli*, February 2011, Bacteriological Analytical Manual, Chapter 4A, Diarrheagenic *Escherichia* coli, which is incorporated herein by reference.

In some embodiments, the specific antibodies specifically bind a causative pathogenic agent in undifferentiated diarrhea selected from the group consisting of: *Campylobacter jejuni*, *Salmonella*, *Salmonella enterica* serovar *Typhi*, *Shigella* dystenteriae, *Plesiomonas shigelloides*, *Escherichia coli* [including (EPEC) enteropathogenic *E. coli*, (ETEC) enterotoxigenic *E. coli*, (EAEC) enteroaggregative *E. coli*, (EIEC) enteroinvasive *E. coli*, (DAEC) diffuse adherent *E. coli* and (EHEC) haemorrhagic *E. coli*], *Clostridium difficile*, *Yersinia enterocolitica*, *Vibrio cholerae* 01, *Vibrio* 0139, Non-O1 Vibrios, *Vibrio parahaemolyticus*, *Aeromonas hydrophila*, *Clostridium perfiingens*, *Clostridium difficile*, enterohepatic *Helicobacter* (including Helicobacter-pylori), *Staphylococcus aureus*, *Klebsiella*, *Candida* spp., rotavirus, coronavirus, norovirus, calicivirus, enteric adenovirus, cytomegalovirus, astrovirus, *Cryptosporidium* spp., *Entamoeba* spp., and *Giardia* spp. In certain embodiments, the pathogen related toxin includes an endotoxin or exotoxin. In certain embodiments, the pathogen related adhesin element includes adhesins, cadherins, cilia, fimbrillae, a viral adhesin structure, or a combination thereof.

In embodiments, the compositions may be useful to treat or prevent conditions such as undifferentiated diarrhea, traveler's diarrhea, rotavirus diarrhea, toxin-mediated diarrhea, antibiotic-associated diarrhea, cholera, *C. difficile* infection, dysentery, typhoid fever, peptic ulcers including gastric ulcers, duodenal ulcers, and gastroduodenal ulcers, gastritis, or for gastrointestinal flora management, for example, to reduce or eliminate small intestinal bacterial overgrowth (SIBO).

In some embodiments, the compositions and methods of the disclosure are employed in the treatment or prevention of diarrhea. There are multiple diarrhea causing pathogenic organisms including viruses, bacteria, parasites, fungi and protozoa; prevalence of these infections varies per geographical location.

The primary causes of bacterial infection, for example in India, include *Escherichia coli* spp., Enterotoxigenic *E. coli*, Entero-adherent *E. coli*, *Auromonas* spp., *Camphylobacter jejuni*, *Shigella* spp., *Vibrio* spp., *Vibrio cholera* 01, *Vibrio parahaemolyticus*, *Salmonella* spp., *Staphylococcus aureus*, *Clostridium difficile*, *Clostridium perfringens*, and *Yersinia enterocolitica*. Secondary causes include *Clostridium difficile* (toxin A or B). The primary cause of viral diarrhea is infection by Rotavirus; although Calcivirus, Astrovirus, Norwalk virus, and Adenovirus are also known to cause diarrhea. Secondary causes of viral diarrhea include enteric adenovirus, herpes simplex virus and viral hepatitis. (John B. Sullivan and Gary R. Krieger, Clinical Environmental Health and Toxic Exposures, $2^{nd}$ Ed., Lippincott Williams & Wilkins, 2001, page 1040).

There are also known to be regional and seasonal differences in prevalence of various pathogenic infections resulting in diarrhea. For example, in Pranam, India, one study reported rotavirus accounted for an average 15-25% of childhood cases of diarrhea. Enterotoxigenic *E. coli* was responsible for 10 to 20% of total diarrhea cases, with Enteropathogenic *E. coli* causing about 1 to 5% of cases. *Camphylobacter jejuni* infection caused about 10 to 15%, and *Shigella* caused an estimated 5 to 15% of cases of childhood diarrhea. *Vibrio cholera* caused about 5 to 10% of cases. *Salmonella* (non-typhoid) caused about 1 to 5% of cases. Protozoan infection was caused by primarily by *Cryptosporidium* (5-15%). No pathogenic cause was identified in about 20 to 30% of cases. (Fricker, Children in the Tropics, Putting an end to diarrheal diseases, 1993-No. 204: 1-66).

Different regions within India ascribe bacterial cases of childhood diarrhea to different pathogens with different degree of prevalence. For example a study in Orissa, India found, among 866 culture-positive samples that *E. coli* sp. (75.5%), pathogenic E. coli (13.2%), *Aeromonas* spp. (2%), *Shigella* spp. (4.5%), *Vibrio cholera* O1 (17.3%), *V. cholera* 0139 (1%) and *Salmonella* spp. (0.7%). Samal et al., Incidence of bacterial enteropathogens among hospitalized diarrhea patients from Orissa, India, Jpn J Infect Dis 2008 September, 61(5): 350-5. A majority of childhood diarrhea cases seem to be caused by bacterial and viral infection, and an alternative to antibiotics is desirable.

Gastrointestinal Flora Management

In some embodiments, the compositions of the disclosure can be used for gastrointestinal flora management, for example, in a method of dietary management to control overgrowth of undesirable species, such as small intestinal bacterial overgrowth (SIBO). The pattern of intestinal flora can fluctuate due to diarrheal illnesses, antibiotic treatment, and to some extent due to dietary interventions.

Major human gut bacteria include the genera *Bacteroides*, *Clostridium*, *Fusobacterium*, *Eubacterium*, *Ruminococcus*, *Peptococcus*, *Peptostreptococcus*, and *Bifidobacterium*. Other genera, such as aerobes such as *Escherichia*, *Enterobacterium*, *Enterococcus*, *Klebsiella*, *Proteus*, and *Lactobacillus*, are present to a lesser extent. Guarner and Malagelada, Lancet 361, Feb. 8, 2003, 512-519.

In some embodiments, the disclosure provides a method for dietary management of one or more species of gut bacteria, or undesirable species, in a subject comprising administering a composition of the disclosure. In some embodiments, the disclosure provides a composition comprising 1) colostrum, 2) one or more additional active agents, and 3) antibody product comprising at least one specific antibody, immunoglobulin, or an active binding fragment thereof, that is specific for binding to an antigenic region of one or more gut bacteria selected from the genera *Bacteroides*, *Clostridium*, *Fusobacterium*, *Eubacterium*, *Ruminococcus*, *Peptococcus*, *Peptostreptococcus*, *Bifidobacterium*, *Escherichia*, *Enterobacterium*, *Enterococcus*, *Klebsiella*, *Proteus*, and *Lactobacillus*. Cirrhotic patients are immunocompromised with a high risk of infection. Gram negative bacteria are a frequent cause of enteric infections, as well as enterococci, *Vibrio* spp., *Aeromonas* spp., *Clostridium* spp., *Listeria monocytogenes*, *Plesiomonas shigelloides* and *Mycobacterium tuberculosis*. In some embodiments, the compositions of the disclosure comprise colostrum, an antibody product comprising specific polyclonal antibodies specific for one or more of enterococci, *Vibrio* spp., *Aeromonas* spp., *Clostridium* spp., *Listeria monocytogenes*, *Plesiomonas shigelloides* and *Mycobacterium tuberculosis*, and an additional active agent.

In some embodiments, the disclosure provides a method of treating a subject with special dietary needs due to an enteric infection or gastrointestinal condition, the method comprising administering a composition comprising 1) colostrum; 2) antibody product comprising specific antibodies derived from a different species than the colostrum, wherein the antibodies are specific for one or more pathogenic or undesirable species, or a toxin or adhesion produced thereby, and optionally, 3) an additional active agent. These compositions are useful as nutritional compositions for administering to the non-neonate human subject in need thereof, wherein the subject is afflicted with a disease that creates special dietary needs. In some embodiments, the disease that creates special dietary needs is selected from the group consisting of Crohn's disease, ulcerative colitis, indeterminate colitis, antibiotic-associated diarrhea, cirrhosis, gastritis, and peptic ulcers including gastric ulcers, duodenal ulcers, and gastroduodenal ulcers. In some embodiments, the disease that creates special dietary needs is selected from the group consisting of pediatric diarrhea, undifferentiated diarrhea, traveler's diarrhea, rotavirus diarrhea, toxin-mediated diarrhea, cholera, *C. difficile* infection, dysentery, typhoid fever, watery diarrhea, acute watery diarrhea, bacterial-mediated diarrhea, protozoal-mediated diarrhea, parasitic-mediated diarrhea, HIV-associated diarrhea, and infectious diarrhea.

Antibiotic-Associated Diarrhea

In some embodiments, the disclosure provides a method of treating or preventing antibiotic-associated diarrhea comprising administering a composition comprising a colostrum, an additional active agent, and an antibody product comprising specific antibodies derived from a different animal species than the colostrum, wherein the antibodies specifically bind to as described herein. Antibiotic-associated diarrhea (AAD) can result from an imbalance in the colonic microbiota. An overgrowth of pathogenic microorganisms or undesirable strains such as *Clostridium difficile* or *Candida* spp. can occur during antibiotic therapy. *Candida* is the most frequently encountered fungal infection in the gastrointestinal tract following antibiotic exposure. The pathogenesis of *Candida* is said to vary with each species. Vaishnavi et al. studied speciation of fecal *Candida* isolates in antibiotic-associated diarrhea in non-HIV patients and found predominant isolates were *C. tropicalis*, *C. albicans*, and *C. krusai*. See Vaishnavi et al., Jpn. J. Infect. Dis. 61, 1-4, 2008. Speciation of fecal *Candida* isolates in antibiotic-associated diarrhea in non-HIV patients. In embodiments, the specific antibodies of the disclosure may be specific for

*C. difficile* or one or more *Candida* species. In embodiments, the specific antibodies may be avian polyclonal antibodies specific for one or more *Candida* species, for example, *C. tropicalis, C. albicans*, and/or *C. krusai*.

Clostridium difficile Infection

In some embodiments, the compositions can be used to treat or prevent diarrhea due to *C. difficile* infection or overgrowth, by administration to a subject or population of subjects diagnosed, suspected, or at risk of contracting, *C. difficile* infection. In some embodiments, the subject population is selected from that of a nursing home facility, hospital, day care facility, school, or military base or encampment.

Specific Antibodies

The disclosure provides compositions comprising colostrum, antibody product comprising specific binding molecules such as immunoglobulins, antibodies, or active binding fragments thereof, derived from a different animal species than the colostrum, and an additional active agent. Antibodies, immunoglobulins, and other biological immune factors (referred to collectively as antibodies), both natural and their synthetic analogues, are known therapeutic agents in humans and animals.

Antibodies operate by binding (via non-covalent forces) between the antigen-combining site on the antibody and a portion of the antigen called the antigenic determinant or epitope. Antibodies are capable of high degrees of specificity. For example, the field of monoclonal antibodies has developed largely under the impetus of producing ever more specific and precise binding characteristics. However, this high specificity can lead to excessively limited binding attributes, where agents or antigens that are functionally identical do not react identically with the immunoreagent or immunotherapeutic. Cross-reactivity on the other hand, usually considered an error or failure, is the reaction between an antigen and an antibody that was generated against a similar but different antigen. Controlled cross-reactivity may constructively be used to broaden the binding range of the antibody.

In various embodiments, the disclosure provides a composition comprising colostrum, an additional active agent and an antibody product comprising one or more specific antibodies, immunoglobulins, or active binding fragments thereof, derived from a different animal species as the colostrum, wherein the specific antibody is specific for binding to an antigenic region of a diarrhea-causing pathogenic organism, or a pathogen related toxin, or adhesin originating therefrom.

In some embodiments, the specific antibodies are specific for binding to a pathogenic organism, or a pathogen related toxin, or adhesin originating therefrom, selected from the group consisting of: *Campylobacter jejuni, Salmonella, Salmonella enterica* serovar *Typhi, Shigella dystenteriae, Plesiomonas shigelloides, Escherichia coli*, enteropathogenic *E. coli*, enterotoxigenic *E. coli*, enteroaggregative *E. coli*, enteroinvasive *E. coli*, haemorrhagic *E. coli*, diffuse adherent *E. coli, Clostridium dificile, Yersinia enterocolitica, Candida* spp., *Vibrio cholerae* 01, *Vibrio* 0139, Non-O1 Vibrios, *Vibrio parahaemolyticus, Aeromonas hydrophila, Clostridium perfringens*, enterohepatic *Helicobacter, Helicobacter pylori, Staphylococcus aureus, Klebsiella, Gardnerella* spp., *Listeria monocytogenes, Neisseria gonorrhoeae, Chlamydiaceae trachomatis, Mycoplasma* spp., *Campylobacter jejuni, Trichomonas vaginalis*, herpes virus type 1, herpes virus type 2, *Candida albicans, Candida glabrata, Candida tropicalis, Candida parapsilosis* and *Candida krusei*, Group A *Streptococcus* spp., rotavirus, coronavirus, norovirus, calicivirus, parvovirus, enteric adenovirus, cytomegalovirus, astrovirus, *S. pneumoniae, H. influenzae*, herpes zoster virus, *Fusarium* spp., and *Acanthamoeba* spp.

In some embodiments, the specific antibodies are specific for binding to a pathogenic organism, or a pathogen related toxin, or adhesin originating therefrom, that is an enteric parasite selected from a protozoa or a helminth. In some embodiments, the pathogenic organism is a protozoan selected from the group consisting of *Giardia lamblia, Cryptosporidium parvum, Trichinella* spp., *Trichinella spiralis, Trichinella pseudospirallis*, and *Entamoeba histolytica*. In some embodiments, the pathogenic organism is a helminth selected from among Nematodes (roundworms, hookworms), Trematodes (Flukes), Cestodes (tapeworms), pinworms and ringworms. In some embodiments, the pathogenic organism is a helminth selected from *Taenia* spp., *Taenia saginata* (beef tapeworm), *Taenia solium* (pork tapeworm). In some embodiments, the pathogenic organism is a parasite selected from *Ancylostoma duodenale* (hookworm), *Necator americanus* (hookworm), *Ancylostoma caninum* (hookworm), and *Ascaris lumbricoides* (roundworm).

In some embodiments, the specific antibodies are specific for binding to a pathogen related toxin selected from an endotoxin or exotoxin. In some embodiments, the exotoxin is an enterotoxin. In some embodiments, the pathogen related toxin include exotoxins are derived from bacterial sources such as *Clostridium difficile, Clostridium perfringens* (*Clostridium perfringens* enterotoxin), *Vibrio cholerae* (Cholera toxin), *Staphylococcus aureus* (Staphylococcal Enterotoxin B), *Yersinia enterocolitica, Shigella dysenteriae* (Shiga toxin), *Campylobacter jejuni* (*Campylobacter jejuni* enterotoxin), *E. coli* (heat stable enterotoxins, LT; LT-II), enterohemorrhagic varieties of *E. coli* including O157:H7 (shiga-like toxin) or viral sources such as rotovirus (NSP4). In other embodiments, the exotoxin is an AB5 toxin.

In some embodiments, the specific antibodies are specific for binding to a pathogen related toxin that is a bacterial toxin or toxoid whose toxicity has been inactivated or suppressed by chemical (formalin) or heat treatment, while immunogenicity is maintained.

In some specific embodiments, the specific antibodies are specific for binding to a pathogen related toxin that is selected from the group consisting of alpha-toxin (CPA), beta-toxin (CPB), epsilon-toxin (ETX), enterotoxin, beta2-toxin (CPB2), and perfringolysin O produced by *Clostridium perfringens* type C or type B.

In some embodiments, the specific antibodies are specific for binding to a pathogen related toxin that is an endotoxin selected from lipopolysaccharides (LPS), or lipooligosaccharides (LOS) found in the outer membrane of various gram-negative bacteria. In some embodiments, the endotoxins are derived from a gram-positive bacteria, for example, *Bacillus thuringiensis* (delta endotoxin).

In some embodiments, the specific antibodies are specific for binding to a pathogen related toxin that is a mycotoxin derived from fungi including, but not limited to *Fusarium* (Trichothecenes, Zearalenone); *Aspergillus* (Aflatoxins, Ochtatoxin A, Patulin); *Gibberella* (Fumonisins, Fusarin C); *Penicillium* (Patulin, Citrinin, Ochratoxin A, Cyclopiazonic acid); *Byssochlamys* (Patulin); *Claviceps* (Ergot alkaloids); and *Alternaria* (Alternariol, Tenuazonic acid). Mycotoxins can exacerbate bacterial and parasitic enteric infections and increase susceptibility to infection.

In another aspect, the specific antibodies are specific for binding to a pathogen related adhesin element is selected from among adhesins, cadherins, cilia, fimbrillae, a viral adhesin structure, or a combination thereof.

In various embodiments, the composition comprises bovine colostrum, an additional active agent, and an antibody product comprising at least one specific avian antibody, immunoglobulin, or an active binding fragment thereof, that is specific for binding to an antigenic region of a diarrhea-causing pathogenic organism, toxin, or adhesin originating therefrom, as described herein.

In another aspect, the specific antibodies are specific for binding to an undesirable species or a species of gut flora.

In some embodiments, the immune egg or antibody product comprises at least one specific antibody, immunoglobulin, or an active binding fragment thereof, that is specific for binding to an antigenic region of one or more gut bacteria selected from the genera *Bacteroides, Clostridium, Fusobacterium, Eubacterium*, Ruminococcus, Peptococcus, *Peptostreptococcus, Bifidobacterium, Escherichia, Enterobacterium, Enterococcus, Klebsiella, Proteus*, and *Lactobacillus*. In some embodiments, the immune egg may be selected from the group consisting of whole immune egg, egg yolk, and antibody product comprising at least one specific antibody, immunoglobulin, or an active binding fragment thereof. In some embodiments, the immune egg is whole immune egg. In some embodiments, the antibody product comprises IgY.

One embodiment of this invention is its use in the production of a broad spectrum therapeutic or dietary formulation. Such a broad spectrum therapeutic or dietary formulation can exploit cross-reactivity of certain antibodies. One method for producing this type of reactive formulation involves the production of avian polyclonal specific antibodies, harvesting the antibodies from an appropriately immunized avian, embedding the antibodies in minimally processed colostrum, and adding an additional active agent.

Polyclonal antibodies (or antisera) are antibodies that are derived from different B cell lines. They are typically harvested en-mass from the blood, serum, plasma, or blood, eggs, tissue, or other biological fluids of an immunized avian. They are a mixture of immunoglobulin molecules secreted against a specific antigen, or group of antigens, recognizing a range of different epitopes. It is possible to have multiple antibodies for a single antigen (binding to different epitopes) or for a single antibody to bind to multiple antigens due to cross-reactivity. This is in contrast to monoclonal antibodies, which are identical and monospecific; being produced by one type of immune cell that are all clones of a single parent cell.

The antibodies used in this invention may be treated in any suitable manner to prepare for formulation and use, including but not limited to separations, plasmapheresis, drying processes, lyophilization, pasteurization, and preservation methods. The antibodies used in this invention may be treated, concentrated, separated, or purified in various ways depending upon their final intended use.

There is a clear need for low cost and effective treatments for many gastrointestinal pathogens, and orally administered antibodies are candidates for this role. In addition demonstrated efficacy, orally administered antibodies are typically non-immunogenic. They are considered typically well tolerated with no adverse side effects reported and comparatively no different reactions than a comparable ingested food product. Notably several products containing orally administered antibody have received GRAS (Generally Recognized as Safe) certification by the FDA.

Avian Antibodies

In some embodiments, the antibody product comprises specific antibodies that are derived from birds (such as laying-hens) that are highly cost-effective as producers of antibodies compared with mammals traditionally used for such production. Avian antibodies have biochemical advantages over mammalian antibodies. Immunologic differences between mammals and birds result in increased sensitivity and decreased background in immunological assays; as well as high specificity and lack of complementary immune effects when administered to mammalian subjects. In contrast to mammalian antibodies, avian antibodies do not activate the human complement system through the primary or classical pathway nor will they react with rheumatoid factors, human anti-mouse IgG antibodies, staphylococcal proteins A or G, or bacterial and human Fc receptors. Avian antibodies can however activate the non-inflammatory alternative pathway. Thus avian antibodies offer many advantages over mammalian antibodies.

In a preferred embodiment, the antibody product in the compositions comprises specific polyclonal antibodies prepared in eggs of hens inoculated with one of or a mixture of pathogenic components. Various preparations of specific antigens can also be employed for inoculation. After inoculation, the hen produces eggs containing substantial quantities of specific IgY immunoglobulin in the yolk, as well as small amounts of IgM and IgA immunoglobulins in the albumin. Therefore eggs are an excellent source for large quantities of economically produced, highly specific and stable antibodies. In one embodiment, chickens are used to produce avian antibody; however, turkeys, ducks, geese, ostriches, etc. may alternatively be used. In one aspect, hens are inoculated by any method known in the art, as described herein. For example, the antigen may be injected intramuscularly or subcutaneously. The preferred muscle for injection in an avian is the breast muscle. Other methods of administration that can be used include subcutaneous injection, intravenous injection, intraperitoneal injection, intradermal, rectal suppository, aerosol or oral administration.

The specific immune state is preferably induced and maintained in the target animal by immunization and repeated booster administrations of an appropriate dosage at fixed time intervals. The time intervals are preferably 1-8 week intervals over a period of 1-12 months. Dosage is selected between about 0.01-5 milligrams of the antigen. In one aspect, the dosage is 0.01 mg to 1.0 mg of antigen per inoculation, preferably 100 mg, 200 mg, 250 mg, 300 mg, 400 mg, 500 mg or 750 mg antigen per inoculation of a hen chicken. The total number of vaccinations can be selected from 1, 2, 3, 4, 5, or 6 in a 12 month period. Typically, a first inoculation is performed on day 1, with booster vaccinations on day 10, and day 20. The hen chicken can be re-vaccinated as needed by monitoring the specific antibody concentration, or titer, in the eggs by, for example, ELISA. A typical subcutaneous dosage volume for a hen chicken is selected from between about 0.2 to 1.0 mL, 0.3 to 0.7 mL, or 0.5 mL. However, it is essential that the booster administrations do not lead to immune tolerance. Such processes are well known in the art.

It is possible to use other inoculation maintenance procedures or combination of procedures, such as, for example, intramuscular injection for primary immunization and intravenous injection for booster injections. Further procedures include simultaneously administering microencapsulated and liquid immunogen, or intramuscular injection for primary immunization, and booster dosages by oral administration or parenteral administration by microencapsulation means. Several combinations of primary and booster immunization are known to those skilled in the art.

Adjuvants, or functional equivalents thereof, may be included in the immunization solution/vaccine composition to enhance the specific immune response of the animal. A large number of adjuvants have been described and used for the generation of antibodies in laboratory animals, such as mouse, rats, rabbits and chickens. In such setting the tolerance of side effects is rather high as the main aim is to obtain a strong antibody response.

Adjuvants pertaining to the present disclosure may be grouped according to their origin, be it mineral, bacterial, plant, synthetic, or host product. The first group under this classification is the mineral adjuvants, such as aluminum compounds. Antigens precipitated with aluminum salts or antigens mixed with or adsorbed to performed aluminum compounds have been used extensively to augment immune responses in animals and humans. In one embodiment, the adjuvant in the immunization composition is from a bacterial origin. Adjuvants with bacterial origins can be purified and synthesized (for example muramyl dipeptides, lipid A) and host mediators have been cloned (Interleukin 1 and 2). Known chemical purification of several adjuvants of active components of bacterial origin includes: *Bordetella pertussis, Mycobacterium tuberculosis*, lipopoly-saccharide, Freund's Complete Adjuvant (FCA) and Freund's Incomplete Adjuvant (Difco Laboratories, Detroit, Mich.) and Merck Adjuvant 65 (Merck and Company, Inc., Rahway, N.J.). In a specific aspect, Freund's Complete Adjuvant or Freund's Incomplete Adjuvant is employed in the immunization compositions of the disclosure. Additionally suitable adjuvants in accordance with the present invention are for example, Titermax Classical adjuvant (SIGMA-ALDRICH), ISCOMS, Quil A, ALUN, see U.S. Pat. Nos. 5,876,735 and 5,554,372, Lipid A derivatives, choleratoxin derivatives, HSP derivatives, LPS derivatives, synthetic peptide matrixes, GMDP, and other as well as combined with immunostimulants (U.S. Pat. No. 5,876,735). *B. pertussis* may of interest as an adjuvant in the context of the present invention due to its ability to modulate cell-mediated immunity through action on T-lymphocyte populations. Freund's Complete Adjuvant is the standard in most experimental studies. Mineral oil may be added to the vaccination composition in order to protect the antigen from rapid catabolism.

Many other types of materials can be used as adjuvants in immunogenic or immunization compositions according to the present disclosure. They include plant products such as saponin, animal products such as chitin and numerous synthetic chemicals.

Chickens immunized by the intramuscular route can produce high specific antibody levels in their eggs by day 28 after immunization and continue producing specific antibodies during more than 200 days making antibody preparations available in a short period of time, for example less than 4-5 weeks. Eggs contain IgY antibody concentrations of from up to about 50 to about 100 mg per egg. Over 100 mg of purified IgY can be obtained from a single egg. The percentage of antigen specific antibodies in one egg yolk can be up to about 2% to 10%. (daSilva et al., IgY: A promising antibody for use in immunodiagnostic and in immunotherapy. Veterinary Immunol. Immunopath., 135(2010):173-180). One chicken of a high egg-laying strain can produce around 20 eggs per month. Eggs weigh from about 33 to about 77 grams, with about 10.5% of the whole egg due to shell. The yolk is about 31% of the weight of the whole egg. Upon optional drying, about 1 kg of dried whole egg powder can be produced from 72 eggs. Therefore, in this calculation, one egg can return about 13.9 g dried whole egg. In another aspect, one egg can return from 10 g to about 15 g dried whole egg. In another aspect, the immune eggs of the disclosure are from 40 to 55 mL per egg with about 1-2 mg/mL total IgY per egg. In another aspect, immune eggs of the disclosure contain about 0.01 mg/mL to 0.05 mg/mL specific IgY per egg. Therefore, in one aspect after processing, one dried whole immune egg contains about 80 to 110 mg total IgY and about 6 to 10 mg of total mixed antigen-specific IgY, for example, from a chicken immunized with, for example a mixed antigen preparation.

It can be determined whether the vaccine has elicited an immune response in the egg-producing animal through a number of methods known to those having skill in the art of immunology. Examples of these include enzyme-linked immunosorbent assays (ELISA), tests for the presence of antibodies to the stimulating antigens, and tests designed to evaluate the ability of immune cells from the host to respond to the antigen. The minimum dosage of immunogen necessary to induce an immune response depends on the vaccination procedure used, including the type of adjuvants and formulation of immunogen(s) used as well as the type of egg-producing animal used as the host.

In one embodiment, hen chickens suitable for the commercial production of eggs are employed in the production of polyclonal antibodies. Any breed of chicken appropriate for egg production can be employed. For example, Rhode Island Reds, White Leghorns, Brown Leghorns, Lohmann Brown hens, sex-linked hybrid crosses, or other breeds suited to large egg size, high volume egg production and ease of handling can be selected. In one aspect, chickens are inoculated as chicks as for standard diseases (for example *Salmonella*, avian influenza, or Newcastle virus etc.). In one aspect, chickens of any age can be inoculated. Hens which are about to reach laying age, about 15-19 weeks for chickens, or any preselected time before or thereafter, are inoculated on a schedule predetermined by the amount and timing of final product to result in a steady continuous production stream. Typically, after a suitable period of isolation and acclimatization of about 2 to 4 weeks, each group will enter into an inoculation program using various antigens or immunization compositions comprising specific antigens to which an antibody is desired.

In one embodiment, the eggs are collected from inoculated chickens and processed as whole eggs. Eggs are stored under refrigeration conditions until enough are collected to prepare a batch. Batches of eggs from predetermined groups of chickens are cracked, the contents are separated from the shells and mixed and preferably pasteurized to eliminate potential contamination from pathogenic microorganisms from the chicken.

In one aspect, the immune egg products are pasteurized. Egg products are processed in sanitary facilities. Shell eggs are processed into immune egg product by automated equipment that removes the shell eggs from flats, washes and sanitizes the shells, breaks the eggs. Optionally, the whites are separated from the yolks. The liquid egg product is optionally filtered, optionally mixed with other ingredients, and is then chilled prior to additional processing. The resulting egg products liquid then receives a lethality treatment such as pasteurization or is heated in the dried form. In the U.S., the 1970 Egg Products Inspection Act (EPIA) requires that all egg products distributed for consumption be pasteurized.

Following pasteurization, the total egg content is optionally dried using standard commercial methods, such as spray drying using ambient or hot air, thermal drying, freeze drying, or lyophilization. In one aspect, an appropriate method of drying the pasteurized liquid egg minimizes damage to the antibodies and molecular components in the egg, resulting in a product that has a high nutrient value and is capable of conferring passive protection.

In one aspect, the dried egg is tested to determine overall titer or antibody level. Standard test procedures are used, such as ELISA, FIA (fluorescent immunoassay), RIA (radioimmunoassay), or the like. In another aspect, the batch is blended with batches from groups of chickens at other average production levels resulting in a lot containing a standardized amount of antibodies. The dried egg containing specific polyclonal antibodies may be stored in an airtight container at room temperature prior to formulation into the compositions of the disclosure. In embodiments, the dried egg material is used as a whole egg and is not separated out. In embodiments, the whole dried egg material contains at least 5 mg per egg of specific IgY.

In another embodiment, IgY is isolated from the eggs. IgY can be isolated by any technique known in the art. In some embodiments, the first step in the isolation of IgY is to separate the water-soluble proteins from lipoproteins. Water-soluble proteins constitute 42.4% of the total proteins in egg yolk (Osuga et al., "Egg Proteins: In Food Proteins, J. R. Whitaker and S. R. Tannenbaum eds., AVI Pub. Co., Westport, Conn. (1977)).

Many methods have been used for the isolation and purification of immunoglobulins from egg yolk (Martin et al., Can J. Biochem. Physiol. 35:241 (1957); Martin et al., Can. J. Biochem Physiol. 36:153 (1958); Jensenius et al., J. Immunol. Methods 46:63 (1981); Bade et al., J. Immunol. Methods 72:421 (1984); Polson et al., Immunol. Invest. 14:323 (1985); Hassl et al., J. Immunol. Methods 110:225 (1988)). Hatta et al. (Agric. Biol. Chem. 54:2531 (1990)) used food-grade natural gums (for example, carrageenan) to remove yolk lipoprotein as a precipitate and to recover IgY in the water-soluble fraction from egg yolk. Methods for recovering antibodies from chicken egg yolk are well known in the art. Several methods can be used for the extraction of IgY from egg yolk, and commercial extraction kits are available (van Regenmortel, M. H. V. (1993). Eggs as protein and antibody factories. In Proceedings of the European Symposium on the Quality of Poultry Meat, pp. 257-263. Tours, France: INRA). IgY can be isolated from egg yolk by polyethylene glycol (PEG)-PBS precipitation; first by 3.5% PEG; centrifugation; subjecting the supernatant to 12% PEG-PBS precipitation and subjecting the pellet containing IgY to dialysis by the technique of Pauly et al 2011, IgY Technology: Extraction of chicken antibodies from egg yolk by polyethylene glycol (PEG) precipitation. JOVE, May 2011, 51:1-6. http://www.jove.com/video/3084/.

Additional Antibodies

In some embodiments, the composition comprises colostrum, antibody product, an additional active agent, and further comprises additional antibodies collected from serum, plasma, colostrum, milk, or other suitable biologically derived fluid.

In some embodiments, the colostrum itself is utilized as an additional source of antibodies. Colostrum itself has a high content of immunoglobulins, particularly IgG. One study compared IgG and IgG1 activity toward 19 microbial pathogens in an early milk colostrum concentrate from non-immunized cows (IMMULAC 15) with a milk concentrate from immunized cows using ELISA. Both products contained IgG and IgG1 which bound to all of the pathogens tested. The early milk colostrum concentrate (IMMULAC 15) demonstrated much higher titers of immunoglobulin (9.57% IgG), compared to immune milk (0.15%). McConnell et al, 2001, Food Res. Int. 34:255-261.

In some embodiments, the additional antibodies used in this invention may be collected from serum of an inoculated animal. Total immunoglobulins in plasma are about 15.7% on a protein basis. In some embodiments, immunoglobulin is isolated from serum or plasma by the method of Lee et al., US 20040182785, incorporated herein by reference. For example, normal liquid animal plasma, which is treated with anticoagulant(s) and separated from animal red blood cells, is mixed with sodium hexametaphosphate, at a level of less than 1% solids against normal liquid plasma or serum weight. Sodium hexametaphosphate is a food-grade, feed-grade or technical-grade chemical, which can be liquid or solid form. Liquid form is easily mixed with the plasma within a few minutes. The pH is adjusted to a range from 3.5 to 4.9. The preferred range is 4.1 to 4.5. The color is changed from plasma red to creamy. Then a settling process is used to let the mixture in a tank set without disruption for a period of time such as overnight or a centrifuge process is used to separate the precipitate and liquid into two products of immunoglobulin rich fraction and albumin rich fraction. The immunoglobulin rich fraction is the liquid phase. The clear solution of immunoglobulin rich fraction can be further concentrated to a higher solids level such as 20-30% by ultrafiltration, nanofiltration or evaporation after the pH is adjusted to above 4.5, which reduces the drying cost. The Ig fraction can then be optionally subjected to spray drying or freeze drying.

For the purposes of this disclosure, additional antibodies are polyclonal antibodies derived from an animal origin, and may be of any isotype: for example, IgA, $IgG_1$, $IgG_2$ and IgM, or any fragments derived therefrom that retain the ability to bind to the pathogenic component.

Antibodies from Hyperimmune Colostrum

In some embodiments, the composition may include hyperimmune colostrum. Hyperimmune colostrum represents an attempt to boost the effectiveness of natural colostrum by immunizing pregnant animals with a specific pathogen. This approach is promising as antibodies are produced to the specific pathogens or antigens used in the original challenge. However, varying response to antigens, biological variability, and low production yield have limited its clinical and commercial utility. Methods of preparing hyperimmune bovine colostrum are described in, for example, WO 2004/078209 and US 20110200610, each of which is incorporated herein by reference. For example, pregnant cows can be inoculated about 10 weeks before parturition (WBP) with, for example, an intramuscular injection with the immunogen, or antigenic preparation, preferably adjuvanted, for example, with Freund's complete adjuvant. Booster innoculations can be administered to the cows, for example at 8, 6 and 4 weeks WBP as, for example, intramammary infusions with the immunogen or antigenic preparation with, for example, Freund's incomplete adjuvant. Colostrum containing antibodies specific for the immunogen or antigen is collected from, e.g., standard colostrum, or the first milking and frozen at −20° C. for later processing. See, for example, Fayer et al., 1990, Infection and Immunity, 58 (9): 2962-2965. Immunotherapeutic efficacy of bovine colostral immunoglobulins from a hyperimmunized cow against Cryptosporidiosis in neonatal mice. However, it is preferred that the booster administrations do not lead to immune tolerance.

The hyperimmune colostrum containing specific antibodies can be optionally processed to concentrate the antibodies, and dried by any known technique that preserves antibody activity, for example by spray drying or lyophilization. Antibodies from Serum In embodiments, immunoglobulins may be isolated from serum by the methods of Stec et al., 2004 Isolation and purification of poluclonal IgG antibodies from bovine serum by high performance liquid chromatography, Bull Vet Inst Pulawy 48, 321-327, incorporated herein by reference. Animals can be bled by venipuncture and serum clarified by centrifugation and diluted with phosphate buffer at pH7.2. Antibodies can be isolated by several techniques including ammonium sulfate precipitation, optionally followed by affinity, ion exchange or gel filtration chromatography. Samples can be optionally desalted by buffer exchange.

The antibodies used in this invention may be treated, concentrated, separated, or purified in various ways depending upon their final intended use.

Many antibody agents are known to be immunogenic when administered systemically, and much of the development work in the field of therapeutic antibodies has been directed toward the development of non- or low-immunogenic versions or analogues of these molecules and factors. It has also been demonstrated that antibodies, immunoglobulins, and other biological immune factors, including those derived from non-human sources, are largely non-immunogenic when ingested by humans and other animals, presumably due to the protective nature of the gastrointestinal system.

In some embodiments, the antibody product comprises specific antibodies that are harvested from the plasma, serum, blood, milk, colostrum, eggs or other component of an inoculated animal, then optionally purified or treated to obtain an antibody product. The antibodies used in this invention may be treated in any suitable manner to prepare for formulation and use, including but not limited to separations, plasmapheresis, drying processes, lyophilization, pasteurization, and preservation methods. The processed antibodies are mixed appropriately and added to a bovine colostrum, which is used as a delivery medium for oral administration of the antibody formulation This approach may provide an effective way of reliably scaling antibody production for formulation in this manner, so as to control titer, consistency, and continuous availability, for commercial use. The antibody product comprises at least one specific avian antibody, immunoglobulin, or active binding fragment, obtained from a bovine animal and that specifically binds to an antigenic region of a diarrhea-causing pathogenic organism, toxin, or adhesion.

In some embodiments, the harvested antibodies can be utilized in crude form, such as spray dried biological material to provide the antibody product, or isolated, or purified by any technique known in the art, to provide the antibody product. The antibody product is combined with the colostrum and additional active agent. In some embodiments, it is preferred that the antibody product is only minimally processed as required by any applicable food standards for use in the compositions.

By altering the mix of antibodies in the antibody product to those appropriate to various embodiments, the disclosure provides compositions and methods appropriate for treating or preventing other gastrointestinal infections such as cholera, C. difficile, dysentery, Salmonella typhi (e.g., typhoid fever), and H. pylori (e.g., peptic ulcers).

In embodiments, antibodies are harvested from an inoculated animal, and may be purified or treated or retained in the native form. In embodiments, the crude antibody source such as colostrum or milk can be processed to isolate the majority of immunoglobulin, for example, by absorbing the antibodies onto an affinity resin (for example Protein G or Protein A Sepharose; or Protein A or Protein G Agarose) in a batch or column format and retaining the eluate for further processing. Immunoglobulin can also be removed by gel filtration chromatography on Sephadex G-200 or DEAE Sephadex A-25 ion exchange chromatography. (Lloyd and Soulsby, Immunology, The role of IgA immunoglobulin in the passive transfer of protection to *Taenia taeniaeformis* in the mouse. 34, 939-945) These processes can be run on a column or a batch format by various methods and techniques known in the art. Optionally purified antibodies can be isolated or combined to obtain the antibody product.

In some embodiments, the specific antibodies are processed to increase content of specific or total immunoglobulins. The antibodies can optionally be suitably separated from the biological fluid, or serum by conventional antibody purification procedures such as, for example, affinity chromatography (for example, using protein A or protein G-Sepharose) or ion-exchange chromatography, hydroxylapatite chromatography, gel electrophoresis, precipitation, dialysis, etc. For example, ammonium sulfate precipitation, gel filtration or size-exclusion chromatography techniques can be employed to isolate the antibodies. Other techniques familiar to the skilled artisan can be alternatively employed to increase the immunoglobulin content of a preparation. For example, ion exchange, hydrophobic interaction, Protein A or Protein G sepharose resins can be employed to isolate total IgGs. Alternatively, various other affinity resins based upon immunogens or antigens can be employed in column or batch format in order to isolate specific immunoglobulins.

The binding specificity of antibodies can be determined by any known method, for example, by immunoprecipitation or by an in vitro binding assay, such as radioimmunoassay (RIA) or enzyme-linked immunosorbent assay (ELISA). The binding affinity of the antibody can, for example, be determined by the Scatchard analysis described in Munson et al., Anal. Biochem. 107:220 (1980), which is incorporated herein by reference.

The optionally processed antibody product is optionally filtered, optionally mixed with other ingredients, and is then preferably chilled prior to additional processing. The resulting antibody product liquid then receives a lethality treatment such as pasteurization or is heated in the dried form. In some embodiments, the antibody products are pasteurized.

Following pasteurization, the antibody product is optionally dried using standard commercial methods, such as spray drying using ambient or hot air, thermal drying, freeze drying, or lyophilization. In one aspect, an appropriate method of drying the pasteurized antibody product minimizes damage to the antibodies and other molecular components, resulting in a product that has a high nutrient value and is capable of conferring passive protection.

In one aspect, the dried antibody product is tested to determine overall titer or antibody level. Standard test procedures are used, such as ELISA, FIA (fluorescent immunoassay), RIA (radioimmunoassay), or the like. In another aspect, the batch is blended with batches from groups of chickens at other average production levels resulting in a lot containing a standardized amount of antibodies. The antibody product containing specific polyclonal antibodies may be stored in an airtight container at room temperature, or at reduced temperature, prior to formulation into the compositions of the disclosure.

Immunogens and Antigens Including Pathogens and Toxins for Production of Antibodies The antigens selected for immunization of various animal species for production of specific immunoglobulins, antibodies or active binding fragments can be bacterial, viral, protozoal, fungal, parasitic, cellular, or any other substances to which the immune system of an animal will respond. In one aspect, the immunogenicity of the antigens is enhanced by use of an adjuvant as described herein.

In various embodiments, the composition comprises colostrum, an additional active agent, and an antibody product comprising at least one specific avian antibody, immunoglobulin, or an active binding fragment thereof, that is specific for binding to an antigenic region of a diarrhea-causing pathogenic organism, or a toxin, or adhesin originating therefrom. In some embodiments, the pathogenic organism is selected from one or a combination of human or veterinary, enteric or gastrointestinal, pathogens causing gastroenteritis. In some embodiments, the pathogenic organism is selected from the group consisting of: *Campylobacter jejuni, Salmonella, Salmonella typhimurium, Salmonella enterica* serovar *Typhi, Shigella dystenteriae, Plesiomonas shigelloides, Escherichia coli* [including (EPEC) enteropathogenic *E. coli*, (ETEC) enterotoxigenic *E. coli*, (EaggEC) enteroaggregative *E. coli*, (EIEC) enteroinvasive *E. coli*, and (EHEC) haemorrhagic *E. coli*], *Yersinia enterocolitica, Vibrio cholerae* 01, *Vibrio* 0139, Non-01 Vibrios, *Vibrio parahaemolyticus, Aeromonas hydrophila, Clostridium perfiingens, Clostridium difficile, Candida* spp., enterohepatic *Helicobacter* (including *Helicobacter pylori*), *Staphylococcus aureus, Klebsiella*, rotavirus, coronavirus, norovirus, calicivirus, enteric adenovirus, cytomegalovirus, and astrovirus. In another aspect, the pathogen related toxin includes an endotoxin or exotoxin. In another aspect, the pathogen related adhesin element includes adhesins, cadherins, cilia, fimbrillae, a viral adhesin structure, or a combination thereof.

In some embodiments, the methods and compositions of the invention are used for a variety of pathogens or agents including, without limitation, cholera toxin (*Vibrio cholera*), *E. coli* (including enterotoxigenic (ETEC)), *Shigella, Salmonella, Campylobacter, Clostridium difficile*, parasites (for example, *Giardia, Entamoeba histolytica*, Cryptosporidiosis, *Cyclospora*), and diarrheal viruses (for example, rotavirus, norovirus).

In various specific aspects the pathogenic components, immunogens or antigens can be derived from, for example, rotavirus, corona virus; *Clostridium Perfringens* Type C; *Escherichia coli* (cellular); Enterotoxigenic strains of, and Enterotoxins from, *E. coli*; any bacteria having K99, K88, 987P, or F41 pili adherence factor antigen; endotoxin (or LPS) caused by *E. coli* and *Salmonella typhimurium* (gram negative bacteria, generally). In a particular aspect, animals are inoculated with antigens or toxins derived from one, two, three, four, five, six, seven, or eight, or a number of pathogenic microorganisms.

In some embodiments, the animal is inoculated with the pathogenic components, antigens, or immunogens in a vaccination composition, inoculant or vaccine. In one aspect, the pathogenic components or specific antigens can be obtained or derived from commercial sources such as the American Type Culture Collection (ATCC). In another aspect, the pathogenic components can be isolated from a wild type strain. In another aspect, the pathogenic components or undesirable strains are present in a mixed antigen preparation. In another aspect, the vaccine can be a commercial vaccine. Any antigens or combination of antigens derived from various undesirable strains or pathogenic components can be employed in the immunization composition.

In one aspect, the immune response is more potent when the distance between the antigen source and the immune system of the vaccinated animal increases.

Antigen Clusters for Production of Cross-Reactive Antibodies

In some embodiments, the specific antibodies are produced by inoculating an animal with an inoculant, antigen or immunogen that is selected from a common or preserved component or region of the targeted antigen cluster, while ignoring the variable or distinguishing components or regions of the individual members of the cluster of related antigens. The method involves the preparation of an appropriate immunogen with characteristics that elicit the production of antibodies that are cross-reactive to desired instances of that epitope, but which are not reactive to other epitopes, and the inoculation or exposure of the producing cells or organism to that immunogen so as to cause the production of antibodies, with the resultant antibodies being embedded within the suitable carrier matrix for administration. Formulations of this type may be developed that use admixtures of antibodies produced according to this method to provide broad coverage of more than one cluster of target antigens. For example, in the case where two clusters of unrelated antigens are associated with a disease or condition, and it is desirable to create a single formulation to address this disease or condition, an admixture of two antibodies, immunoglobulins, or biological immune factors may be prepared using this method that simultaneously provides two broad domains of reactivity. One example of this embodiment is for the production of antitoxin antibodies that are specifically reactive to clusters of structurally related toxins.

After entering the gastrointestinal tract many pathogens, including but not limited to bacteria such as *E. coli*, bind to epithelial, mucosal, or other tissue and become embedded in gastrointestinal tract tissue, such as the wall of the intestine. After binding to tissue in the gastrointestinal tract the pathogens replicate, causing an increase in toxin concentrations, either directly from production or indirectly from increased lysing of pathogen cells by immune system action. Inhibiting the ability of pathogens to bind to the gastrointestinal tract tissue promotes a more effective mobilization of the pathogens, digestion and excretion before colonies of sufficient size to cause lesions and other symptoms are formed. By blocking the class of receptors and ligands on the pathogen that would be used to adhere to the gastrointestinal tract, including but not limited to Adhesins, Cadherins, Cilia, Fimbrillae, and/or viral adhesin structures, adhesion to gastrointestinal tract tissue can be prevented or minimized, ultimately resulting in substantially decreased pathology from pathogens that utilize this mode of action.

In some embodiments, this approach is used to make a broadly reactive antibody to lipopolysaccharide (LPS) (endotoxin) from any Gram-negative bacteria (*Escherichia coli, Salmonella, Shigella*, and other Enterobacteriaceae, *Pseudomonas, Moraxella, Helicobacter, Stenotrophomonas*, and others), or for example a broadly reactive antibody to AB5 toxins (including *Campylobacter* enterotoxin, cholera toxin, heat-labile enterotoxins (LT and LT-II) (*E. coli*), pertussis toxin, shiga toxin (*Shigella*), shiga-like toxin (or verotoxin)).

In some preferred embodiments, the specific avian antibodies are anti-toxin antibodies have effect without regard to the species originating the toxin. In another aspect, the antibodies produced are neutralizing antibodies, capable of neutralizing or inactivating the biological activity of the target toxins. Such a broad-spectrum neutralizing antibody could be used to intervene in pathology cases (for example certain types of diarrhea) where the toxin mediating the symptoms was one of the cluster targeted (in these examples, AB5 or LPS), without requiring knowledge of which organism was causative. Further, if an admixture was prepared containing both the anti AB5 antibody and the anti LPS antibody in clinically effective amounts, the formulation could be used to intervene in case where the active toxin was either AB5 or LPS or both.

This method can be extended to include any number of (in this example) toxin clusters, and to include broad-spectrum neutralizing antibodies to mediators of other toxin-like reactions (for example viral toxin-like phenomena), to create a broadly applicable intervention (in this example to) diarrhea where symptoms and pathology can be managed without knowledge of the infectious causes, or where there are multiple infectious causes. In one aspect, the disclosure provides a composition comprising a synergistic combination of anti-toxin antibodies in a colostrum matrix.

In embodiments, various preparations of specific antigens can also be employed for inoculation. In embodiments, the inoculant or immunogen is selected to a common or preserved component or region of the targeted antigen cluster, while ignoring the variable or distinguishing components or regions of the individual members of the cluster of related antigens. The method involves the preparation of an appropriate immunogen with characteristics that elicit the production of antibodies that are cross-reactive to desired instances of that epitope, but which are not reactive to other epitopes, and the inoculation or exposure of the producing cells or organism to that immunogen so as to cause the production of antibodies, with the resultant antibodies being embedded within a suitable colostrum for administration.

Certain embodiments provide formulations of this type comprising admixtures of antibodies produced to provide broad coverage of more than one cluster of target antigens. For example, in the case where two clusters of unrelated antigens are associated with a disease or condition, and it is desirable to create a single formulation to address this disease or condition, an admixture of two antibodies, immunoglobulins, or biological immune factors may be prepared using this method that simultaneously provides two broad domains of reactivity.

One example of this embodiment is for the production of antitoxin antibodies that are specifically reactive to clusters of structurally related toxins.

In embodiments, antibodies would have effect without regard to the species originating the toxin.

In other embodiments, the antibodies produced are neutralizing antibodies, capable of neutralizing or inactivating the biological activity of the target toxins.

In some embodiments, broad-spectrum neutralizing antibodies can be used to intervene in pathology cases (for example certain types of diarrhea) where the toxin mediating the symptoms was one of the cluster targeted (in these examples, AB5 or LPS), without requiring knowledge of which organism was causative. Further, if an admixture was prepared containing both the anti AB5 antibody and the anti LPS antibody in clinically effective amounts, the formulation could be used to intervene in case where the active toxin was either AB5 or LPS or both.

In other embodiments, the method can be extended to include any number of (in this example) toxin clusters, and to include broad-spectrum neutralizing antibodies to mediators of other toxin-like reactions (for example viral toxin-like phenomena), to create a broadly applicable intervention (in this example to) diarrhea where symptoms and pathology can be managed without knowledge of the infectious causes, or where there are multiple infectious causes.

Immunization

In one embodiment, antibodies are preferably raised in animals by, for example, multiple intramuscular (im), subcutaneous (sc), intramammary infusion, or intraperitoneal (ip) injections of the relevant antigen and optionally an adjuvant. In one aspect, it may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or R N=C=NR, where R and R are different alkyl groups. Animals are immunized against the antigen, immunogenic conjugates, or derivatives as described herein. In other embodiments, the antibodies may be synthetic or semisynthetic, for example, as are obtained in a phage display library, or prepared as humanized or chimeric antibodies.

The specific immune state is preferably induced and maintained in the target animal by immunization and repeated booster administrations of an appropriate dosage at fixed time intervals. However, it is important that the booster administrations do not lead to immune tolerance. The time intervals are preferably 1-8 week intervals over a period of 1-18 months. Dosage is selected between about 10-5000 micrograms, 3-3000 micrograms, or 50-2000 micrograms of the antigen. In one aspect, the dosage is 0.01 mg to 1.0 mg of antigen per inoculation, preferably 100 ug, 200 ug, 250 ug, 300 ug, 400 ug, 500 ug, 750 ug, 1000 ug, 1500 µg or 2000 ug antigen per inoculation. The total number of vaccinations can be selected from 1, 2, 3, 4, 5, or 6 in a 12 month period. Typically, a first inoculation is performed on day 1, with booster vaccinations, for example, on day 10, and day 20. In the case of milk, serum, or blood, the cow can be re-vaccinated as needed by monitoring the specific antibody concentration, or titer, in the milk or blood by, for example, ELISA. Such processes are well known in the art.

In a specific embodiment, a first herd of cattle, for example, pregnant cows, is inoculated with a first one mixed antigenic preparation. In one aspect, a second herd is inoculated with a second mixed antigenic preparation containing a different set of antigens than the first. In another aspect, a third herd is inoculated with a third mixed antigenic preparation. In a further aspect, a fourth herd is inoculated with a fourth mixed antigenic preparation. While not meant to limit the scope of the invention, it is believed to be advantageous to immunize different herds with different antigens, or a small number of different antigens, in order to avoid antigen overload.

It is possible to use other inoculation maintenance procedures or combination of procedures, such as, for example, intramuscular injection for primary immunization and intravenous injection for booster injections. Further procedures include simultaneously administering microencapsulated and liquid immunogen, or intramuscular injection for primary immunization, and booster dosages by oral administration or parenteral administration by microencapsulation means. Several combinations of primary and booster immunization are known to those skilled in the art.

In embodiments, the immunogen or antigen is utilized with an adjuvant for inoculation of the animal for production of the specific antibodies.

Adjuvants, or functional equivalents thereof, may be included in the immunization solution/vaccine composition to enhance the specific immune response of the animal. Adjuvants pertaining to the present disclosure may be grouped according to their origin, be it mineral, bacterial, plant, synthetic, or host product. The first group under this classification is the mineral adjuvants, such as aluminum compounds. Antigens precipitated with aluminum salts, such as aluminum phosphate, aluminum hydroxide or antigens mixed with or adsorbed to performed aluminum compounds have been used extensively to augment immune responses in animals and humans. In one embodiment, the adjuvant in the immunization composition is from a bacterial origin. Adjuvants with bacterial origins can be purified and synthesized (for example muramyl dipeptides, lipid A) and host mediators have been cloned (Interleukin 1 and 2). Known chemical purification of several adjuvants of active components of bacterial origin includes: *Bordetella pertussis, Mycobacterium tuberculosis*, lipopoly-saccharide, Freund's Complete Adjuvant (FCA) and Freund's Incomplete Adjuvant (Difco Laboratories, Detroit, Mich.) and Merck Adjuvant 65 (Merck and Company, Inc., Rahway, N.J.). In a specific aspect, Freund's Complete Adjuvant or Freund's Incomplete Adjuvant is employed in the immunization compositions of the disclosure. Additionally suitable adjuvants in accordance with the present invention are for example, Titermax Classical adjuvant (SIGMA-ALDRICH), ISCOMS, QS21, Quil A, ALUN, see U.S. Pat. Nos. 5,876, 735 and 5,554,372, Lipid A derivatives, choleratoxin derivatives, HSP derivatives, LPS derivatives, synthetic peptide matrixes, GMDP, and other as well as combined with immunostimulants (U.S. Pat. No. 5,876,735), ISCOM matrix, calcium phosphate, calcium hydroxide, zinc hydroxide, a glycolipid analog, an octadecyl ester of an amino acid, a muramyl dipeptide, polyphosphazene, ISCOPREP, DC-chol, DDBA, CpG oligonucleotides, a lipoprotein and other adjuvants. Freund's Complete Adjuvant is the standard in most experimental studies. Mineral oil may be added to the vaccination composition in order to protect the antigen from rapid catabolism.

Colostrum, milk, serum, eggs or blood is/are collected, optionally titered as to specific and/or total immunoglobulin, optionally isolated and/or purified, and processed separately to optionally prepare a dry powder. In another aspect, antibody preparations from multiple flocks, for example, a first and second; first, second and third; or first, second, third and fourth flocks are blended, or packaged, with a carrier matrix to prepare a composition of the disclosure.

In some embodiments, the antigenic preparation used for immunization is a mixed antigenic preparation comprising two or more pathogenic organisms, pathogen related toxins, and/or pathogen related adherence factors. In some embodiments, the mixed antigenic preparation comprises a rotavirus preparation. In some embodiments, the mixed antigenic preparation comprises a coronavirus preparation. In some embodiments, the mixed antigenic preparation comprises an enterotoxigenic *E. coli* strain. In some embodiments, the mixed antigenic preparation comprises an enteropathogenic *E. coli* strain. In some embodiments, the mixed antigenic preparation comprises an atypical enteropathogenic *E. coli* strain. In some embodiments, the mixed antigenic preparation comprises a *Camphylobacter jejuni* preparation. In some embodiments, the mixed antigenic preparation comprises a *Shigella dysenteriae* preparation. In some embodiments, the mixed antigenic preparation comprises an *E. coli* strain with K99 pili adherence factors. In some embodiments, the mixed antigenic preparation comprises an atypical enteropathogenic *E. coli* strain *Clostridium perfringens* type C toxoid. In some embodiments, the mixed antigenic preparation comprises a *Clostridium difficile* preparation. In some embodiments, the mixed antigenic preparation comprises a *Vibrio cholera* O1 preparation. In some embodiments, the mixed antigenic preparation comprises an enterotoxigenic strain of *E. coli* having K88 adherence factors. In some embodiments, the mixed antigenic preparation comprises a *Clostridium perfringens* preparation. In some embodiments, the mixed antigenic preparation comprises a *Yersinia enterocolitica* preparation. In some embodiments, the mixed antigenic preparation comprises a strain of *E. coli* having F19 pili adherence factors. n some embodiments, the mixed antigenic preparation comprises an *E. coli* endotoxin preparation. In some embodiments, the mixed antigenic preparation comprises an enterotoxigenic strain of *E. coli* having 987P pili adherence factors. In some embodiments, the mixed antigenic preparation comprises a Norovirus preparation. In some embodiments, the mixed antigenic preparation comprises an enterotoxigenic strain of *E. coli* having F41 pili adherence factors. In some embodiments, the mixed antigenic preparation comprises a wild-type isolated strain of *E. coli*.

In some embodiments, the strains are selected from two or more of rotavirus, norovirus, coronavirus, *Camphylobacter jejuni* strains, enterotoxigenic strains of *Escherichia coli*, *Yersinia enterocolitica* strains, *Clostridium perfringens* strains, enterotoxigenic strains of *Escherichia coli* producing heat-labile toxin, *E. coli* strains having F41 adherence factors, *Shigella dysenteriae* strains, killed *E. coli*, or *Salmonella typhimurium* endotoxins.

In some embodiments, the antigens are prepared by any means known in the art. For example, cells from a wild type source, such as an animal suffering from, for example, *E. coli* diarrhea. The isolate cells can be cultured in, for example, Trypticase Soy Broth (TSB) at 37° C. overnight and concentrated by centrifugation. The resulting pellet can be re-suspended with 0.4% formaldehyde in PBS buffer and incubated at 37° C. for inactivation. Formaldehyde can be removed by centrifugation. The pellet can be resuspended in PBS and used as antigen. In one aspect, the antigens are emulsified with an equal volume of adjuvant prior to inoculation.

It can be determined whether the vaccine has elicited an immune response in the animal through a number of methods known to those having skill in the art of immunology. Examples of these include enzyme-linked immunosorbent assays (ELISA), tests for the presence of antibodies to the stimulating antigens, and tests designed to evaluate the ability of immune cells from the host to respond to the antigen. The minimum dosage of immunogen necessary to induce an immune response depends on the vaccination procedure used, including the type of adjuvants and formulation of immunogen(s) used as well as the bovine breed of cattle used as the host. Any appropriate biological fluid can be tested for antibody titer to help guide the vaccination schedule. If the intended antibody-containing biological fluid is colostrum, for example, serum can be tested by any known method as an indication of immune response.

Thermal Stability of Antibodies

In certain embodiments, the antibody product comprises specific antibodies that are secretory IgA antibodies, encapsulated antibodies, or comprise added sugars or glycerol, in order to enhance the thermal stability of the specific antibodies in the composition, compared to colostrum alone.

Immunoglobulins are thermolabile.

In the compositions of the disclosure, colostrum, egg product, specific antibodies, and/or antibody product comprising specific antibodies derived from eggs, blood, plasma and/or serum are subjected to pasteurization, or exposure to elevated temperatures for a period of time so as to reduce bacterial contamination of the product. In some embodiments, the additional active agent is added to the composition after pasteurization of one or more of the colostrum, antibody product or specific antibodies. In some embodiments, the additional active agent is added to the composition before pasteurization of one or more of the colostrum, antibody product or specific antibodies. For example, batch pasteurization can be employed, where a tank or vat of the biological material is heated to 63° C. for about 30 minutes. Batch pasteurization has been noted to reduce IgG concentration in colostrum samples by an average of 26%. Exposure to temperatures of 75° C. for 5 min can reduce detectable isolated bovine IgG by 40%. Hurley et al., 2011, Perspectives on Immunoglobulins in Colostrum and Milk, Nutrients, 2011, 3, 442-474, incorporated herein by reference. Heat treatment of bovine colostrum at 60° C. for 1-2 hours does not alter measurable IgG concentrations. p. 457-459. The colostrum or immune egg product may be pasteurized. Pasteirization may be a temperature of 60° C. for 3 to 4 minutes. The colostrum or immune egg product may be subjected to flash pasteurization, also known as high temperature, short time (HTST) pasteurization. High temperature short term pasteurization may involve heating, e.g., to about 72° C. for 15 seconds to 2 minutes, usually by circulation in heated tubes or coils. For example, the liquid colostrum or egg product may be flash pasteurized by subjecting to 71.5° C. to 74° C., for about 15 to 30 seconds, followed by rapid cooling from about 4° C. to 5.5° C. Flash heat treatment of human breast milk of a maximum temperature of 72-73° C., with a temperature above 56° C. for 6 min has minimal effects on IgA in human breast milk. Thermal protectants such as sugars or glycerol can also increase the stability of IgG to heat treatment.

Proteolytic Enzymes

In some embodiments, the specific antibodies are protected from rapid enzymatic degradation by embedding in an effective amount of colostrum, preferably whole colostrum. Immunoglobulins are more resistant to intestinal digestion than other milk or colostral proteins, but are still subject to degradation by various proteolytic enzymes in the digestive tract, such as pepsin and trypsin. IgA is more resistant towards digestion than IgG. Secretory IgA is somewhat protected from proteolytic enzymes by the secretory component. Bovine $IgG_1$ is said to be more susceptible to hydrolysis by pepsin than $IgG_2$, but $IgG_2$ is more susceptible to trypsin degradation. See Hurley et al., 2011, Perspectives on Immunoglobulins in Colostrum and Milk, Nutrients, 2011, 3, 442-474; see P.453-455. p. 456. In other embodiments, the antibodies may be protected from rapid enzymatic degradation by encapsulation.

Antibody Encapsulation

In some embodiments, the antibody product comprises specific antibodies protected by encapsulation. Lipid or polysaccharide encapsulation can be employed to enhance antibody stability and/or absorption. It is contemplated that encapsulated avian specific antibodies are more resistant to degradation caused by thermal, acidic and enzymatic conditions within the gastrointestinal environment upon ingestion.

In some embodiments, the antibody product comprises antibodies that are encapsulated by liposomes. Bangham et al. found that when phospholipids, which are surfactants derived from biomembranes, were suspended in water, closed vesicles composed of lipid bilayers were formed (J. Mol. Biol. 13, 238 (1965)). Any known method for producing liposomes can be employed, for example, liposomes can be formed by phospholipids such as natural lecithins (for example, egg yolk lecithin, soybean lecithin, etc.), dipalmitoyl phosphatidyl choline (DPPC), dimyristoyl phosphatidyl choline (DMPC), distearoyl phosphatidyl choline (DSPC), dioleoyl phosphatidyl choline (DOPC), dimyristoyl phosphatidyl ethanolamine (DMPE), dipalmitoyl phosphatidyl glycerol (DPPG), dimyristoyl phosphatidic acid (DMPA), and the like alone or in combination of two or more thereof, and mixtures thereof with cholesterols, etc. Kida et al., U.S. Pat. No. 4,861,597, which is incorporated herein by reference, discloses liposomes having a very high encapsulation efficiency can be obtained when LPS or a LPS-like compound is used as a amphiphilic compound to generate the liposomes. Many conventional methods for preparing encapsulating liposomes have been reported, for example, formation of a lipid thin film, followed by treatment by vortexing (A. D. Bangham et al, J. Mol. Biol., 13, 238 (1965)), sonication or the like (C. Hudng et al, Biochemistry, 8, 344 (1969)), the reverse-phase evaporation method (REV method) using organic solvents (F. Szoka et al, Proc. Natl. Acad. Sci., U.S.A., 75, 4194 (1978)), the ethanol infusion method (S. Batzri et al, Biochem. Biophs. Acta., 298, 1015 (1973)), the ether infusion method (D. Deamer et al, Biochim. Biophys. Acta., 443, 629 (1976)), and methods using surfactants (J. R. Slack et al, Biochim. Biophys. Acta., 323, 547 (1973)). Any appropriate known method can be employed for liposomal encapsulation of the avian antibodies. As a method for producing the liposomes of this invention, there may be exemplified all the per se well-known methods for producing liposomes, for example, heretofore well known methods such as the vortexing method, sonication method, surfactant method, reverse-phase evaporation method (REV method), ethanol infusion method, ether infusion method, pre-vesical method, French press extrusion method, $Ca^{2+}$ fusion method, annealing method, and the freeze-thaw-fusion method.

In some embodiments, the antibody product comprises antibodies that are encapsulated in chitosan-polyglutamic acid nanoparticles, for example, by the method of Sung et al., U.S. Pat. No. 7,541,028, which is incorporated herein by reference. Chitosan is a cationic polysaccharide. Sung et al. encapsulates monoclonal antibodies in nanoparticles for oral administration using a shell portion of biodegradable chitosan that is positively charged, and a core portion of negatively charged substrate of polyglutamic acid (PGA) that is neutralized with a portion of positively charged chitosan.

In some embodiments, the antibody product comprises antibodies that are encapsulated by chitosan-alginate microcapsules by the method of Li et al., 2007, Chitosan-alginate microcapsules for oral delivery of egg yolk immunoglobulin (IgY). J Agric Food Chem 2007 55(8):2911-7, which is incorporated herein by reference. Li reported that the stability of IgY in simulated gastric fluid at low pH was greatly improved by microencapsulation in chitosan-alginate microcapsules. The microencapsulated IgY exhibited increased resistance to pepsin hydrolysis and IgY was released from microcapsules upon exposure to simulated gastric fluid at pH 6.8.

In some embodiments, the antibodies are encapsulated by the method of Lin, U.S. Pat. No. 7,935,334, which is incorporated herein by reference. Encapsulation in a mixture of xanthan gum and chitosan, or in gelatin, can be employed.

Colostrum

Colostrum, or "first milk" is produced by mammals immediately postpartum and delivers it nutrients to the neonate in a very concentrated low-volume form. Colostrum contains a host of immuno-complimentary factors and growth factors. For example, colostrum includes interferons, immunglobulins (including $IgG_1$, $IgG_2$, IgM and secretory IgA), polyrnorphonuclear leukocytes, macrophages, and lymphocytes. Colostrum also contains proline-rich polypeptide, or PRP, a T-cell activator.

Colostrum alone can deliver passive immunity to the neonate, but less so to the non-neonate. At birth, neonate gastric pH ranges are relatively neutral and vary from pH 6-8 due to residual amniotic fluid in the stomach. Gastric pH then falls to a pH of 1.5 to 3 in 24 to 48 hours. Therefore, The GI conditions of the newborn are conducive to passive immunization. In addition, gastric emptying time in neonates and premature infants is prolonged, allowing for greater contact time, with adult values being reached at 6-8 months of age.

The gastrointestinal tract of non-neonatal babies, children, adolescents and healthy adults is a more hostile environment than that of a neonate, with respect to oral administration of immunoglobulins. Immunoglobulins are less stable under the acidic gastrointestinal conditions of the non-neonate compared to that of the neonate. Therefore, an increased amount of antibodies relative to that provided in colostrum alone, is desired for consistent efficacy. However, mere concentration of antibodies can result in removal of protective components found in minimally processed, full fat colostrum.

In some embodiments, the disclosure provides a composition comprising an effective amount of colostrum and specific antibodies derived from a different species than the colostrum, and an additional active agent, wherein the composition is useful for the treatment and prevention of diarrhea and management of gastrointestinal conditions.

In some embodiments, the colostrum may be derived from any appropriate mammalian source. For example, the colostrum may be derived from Alpaca, Banteng, Bison, Camel, Cat, Cow, Deer, Dog, Donkey, Gayal, Goat, Sheep, Guinea pig, Horse, Human, Llama, Mule, Pig, Rabbit, Reindeer, Sheep, Water buffalo, or Yak. In a specific embodiment, the colostrum is a bovine colostrum.

In some embodiments, the colostrum is selected from non-hyperimmune colostrum; hyperimmune colostrum; whole, non-defatted colostrum; defatted colostrum; fractionated colostrum; immune milk; whole milk; fractionated milk; milk; whole hyperimmune colostrum, whole non-hyperimmune colostrum; non-defatted hyperimmune colostrum; or non-defatted non-hyperimmune colostrum. In some embodiments, the fractionated colostrum is defined as two or more, three or more, four or more, five or more or six or more components of colostrum. In specific embodiments, the colostrum is selected from non-hyperimmune colostrum; whole non-hyperimmune colostrum; or non-defatted non-hyperimmune colostrum. In a specific embodiment, the colostrum is whole non-hyperimmune bovine colostrum.

In contrast to known colostrum derived products such as TRAVELAN™, it is disclosed herein that at least a minimum effective amount of colostrum needs to be present in an oral antibody formulation to effectively protect and improve the stability of the specific antibodies in the gastrointestinal tract, as well as to enhance the immune response of the subject. In some embodiments, the colostrum in the composition is whole colostrum. In some embodiments, the colostrum in the composition is full fat colostrum. In some embodiments, the colostrum is minimally processed colostrum. In some embodiments, the colostrum is present in the composition in an amount sufficient to adequately protect the immune egg antibodies from thermal, pH and enzymatic degradation within the gastrointestinal environment.

Colostrum contains elements, co-factors, and other components in appropriate ratios and concentrations so as to supply elements required to propagate, promote, support, or enhance an in situ immune-type response, cascade, or reaction. These elements may variously promote cleavage and maturation reactions, the formation of assemblies and complexes, depletion and adsorption functions, supply essential elements, biologics, or compounds, and provide protective functions for active elements or components. In embodiments, the colostrum may or may not contain endogenous antibodies (immune factors), which may or may not be specific to targeted antigens. Colostrum has evolved naturally in mammals specifically to deliver its components to neonates to and through the gastrointestinal tract in a very concentrated low-volume form.

Colostrum is known to contain major components of the adaptive immune system including antibodies such as secretory IgA, $IgG_1$, $IgG_2$, and IgM, as discussed herein.

Colostrum contains several components of the innate immune system. For example, colostrum can include any of lysozyme, phospholipase, defensins, opsonins, components of the complement system, beta-lysin, lactoferrin, transferrin, cytokines, interleukins, chemokines, interferons, TNF-alpha, fibronectin, leukocytes (including white blood cells), phagocytes (including macrophages, monocytes, neutrophils, polyrnorphonuclear cells, and dendritic cells), mast cells, eosinophils, basophils, natural killer (NK) cells, lymphokine activated killer (LAK) cells, cationic proteins including defensins, proteolytic enzymes including elastase, cathepsin G, myeloperoxidase, NADPH oxidase components, lactoperoxidase, complement, and proline-rich polypeptides (PRP), or a combination thereof. Other immune components of colostrum include the major components of the innate immune system, including lactoferrin, lysozyme, lactoperoxidase, complement, and proline-rich polypeptides (PRP). A number of cytokines (small messenger peptides that control the functioning of the immune system) are found in colostrum as well, including interleukins, tumor necrosis factor, chemokines, and others.

Colostrum also contains a number of growth factors, such as insulin-like growth factor I (IGF-I), insulin-like growth factor II (IGF-II), transforming growth factors alpha, beta 1 and beta 2(TGF-α, TGF-β1, TGFβ2), fibroblast growth factors, epidermal growth factor (EGF), granulocyte-macrophage-stimulating growth factor(GM-CSF), platelet-derived growth factor (PDGF), vascular endothelial growth factor (VEGF), and granulocyte colony-stimulating factor (GCSF). A review of growth factors found in colostrum is found in Playford, 2001 J Clin Nutr 20 (Suppl. 1): 101-106 Peptide therapy and the gastroenterologist: colostrum and milk-derived growth factors, which is incorporated herein by reference.

Colostrum components help to regulate the intestinal environment, rendering it hostile to foreign pathogens. For example, colostrum contains lactoferrin, an iron-binding protein that prevents bacteria and viruses from obtaining iron necessary for replication. Colostrum is a natural source of two major growth factors, Transforming Growth Factors (TGF)-alpha and -beta, as well as a source of Insulin-Growth Factors 1 and 2. These factors promote tissue repair and development. Colostrum is also a source of Hepatocyte Growth Factor, which stimulates the growth and expansion of intestinal wall cells. Colostrum is naturally designed to serve as a carrier matrix within a gastrointestinal environment.

A number of cytokines (small messenger peptides that control the functioning of the immune system) are found in colostrum as well, including interleukins, tumor necrosis factor, chemokines, and others. Colostrum also contains a number of growth factors, such as insulin-like growth factors I, and II, transforming growth factors alpha, beta 1 and beta 2, fibroblast growth factors, epidermal growth factor, granulocyte-macrophage-stimulating growth factor, platelet-derived growth factor, vascular endothelial growth factor, and colony-stimulating factor-1.

The antibodies and cofactors in colostrum can, under certain circumstances (for example, breastfeeding) provide a passive immunity to the recipient. The antibodies and cofactors are passed to the neonate from the mother and provide the first protection against pathogens. Growth factors also stimulate the development and repair of the gut.

Livestock husband/breeders commonly bank colostrum from their animals. Colostrum produced on their own premises is considered to be superior to colostrum from other sources, because it is produced by animals already exposed to (and thus making antibodies to) pathogens occurring on the premises. Generally, colostrum from animals exposed to relevant pathogens will have superior immunological characteristics.

Bovine colostrum and its components are safe for human consumption, except in the context of intolerance or allergy to lactose or other components. Bovine colostrum from pasture-fed cows typically contains immunoglobulins specific to many human pathogens, including *Escherichia coli, Cryptosporidium parvum, Shigella flexneri, Salmonella, Staphylococcus*, and rotavirus, depending upon their natural exposure to these pathogens. Before the development of antibiotics, colostrum was the main source of immunoglobulins used to fight infections.

One important limitation of using natural food based products is that preparations are limited to the results allowed by natural processes. The present invention allows for the selective addition of levels of specific antibodies and general immune factors (formulation) that are significantly higher than physiological levels that can normally be achieved in nature. The present invention also allows for a weighting of various factors in a manner so as to create greater specificity to targeted diseases, pathogens, or substances. In addition, in embodiments, the use of a minimum amount of colostrum is important to maximize protection of the antibodies in the gastrointestinal tract, and to enhance the immune response of the patient.

In some embodiments, the disclosure provides a composition comprising colostrum that is not hyperimmune colostrum or that does not contain a measurable or significant amount of antibodies specific for the pathogenic or target antigen components. In preferred embodiments, the non-hyperimmune colostrum has been minimally processed and is not defatted. Whole colostrum or partially defatted colostrum is considered to be minimally processed. The colostrum may be dried non-hyperimmune full-fat colostrum. The colostrum may be dried non-hyperimmune whole colostrum.

In other embodiments, the colostrum is hyperimmune colostrum that has been minimally processed, such as whole hyperimmune colostrum or partially defatted hyperimmune colostrum.

Minimally processed colostrum is hypothesized herein to act as a more effective protective/reactive matrix for formulations containing specific antibodies. Further, a minimal amount of colostrum is necessary to be effective in the formulation. For example, without being bound by theory, the colostrum protects and helps stabilize the specific antibodies in the gastrointestinal environment. Therefore, although a buffer can be added to the formulation, use of a buffer to protect the antibodies in the context of the gastrointestinal environment is not necessary provided an effective amount of colostrum is present. Colostrum also contains components of the innate immune system that enhance the effect of the specific antibodies in the formulation. Colostrum further contains various growth factors to help reduce symptomology of diarrhea in the subject following ingestion.

Colostrum serves to provide additional protective and efficacious attributes to the antibody formulation. Any combination of antibodies can be used in within the colostrum, including but not limited to a combination of anti-pathogen, anti-toxin, and anti-adhesin antibodies.

Colostrum is also very rich in proteins, vitamin A, and sodium chloride, but contains lower amounts of carbohydrates, lipids, and potassium than normal milk. Some of the most pertinent bioactive components in colostrum are growth factors and antimicrobial factors. The antibodies in colostrum provide passive immunity, while growth factors stimulate the development of the gut. They are passed to the neonate and provide the first protection against pathogens. The passive immunity from the mother gets transferred to the newborn.

In some embodiments, the compositions of the disclosure provide improved activity upon oral administration compared to oral administration of the same antibodies alone, due to a protective effect with respect to the antibodies provided by the colostrum, preferably whole colostrum, in the gastrointestinal tract.

In some embodiments, the disclosure provides compositions comprising 1) colostrum and 2) antibody product comprising at least one specific antibody, immunoglobulin, or an active binding fragment thereof, obtained from a different species as the colostrum, that is specific for binding to an antigenic region of a diarrhea-causing pathogenic organism, or a toxin, or adhesin originating therefrom, and 3) an additional active agent. The compositions provide improved activity upon oral administration compared to oral administration of the same antibodies alone, due to a protective effect provided by the colostrum, preferably whole colostrum, in the gastrointestinal tract. The compositions also are contemplated to provide improved activity upon oral administration compared to oral administration of the additional active agent alone.

In some embodiments, the colostrum is bovine colostrum. Bovine colostrum is produced by cows for their newborn calves. In many dairy cow herds the calves are not permitted to nurse; rather, they are fed colostrum and later milk from a bottle then a bucket. Various compositions including colostrum and processes for preparing colostrum have been disclosed in U.S. Pat. Nos. 5,846,569, 6,410,058, 6,475,511, and 6,521,277, the contents of which are incorporated by reference in their entireties.

In embodiments, commercial colostrum is employed in an amount effective to act as a protective/reactive matrix in which to formulate the specific antibodies, derived from a different animal species than the colostrum. In preferred aspects, the commercial colostrum is an agglomerated and instantized, pasteurized, full cream, whole colostrum powder produced from first milking colostrum only. In another aspect, the colostrum is processed at low pressures and low temperatures and is spray dried using indirect steam to maintain maximum bioactivity. In another aspect the commercial colostrum is from antibiotic free sources. In another aspect, the colostrum is subjected to microbiological analysis and is found to be negative, or below acceptable levels with respect to a variety of pathogens. In various other aspects, the colostrum is assayed for other contaminants such as nitrates, aflatoxin, nitrofuran, dioxins, melamine, and heavy metals and found to be negative or below specified levels.

In embodiments, the compositions can be composed of colostrum of several hyper-immunized sources, each targeting a different cluster or class of antigen, where the colostrums are admixed to provide a broad-spectrum antibody formulation. In another embodiment, additional antibodies derived from one or more pools of hyperimmune colostrum are added to non-hyperimmune colostrum as an additional component of the composition. In embodiments, a minimum amount of colostrum is utilized to protect the antibodies in the gastrointestinal tract and to enhance the immune response. For example, at least a minimum of 1 gram, 1.5 grams, 2 grams, 2.5 grams, 3 grams, 4 grams, 5 grams, 6 grams, 7 grams, 8 grams, 9 grams, 10 grams, 11 grams, 12 grams, 13 grams, 14 grams, 15 grams, 16 grams, 16 grams, 17 grams, 18 grams, 19 grams, 20 grams or more of colostrum per dose is to be employed. In one specific embodiment, 3 grams of whole non-hyperimmune bovine colostrum is used per dose. In another specific embodiment, 4 grams of whole non-hyperimmune bovine colostrum is employed per dose. In another specific embodiment, 5 grams of whole non-hyperimmune bovine colostrum is employed per dose.

The colostrum carrier matrix may act as a protective and reactive matrix for combination with the antigen-specific binding molecules in the immune egg. In some embodiments, the colostrum may stabilize the antibodies under GI tract conditions including in the presence of low pH and/or digestive enzymes. In some embodiments, the colostrum is non-hyperimmune colostrum. In some embodiments, the colostrum is full-fat colostrum. In some embodiments, the colostrum is full-fat, non-hyperimmune colostrum. In some embodiments, the colostrum is hyperimmune colostrum.

An effective amount of colostrum in the composition can be determined by evaluating one or more of (1) increased stability with respect to retention of binding activity of a specific antibody within a colostrum containing composition over time when exposed to conditions encountered in the gastrointestinal environment of the subject, compared to the binding activity of the same specific antibody without colostrum, (2) reduction in one or more symptoms of pathogenic infection including consistency, volume, and/or duration of diarrhea, (3) reduction of viral shedding, and (4) improvement in overall health and well-being of the subject, compared to the same formulation without the colostrum. In embodiments, the effective amount of colostrum per dose is the equivalent of at least 1 gram, 1.5 grams, 2 grams, 2.5 grams, 3 grams, 4 grams, 5 grams, 6 grams, 7 grams, 8 grams, 9 grams, 10 grams, 11 grams, 12 grams, 13 grams, 14 grams, 15 grams, 16 grams, 17 grams, 18 grams, 19 grams, 20 grams, 21 grams, 22 grams, 23 grams, 24 grams, 25 grams, or more of dried colostrum per dose on a dry weight equivalent per dose compared to the total amount of combined dried colostrum and dried antibody product.

Additional Active Agents

In some embodiments, the composition comprises colostrum, antibody product, and further comprises one or more additional active agents known to be useful in the treatment of diarrhea.

Antiinfectives

In some embodiments, the composition may further comprise one or more anti-infective drugs. Anti-infective drugs include antibiotics, antifungals, antivirals, antiprotozoal drugs and various fixed-dose combinations.

Antibiotics

Emerging markets typically lack adequate diagnostics, and have frequent mixed infections, so there is a natural requirement for broad spectrum interventions. Current Standard of Care (SOC) for infectious diarrhea in most of the emerging markets centers on administration of oral rehydration solution (ORS), or other palliative interventions (symptomatic relief only) as needed, and antibiotics as a broad defense against what may be the underlying cause of the disease. Antibiotics are currently used to control bacterial infection of *Shigella* spp., *Salmonella, Camphylobacter* spp., enterotoxigenic *E. coli* spp., enteropathogenic *E. coli* spp., Enteroinvasive *E. coli* spp., enteroaggregative *E. coli* spp., enterohemmorrhagic (STEC) *E. coli* spp., *Aeromonas/Plesiomonas, Yersinia* spp., *Vibrio cholera* 01 or 0139, and *Clostridium difficile*.

In some embodiments, compositions provided herein comprising a carrier matrix, for example, colostrum and specific avian polyclonal antibodies, for example, IgY, further comprise one or more antibiotics. Compositions comprising colostrum, IgY and one or more antibiotics may be useful for treating small intestine bacterial overgrowth, a subclinical infection, diarrhea, for example, undifferentiated diarrhea, pediatric diarrhea, or traveller's diarrhea.

In some embodiments, the antibiotic is selected from antibiotics or antibiotic/antimicrobial combinations, selected from, for example, Prulifloxacin (Pruvel, Pruquin), Ulifloxacin, Fidaxomicin, Mestacine (Minocyclin), Metrogyl (Metronidazole), Metronidazole, Sulfamethoxazole, Trimethoprim, and Co-Trimoxazole (Sulfamethoxazole, Trimethoprim), Bactrim (trimethoprim/sulfamethoxazole), Orinet-M (Ofloxacin & Metronidazole), Tiniflox (Norfloxacin, Tinidazole), Norfloxacin, Oxacin (Ofloxacin/Ornidazole), Ofloxacin, Levofast/Levofloxacin, nalidixic acid, ceftriaxone, azithromycin, and Septra (Sulfamethoxazole, Trimethoprim). In some embodiments, the antibiotic is a cephalosporin antibiotic, for example, Cefimax (Cefixime), Mahacef (Cefixime), Milixim, Ceftriaxone, Phexin(Cefalexin), Swizin (Cefixime), Topcef (Cefixime), Zofix (Cefixime), Cefaxone (Ceftriaxone), Ceftriaxone, and Rifaximin, (e.g., Xifaxan). In some embodiments, the antibiotic is a nitrofuran antibiotic, for example, Furazolidone. In some embodiments, the antibiotic is a fluoroquinoline antibiotic, such as fluoroquinolone, ciprofloxacin, erythromycin, doxycycline, diiodohydroxyquin, paromomycin, Cipro. In some embodiments, the antibiotic is a macrolide antibiotic, such as Macrotor (azithromycin). In some embodiments, the antibiotic is an aminoglycoside. In some embodiments, the aminoglycoside can be selected from one or more of Amikacin, Gentamycin, Kanamycin, Mikacin (Amikacin), and Tobacin (Tobramycin). In some embodiments the antibiotic is a penicillin or aminopenecillin antibiotic such as ampicillin, or amoxicillin.

In some embodiments, the antibiotic is a quinolone, such as a fluoroquinolone. The fluoroquinolone can be selected from Ciprofloxacin, Norfloxacin, Ofloxacin, Levofloxacin, Gatifloxacin, Gemifloxacin, Prufloxacin, Ulifloxacin, and Moxifloxacin.

In some embodiments, the antibiotic is Prulifloxacin (PRUVEL, Optimer). Prulifloxicin, a prodrug of ulifloxacin, is a broad spectrum oral fluoroquinoline antibacterial agent. Prulifloxacin is metabolized by esterases to ulifloxacin. Prulifloxacin has a long elimination half-life, and therefore can be administered once per day. Fluoroquinolines act by preventing bacterial DNA replication, transcription through inibotion of bacterial gyrase. Prulifloxacin is licensed in Japan for treatment of gastroenteritis, including infectious diarrhea.

In some embodiments, the antibiotic is Ulifloxacin. Ulifloxacin is active in vitro against a variety of clinical isolates of Gram-negative bacteria, including community and nosocomial isolates of *Escherichia coli, Klebsiella* spp., *Proteus, Providencia* and *Morganella* spp., *Moraxella catarrhalis* and *Haemophilus* spp. Gram-positive organisms, including meticillin- or oxacillin-susceptible *Staphylococcus aureus, Enterococcus* spp. and Italian community isolates of *Streptococcus pneumoniae* are susceptible to ulifloxacin.

In some embodiments, the antibiotic is ciprofloxacin hydrochloride.

Antifungals

In some embodiments, the composition comprising a carrier matrix, for example, colostrum and a specific avian antibodies, for example, IgY further comprises an antifungal compound. In some embodiments, the antifungal compound is selected from nystatin, amphotericin B, flucytosine, ketoconazole, posaconazole, clotrimazole, voriconazole, griseofulvin (for example Pedinol), miconazole nitrate, and fluconazole (for example Zorca).

Antimicrobials

Diarrhea caused by protozoal infection is common. Intestinal protozoal diseases include Giardiasis, Amoebiasis and intestinal coccidian infection by Cryptosporidiosis, Microsporidium and *Cyclospora* species, and *Isospora belli*. Clinically important human intestinal pathogenic protozoa include *Entamoeba histolytica, Giardia intestinalis*, (syn. *Giardia lamblia, Giardia duodenalis*), *Balantidium coli, Cryptosporidium parvum, Cryptosporidium hominis, Isospora belli, Cyclospora cayetanensis, Sarcocystis* spp., *Enterocytozoon bieneusi*, and *Encephalitozoon intestinalis*. The small intestinal protozoa *Giardia intestinalis* and Cryptosporidiumparvum are said to particularly impact children, whereas the large bowel pathogen *Entamoeba histolytica* affects all ages. Farthing, 2006, Treatment options for the eradication of intestinal protozoa. Nature Clinical Practice 3(8): 436-445.

Typical antimicrobial treatment for diarrhea caused by protozoa varies depending on the infection.

Treatment of *Giardia intestinalis* involves administration of, for example, Metronidazole, 1 g per dose on 3 successive days, or Tinidazole, 2 g single dose.

Typical treatment of *Cryptosporidium parvum* is Nitazoxanide, 500 mg twice a day for 3-14 days, or Albendazole 400 mg twice a day for 7-14 days, or Paromomycin, 500 mg four times a day for 7-14 days.

Typical treatment of *Cyclospora cayetanensis* infection is administration of Co-trimoxazole (trimethoprim 160 mg plus sulfamethoxazole 800 mg) twice a day for 7 days; or Ciprofloxacin, 500 mg twice a day for 7 days.

Typical treatment of *Isospora belli* is administration of Co-trimoxazole (trimethoprim 160 mg plus sulfamethoxazole 800 mg) four times a day for 10 days; or Ciprofloxacin 500 mg twice a day for 7 days.

Typical treatment of *Entamoeba histolytica* infection involves administration of Metronidazole, 750 mg three times a day for 5 days; or Diloxanide furoate, 500 mg three times a day for 10 days; or Paromomycin 25-35 mg/kg three times a day for 7-10 days.

Typical treatment of *Balantidium coli* involves administration of Metronidazole 400 mg three times a day for 10 days; or Tetracycline, 500 mg four times a day for 10 days.

Typical treatment of *Blastocystis hominis* infection is Nitazoxanide, 500 mg twice a day for 3 days; or Metronidazole 800 mg three times a day for 5-10 days; or Co-trimoxazole (trimethoprim 160 mg plus sulfamethoxazole 800 mg) twice a day for 7 days.

Typical treatment of *Encephalitozoon intestinalis* infection is administration of Albendazole, 400 mg twice a day for 14-28 days.

Typical treatment of *Enterocytozoon bieneusi* infection is administration of Albendazole, 400 mg twice a day for 28 days; or Fumagillin 60 mg daily for 14 days.

Disadvantages of the sole use of antimicrobials to treat diarrhea is the need to diagnose the protozoal infection, selection of the correct antimicrobial drug and dose, and the need for patient compliance over several days or weeks.

In some embodiments, a composition comprising a carrier matrix, for example, bovine colostrum, and a specific binding molecule, for example, antibody product, and further comprising one or more antiprotozoal or antimicrobial drugs is used to treat diarrhea. In some embodiments, animicrobial drug is selected from one or more of Metronidazole, Aristogyl (Metronidazole), Tinidazole, Nitazoxanide, Satranidazole, Ornidazole, Oxacin-oz (ofloxocin/ornidazole), Tinilox MPS (tinidazole, diloxanide furoate, polydimethylsiloxane), Bactrim (trimethoprim/sulfamethoxazole), Co-trimoxazole (trimethoprim plus sulfamethoxazole), tetracycline, albendazole, rifampicin, secnidazole, paromomycin, Ciprofloxacin, Diloxanide furoate, and Fumagillin. The amount of the antimicrobial component per dose of composition can be adjusted by techniques known to the skilled artisan. It is contemplated that one or both of the duration of administration, or the dose of microbial drug, can be reduced by incorporation into the compositions of the invention when compared to administration of the antimicrobial drug alone. In some embodiments, the composition comprises colostrum, antibody product, one or more antibacterial drugs and one or more antimicrobial drugs.

Antivirals

In some embodiments, the disclosure provides a composition comprising colostrum, antibody product derived from a different species than the colostrum, and an additional active agent that is an antiviral agent; the composition is useful to treat or prevent diarrhea due to a viral infection, such as rotavirus infection, in a subject. In some embodiments, the additional active agent is nitazoxanide. Nitazoxanide (ALINIA®, Romark), is known as an antimicrobial but has also been found to be effective to reduce the duration of rotavirus disease in pediatric patients following a 3 day course of administration when administered in a 7.5 mg/kg suspension. Rossignol et al., 2006, Effect of nitazoxanide for treatment of severe rotavirus diarrhea:randomized double-blind placebo controlled trial. Lancet 2006; 368:124-129.

In some embodiments, the composition comprises colostrum, antibody product, one or more antibacterial drugs and one or more antiprotozoal drugs. In some embodiments, the composition comprises bovine colostrum, antibody product and nitazoxanide. In some embodiments, the nitazoxanide is present in an effective amount in the composition in the range of 50 to 1,000 mg per dose.

Generally used nutritional plant extracts of *Nelumbo nucifera* Gaertn., *Aspalathus linearis* (Burm. f.) R. Dahlgren, *Urtica dioica* L., *Glycyrrhiza glabra* L. and *Olea europaea* L. were recently reported to have in vitro antiviral activity against rotavirus. Two components of *Aspalathus linearis*, luteolin and vitexin; and apigenin 7-O-glucoside also were reported to show antiviral activity against rotavirus infection in MA-104 cells in an antiviral titration assay, as reported by Knipping et al, 2012, An evaluation of the inhibitory effects against rotavirus infection of edible plant extracts. Virology J 9:137, incorporated herein by reference. In some embodiments, a composition comprising bovine colostrum, antibody product, and an antiviral agent selected from Nitazoxanide or one or more extracts of *Nelumbo nucifera* Gaertn., *Aspalathus linearis* (Burm. f.) R. Dahlgren, *Urtica dioica* L., *Glycyrrhiza glabra* L. and *Olea europaea* L; or luteolin and vitexin, and apigenin 7-O-glucoside is useful to treat or prevent diarrhea due to a viral infection, such as rotavirus infection, in a subject.

In some embodiments, the composition comprises colostrum, antibody product and one or more bacteriocins. Bacteriocins are specific inhibitors which are secreted by microorganisms and are lethal for other microorganisms—principally bacteria. Bacteriocins are peptides, polypeptides, proteins or substances which have at least proteinogenic structures and are composed of amino acids. It is moreover possible for these bacteriocins which are composed of amino acids also to contain unusual amino acids such as, for example, lanthionine or beta-methyllanthionine. For example, pediocin L50 contains other modified amino acids. Pediocin has been used in meat preservation formulations. Nicin is a bacteriocin that is Generally Recognized as Safe (GRAS) in the U.S. Cleveland et al., 2001, Int. J. Food Microbiol.71, 1-20. Nisin is commercially available food ingredient as a concentrate or dry material. In some embodiments, the bacteriocin is Nicin A, Pediocin AcH, Enterocin 4, Linocin M-18, Piscicolin 126, Leucocin A, Lactocin 705, Pediocin, Pediocin PA-1 or Enterocin. A number of bacteriocins are described in U.S. Pat. No. 6,780,447, which is incorporated herein by reference.

Micronutrients

Current standard of care for treating childhood diarrhea can include fluid and electrolyte replacement (ORS), nutritional therapy (the early restart of normal feeding and supplementation for micronutrient deficiencies), and, if possible, elimination of the underlying cause of the diarrhea. Micronutrients are nutritional supplements providing support for immune function in the recipient. Zinc supplements may be useful as an adjunct to provide increased future resistance to infection, and may marginally shorten the duration of some types of diarrhea. However, this intervention does not have sufficient curative or palliative effect to be seen as a 'cure' when used alone in active disease. Vitamin A deficiency may also be a factor in emerging nations, but may not be specifically related to infectious diarrhea.

In some embodiments, the compositions comprising colostrum and antibody product further comprise one or more micronutrients selected from the group consisting of vitamins, minerals, and a combination of thereof. Vitamins may be selected from vitamin A, vitamin D, vitamin E, vitamin $B_{12}$, riboflavin, niacin, pantothenic acid, thiamine, choline, folic acid, biotin, vitamin K, vitamin C, and a combination thereof. Minerals may be selected from cobalt, copper, iron, manganese, zinc, selenium, and a combination thereof. In some embodiments the micronutrient is selected from one or more of zinc or vitamin A. One or more, two or more, three or more, four or more, five or more, or from 1 to 25, 2 to 22, 3 to 15, 4 to 10 micronutrients may be employed in the copositions or methods according to the disclosure. In certain embodiments, combinations of micronutrients may be employed according to World Health Organization (WHO) guidelines. Combinations of micronutrients may be employed according to Table 2.

TABLE 2

Exemplary Micronutrient Combinations.

| | Formula A | Formula B | Formula C |
|---|---|---|---|
| Micronutrient | 22-nutrient | 15-nutrient | 5-nutrient |
| Vitamin A, μg | 100 to 1000 | 100 to 1000 | 100 to 1000 |
| Vitamin D, μg | 2 to 25 | 2 to 25 | NA |
| Vitamin E, mg | 3 to 15 | 3 to 15 | NA |
| Vitamin C, mg | 15 to 60 | 15 to 60 | 15 to 60 |
| Thiamin, mg | 0.2 to 1.5 | 0.2 to 1.2 | NA |
| Riboflavin, mg | 0.2 to 1.3 | 0.2 to 1.3 | NA |
| Vitamin B-6, mg | 0.2 to 2 | 0.2 to 2 | NA |
| Vitamin B-12, μg | 0.2 to 5 | 0.2 to 5 | NA |
| Niacin, mg | 3 to 16 | 3 to 16 | NA |
| Folic acid, μg | 80 to 600 | 80 to 600 | 80 to 600 |
| Iron, mg | 0.5 to 18 | 0.5 to 18 | 0.5 to 18 |
| Zinc, mg | 1 to 50 | 1 to 20 | 1 to 15 |
| Copper, mg | 0.2 to 1.6 | 0.2 to 1.6 | NA |
| Selenium, μg | 10 to 80 | NA | NA |
| Iodine, μg | 45 to 290 | 45 to 290 | NA |
| Calcium, mg | 50 to 1300 | NA | NA |
| Magnesium, mg | 10 to 420 | NA | NA |
| Phosphorus, mg | 50 to 1250 | NA | NA |
| Manganese, mg | 0.3 to 2.6 | NA | NA |
| Vitamin K, μg | 2 to 120 | NA | NA |
| Pantothenic acid, mg | 0.9 to 7 | NA | NA |
| Biotin, μg | 3 to 35 | NA | NA |

Zinc

The compositions of colostrum and antibody product may further comprise the micronutrient zinc in the form of one or more zinc supplements. The antibody product may be egg antibody product, for example, dried immune egg antibody product. The colostrum may be whole bovine colostrum, for example, dried whole bovine colostrum. In some embodiments, a zinc supplement is employed supplying a daily dose of, for example, from 1 mg to 50 mg, 2 mg to 20 mg, or 4 mg to 15 mg zinc equivalents. In some embodiments, zinc supplements may be employed supplying a zinc equivalent dose of 10 mg or 20 mg per day. Several trials have been conducted using zinc supplementation with oral rehydration solution for management of childhood diarrhea. WHO/UNICEF Joint Statement Integrated Community Case Management (iCCM), June 2012, p. 5. Zinc can be used in any acceptable zinc supplement form, for example, inorganic zinc salts and/or organic zinc salts. Inorganic zinc salts may include zinc sulfate, or zinc oxide. Organic zinc salts may include zinc carnosine, zinc acetate, zinc gluconate, zinc monomethionine, zinc picolinate, or zinc glycinate. The zinc carnosine may be zinc L-carnosine.

One composition according to the disclosure may comprise colostrum, antibody product and a zinc supplement. The zinc supplement may be zinc carnosine. Use of zinc carnosine for treatment or prevention of irritable bowel syndrome is disclosed in US20100040711, Playford et al., which is incorporated herein by reference. Zinc carnosine has been studied in models of gut injury and gut repair. In the case of a human averaging 50 kg or more in weight, the zinc carnosine composition may be administered in a single or multiple daily doses amounting in total from about 5 to about 200 mg/day, more preferably about 15 to about 150 mg/day, even more preferably about 75-150 mg/day, or a daily dose of 5 mg, 10 mg, 15 mg, 20 mg, 30 mg, 37.5 mg, 50 mg, 75 mg, 100 mg, 125 mg, 150 mg, 175 mg, 200 mg, or 250 mg, or any intermediate value, of zinc L-carnosine. One dose of the composition may include, for example, 1 g-15 g dried immune egg, 1 g-15 g dried whole bovine colostrum, and 1 mg-200 mg zinc carnosine; 2 g-7 g dried immune egg, 2 g-7 g dried whole bovine colostrum, and 5 mg-150 mg zinc carnosine; or 3 g-4 g dried immune egg, 3 g-4 g dried whole bovine colostrum, and 10 mg-100 mg zinc carnosine. The daily dose may be provided for administration in one or more, two or more, three or more times daily.

Vitamin A

The micronutrient composition may include vitamin A. Vitamin A is a fat soluble vitamin. The vitamin A may be included in compositions of the disclosure or co-administered with compositions of the disclosure in an amount of about 100 to about 1,000 µg, 150 to 500 µg, or 200 to 400 µg per day. Vitamin A deficiency diminishes the ability to fight infections. Even mild, subclinical deficiency can be a problem, as it may increase children's risk of developing respiratory and diarrheal infections, decrease growth rate, slow bone development, and decrease likelihood of survival from serious illness. In some embodiments, the compositions comprising colostrum and antibody product further comprise an acceptable source or form of vitamin A. In some embodiments the vitamin A source is selected from one or more of retinol, retinyl acetate, retinyl palmitate, or a carotenoid. The vitamin A source is converted to vitamin A in the body. In some embodiments, the vitamin A is a pro-vitamin A carotenoid. The carotenoid is selected from, for example, one or more of beta-carotene, alpha-carotene, gamma-carotene or beta-cryptoxanthin. Lipids are known to enhance the uptake of vitamin A. Therefore, in some embodiments, the composition comprises whole colostrum, antibody product and one or more sources or forms of vitamin A.

Vitamin D

The micronutrient composition may include vitamin D. Vitamin D is a fat soluble vitamin. Vitamin D is important for bone growth, bone remodeling, modulation of cell growth, neuromuscular and immune function, and reduction of inflammation. https://ods.od.nih.gov/factsheets/VitaminD-HealthProfessional/. Vitamin D may be included in compositions of the disclosure or co-administered with compositions of the disclosure in an amount of about 2 to 25 micrograms, or 10 to 20 micrograms per day per day. Vitamin D may be in the form of ergocalciferol ($D_2$) and/or cholecalciferol ($D_3$).

Vitamin E

A micronutrient composition provided herein may include vitamin E. Vitamin E is a fat soluble vitamin. Vitamin E may act as an antioxidant, and may contribute to immune system function. https://ods.od.nih.gov/factsheets/VitaminE-Consumer/The vitamin E may be included in compositions of the disclosure or co-administered with compositions of the disclosure in an amount of about 2 to 20 milligrams, or 3 to 15 milligrams per day per day. Vitamin E may be in the form of d-alpha-tocopherol, dl-alpha-tocopherol, gamma-tocopherol, tocotrienols, or mixed tocopherols.

Vitamin C

A micronutrient composition provided herein may include vitamin C. Vitamin C is a water soluble vitamin. Vitamin C, also known as L-ascorbic acid, is important for biosynthesis of collagen, L-carnitine, and certain neurotransmitters. Collagen is an essential component of connective tissue and plays a role in wound healing. Vitamin C also acts as an anti-oxidant, plays a role in immune function, and improves absorption of non-heme iron. dhttps://ods.od.nih.gov/factsheets/VitaminC-HealthProfessional/. Vitamin C may be in the form of L-ascorbic acid, ascorbyl ester or ascorbate including either or both water-soluble and fat-soluble forms. The water soluble form of ascorbic acid can be selected from ascorbic acid, a biologically acceptable mono or divalent metal ion salt of ascorbic acid and niacinamide ascorbate, and mixtures thereof. Suitable metal ion salts of ascorbic acid are those selected from the group consisting of calcium ascorbate; magnesium ascorbate; potassium ascorbate; and sodium ascorbate, either alone or some mixture thereof. Other water soluble forms can include manganese ascorbate; zinc ascorbate; iron ascorbate; copper ascorbate; boron ascorbate; molybdenum ascorbate; and chromium ascorbate. The fat soluble ascorbyl esters preferably comprise fatty acid esters of saturated or unsaturated carboxylic acids with ascorbyl palmitate being one preferred form. Other fat soluble esters of ascorbic acid which are preferred include: ascorbyl palmitate; ascorbyl arachidonate; ascorbyl stearate; ascorbyl linoleate; ascorbyl linoleneate; and ascorbyl oleate. Vitamin C may be included in compositions of the disclosure or co-administered with compositions of the disclosure, for example, as an ascorbic acid or ascorbate form in an amount of about 10 to 1,200 mg, 15 to 500 mg, or 20 to 60 mg per day.

Thiamin

A micronutrient composition provided herein may include Thiamin. Thiamin is a water-soluble B vitamin, also known as B1. Thiamin may play a role in emergy metabolism and therefore in growth, development, and function of cells. https://ods.od.nih.gov/factsheets/Thiamin-HealthProfessional/. Thiamin may be in the form of thiamin mononitrate, thiamin hydrochloride, or benfotiamine. Thiamine may may be included in compositions of the disclosure or co-administered with compositions of the disclosure, for example, at 0.2 to 1.4 mg, or 0.4 to 1.1 mg.

Riboflavin

A micronutrient composition provided herein may include riboflavin. Riboflavin is a water-soluble B vitamin, also known as B2. Riboflavin is a component of two coenzymes, flavin mononucleotide (FMN) and flavin adenine dinuceotide (FAD). These enzymes play a role in energy production, cellular function, growth and development and metabolism and conversion of tryptophan to niacin. https://ods.od.nih.gov/factsheets/Riboflavin-HealthProfessional/.

Riboflavin may be included in compositions of the disclosure or co-administered with compositions of the disclosure, for example, at 0.2 to 1.6, or 0.4 to 1.0 mg per day.

Vitamin B6

A micronutrient composition provided herein may include vitamin B6. Vitamin B6 is a water-soluble vitamin. Vitamin B6 is involved in enzyme reactions in protein metabolism, amino acid metabolism, and biosynthesis of neurotransmitters, gluconeogenesis, immune function, and hemoglobin formation. https://ods.od.nih.gov/factsheets/VitaminB6-HealthProfessional/. Vitamin B6 may be included in compositions of the disclosure or co-administered with compositions of the disclosure, for example, at 0.1 to 2 mg, 0.2 to 1.3, or 0.4 mg to 0.8 mg per day.

Vitamin B12

A micronutrient composition provided herein may include vitamin B12. Vitamin B12 is a water-soluble vitamin. Vitamin B12 is involved in red blood cell formation, neurologic function, and DNA synthesis. https://ods.od.nih.gov/factsheets/VitaminB12-HealthProfessional/. Vitamin B12 may be administered in any acceptable form, for example in the form of cyanocobalamin or hydroxocobalamin. Vitamin B12 may be included in compositions of the disclosure or coadministered with compositions of the disclosure, for example, at 0.2 to 5 mcg, 0.3 to 2.8 mcg, or 0.4 mg to 0.8 mcg per day.

Niacin

A micronutrient composition provided herein may include niacin. Niacin is a water-soluble B vitamin also known as B3. Niacin is a generic name for nicotinic acid, niacinamide, or pyridine-3-carboxamide. In the body, niacin is converted to its main active form of coenzyme nicotinamide adenine dinucleotide (NAD). Hundreds of enzymes within the body require NAD to catalyze reactions in the body, Nicotine may also be converted in the body to another active form nicotinamide the coenzyme nicotinamide adenine dinucleotide phosphate (NADP). NAD is involved in catabolic reactions that transfer energy in carbohydrates, fats and proteins to adenine triphosphate (ATP), involved in cellular energy. NADP enables catabolic reactions such as synthesis of cholesterol and fatty acids, and plays a role in cellular antioxidant function. https.//ods.od.nih.gov/factsheets/Niacin-HealthProfessional/. Niacin may be administered in the form of nicotinic acid, nicotinamide, or inositol hexanicotinate. Niacin may be included in compositions of the disclosure or co-administered with compositions of the disclosure, for example, at 2 to 20 mg, 4 to 15 mg, or 5 to 10 mg per day.

Folic Acid

A micronutrient composition provided herein may include folic acid. Folic acid is a water-soluble B vitamin also known as folate, folacin, or vitamin B9. Folate functions as a coenzyme or cosubstrate in the synthesis of nucleic acids and metabolism of amino acids. One folate-dependent reaction is the conversion of homocysteine to methionine in the synthesis of S-adenosyl-methionine, an imortant methyl donor. Another folate dependent reaction is the methylation of deoxyuridylate to thymidylate in the formation of DNA, is required for proper cell division. An impairment of this reaction initiates a process resulting in megaloblastic anemia, an indication of folate deficiency. https://ods.od.nih.gov/factsheets/Folate-HealthProfessional/. Folic acid may be administered in the form of monoglutamyl folate, tetrahydrofolate, 5-methyl THF also known as methyl folate, or a reduced from of folate. Folic acid may be included in compositions of the disclosure or co-administered with compositions of the disclosure, for example, at 50 to 1,000 mcg, 80 to 600 mcg, or 100 to 200 mcg per day.

Iron

A micronutrient composition provided herein may include iron. Iron is a mineral required fro growth and development, hemoglobin and myoglobin formation, and synthesis of hormones and connective tissues. https://ods.od.nih.gov/factsheets/Iron-Consumer/Iron may be administered, for example, in the form of ferrous sulfate, ferrous gluconate, ferric citrate, or ferric sulfate. Iron may be included in compositions of the disclosure or co-administered with compositions of the disclosure, for example, at 0.2 to 30 mg, 0.5 to 18 mg, or 5 to 15 mg per day.

Copper

A micronutrient composition provided herein may include copper. Copper is a trace element. Copper is a cofactor for oxidation-reduction reactions involving copper containing oxidases. Copper enzymes regulate physiologic pathways including energy production, iron metabolism, connective tissue maturation, bone development, and neurotransmission. https://lpi.oregonstate.edu/mic/minerals/copper. Copper may be included in compositions of the disclosure or co-administered with compositions of the disclosure, for example, at 0.2 to 1.6 mg, or 0.3 to 0.9 mg per day.

Selenium

A micronutrient composition provided herein may include selenium. Selenium is a trace element. Selenium is important for reproduction, thyroid hormone metabolism, DNA synthesis, and protection from oxidative damage and infection. https://ods.od.nih.gov/factsheets/Selenium-HealthProfessional/. Selenium may be administered in inorganic or organic forms. Inorganic forms may include selenate and selenite; organic forms may include selenomethionine and selenocysteine. Selenium may be included in compositions of the disclosure or co-administered with compositions of the disclosure, for example, at 3 to 80, 5 to 55, or 10 to 30 mcg per day.

Iodine

A micronutrient composition provided herein may include iodine. Iodine is a trace element. Iodine is a component of thyroid hormmose thyroxine (T4) and triiodothyronine (T3). Thyroid hormoned regulate many biochemical reactions, including protein synthesis, enzymatic activity, and metabolic activity. Thyroid hormones are also used in skeletal and central nervous system development. https://ods.od.nih.gov/factsheets/Iodine-HealthProfessional/. Iodine may be administered in the form of potassium iodide, sodium iodide, or iodine-containing kelp. Iodine may be included in compositions of the disclosure or co-administered with compositions of the disclosure, for example, at 45 to 300 mcg, or 50 to 220 mcg, or 60 to 150 mcg per day.

Calcium

A micronutrient composition provided herein may include calcium. Calcium is a mineral important for vascular contraction, vasodilation, muscle function, nerve transmission, intracellular signalling, and hormonal secretion. Serum calcium is highly regulated and the body uses bone tissue as a reservoir for and a source of calcium to maintain constant levels in blood, muscle, and intracellular fluids. https://ods.od.nih.gov/factsheets/Calcium-HealthProfessional/Calcium may be administered as calcium carbonate, calcium citrate, calcium phosphate, calcium gluconate, calcium lactate or calcium citrate malate. Calcium may be included in compositions of the disclosure or co-administered with compositions of the disclosure, for example, at 50 to 1,300 mg, or 75 to 500 mg, or 60 to 200 mg per day.

Magnesium

A micronutrient composition provided herein may include magnesium. Magnesium is a mineral that acts as a cofactor in many enzyme systems, protein synthesis, muscle and nerve function, blood glucose control, and blood pressure regulation. https://ods.od.nih.gov/factsheets/Magnesium-HealthProfessional/. Magnesium may be administered in inorganic or organic forms. Inorganic forms may include magnesium oxide, magnesium sulfate, or magnesium chloride. Organic forms may include magnesium citrate, magnesium aspartate, or magnesium lactate. Magnesium may be included in compositions of the disclosure or co-administered with compositions of the disclosure, for example, at 5 to 500 mg, or 10 to 200 mg, or 15 to 50 mg per day.

Phosphorus

A micronutrient composition provided herein may include phosphorus. Phosphate is a mineral that is a major component of bone. Phosphorus is also a component of DNA, RNA, ATP, phospholipids and sugar phosphates. Phosphorus may be administered in the form of sodium phosphate, calcium phosphate, or potassium phosphate. Phosphorus may be included in compositions of the disclosure or co-administered with compositions of the disclosure, for example, at 50 to 1200 mg, 75 to 500 mg, or 100 to 200 mg per day.

Manganese

A micronutrient composition provided herein may include manganese. Manganese is a mineral involved in bone formation, metabolism of carbohydrates, cholesterol and amino acid formation. Manganese metalloenzymes include manganese supeoxide dismutase, arginase, phosphoenolpyruvate decarboxylase, and glutamine synthestase. Manganese may be administered in the form of maganese gluconate, manganese sulfate, manganese ascorbate, or amino acid chelates of managnese. Manganese may be included in compositions of the disclosure or co-administered with compositions of the disclosure, for example, at 0.3 to 3 mg, 0.4 to 2 mg, or 0.5 to 1 mg per day.

Vitamin K

A micronutrient composition provided herein may include vitamin K. Vitamin K is a generic name for a family of compounds with a common chemical structure of 2-methyl-1,4-naphthoquinone. Vitamin K is a fat soluble vitamin. Vitamin K may be administered in a form selected from phylloquinone (vitamin K1) and a series of menaquinones (vitamin K2). Manaquinones have unsaturated isoprenyl side chains and are designated MK-4 to MK-13, based on length of the side chain, for example, MK-4, MK-7 and MK-9. https://ods.od.nih.gov/factsheets/VitaminK-Health-Professional/. Vitamin K functions as a coenzyme for vitamin-K depsndent carboxylase, an enzyme required for synthesis of proteins involved in homeostasis (blood clotting) and bone metabolism. Vitamin K may be included in compositions of the disclosure or co-administered with compositions of the disclosure, for example, at 2 to 120 mcg, 5 to 80 mcg, or 10 to 30 mcg per day.

Pantothenic Acid

A micronutrient composition provided herein may include pantothenic acid. Pantothenic acid, also known as vitamin B5, is a water soluble B vitamin. Pantothenic acid is involved in synthesis of coenzyme A (CoA) and acyl carrier protein. CoA is used in fatty acid synthesis and degradation, transfer of acetyl and acyl groups, and other anabolic anc catabolic processes. https://ods.od.nih.gov/factsheets/PantothenicAcid-HealthProfessional/. Pantothenic acid may be administered in a form of CoA, phosphopantetheine, D-pantothenic acid, DL-pantothenic acid, pantetheine, pantethine, or calcium pantetheinate. Pantothenic acid may be included in compositions of the disclosure or co-administered with compositions of the disclosure, for example, at 0.5 to 10 mg, 0.9 to 5 mg, or 1 to 3 mg per day.

Biotin

A micronutrient composition provided herein may include biotin. Biotin is a water-soluble B vitamin. Biotin is a cofactor for five carboxylases that catalyze steps in metabolism of fatty acids, glucose and amino acids. Biotin also may play a role in histone modifications, gene regulation by modifying activity of transcription factors, and cell signalling. https://ods.od.nih.gov/factsheets/Biotin-HealthProfessional/. Biotin may be included in compositions of the disclosure or co-administered with compositions of the disclosure, for example, at 3 mcg to 35 mcg, or 5 mcg to 25 mcg.

Oral Rehydration Salts

Oral rehydration therapy is part of the Standard of Care used to treat dehydration associated with diarrhea in many countries. However, ORS does not reduce stool output or duration of diarrhea. ORS consists of a solution of salts and sugars that is taken orally. WHO recommends oral rehydration solution (ORS) with zinc supplementation for management of childhood diarrhea. In many cases, ORS with zinc is the standard of care for childhood diarrhea in developing countries. WHO/UNICEF Joint Statement Integrated Community Case Management (iCCM), June 2012, p. 5. A homemade ORS consists of one liter of water with 1 teaspoon (3 g) of sodium chloride, and two tablespoons (18 g) of sugar. WHO, The Treatment of diarrhoea: a manual for physicians and other senior health workers. 4th rev., 1995. Glucose, fructose, dextrose are used in place of sucrose in some ORS formulations. For example, PEDIALYTE® (Abbott Nutrition) comprises water, dextrose, potassium citrate, sodium chloride, and zinc gluconate in flavored or unflavored formulations. A reduced osmolarity ORS includes sodium chloride (2.6 g/L), anhydrous glucose (13.5 g/L), potassium chloride (1.5 g/L), and trisodium citrate, dihydrate (2.9 g/L). See UNICEF Technical Bulletin No. 9, New formulation of Oral Rehydration Salts (ORS) with reduced osmolarity.

In some embodiments, the compositions comprising colostrum and specific antibody product further comprise oral rehydration salts. In some embodiments, the oral rehydration salts are selected from sodium chloride, sodium citrate, potassium chloride, potassium citrate. Various carbohydrates are optionally included. For example, in some embodiments, the compositions comprising colostrum and antibody product further comprise one or more carbohydrates selected from glucose, glucose polymer, dextrose, sucrose, and fructose.

In some embodiments, the compositions comprising colostrum and antibody product can be administered with one or more of various commercially available ORS, or the composition may further comprise the oral rehydration salts of, for example, Pedialyte, Ceralyte, Isolyte P and Ringer lactate, Jal Jeevan (NaCl, KCl, glucose), Walyte (NaCl, KCl, glucose), Coslyte (NaCl, KCl, Dextrose), Rebalanz and Glucon-D for the treatment of diarrhea. In some embodiments, the composition comprising ORS can further comprise zinc formulation such as Zincofer Syrup.

Antidiarrheal Adsorbants

The use of antidiarrheal adsorbants extends back to the ingestion of certain soils, clays, or fibrous materials in folk medicine. Absorbents that are taken orally bind water in the small intestine and colon and make diarrheal stools less watery (although not decreasing fluid loss). Traditionally it was thought that they also bind toxic chemicals produced by bacteria that cause the small intestine to secrete fluid. Antidiarrheal adsorbants include over the counter anti-diarrhea medicine including bismuth subsalicylate (Pepto-Bismol), kaolin-pectin, activated charcoal, attapulgite (Kaopectate). It is recommended that these products not be used in children under 12 years of age. In some embodiments, the compositions comprise colostrum, antibody product and an anti-diarrheal adsorbant. In addition, it has been found that synthetic bismuth compounds have activity against *Clostridium difficile*. In some embodimets, the anti-diarrheal adsorbant is selected from bismuth subsalicylate, kaolin, attapulgite and pectin.

Anticholinergics

Anticholinergics decrease intestinal muscle tone and peristalsis of the gastrointestinal tract. Anticholinergics used for this purpose include *belladonna* alkaloids (Donnatal), atropine, and hyoscyamine. In some embodiments, the composition comprises colostrum, antibody product and one or more anticholinergic drugs. In some embodiments, the anticholinergic drug is selected from a *belladonna* alkaloid, atropine and hyoscyamine.

Antisecretory Agents

An antisecretory is any drug that reduces the normal rate of secretion of a body fluid into the GI tract. As used herein, the antisecretory action refers to the loss of water and electrolytes associated with diarrheal symptoms. Anti-secretories are palliative interventions that do not affect the control, clearance, or resolution of the underlying condition causing the secretion. In this respect they are complementary to ORS; where ORS is adding water and electrolytes, and the antisecretory is slowing the loss of water and electrolytes.

Anti-secretories are a relatively recent development. Only one dedicated product is in the market, although several older products have had some antisecretory effect. Several other new antisecretory drugs are in development or trials. In the absence of alternatives beyond the current standard interventions (ORS and anti-infectives), anti-secretories are seen as an important advance in the management of diarrhea associated dehydration.

Racecadotril (Acetorphan, Bioprojet) is the only currently marketed antisecretory drug for infectious diarrhea. It has received regulatory approval in Europe, is a generic drug in India, but it is not available in the US. It acts by inhibiting neprilysin (enkephalinase) and thus the degradation of enkephalin, an endogenous peptide that inhibits intestinal secretion.

Crofelemer (Napo/Salix/Glenmark) is a Transmembrane Conductance Regulator (CFTR) chloride channel blocker. Inhibitors of the CFTR chloride ion channel have been proposed to be useful for the treatment of acute secretory diarrhea. Crofelemer is a proanthocyanidin oligomer extracted from Croton lecheri. Crofelemer is in clinical trials for treatment of infectious diarrhea, primarily from enterotoxigenic E. coli infection, in adults. Crofelemer also was in clinical trials for the treatment of cholera infection with azithromycin. Crofelemer is in a third trial for treatment of pediatric diarrhea. Crofelemer is said to represent a first in class treatment option for treatment of acute watery diarrhea with or without antibiotics. Some older approaches with antisecretory effect, such as the astringent albumin tannate (circa 1900), have been resurrected as medical food products. Albumin tannate (Tannalbin; Cesinex) is also categorized as an astringent.

iOWH032 (3-(3,5-dibromo-4-hydroxyphenyl)-N-(4-phenoxybenzyl)-1,2,4-oxadiazole-5-carboxamide) (One World Health/Novartis) is a CFTR channel regulator in Phase I clinical trials.

Other (typically anti-inflammatory or immunosuppressive) drugs with known antisecretory effect include Sulfasalazine, Mesalazine, Olsalazine, and Octreotide. These drugs are typically used for inflammatory bowel disease, Crohn's disease, ulcerative colitis, and in AIDS-induced diarrhea.

In some embodiments, the composition comprising colostrum and antibody product further comprises an antisecretory agent. In some aspects, the antisecretory agent is selected from one or more of Racecadotril, Crofelemer, iOWH032, albumin tannate, Sulfasalazine, Mesalazine, Olsalazine, and Octreotide. In specific aspects, the composition comprises colostrum, antibody product and one or more of Racecadotril, Crofelemer, and iOWH032.

Antimotility Drugs

Antimotility drugs are palliative with respect to diarreal symptoms, and do not have an effect on the underlying course of the disease. These agents include loperamide (Imodium) (opioid-receptor agonist), diphenoxylate with atropine (Lomotil) (tropane alkaloid), and opiates such as paregoric, tincture of opium, codeine, and morphine. They operate as a complement to ORS in treatment of infectious diarrhea by diminishing the amount of water that is lost through the stool, either by reducing secretion or increasing the transit time through the GI tract. The antimotility drug Loperamide (Imodium) is an orally administered synthetic piperidine derivative (opioid drug) classified as an antiperistaltic antidiarrheal agent, used for diarrhea of diverse etiology. In some embodiments, the composition comprising colostrum and antibody product further comprises an antimotility drug. In some embodiments, the antimotility drug is selected from loperamide and diphenoxylate.

Egg Bioactive Molecules

The additional active agent may be an isolated egg bioactive molecule. The isolated egg bioactive molecule may be a non-immunoglobulin active molecule. For example, the isolated egg bioactive molecule may be isolated from egg white, egg yolk and/or vitelline membrane. Isolated egg white bioactive molecule include ovalbumin, ovomucoid, ovotransferrin, lysozyme, ovomucin. Isolated egg yolk bioactive molecule may include phosvitin, lipovitellins, livetins, low-density lipoproteins, apovitellenin-1, or vitellogenins. Isolated egg bioactive molecules may include egg antimicrobial proteins, for example, avian beta-defensin, avidin, beta-microseminoprotein-like, cystatin, gallin, lysozyme, ovalbumin-related protein X, ovoglobulinG2/TENP, ovoinhibitor, ovomucin (alpha and or beta subunits), ovotransferrin, phosvitin, pleiotrophin, vitelline membrane outer layer protein 1.

Non-Immunoglobulin Colostrum Components

Previous studies have suggested that colostral fractions, or individual peptides present in colostrum, might be useful for the treatment of certain gastrointestinal conditions such as inflammatory bowel disease, or non-steroidal antiinflammatory drug-induced gut injury, or chemotherapy-induced mucositis. Playford et al., 2000, Am J Clin Nutr 72; 5-14.

In some embodiments, the composition comprises colostrum and antibody product and further comprises an additional active agent comprising one or more non-immunoglobulin colostrum components (colostrum components). The colostrum components may be non-immunoglobulin components found in colostrum and are obtained by one or more of i) further fractionation or processing of one or more of bovine colostrum, or other biological fluids such as milk, blood, plasma or serum to provide fractions enriched in the desired colostrum component(s); ii) commercially available colostrum components; or iii) recombinant colostrum components.

In some embodiments, the additional active agent may be an additional colostrum component are selected from one or more of soluble secretory component, free secretory component, lactoferrin, lysozyme, lactoperoxidase, growth factor, lactalbumin, beta-lactoglobulin, proline-rich polypeptides (PRPs), kappa-caseino glycomacropeptide, clusterin, orotic acid, fats, cytokines, phospholipase, defensins, opsonins, components of the complement system, beta-lysin, transferrin, interleukins, chemokines, interferons, TNF-alpha, fibronectin, leukocytes (including white blood cells), phagocytes (including macrophages, monocytes, neutrophils, polyrnorphonuclear cells, and dendritic cells), mast cells, eosinophils, basophils, natural killer (NK) cells, lymphokine activated killer (LAK) cells, cationic proteins including defensins, proteolytic enzymes including elastase, cathepsin G, myeloperoxidase, and NADPH oxidase components. See Keech, Peptide Immunotherapy. Colostrum, 2009, $2^{nd}$ Ed. AKS Publishing, China. Chapter 6, pp. 67-97, which is incorporated herein by reference.

In some embodiments, the additional active agent may be a colostrum component is a growth factor selected from or derived from one or more of colony stimulating factor-1 (macrophage colony-stimulating factor), epidermal growth factor (EGF), betacellulin, fibroblast growth factor (FGF), granulocyte colony-stimulating factor (G-CSF), insulin-like growth factor 1 (IGF-1), insulin-like growth factor 2 (IGF-2), insulin, insulin-like growth factor binding proteins (IGFBP), platelet-derived growth factor, transforming growth factor-alpha (TGF-α), transforming growth factor-beta (TGF-β), and vascular endothelial growth factor (VEGF).

In some embodiments, the additional active agent may be a colostrum component is a fat selected from one or more of phospholipids, fatty acids (oleic acid, linoleic acid, dihomo-gamma-linoleic acid, alpha-linoleic acid, octadecatetraenoic acid, eicosatrienoic acid, docosahexaenoic acid, docosapenteanoic acid, arachidonic acid), saposins (A, B, C, D), prosaposin, tocopherols, and cholesterol.In some embodiments, the additional active agent is a colostrum component is a cytokine selected from one or more of interleukin-1 (IL-1), IL-1β, IL-1ra, IL-3, IL-4, IL-5, IL-6, IL-8, IL-10, IL-12, IL-13, IL-16, IL-18, interferon-gamma (INF-γ), tumor necrosis factor-alpha (TNF-α) and TNF-α receptors.

Methods

The present invention is based on a method to create a targeted antibody-based formulation combined, embedded or subsumed within a colostrum, where the antibodies use a controlled form of cross-reactivity to multiple clusters of related target antigens, and where the colostrum contains effective amounts of support and cofactors that enhance the effect of the antibodies. The utility of such antibody/colostrum formulations may include providing broad-spectrum therapeutic interventions under conditions where the class of causative agent, but not the precise or specific causative agent is known or suspected or under circumstances where multiple (mixed) causative agents are active.

A novel approach to the use of antibodies in this manner has been developed, that takes advantage of both the specificity and cross-reactive attributes of antibodies, and then further utilizes the components within the colostrum matrix to generate a multi-component in situ immune response. In this embodiment, antibodies are designed to bind to several closely related epitopes that represent a structurally related cluster of antigens. These antigens may differ markedly in other respects, and may originate from diverse sources, organisms, or species.

One embodiment of the invention involves the method of using specific avian antibodies (immunoglobulins), within a colostrum matrix, where the antibodies have specificity to a class of related antigens, and are specifically cross-reactive to different instances of members of that class; and an additional active agent. There exists a degree of structural similarity in related clusters of target antigens, without regard to the organism or pathogen that is the source of the antigen. Similarity in structure can result in a phenomenon known as "cross-reactivity" (the steric binding of a reactive molecule to an antigen other than the antigen intended). Cross-reactivity is often unintentional, and is considered a source of error and nonspecificity. However, in this embodiment the extent and degree of cross-reactivity is controlled by various means to limit and channel its expression so as to provide desired characteristics.

This treatment confers passive immunity to patients. The nature of the treatment makes the associated risk factors comparable to that of eating food from the source where the antibodies were harvested (for example, risk factors would be similar to that of drinking a glass of milk). This is an effective treatment with less toxicity than the currently available alternative medicines.

In some embodiments, the present invention provides methods for conferring immunity to a subject. The methods include administering to the subject a clinically effective amount of the composition of the invention, thereby conferring immunity to the subject. In one aspect, the administering step includes delivery to the gastrointestinal tract, including oral, rectal, sublingual, sublabial, topical and enteral administration as well as administration by gastric feeding tube or gastrostomy. Formulations for administration can be in any practical form, such as powders, liquids, suspensions, capsules, tablets, and soft chews.

In another embodiment, the present invention provides a method for preparing an immunity conferring composition. The method includes (a) obtaining at least one antibody product source of specific avian antibodies; (b) preparing a powderized form of an antibody product comprising at least one specific avian antibodies; (c) obtaining at least one colostrum, optionally containing one or more endogenous specific bovine antibodies; (d) preparing a powderized form of the at least one colostrum; and (e) mixing the powderized form of step (b) with the powderized form of step (d), thereby obtaining the immunity conferring composition. In one embodiment, the immunity conferring composition includes a dose controlled formulation. In various embodiments, the immunity conferring composition includes a pharmaceutically acceptable carrier. In various embodiments, the immunity conferring composition does not include a polymer, copolymer, liposome, hydrogel, or fibrin. In various embodiments, the immunity conferring composition does not include microspheres or microcapsules. In various embodiments, the immunity conferring composition does not include a specific immunogen or antigen.

In embodiments, the method includes at least one of the following distinguishing attributes: (a) it enables customized design of the matrix, specific factors, and the activating events for specified or targeted diseases; (b) it enables dose controlled formulation of a variety of mixtures of components, which may be tuned or adjusted for effect; (c) it enables dose controlled formulation that provides specified components in excess of normal physiological levels that can be achieved in natural systems; (d) it uses complex multi-component multi-pathway interactions to create a systems effect that emulates a native immune system response; (e) it enables creation of a preconditioned or potentiated immune response that can be administered in its potentiated state, and subsequently activated by the presence of the target pathogens, toxins, disease state, or syndrome; (f) it enables the creation of formulations that have a defined specificity or broad-spectrum effect, to match the needs of the specific target disease state or syndrome, or of the practice environment within which the product is to be used; and (g) it enables the creation of formulations that can be targeted for prophylaxis as well as for therapeutic intervention.

In embodiments, the composition is administered as a prophylactic or therapeutic composition.

The compositions of the disclosure comprise a specific antibody (immunoglobulin) embedded within a colostrum and an additional active agent. In various embodiments, the composition is administered as a prophylactic or therapeutic composition. The compositions can be administered in any method suitable to their particular immunogenic or biologically or immunologically reactive characteristics. The composition of the invention can be administered via oral delivery, rectal delivery, enteral delivery, gastric feeding tube, mucosal delivery, or a combination thereof. A specific embodiment involves the oral administration of the composition of the disclosure.

One embodiment of this invention uses oral administration. It has been demonstrated in both human and animal systems that oral (ingested) administration of antibodies, immunoglobulins, and other biological immune factors can have measurable effects on the course, severity and duration on diseases of, in, associated with, or influenced by, the gastrointestinal system.

In some embodiments, the methods and compositions of the invention are used for treatment of a subject with undifferentiated diarrhea as a result of infection by a variety of pathogens or agents including, without limitation, cholera toxin (*Vibrio cholera*), *E. coli* (including enterotoxigenic (ETEC)), *Shigella, Salmonella, Campylobacter, Clostridium difficile*, protozoal parasites (for example, Giardia, *Entamoeba histolytica, Cryptosporidiosis, Cyclospora*), and diarrheal viruses (for example, rotavirus).

In one aspect, the compositions of the disclosure are used to treat patients suffering from various pathogenic infections. The compositions and formulations for oral administration can be administered once, twice, three times, or four times a day for two, three, four, five, six, seven, eight, nine, 10, 11, or 12 consecutive days for the treatment of a pathogenic infection. In one aspect, the composition is administered twice per day for five days for the treatment of a pathogenic infection. In another specific aspect, the composition is administered once per day for three consecutive days for the effective treatment of undifferentiated diarrhea in non-neonatal children, or in the treatment of traveler's diarrhea in non-neonatal children or adults. In another aspect, the composition may be regularly administered for the prophylaxis of a pathogenic infection. In one embodiment, the amount of the composition effective for prophylaxis of a particular infection is the same as the amount effective to treat the same infection. In another embodiment, the amount of the composition effective for prevention, or prophylaxis, of a certain infection is less than the amount effective to treat the same infection. In embodiments, the amount effective to prevent an infection is selected from 20%, 30%, 40%, 50%, 60%, 70%, 80%, 90% or 100% by weight of the amount of the composition effective to treat the same infection.

In the case of a composition for the treatment of a pathogenic infection of a mucosal membrane by topical administration to a mucosal membrane, the composition can be administered two to six times per day for a period of three to 12 days.

In a specific aspect, the composition comprises an equivalent weight amount of dried immune antibody product from each of three herds of cattle inoculated with different antigens or different mixed antigen preparations is co-packaged with a specific weight amount of commercial dried non-hyperimmune bovine colostrum.

In various aspects, the composition includes a pharmaceutically acceptable carrier. In various aspects, the composition does not include a polymer, copolymer, liposome, hydrogel, or fibrin. In various aspects, the composition does not include microspheres or microcapsules. In various aspects, the composition does not include an immunogen or antigen. In one embodiment, 0.1 to 50 g, 0.5 to 30 g, 0.7 to 20 g, 2 to 15 g, or 3 to 10 g, or 0.05 g, 0.1 g, 0.3 g, 0.5 g, 0.7 g, 1.0 g, 1.3 g, 1.5 g, 2 g, 2.5 g, 3 g, 3.5 g, 4 g, 5 g, 6 g, 7 g, 8 g, 9 g, or 10 g, or any number in between, is contained in a single dose packet. In another aspect, 1 to 50 g, 2 g to 40 g, or 3 to 10 g, or 1.0 g, 1.5 g, 2.0 g, 2.5 g, 3.0 g, 3.5 g, 4.0 g, 4.5 g, 5 g, 5.5 g, 6 g, 7 g, 8 g, 9 g, 10 g, 11 g, 12 g, 13 g, 14 g, 15 g, 16 g, 17 g, 18 g, 19 g, 20 g, 25 g, 30 g, 40 g, or 45 g, or any value in between, of dried colostrum is contained in the same single dose packet.

In another embodiment, the additional active agent is utilized in a dry form and is added to the same packet as the colostrum and the antibody product. The additional active agent may be selected from an antibiotic, antifungal, antiviral, antimicrobial, micronutrient, oral rehydration salt, antidiarrheal adsorbant, anticholinergic, antisecretory agent, antimotility drug, isolated egg bioactive molecule, or additional colostrum component, or a combination thereof. In some embodiments, the additional active agent is a micronutrient. n some embodiments, the additional active agent is an antibiotic or an antimicrobial agent. In other embodiments, the additional active agent is an oral rehydration salt.

In one embodiment, prior to use, the contents of the packet, or sachet, are mixed into approximately 2 ounces of purified water, or some other oral liquid. The entire reconstituted formulation is administered orally to the subject in need thereof. The composition can be administered one to four times per day for two to ten days. In a specific embodiment, the composition is administered once per day for 3 consecutive days. In another specific embodiment, one packet is administered once, twice, three, or four or more times a day on a daily basis for 1-30, 3-20, 5-15, or 1, 2, 3, 4, 5, 6, 7, 8, 9, 10, 11, 12, 13, 14, 15, 16, 17, 18, 19, 20, 21, 22, 23, 24, 25, 26, 27, 28, 29, or30 consecutive days, or 1-24 months, 2-18 months, 3-12 months, or 4-9 months. In another embodiment, the composition is administered on a daily basis until alleviation or improvement of one or more symptoms. The disclosure provides a method of treating environmental enteric dysfunction (EED), tropical sprue, TBD, TBS, or severe acute malnutrition, by administration of the composition of the disclosure daily for 7 or more, 14 or more, 28 or more, 56 or more, 84 or more, 112 or more, 140 or more, 168 or more, 252 or more, or 356 or more consecutive days. Daily administration may include administration of the composition one or more, two or more, three or more, or four or more times daily.

When used in the prophylactic mode, a reduced dosage can be optionally be employed wherein the same ratio of antibody preparation to colostrum used for the therapeutic dosage is employed, but optionally one half, one third, or one quarter of the total amount of the composition is packaged and administered daily for a period of potential exposure for example, lasting from between about one day to several months.

In one aspect, the composition of the disclosure is administered as an adjunct therapy to antibiotic treatment. In this aspect, the composition may be administered once per day for the first three days of treatment. In another aspect, the composition of the disclosure is administered with oral rehydration solution (ORS). In another aspect, the composition of the disclosure is co-administered with an oral zinc formulation. In another aspect, the composition of the disclosure is administered as an adjunct to antibiotic treatment to prevent overgrowth of a particular pathogenic organism that is resistant to the antibiotic. As described in detail in the examples, the composition and method is effective to rapidly resolve the symptoms of undifferentiated pediatric diarrhea, resulting in significantly decreased stool volume, stool frequency and duration of diarrhea, as well as significantly improved physician reported well-being.

In one alternative embodiment, the compositions of the disclosure are used to treat traveler's diarrhea. The onset of TD usually occurs within the first week of travel but may occur at any time while traveling, and even after returning home. The most important determinant of risk is the traveler's destination. High-risk destinations are the developing countries of Latin America, Africa, the Middle East, and Asia. Persons at particular high-risk include young adults, immunosuppressed persons, persons with inflammatory-bowel disease or diabetes, and persons taking H-2 blockers or antacids. Most TD cases begin abruptly. The illness usually results in increased frequency, volume, and weight of stool. Altered stool consistency also is common. Typically, a traveler experiences four to five loose or watery bowel movements each day. Other commonly associated symptoms are nausea, vomiting, diarrhea, abdominal cramping, bloating, fever, urgency, and malaise.

Infectious agents are the primary cause of TD. Bacterial enteropathogens cause approximately 80% of TD cases. The most common causative agent isolated in countries surveyed has been enterotoxigenic *Escherichia coli* (ETEC). ETEC produce watery diarrhea with associated cramps and low-grade or no fever. Besides ETEC and other bacterial pathogens, a variety of viral and parasitic enteric pathogens also are potential causative agents.

In one aspect, the composition of the disclosure is administered to the subject once per day for three consecutive days as an alternative or adjunct to antibiotic treatment of traveler's diarrhea. Limited field study evidence suggests improvement in diarrheal symptoms within 24 or 48 hours of the first dose. Alternatively, two doses per day of the composition of the disclosure are administered on day 1, followed by a single dose on days 2 and 3. In one aspect, the composition of the disclosure is administered on an alternate daily or weekly schedule, or on a reduced dosage schedule to for prophylaxis of traveler's diarrhea.

In another alternative embodiment, the compositions of the disclosure may be used for gastrointestinal flora management of a subject, for example, to reduce or eliminate small intestinal bacterial overgrowth (SIBO). As used herein, the term "prebiotic" refers to a composition that allows specific changes, both in the composition and/or the activity of the gastrointestinal microflora that confers benefits upon the subject's well-being and health. In one aspect, the composition is useful to manage gastrointestinal flora so as to reduce or eliminate one or more undesirable strains of bacteria. In one aspect, the anti-antigenic immunoglobulin composition is tailored to manage gastrointestinal flora so as to reduce or eliminate one or more undesirable strains of bacteria.

In another aspect, the disclosure provides a method of gastrointestinal flora management in a subject comprising the steps of administering the composition of the disclosure to reduce or eliminate one or more undesirable strains of bacteria. In another aspect, the composition of the disclosure is administered as an adjunct to antibiotic treatment to prevent overgrowth of a particular pathogenic organism that is resistant to the antibiotic.

Carriers and Excipients

In some embodiments, the composition comprises a colostrum, an immune egg antibody product, optionally an additional active agent, and further comprises a pharmaceutically acceptable carrier or excipient. In various embodiments, the composition does not include a polymer, copolymer, liposome, hydrogel, or fibrin. In various aspects, the composition does not include microspheres or microcapsules. In some embodiments, the composition does not include an immunogen or antigen. In some embodiments, the composition further comprises a buffer, flavoring, coloring, rehydration salts or excipients.

In some embodiments, the composition comprises a colostrum, an antibody product derived from a different species than the colostrum and an additional active agent and further comprises a carrier medium, such as fructo-oligo-saccharides (FOS), or other soluble fiber, sugar, nutrient or base material, mannitol, inulin, polydextrose, arabinogalactan, polyolslactulose, lactitol, etc. The carrier medium can comprise an oligosaccharide selected from the group consisting of fructo-, galacto-, malto-, isomalto-, gentio-, xylo-, palatinose-, soybean- (includes raffinose and stachyose), chito-, agaro-, neoagaro-, .alpha.-gluco-, .beta.-gluco-, cyclo-inulo-, glycosylsucrose, lactulose, lactosucrose and xylsucrose. In some embodiments, the composition further comprises a carrier medium and is incorporated in an oral dose form such as a pill, capsule, powder or sachet.

In some embodiments, a lipid-based nutrient supplement (LNS) carrier formulation may be employed. The LNS carrier may include macronutrients including protein, carbohydrates and fats. The LNS carrier may include from 10-15 g protein, 30-40 g fat, and 90-140 g carbohydrate on a daily equivalent basis. For example the LNS carrier may include (i) at least one powdered protein product which provides proteins selected from skimmed milk powder, powdered yogurt, defatted soy flour, or whey; (ii) at least one product that supplies additional carbohydrates, for example, selected from sucrose, glucose, fructose, maltodextrin, skimmed milk, whey, or flour made from maize, wheat, millet, oats, rice, *quinoa*, cassava, or potato starch, and (iii) at least one product that supplies lipids, selected from the group consisting of vegetable fats, such as a vegetable oil, and animal fats. The fats may include linoleic acid from 4-7 g daily, and alpha-linolenic acid at from 0.5 to 0.8 g daily. The composition may also comprise a lipid-rich substance derived from oleaginous seeds, for example, selected from peanuts, cocoa, beans, almonds, walnuts, hazelnuts, coconuts, and pistachio nuts. In one example, the LNS carrier may comprise skimmed milk powder, whey, maltodextrin, sucrose, micronutrient blend, peanut paste, and a plant-based fat.

Another embodiment of the present invention relates to the pharmaceutical acceptable diluents for formulating the composition, wherein said pharmaceutical acceptable diluents are selected from the group consisting of a lactose, mannitol, sorbitol, microcrystalline cellulose, sucrose, sodium citrate, dicalcium phosphate, or any other ingredient of the similar nature alone or in a suitable combination thereof; binder selected from the group consisting of gum tragacanth, gum acacia, methyl cellulose, gelatin, polyvinyl pyrrolidone, starch or any other ingredient of the similar nature alone or in a suitable combination thereof, excipients selected from the group consisting of agar-agar, calcium carbonate, sodium carbonate, silicates, alginic acid, corn starch, potato tapioca starch, primogel or any other ingredient of the similar nature alone or in a suitable combination thereof, lubricants selected from the group consisting of a magnesium stearate, calcium stearate or steorotes, talc, solid polyethylene glycols, sodium lauryl sulfate or any other ingredient of the similar nature alone; glidants selected from the group consisting of colloidal silicon dioxide or any other ingredient of the similar nature alone or in a suitable combination thereof; a sweetening agent selected from the group consisting of such as sucrose, saccharin or any other ingredient of the similar nature alone or in a suitable combination thereof, a flavoring agent selected from the group consisting of peppermint, methyl salicylate, orange flavor, vanilla flavor, or any other pharmaceutically acceptable flavor alone or in a suitable combination thereof; wetting agents selected from the group consisting of acetyl alcohol, glyceryl monostearate or any other pharmaceutically acceptable wetting agent alone or in a suitable combination thereof; absorbents selected from the group consisting of kaolin, bentonite clay or any other pharmaceutically acceptable absorbents alone or in a suitable combination thereof, retarding agents selected from the group consisting of wax, paraffin, or any other pharmaceutically acceptable retarding agent alone or in a suitable combination thereof.

In some embodiments, the composition further comprises a flow agent. For certain applications, ingredients may be required to flow freely and not agglomerate. Flow agents may be utilized to prevent agglomeration or clumping of the compositions, colostrums, or antibody products of the composition. In certain embodiments of the present disclosure, the free-flowing composition may further comprise a flow agent. In some embodiments, the flow agent is a food grade flow agent. In some embodiments, the flow agent is a pharmaceutically acceptable flow agent. In some embodiments, the flow agent is selected from the group consisting of silicon dioxide, calcium stearate, magnesium stearate, maltodextrin, shellac, kaolin, kaolinite, calcium phosphate, tricalcium phosphate, sodium bicarbonate, potassium bicarbonate, sodium ferrocyanide, powdered cellulose, silicate, stearic acid and salts thereof, talcum, a starch, and combinations of any thereof. In some embodiments, the flow agent is present in the composition at 1-30% total weight (w/w) of the composition, on a dry weight basis.

In some embodiments, flavorings and synthetic sweeteners can also be used such as acesulfame potassium, and sucralose. The troche, powder, tablet, capsule, soft chew and caplet forms of the disclosure may comprise, aside from those components specified above, other various additives, such as vehicle, binder, disintegrating agent, lubricant, thickener, surfactant, osmotic pressure regulator, electrolyte, sweetener, flavoring, perfume, pigment, pH regulator and others appropriately as required.

Additives may include starches such as wheat starch, potato starch, corn starch, and dextrin, sugars such as sucrose, glucose, fructose, maltose, xylose, and lactose, sugar alcohols such as sorbitol, mannitol, maltitol, and xylitol, isotransposable glycosides such as coupling sugar and paratinose, vehicles such as calcium phosphate and calcium sulfate, binders and thickeners such as starch, sugar, gelatin, gum arabic, dextrin, methyl cellulose, polyvinyl pyrrolidone, polyvinyl alcohol, hydroxy propyl cellulose, xanthan gum, pectin, tragacanth gum, casein, and alginic acid, lubricants such as leucine, isoleucine, valine, sugar-ester, hardening oil, stearic acid, magnesium stearate, talc, and macrogol, disintegrating agents such as avicel, CMC, CMC-Na and CMC-Ca, surfactants such as polysorbate and lecithin, and sweeteners such as sugars, sugar alcohols, aspartame, alitame, other dipeptides, *stevia*, and saccharin, and they may be used in proper amounts selectively in consideration of the relation with the essential components, property of the composition, manufacturing method, etc.

In another embodiment, compositions of the disclosure can optionally further comprise one or more flavoring agents. The optional flavoring agent is added to increase patient acceptability and compliance with the recommended dosing schedule. The flavoring agents that may be used include those flavors known to the skilled artisan, such as natural and artificial flavors. These flavorings may be chosen from synthetic flavor oils and flavoring aromatics and/or oils, oleoresins and extracts derived from plants, leaves, flowers, fruits, and so forth, and combinations thereof. Non-limiting representative flavor oils include spearmint oil, cinnamon oil, oil of wintergreen (methyl salicylate), peppermint oil, clove oil, bay oil, anise oil, *eucalyptus* oil, thyme oil, cedar leaf oil, oil of nutmeg, allspice, oil of sage, mace, oil of bitter almonds, and *cassia* oil. Also useful flavorings are artificial, natural and synthetic fruit flavors such as vanilla, and citrus oils including, without limitation, lemon, orange, lime, grapefruit, and fruit essences including apple, pear, peach, grape, strawberry, raspberry, cherry, plum, pineapple, apricot, mango, *papaya*, as well as peppermint, menthol, artificial vanilla, cinnamon derivatives, and other various fruit flavors, whether employed individually or in admixture. Other useful flavorings include aldehydes and esters such as cinnamyl acetate, cinnamaldehyde, citral diethylacetal, dihydrocarvyl acetate, eugenyl formate, p-methylamisol, and so forth may be used. These flavoring agents may be used in liquid or solid form and may be used individually or in admixture. The flavor is optionally present from about 0.1% to about 5% by weight of the composition.

In another aspect, the daily dose for the non-neonate human is standardized by any method of quantifying the specific antibodies. In one aspect, the dose of the composition is standardized by use of an ELISA to evaluate the concentration of specific anti-antigen antibody in the formulation. In one aspect, one dose of the oral composition effective to treat a pathogenic infection contains antigen-specific binding molecule in an amount from about 0.0001 mg to 20 mg; from 0.001 mg to 15 mg; from 0.01 to 10 mg; from 0.05 to 5 mg; from 0.1 to 1 mg of mixed antigen specific antibodies.

The term "solid form" refers to a dried form of a specific binding molecule, or a dried form of a carrier matrix, or a solid dosage form comprising both the dried specific binding molecule and the carrier matrix as a powder, compressed tablet, soft chew, troche, or capsule. In one aspect, the solid dosage form is intended for oral administration. In one aspect, the powder is a formulation for suspension. In one aspect, powdered dried antibody product, powdered dried colostrum, and a dry powder additional active agent, are combined and packaged in an airtight packet. Immediately prior to oral administration, the contents of the packet are suspended, or dissolved, in about a liquid and administered orally.

In one aspect, the composition may also be provided in a liquid form. The liquid form may be suitable for oral administration.

In one aspect, one dose contains 2 g-10 g of dried immune egg antibody product; 2 g-10 g of dried bovine colostrum; and an additional active agent in an amount about equivalent to that used alone in standard of care. In one aspect, one dose of the dried dosage form contains 2-10 g dried antibody product and 2-10 g dried bovine colostrum and 20 mg zinc gluconate. In one aspect, one dose of the dried dosage form contains 3 g dried antibody product, 4 g dried bovine colostrum and 300 mg metronidazole. In one aspect, one dose of the dried dosage form contains 3 g dried antibody product, 4 g dried bovine colostrum, and 37.5 mg zinc carnosine.

The dose of additional active agent is tailored to the category and dosage as known in the art. In another aspect, the contents of a single dose packet are dissolved in about 2 ounces of water and administered orally.

In some embodiments, the formulation comprising the specific binding molecule is a dry solid (antibody product powder) formulation. The powdered formulation is sealed in airtight packets, optionally layered with an inert gas. The formulation can be stored for extended periods of time at room temperature, under refrigeration, or frozen temperatures. In other embodiments, the dried composition is formulated into capsules or tablets for oral administration. In another embodiment, the formulation is compressed into chewable tablets.

Formulations for oral use may also be prepared as troches, chewable tablets, soft chews, or as hard gelatin capsules wherein the active ingredient is mixed with an inert solid diluent (for example, potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, for example, a mixer, a fluid bed apparatus or a spray drying equipment.

The colostrum carrier matrix is a protective and reactive matrix for combination with the antigen-specific binding molecules. In another aspect, the compositions of the disclosure are provided in a powdered, solid form for suspension immediately prior to administration. In one aspect, the suspended, or reconstituted, dosage form has the advantage of being very palatable to infants and children, even when suffering from the symptoms of a pathogenic infection. This has the advantage that the full dose is easily administered and ingested by the subject suffering from the pathogenic infection. In some embodiments, the compositions are provided in a liquid form.

It is to be understood that the embodiments of the invention herein described are merely illustrative of the application of the principles of the invention. Reference herein to details of the illustrated embodiments is not intended to limit the scope of the claims, which themselves recite those features regarded as essential to the invention. The following examples are intended to illustrate but not limit the invention.

EXAMPLES

Example 1. Compositions for the Treatment or Prevention of Infectious Diarrhea, Enteric Infection, or Diseases or Conditions Associated with Inflammation or Damage of the Gastrointestinal Tract Infectious diarrhea, enteric infection, or small intestinal bacterial overgrowth may be a pre-condition or subclinical condition associated with inflammatory diseases and conditions of the gastrointestinal tract as provided herein.

Diarrhea is a symptom of a broad range of causes including bacterial, viral, protozoal and parasitic infections. Bacterial diarrhea is induced by multiple organisms, including various forms of *Escherichia coli, Salmonella, Vibrio cholerae* and *parahemolyticus, Shigella, Campylobacter, Yersinia* and others. Viral pediatric diarrhea is often caused by Rotavirus, but also may be caused by several other viruses. Current treatment of rotovirus infection is non-specific and involves management of symptoms and hydration. In 2004, the WHO and UNICEF recommended the use of low-osmolarity oral rehydration solution and zinc supplementation as a two-pronged treatment of acute diarrhea.

There are known to be multiple causative organisms in infectious diarrhea or enteric infection. These causative organisms can be organized into common clusters that produce structurally related toxins, to which a series of broad-spectrum neutralizing antibodies can be created that, when admixed into a formulation with clinically effective titers, can be used as a broad-spectrum organism-independent therapeutic intervention for toxin-mediated diarrhea.

In some embodiments, the composition comprises bovine colostrum, immune egg, and a zinc supplement. Briefly, immune egg comprising antibodies specific to one or more, two or more, three or more, or a multiplicity of causative organisms of diarrhea are generated by inoculation of chickens with antigen. Immune eggs are collected and whole egg may be pasteurized and spray dried to obtain a powderized form. Commercial bovine colostrum is mixed in a powderized form. A dry powderized zinc supplement salt is selected from zinc carnosine, zinc sulfate, zinc acetate, zinc citrate, zinc oxide, zinc gluconate, zinc monomethionine, zinc picolinate, or zinc glycinate and is added at an equivalent dose of 1 mg to 40 mg per dose. Additional micronutrients may be added or co-packaged in a kit for co-administration. The powders are prepared in bulk form or may be added sequentially to a single dose packet and sealed, and distributed in dried form for an oral formulation. The bulk form may be further processed. Alternatively, the three ingredients are mixed and then added to a single dose packet, then sealed. Before administration, the powdered oral formulation may be mixed with a small quantity of water prior to oral consumption.

This treatment confers passive immunity to patients, as demonstrated in the Examples herein. The nature of the treatment makes the associated risk factors comparable to that of eating food from the source where the antibodies were harvested (for example, risk factors would be similar to that of eating an egg and a glass of milk). This is an effective treatment with less toxicity than the currently available alternative medicines.

Example 1A. Chickens were individually inoculated with purified antigens derived from 5 *E. coli* strains: four ATCC strains, containing *E. coli* adherence pili antigens F41, 97P, F19 and K99, and one wild type *E. coli* strain derived from milk. Each chicken was inoculated with only one antigen. Chickens were inoculated once per week for three weeks. Freund's adjuvant was employed for the first inoculation, followed by Freund's incomplete adjuvant for the second and third inoculations. Two shots, left and right breast were used per inoculation. Eggs were housed separately; after a period of time eggs were collected, flash pasteurized and spray dried. Each of the five antibody preparations were mixed in equal parts. The dried egg powder anti-*E. coli* antibody preparation was stored frozen for up to about 2 years.

A second flock of chickens was inoculated with a mixed antigen preparation containing rotavirus, coronavirus and *E. coli* antigens. The same inoculation, collection and egg processing protocols were employed as above. The dried egg powder anti-scours antibody preparation was stored frozen for 1.5 years. ELISA was used to characterize the antibody preparations.

One gram each of the dried anti-*E. coli* antibody preparation and the dried anti-scours antibody preparation were added with 3 grams or 4 grams of commercial dried full-fat bovine colostrum in a single dose packet. In some embodiments, 20 mg of zinc carnosine, zinc gluconate, or zinc acetate dehydrate can be added per single dose packet.

Example 1B. Three flocks of chickens were individually inoculated with one each of different mixed antigen preparations: a first antigen preparation containing rotavirus (serotypes G6 and G10), coronavirus, enterotoxigenic *E. coli* stains with K99 pili adherence factor, and *Clostridium perfringens* type C toxoid with adjuvant); a second preparation containing enterotoxigenic strains of *E. coli* having K99, K88, 987P or F41 adherence factors); and a third mixed antigen preparation containing various *E. coli* endotoxin; with adjuvant). Each of three flocks only received a single mixed antigen preparation. The commercial laying hens also were inoculated with *salmonella* vaccine. Eggs were collected, cleaned, broken, pasteurized and spray dried or thermal dried to create three dried immune egg products. Dried egg product was optionally evaluated by ELISA for specific IgY activity. An equal weight of each of the three dried immune egg products was combined with 3 g or 4 g of dried colostrum in a single dose packet. Either 2 g, 3 g, or 4 g of combined weight of dried immune egg product was employed per single dose packet, as described below. In one aspect, the commercial dried colostrum did not exhibit specific activity toward the antigens of the vaccines.

Example 1C. Different flocks of chickens are individually inoculated with one each of different mixed antigen preparations. In some embodiments, the mixed antigen preparations are prepared with two or more, three or more, four or more, five or more, six or more, or seven or more antigenic preparations selected from rotavirus, norovirus, calicivirus, enteric adenovirus, coronavirus, parvovirus, cytomegalovirus, astrovirus, herpes zoster virus, *Clostridium* spp., *Clostridium perfringens, Clostridium perfringens* type C toxoid, *Clostridium difficile, Clostridium perfringens* enterotoxin, *Clostridium* perfiingens, *Clostridium difficile*, perfringolysin 0 produced by *Clostridium perfringens* type C or type B, enteropathogenic *E. coli* (EPEC) strains, typical EPEC strains, atypical EPEC (aEPEC) strains, enterotoxigenic *E. coli* (ETEC) strains, enteroinvasive *E. coli* (EIEC) strains, enterohemorrhagic *E. coli* (EHEC) strains, Shiga toxin-producing *E. coli* (STEC) strains, enteroaggregative *E. coli* (EAEC) strains, diffusely adherent *E. coli* (DAEC) strains, *E. coli* K99 pili adherence factor, *E. coli* K88 pili adherence factor, *E. coli* 987P pili adherence factor, *E. coli* F41 pili adherence factor, *E. coli* F41 pili adherence factor, *E. coli* endotoxin, *Campylobacter* spp., *Shigella* spp., *Salmonella* spp., *Salmonella typhimurium, Salmonella enterica* serovar *Typhi*, endotoxin derived from gram negative bacteria (LPS, lipopolysaccharides), *Plesiomonas shigelloides Vibrio cholera, Vibrio cholerae* O1, *Vibrio* O139, Non-O1 Vibrios, *Vibrio parahaemolyticus, Aeromonas hydrophila, Candida* spp., enterohepatic *Helicobacter* (including *Helicobacter pylori*), *Staphylococcus aureus, Klebsiella*, Cholera toxin, *Staphylococcus aureus*, Staphylococcal Enterotoxin B, *Yersinia enterocolitica, Shigella dysenteriae, Shiga toxin, Campylobacter jejuni, Campylobacter jejuni* enterotoxin, *E. coli* heat stable enterotoxins LT and LT-II, alpha-toxin (CPA), beta-toxin (CPB), epsilon-toxin (ETX), enterotoxin, beta2-toxin (CPB2), lipooligosaccharides (LOS), *Bacillus thuringiensis Bacillus thuringiensis* delta endotoxin, *Fusarium* spp., *Fusarium* mycotoxin, Trichothecenes, Zearalenone, *Aspergillus* spp., *Aspergillus* mycotoxin, Aflatoxins, Ochtatoxin A, Patulin, *Gibberella* spp., *Gibberella* mycotoxins, Fumonisins, Fusarin C, *Penicillium* spp., *Penicillium* mycotoxins, Patulin, Citrinin, Ochratoxin A, Cyclopiazonic acid, *Byssochlamys* spp., *Byssochlamys* mycotoxins, Patulin, *Claviceps* spp., *Claviceps* mycotoxins, Ergot alkaloids, *Alternaria, Alternaria* mycotoxins, Alternariol, Tenuazonic acid, *Gardnerella* spp., *Listeria monocytogenes, Neisseria gonorrhoeae, Chlamydiaceae trachomatis, Mycoplasma* spp., *Trichomonas vaginalis*, herpes virus type 1, herpes virus type 2, *Candida albicans, Candida glabrata, Candida tropicalis, Candida parapsilosis, Candida krusei*, Group A *Streptococcus* spp., *Giardia* spp., *Entamoeba* spp., *Acanthamoeba* spp., *Cryptosporidium* spp., *Cyclospora* spp., *Taenia* spp., *Taenia saginata, Taenia solium, Ancylostoma duodenale, Necator americanus, Ancylostoma caninum*, and *Ascaris lumbricoides* preparations.

The mixed antigenic preparation may include one or moe, two or more, three or more, four or more, or five or more of a rotavirus preparation, coronavirus preparation, enterotoxigenic *E. coli* strain, enteropathogenic *E. coli* strain, atypical enteropathogenic *E. coli* strain, *Camphylobacter jejuni* preparation, *Shigella dysenteriae* preparation, *E. coli* strain with K99 pili adherence factors, *Clostridium perfringens* type C toxoid, *Clostridium difficile* preparation, *Vibrio cholera* 01 preparation, enterotoxigenic strain of *E. coli* having K88 adherence factors, Clostridiumperfringens preparation, *Yersinia enterocolitica* preparation, strain of *E. coli* having F19 pili adherence factors, *E. coli* endotoxin preparation, enterotoxigenic strain of *E. coli* having 987P pili adherence factors, a Norovirus preparation, enterotoxigenic strain of *E. coli* having F41 pili adherence factors, or a wild-type isolated strain of *E. coli*.

Alternatively, a single flock of chickens may be individually inoculated with a single mixed antigen preparation.

An adjuvant may be used to enhance the immune response of the animal. For example, following a period of time, each flock of chickens may be boosted with the same antigenic preparation.

Eggs are collected, cleaned, broken, pasteurized and spray dried or thermal dried to create three dried immune egg products. Dried egg product is optionally evaluated by ELISA for specific IgY activity. One or more dried immune egg products may be combined with dried bovine colostrum. For example, a dried powdered mixture may be prepared comprising dried immune egg and dried bovine colostrum in a weight ratio of from about 1:5 to 5:1, 1:3 to 3:1 or about 1:2 to 2:1, and optionally one or more pharmaceutically acceptable excipients, diluents, or one or more additional active ingredients. For example, a composition may include 0.5 g to 50 g, 1 g to 30 g, 2 g to 20 g, 3 g to 10 g, or 3 g, 4 g, 5 g, 6 g, 7 g, 8 g, 9 g, 10 g, 11 g, 12 g, 13 g, 14 g, or 15 g, or any intermediate amount, of dried bovine colostrum combined with 0.5 g to 50, 1 g to 30 g, 2 g to 20 g, 2 g to 10 g, 2 g to 4 g, or about 2 g, 3 g, 4 g, 5 g, 6 g, 7 g, 8 g, 9 g, 10 g, 11 g, 12 g, 13 g, 14 g, or 15 g, or any intermediate amount, of dried immune egg product per single dose, as described below. The bovine colostrum may be non-hyperimmune colostrum. The colostrum may be whole colostrum. The immune egg may be whole immune egg. The weight ratio of dried colostrum to dried immune egg may be from 10:1 to 1:10, 5:1 to 1:5, or 3:1 to 1:3. The weight ratio of dried egg to dried colostrum may be about 20:80 to about 80:20, about 30:70 to about 70:30, about 50:50, or about 40:60. The dried immune egg may be dried whole immune egg, dried yolk of immune egg, or dried defatted immune egg, or dried defatted egg yolk. The dried bovine colostrum may be whole or full-fat standard colostrum which may have been collected over the first 48 hours, first 36 hours, first 24 hours, or first milking after calving. Alternatively, the dried bovine colostrum may defatted. The dried bovine colostrum may be non-hyperimmune colostrum, in which the cow has not been vaccinated beyond the recommendations for health of the animal. In some embodiments, about 1-50 mg, 10-30 mg, or about 20 mg of an organic zinc salt, for example, zinc carnosine, zinc gluconate or zinc acetate dehydrate may be added to the composition per single dose.

Example 1D. Immunization of Chickens for IgY Production.

The following immunization protocol was adapted from a Gallus Immunotech, Inc. protocol and can be utilized for generation of IgY polyclonal antibodies. A few eggs are optionally collected prior to immunization to serve as a baseline control. If a mixed antigen preparation is employed, it may be diluted at 1:2, 1:4, 1:8, 1:16, 1:32 or more prior to administration. On day 0, chickens are injected with between 0.02 and 0.5 mg antigen with Freund's complete adjuvant. Injections can be either subcutaneous or intramuscularly into the breast tissue of the hen at multiple sites. The total volume of antigen/adjuvant mixture can be about 1 mL with adjuvant from one-half to two-thirds of the volume. Immunizations are repeated, typically, on days 14, 21 and 28, using Freund's incomplete adjuvant, with about half the initial amount of antigen. Typically, specific antibody can be detected at about day 30 in eggs. For prolonged antibody production, hens are boosted every couple of months. Eggs can be stored in cold storage prior to processing and/or purification of IgY. In one aspect, eggs can be held in cold storage for up to one month, or up to two months, prior to processing or purification. In another aspect, IgY can be generated in a similar fashion in duck, goose, ostrich, quail, or turkey eggs, with use of appropriate amounts of antigen.

Example 2. ELISA Assay to Determine Antibody Titer

Generally, the antigen used for bovine immunization in order to raise antigen-specific antibodies is coated to an ELISA plate. After blocking the plate to reduce non-specific binding, the antibody-containing crude, isolated or purified preparation is tested for antigen-specific antibody titer. Any appropriate ELISA assay can be employed to assess antibody titer. For example, WO2004/078209, Example 7, page 27, which is incorporated herein by reference, may be adapted to coat other antigens to the ELISA plate. *E. coli* cells are coated to the microtiter plate. The assay is an antibody titer assay and color development is catalyzed by goat anti-bovine IgG-peroxidase conjugate.

For example, 0.5 micrograms of heat-killed *E. coli* cells in 100 uL carbonate-bicarbonate coating buffer is dispensed into each well of a 96-well MAXISORP™ immunoplate (Nunc, Roskilde, Denmark), and left at 4° C. overnight. Plates are washed 6 times in PBS-0.05% TWEEN® (polysorbate) buffer, comprising 137 mM NaCl, 1.5 mM $KH_2PO_4$, 8 mM $Na_2HPO_4$, pH 7.4. 100 µL of each test serum or colostrum, diluted in PBS-TWEEN® containing 12 mg/ml casein, are added to each well and incubated at 37° C. for 2 h. Plates are washed 6 times in PBS-TWEEN® buffer, after which 100 uL goat anti-bovine IgG-peroxidase conjugate (Southern Biotechnology Associates, Inc., Birmingham, AL, USA), diluted 1:4000 in PBS-TWEEN®-casein, are added to each well. Plates are incubated for 1 h at 37° C. and washed 6 times. 100 uL peroxidase substrate (Kirkegaard and Perry Lab. Inc., Gaithersburg, MD, USA) is added to each well and left at room temperature until color develops. The reaction is stopped by the addition of 2 M sulfuric acid and the plates are read in a Diagnostics Pasteur LP400™ plate reader (Sanofi, Marnes-la-Coquette, France) at 450 nm. Results are expressed as the mean net O.D. (after subtraction of the blank reaction) of duplicate wells assayed on at least two separate occasions.

Example 3. Combinations

Example 3A. Combination Kit with Micronutrients.

A kit is provided having a composition comprising whole bovine colostrum and specific antibody preparation of Example 1B in individual 7 g dose packets comprising 3 g dried whole immune egg and 4 g dried whole bovine colostrum (PTM202). The kit further comprises packets comprising a daily dose of a combination of micronutrients sprinkles to be added to food immediately prior to consumption. The micronutrient (MNP) sprinkles included a 22-micronutrient composition according to Formula A in a daily packet form comprising Vitamin A, 300 µg; Vitamin D, 5 µg; Vitamin E, 6 mg; Vitamin C, 30 mg; Thiamin, 0.5 mg; Riboflavin, 0.5 mg; Vitamin B-6, 0.5 mg; Vitamin B-12, 0.5 µg; Niacin, 6 mg; Folic acid, 160 µg; Iron, 10 mg; Zinc, 10 mg; Copper, 0.5 mg; Selenium, 20 µg; Iodine, 90 µg; Calcium, 100 mg; Magnesium, 20 mg; Phosphorus, 100 mg; Manganese, 0.6 mg; Vitamin K, 20 µg; Pantothenic acid, 1.8 mg; and Biotin, 6 µg. This micronutrient composition is disclosed in Shafique et al. 2016, Am J Clin Nutr doi: 10.3945/ajcn.115.117770. pp. 1-13, which is incorporated herein by reference. The kit may be used in the treatment or prevention of environmental enteric infection, as illustrated in example 4 herein.

Example 3B. Combination Composition with Micronutrients.

A composition may be provided comprising whole colostrum and specific antibody preparation of Example 1B in individual single dose packets comprising 3 g dried whole immune egg, 4 g dried whole bovine colostrum, Vitamin A, 300 µg; Vitamin C, 30 mg; Folic acid, 160 µg; Iron, 10 mg; and Zinc, 10 mg.

Example 3C. Combination Kit with Zinc Carnosine.

A kit is provided having a composition comprising whole colostrum and specific antibody preparation of Example 1B in individual 7 g dose packets comprising 3 g dried whole immune egg and 4 g dried whole bovine colostrum. The kit further comprises the micronutrient zinc carnosine in a capsule, tablet, or powder single dose form of 25 mg, 37.5 mg, 50 mg, 75 mg, 100 mg, 150 mg, 200 mg, or 250 mg.

Example 3D. Combination Composition with Zinc Carnosine.

A composition is provided comprising whole colostrum and specific antibody preparation of Example 1B in individual 7 g dose packets comprising 3 g dried whole immune egg and 4 g dried whole bovine colostrum and further comprising 35.7 mg zinc carnosine.

Example 3E. Kit Combination with Oral Rehydration Salts.

The formulation comprising whole colostrum and dried immune egg according to of Example 1B, is further combined in a kit with oral rehydration salts. One gram of each of three dried immune antibody products can be combined with 4 g of dried non-hyperimune whole colostrum and sealed in a first single dose packet. Trisodium citrate dihydrate 2.9 g, sodium chloride 2.6 g, potassium chloride 1.5 g and glucose, anhydrous 13.5 g are added to a second single dose packet. Zinc gluconate 20 mg or zinc acetate 20 mg can optionally be added to the second single dose packet. In a typical usage, the first single dose packet is reconstituted with 2 ounces of water and administered orally to the subject. The second packet is reconstituted into 1 L of water and co-administered orally to the subject. The co-administration of the reconstituted second packet may occur before or after administration of the reconstituted first single dose packet; however, it should be administered within the same day. The first and/or second dose packet may also comprise a coloring or flavoring as described herein.

Example 3F. Combination with Antibiotics.

The formulation comprising whole colostrum and specific antibody preparation of Example 1B can be coadministered with an antibiotic. Alternatively, the composition comprising immune egg and dired colostrum may be combined with an antibiotic. A composition is provided comprising 3 g dried immune egg antibody products combined with 4 g of dried non-hyperimune whole colostrum in a single dose packet. 250 mg of ciprofloxacin hydrochloride is added to the packet.

Example 3G. Combination kit with Micronutrients.

A kit is provided having a composition comprising whole bovine colostrum and specific antibody preparation of Example 1B in individual 10 g dose packets comprising 4.3 g dried whole immune egg and 5.7 g dried whole bovine colostrum (PTM1001). The kit further comprises packets comprising a daily dose of a combination of micronutrients sprinkles to be added to food immediately prior to consumption. The micronutrient (MNP) sprinkles include a 22-micronutrient composition according to Formula A in a daily packet form comprising Vitamin A, 300 µg; Vitamin D, 5 µg; Vitamin E, 6 mg; Vitamin C, 30 mg; Thiamin, 0.5 mg; Riboflavin, 0.5 mg; Vitamin B-6, 0.5 mg; Vitamin B-12, 0.5 µg; Niacin, 6 mg; Folic acid, 160 µg; Iron, 10 mg; Zinc, 10 mg; Copper, 0.5 mg; Selenium, 20 µg; Iodine, 90 µg; Calcium, 100 mg; Magnesium, 20 mg; Phosphorus, 100 mg; Manganese, 0.6 mg; Vitamin K, 20 µg; Pantothenic acid, 1.8 mg; and Biotin, 6 µg. This micronutrient composition is disclosed in Shafique et al. 2016, Am J Clin Nutr doi: 10.3945/ajcn.115.117770. pp. 1-13, which is incorporated herein by reference. The kit may be used in the treatment or prevention of environmental enteric infection, as illustrated in example 9 herein.

Example 4. Treatment of Environmental Enteric Dysfunction (EED)

A prospective, randomized, trial in malnourished Bangladeshi children was conducted to assess test article PTM202 in the treatment of Environmental Enteric Dysfunction (EED). Children aged 6 to 9 months were screened for enrollment which included a physical exam, anthropometry, and measurement of serum creatinine, aspartate aminotransferase (AST) and alanine aminotransferase (ALT). Children with known medical conditions, abnormal liver or renal testing, or whose weight-for-age Z score (WAZ) was greater than −1 SD or less than −3 SD were excluded. 200 6 to 9 month old children who exhibited moderate wasting, normal liver and kidney function and no known medical conditions were randomized (100 children per arm) to receive either PTM202 plus micronutrient sprinkles (intervention arm) or micronutrient sprinkles alone (control arm) for 30 days via directly observed therapy. PTM202 was administered 7 g twice daily with micronutrient sprinkles. Families were visited twice per day on days 0 to 30 by field workers who administered 12 of the daily dose at each visit. Biomarkers of EED (Reg 1B, C-reactive protein (CRP), sCD14, Lactulose:Mannitol [L:M] ratio, and myeloperoxidase [MPO]) and glucose hydrogen breath testing for small intestine bacterial overgrowth were assessed both at enrollment and on day 30 of the intervention. Anthropometry was collected prior to the start of the intervention (day 0) and on days 30, 60, and 90.

Specific objectives included the determination of the effectiveness of PTM202 with micronutrient powder (MNP), compared to MNP alone, in treating EED, as measured by fecal Reg 1B, fecal myeloperoxidase (MPO), serum C-reactive protein (CRP), serum soluble CD14 (sCD14), and the lactulose mannitol test (L:M) ratio, in children aged 6 to 9 months.

PTM202 is a nutritional supplement that is designed to limit intestinal inflammation and decrease pathogen burden. PTM202 comprises a combination of bovine colostrum and immune egg protein. The colostrum is obtained from cows that are routinely vaccinated for the health of the animal and may be naturally exposed to various pathogens, but are not hyper-vaccinated. Bovine colostrum is also rich in lactoferrin, oligosaccharides, and anti-inflammatory cytokines and peptides. Stelwagen, K., et al. "Immune components of bovine colostrum and milk." Journal of animal science 87.13_suppl (2009): 3-9. The egg protein component comes from chickens that have routine environmental exposure to ETEC, Salmonella, and C. jejuni. These chickens are also immunized against specific pathogens which are common in the developing world. This occurs such that the immunoglobulin is transmitted vertically into the eggs (proprietary protocol). Thus, PTM202 is designed to not only facilitate increased clearance of common enteric pathogens via specific immunoglobulin but also to temper enteric inflammation through the anti-inflammatory components of colostrum.

PTM202 comes as a powder that is reconstituted in water. A dose is one 7 g packet comprising 3 g dried whole immune egg and 4 g dried whole bovine colostrum. Micronutrient sprinkle packets comprise vitamin A, vitamin C, folic acid, iron, and zinc supplement. Both groups received 1 packet of micronutrient sprinkles per day. The interventional group also received 2×7 g packets of PTM202 per day. All doses of both micronutrient sprinkles and PTM202 were given via directly observed therapy twice daily for 30 days.

Biomarkers for EED. Two fecal biomarkers and two serum biomarkers were assessed at day 0 and day 30 for EED. These include fecal Reg 1B, fecal MPO, serum sCD14, and serum CRP. Analyses were conducted via commercially available ELISA kits. Exploratory analysis on non-discretized data was conducted for each biomarker comparing the PTM202+MNP and control groups using a Wilcoxon signed-rank test.

L:M Ratio. The lactulose and mannitol were given to children as 2 ml/kg of body weight of a solution in water that contains 50 mg/ml of mannitol and 250 mg/ml of lactulose. Urine will be collected up to 2 hours after lactulose and mannitol ingestion. The lactulose and mannitol assays were conducted using high performance liquid chromatography (HPLC) in our laboratory. Children were screened with history of diarrhea and fever prior to collection of urine samples for L:M ratio testing. If a child currently had a diarrheal illness or had had a diarrheal illness in the preceding 2 weeks, the child was not be tested. Such children were rescheduled within 1 week after evaluation by a study physician. Fecal and serum EED biomarkers as well as urine L:M ratio analysis were conducted at icddr,b laboratories.

Glucose-hydrogen breath testing. Hydrogen breath testing may be useful for diagnosing small intestinal bacterial overgrowth (SIBO) and carbohydrate intolerance such as lactose and fructose malabsorption. Ghoshal 2011, "How to interpret hydrogen breath tests", J neurogastroenterol Motil 17(3):312-317. Glucose hydrogen breath test may be employed to determine small intestinal bacterial overgrowth (SIBO), lactulose hydrogen breath test may be employed to determine oro-cecal transit time or SIBO, lactose hydrogen breath test may be employed to determine lactose malabsorption, and fructose hydrogen breath test may be employed to determine fructose malabsorption. For example, SIBO may be diagnosed if there is a rise in breath hydrogen by 12 ppm above basal in glucose hydrogen breath test.

In the present study, a glucose-hydrogen breath testing is employed for testing for small intestine bacterial overgrowth (SIBO). For this test, the child will be required to fast with only water allowed during the fasting period. Children will fast for 2 hours prior to the initiation of the test. After the fast, the child will be given a 1 g/kg (5 ml/kg) of glucose solution. Hydrogen breath chromatography will be measured prior to administration of the glucose solution and then every 20 minutes for 2 hours after solution administration. Breath samples will be collected using the Quintron Breath Sampler Neonate and Infant System and samples will be analyzed using the QuintronBreathTracker SC breath chromatograph. Children who have WAZ<−3SD will not be breath tested or fasted. Children who have had antibiotics within 14 days of a breath test were not tested. They were rescheduled until after a 14-day antibiotic free period. A positive breath test was defined as an increase in exhaled hydrogen of >12 ppm over baseline which has been shown to correlate to >$10^5$ bacteria/ml of upper GI aspirate and is considered diagnostic of SIBO by expert consensus opinion. Gasbarrini, et al. "Methodology and indications of H2-breath testing in gastrointestinal diseases: the Rome Consensus Conference." Alimentary pharmacology & therapeutics 29 (2009): 1-49. All children had glucose-hydrogen breath testing for SIBO at enrollment and at the end to therapy (day 30). Only children with positive breath tests at enrollment will be included in this analysis. Based on previous studies of this population, we estimate 35% of children will have positive tests. A 2×2 contingency table will be created with rows for DiaResQ® and Control and columns for SIBO positive at 30 days and SIBO negative at 30 days. A Fisher's exact test will be utilized to evaluate the effect of DiaResQ® on SIBO. Glucose-hydrogen breath testing was conducted at the field site in Mirpur, Dhaka, Bangladesh.

Liver and renal function tests: Aspartate transaminase (AST) and Alanine transaminase (ALT) are commonly used markers of hepatic health. Blood Urea Nitrogen (BUN) and Creatinine (Cr) are commonly used clinical markers of renal function. Children were screened with these labs on enrollment. Children with abnormal results were excluded and referred for further testing/treatment. These screening labs were retested at the end of therapy and results reviewed by a blinded study physician. If abnormal results were identified, the subject was unblinded and referred for further evaluation/treatment at our expense. The clinical laboratory at icddr,b was utilized for this testing and results reviewed by a study physician within 24 hours. Hepatic and renal function labs were conducted at the icddr,b clinical laboratories.

Primary outcome was change in EED score. If a biomarker measurement is in top $50^{th}$ percentile of all 200 children, then that child gets 1 point. All 5 EED biomarkers are assessed and thus each child received a score of 0 to 5. Another study ne objective was weight gain at 30 days. Children had anthropometrics measured by trained staff in pediatric anthropometric assessment. Weight-for-age z-scores (WAZ) were calculated using the World Health Organization softwareWHO Anthro (version 3.2.2, January 2011). See also WHO child growth standards and the identification of severe acute malnutrition in infants and children, a joint statement of the World Health Organization and the United Nations Children's Fund, 2009. The z-score is defined as number of standard deviations (SD) below or above the reference median value. The change in WAZ score from randomization to 30 days was one objective. Additional objectives included 90 day weight gain and linear growth, normalization of EE biomarkers at 30 days, number of diarrheal episodes of diarrhea at 30 days, and glucose-hydrogen breath testing at 30 days.

Figure 2:
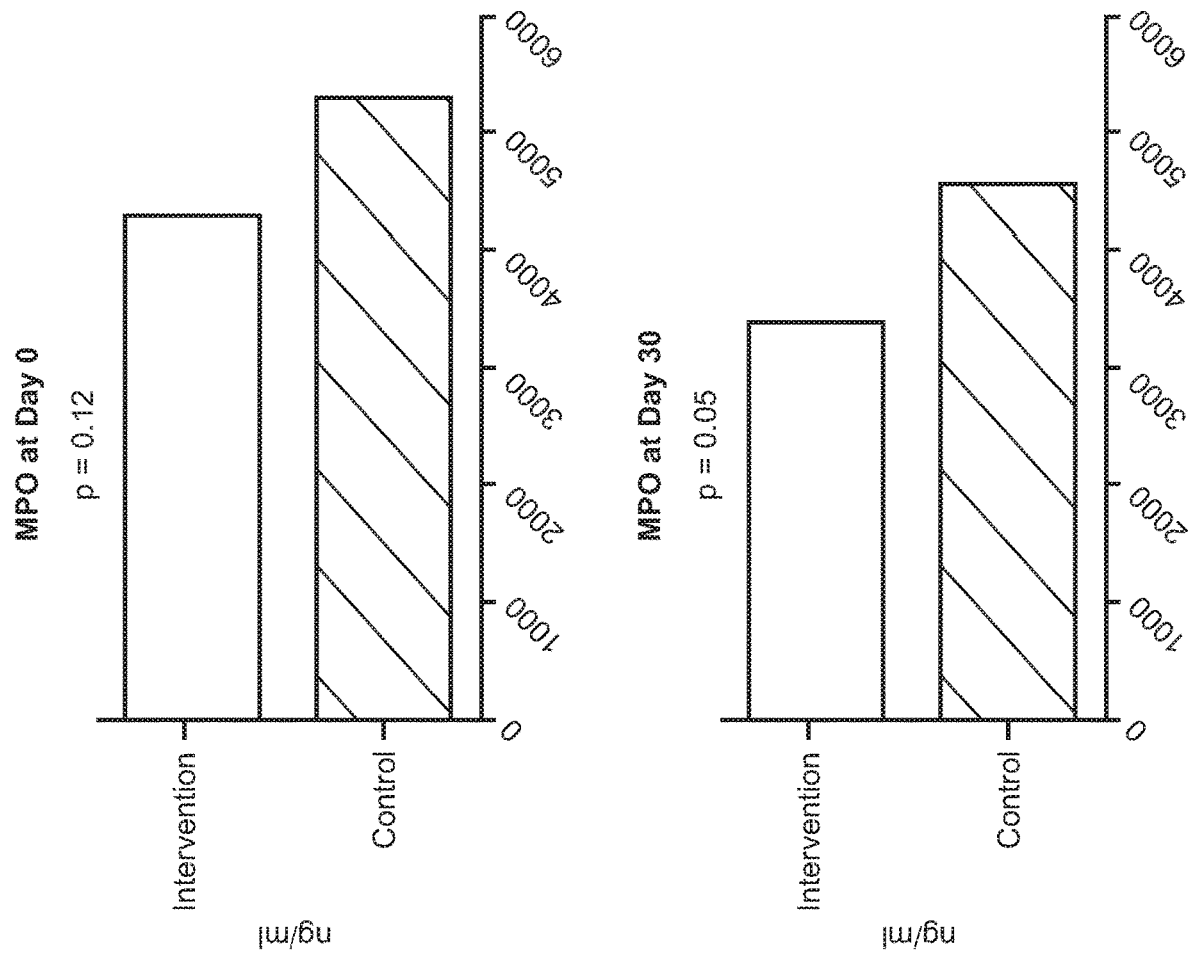
FIG. 2 shows a bar graph illustrating average fecal myeloperoxidase (MPO) levels in children at 0 and 30 days after twice daily administration of PTM202 (7 g BID) with micronutrient sprinkles (intervention, n=100) compared to micronutrient sprinkles alone (control, n=100). At day 0, differences in fecal MPO between intervention and control arm were not significant (upper panel)(p=0.12). At day 30, PTM202 with micronutrient sprinkles significantly decreased fecal myeloperoxidase (MPO) in children when compared to children who had micronutrient sprinkles alone (control)(lower panel)(p=0.05).
Figure 3:
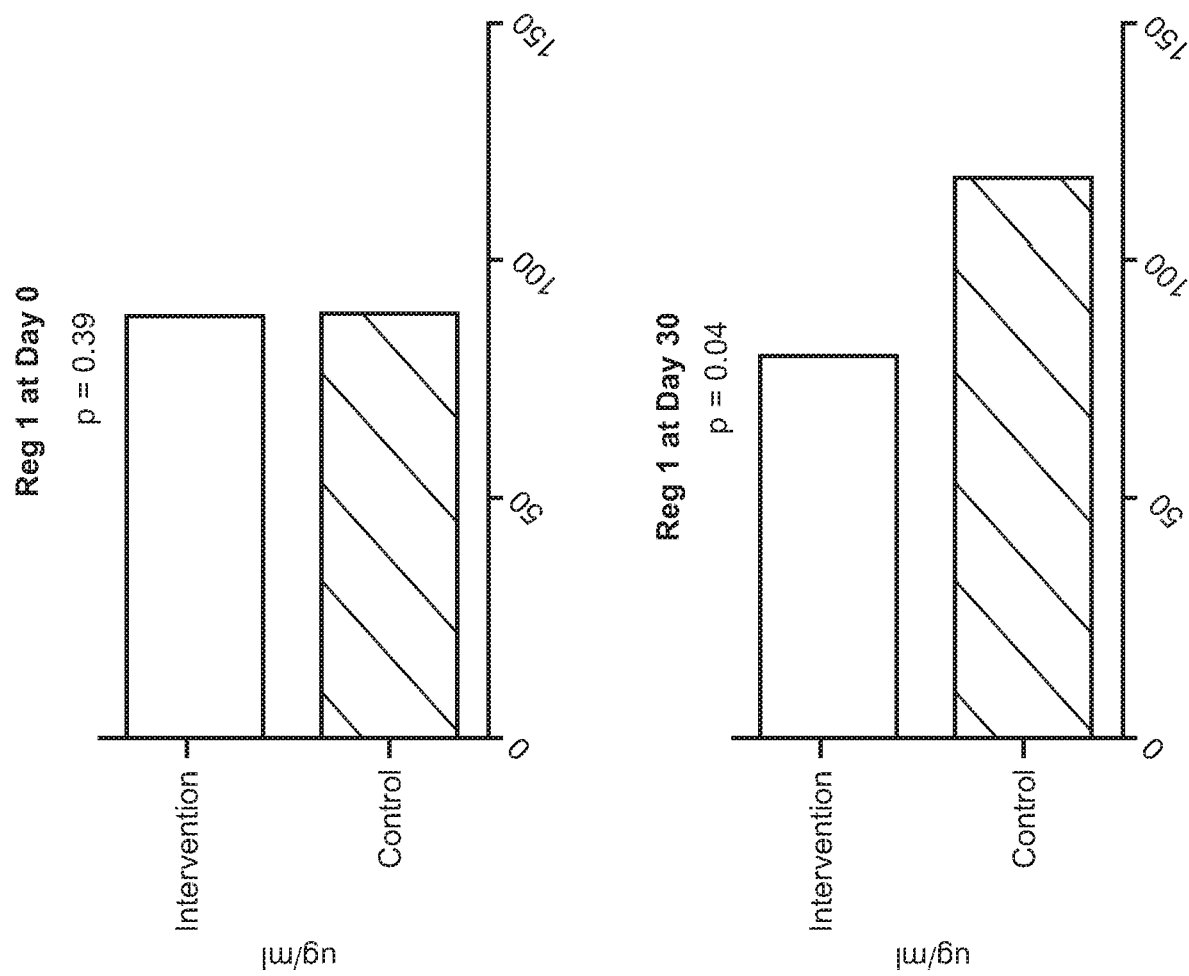
FIG. 3 shows a bar graph illustrating average fecal Reg 1B levels in children at 0 and 30 days after twice daily administration of PTM202 (7 g BID) with micronutrient sprinkles (intervention, n=100) compared to micronutrient sprinkles alone (control, n=100). At day 0, differences in fecal Reg 1B between intervention and control arm were not significant (upper panel)(p=0.039). At day 30, PTM202 with micronutrient sprinkles (intervention) significantly decreased fecal Reg 1B in children when compared to children who had micronutrient sprinkles alone (control) (lower panel)(p=0.04).
Figures 4, 5:
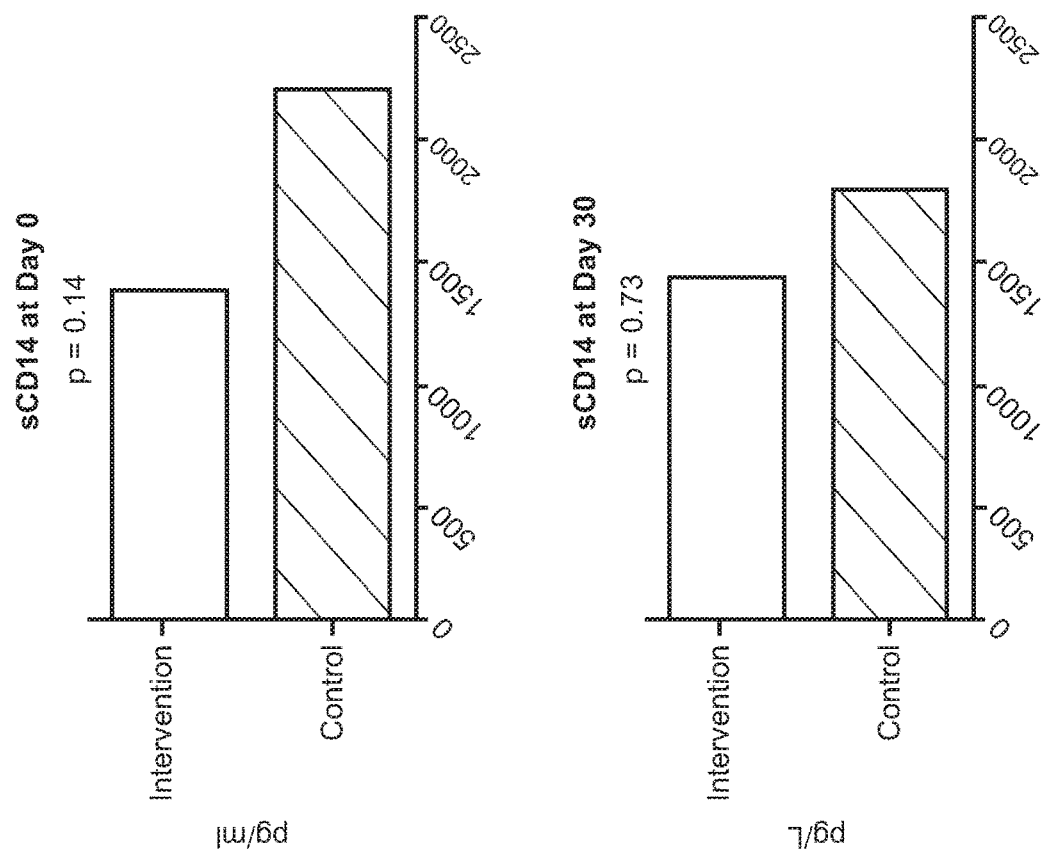
FIG. 4 shows a bar graph illustrating serum C-reactive protein (CRP) levels in children at days 0 and 30 after twice daily administration of PTM202 (7 g BID) with micronutrient sprinkles (intervention, n=100) compared to micronutrient sprinkles alone (control, n=100). At day 30, differences in serum CRP between intervention and control arm were not significant (lower panel)(p=0.40).
FIG. 5 shows a bar graph illustrating serum soluble CD14 (sCD14) levels in children at days 0 and 30 after twice daily administration of PTM202 (7 g BID) with micronutrient sprinkles (intervention, n=100) compared to micronutrient sprinkles alone (control, n=100). At day 30, differences in serum sCD14 between intervention and control arm were not significant (lower panel)(p=0.73).

Summary of Preliminary EED Study Results
PTM202 Improved Environmental Enteric Dysfunction (EED) Biomarkers Intestinal inflammation and damage were significantly improved in the intervention arm compared to the control arm, as measured by fecal myeloperoxidase (MPO) and fecal Reg 1B at the completion of the 30-day intervention. At 30 days, fecal Reg 1B in children was significantly reduced to 121.8 ug/ml in the PTM202 group from 145.3 ug/ml in the control group (p=0.04) as shown in FIG. 2. At 30 days, fecal MPO was significantly reduced to 5972 ng/ml in the PTM202 group from 7849 ng/ml in the control group (p=0.05) as shown in FIG. 3. In contrast markers of systemic inflammation serum sCD14 and serum CRP in children were not significantly different after 30 days between intervention and control arms, as shown in FIG. 4 and FIG. 5. Therefore, 7 g of PTM202 twice per day for 30 days significantly decreased markers of intestinal inflammation and damage but did not affect systemic inflammation biomarkers sCD14 or CRP in this study.

Example 5. PTM202 in Models of Gut Proliferation and Repair

This example shows compositions of the disclosure exhibited improved gut repair bioactivity, for example, as compared to colostrum alone. In addition, activity of the whole (full-fat) standard colostrum and whole (full-fat) first milking colostrum was significantly higher than that of defatted colostrum, or defatted fractionated colostrums, in cell proliferation in vitro assays, e.g., in human gastrointestinal (AGS) cells.

Selected components and compositions of the disclosure were evaluated in cell proliferation and restitution assays as disclosed in Playford et al., 1999, Gut, 44:653-658, which is incorporated herein by reference.

Example 5A. Cell Proliferation Assays (In Vitro).

Human gastrointestinal cells (AGS cells) or rat intestinal epithelial cells (RIE cells) are seeded at 2000 cells/well in an appropriate growth medium containing glutamine and 10% foetal calf serum in 96 well plates overnight. The following day, cells are washed twice with serum-free medium and then incubated in serum-free medium alone (SFM negative control) or also containing colostrum at various concentrations or epidermal growth factor (EGF, positive control) overnight. The following day ALAMARBLUE™ is added to each well. ALAMARBLUE™ is a coloured substrate that changes colour from blue to pink in response to cellular metabolic reduction. This change can be determined by reading the absorbance of the wells at 570 nm using a spectrophotometer at 0 h when the substrate is added and 4 hours later.

Figure 6:
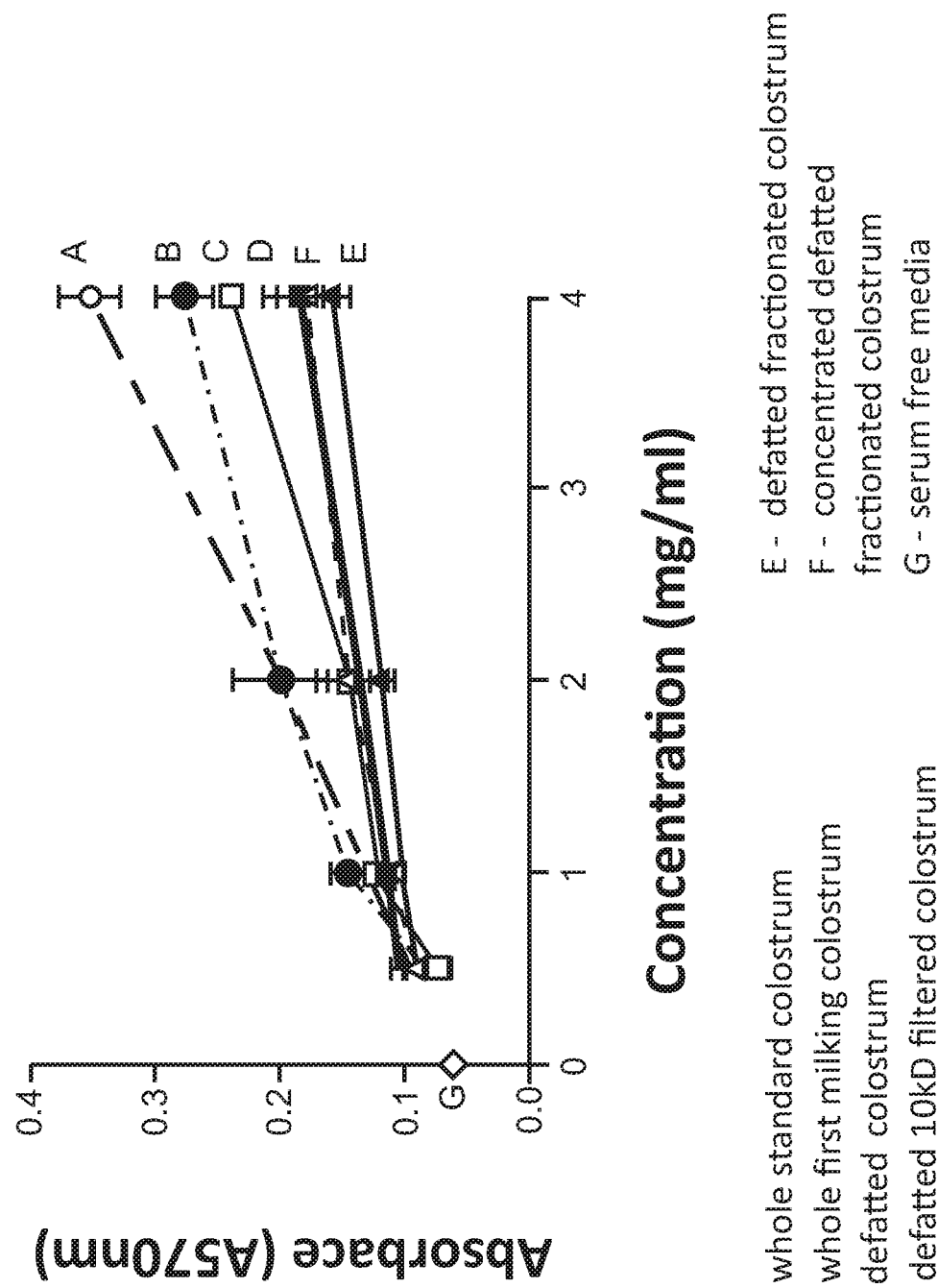
FIG. 6 shows a line graph of an in vitro Proliferation Assay in AGS cells and activity of several types of bovine colostrum including whole standard colostrum (full-fat) (A), whole first milking colostrum (full-fat) (B), defatted colostrum (C), defatted 10 kD filtered colostrum (D), defatted fractionated colostrum (E), and concentrated defatted fractionated colostrum (F) compared to serum free media (G) at various concentrations of 0.5, 1, 2, 3 and 4 mg/mL. Each of the bovine colostrum samples exhibited activity greater than that of the negative control (SFM). The activity of the full-fat colostrums including whole standard colostrum (A) and whole first milking colostrum (B) was significantly higher than that of the defatted (C), or defatted fractionated colostrums (D), (E), and (F).

As shown in FIG. 6, AGS cells were employed in the in vitro cell proliferation assay to evaluate several types of bovine colostrum, including whole standard colostrum (full-fat)(57.4% protein)(A), whole first milking colostrum (full-fat)(52.5% protein)(B), defatted colostrum (69.7% protein)(C), defatted 10 kD filtered colostrum (106.3% protein)(D), defatted fractionated colostrum (39.4% protein)(E), and concentrated defatted fractionated colostrum (46.3% protein)(F) compared to serum free media (G) at various concentrations of 0.5, 1, 2, 3 and 4 mg/mL. The activity of the whole standard colostrum and whole first milking colostrum was significantly higher than that of the defatted, or defatted fractionated colostrums, at 2, 3 and 4 mg/mL, as shown in FIG. 6. The protein concentration did not correlate with activity level in vitro. Results confirmed selection of whole standard colostrum for use in compositions such as PTM202 for treating or prevention of conditions associated with inflammation and/or damage of the gastrointestinal tract.

Figure 7:
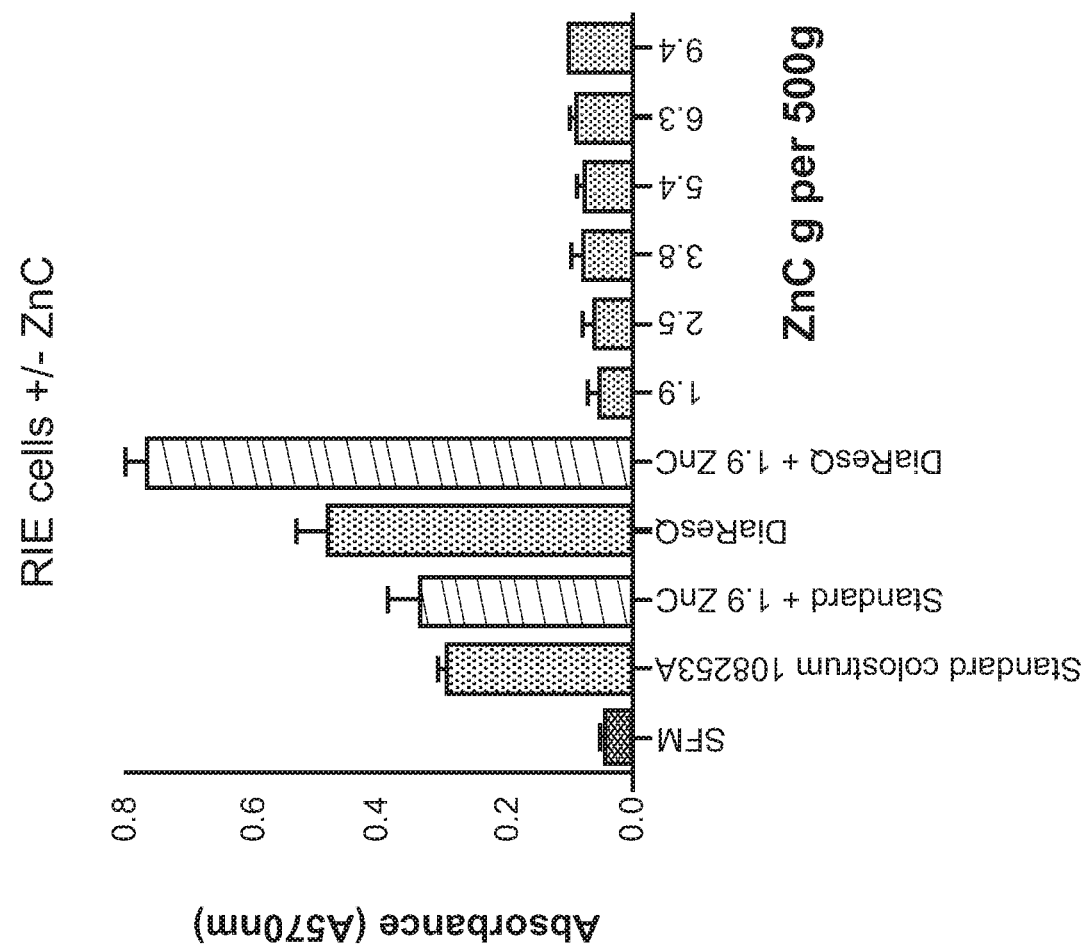
FIG. 7 shows a bar graph illustrating results (A570 nm) in a cell proliferation assay in RIE cells in vitro using standard bovine colostrum, zinc carnosine (ZnC), and/or PTM202 compared to serum free media (SFM, negative control). Standard colostrum and zinc carnosine stimulate cell proliferation compared to negative control SFM. PTM202 used alone exhibits increased cell proliferation compared to either standard colostrum or ZnC alone, or in combination. Remarkably, addition of ZnC to PTM202 exhibits significantly and synergistically increased cell proliferation compared to PTM202 or ZnC alone.

As shown in FIG. 7, RIE cells were employed in the cell proliferation assay to evaluate the effects of cell proliferation of standard whole colostrum, PTM202 comprising immune egg and whole colostrum, and various amounts of zinc-L-carnosine compared to SFM (negative control). PTM202 exhibits improved cell proliferation compared to standard colostrum. Zinc carnosine added to standard colostrum also exhibited enhanced proliferation in cells compared to standard colostrum. Remarkably, addition of zinc-L-carnosine to PTM202 exhibits unexpectedly improved synergistic effect in cell proliferation assay in RIE cells.

Example 5B. Restitution/Cell Migration Assays (In Vitro).

Gastrointestinal human cells are grown in vitro until they form confluent monolayers in 12 well tissue culture plates in an appropriate growth medium containing glutamine and 10% foetal calf serum. The monolayers are wounded by scraping a disposable pipette tip across the dishes, washed with fresh serum free medium, and cultured in serum free medium in the presence of various doses of colostrum. Monolayers grown in the presence of EGF are used as a positive control and monolayers grown in serum free medium alone are used as a negative control. The rate of movement of the anterior edges of the wounded monolayers is then determined by taking photomicrographs (pictures taken through a microscope) directly after wounding (0 hours) and 24 hours later. Identical regions are examined at each time point by premarking the base of the plates to facilitate alignment. Twenty measurements per field are performed by placing a transparent grid over the photograph and measuring the distance moved from the original wound line.

Figure 8:
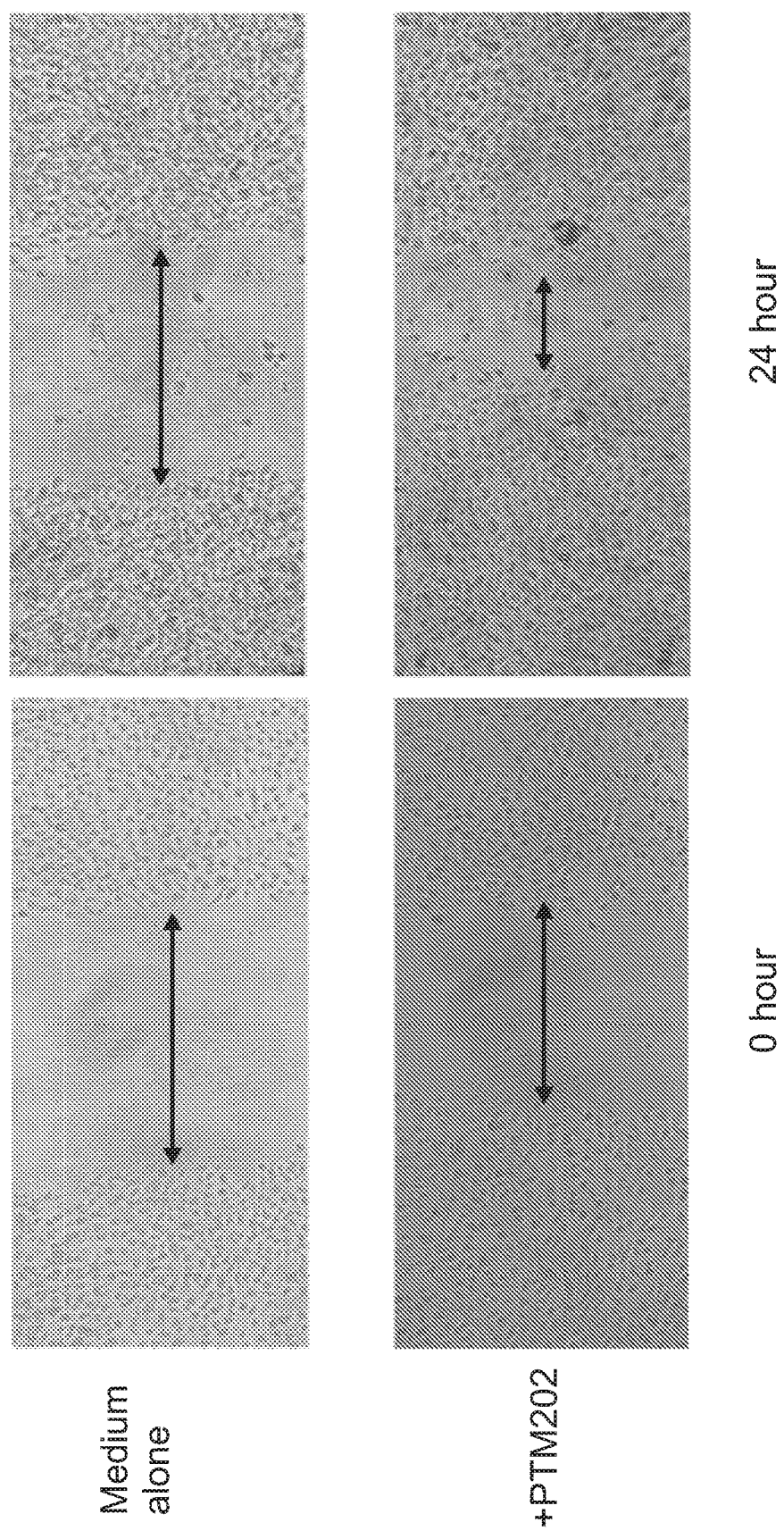
FIG. 8 shows photographs illustrating effect of PTM202 on rate of closure of wounded AGS cell monolayers in restitution/cell migration assay in vitro. Distance migrated by leading edge of wounded monolayer is measured (μm) by microscopy at t=0 h and t=24 hours as illustrated by horizontal arrows. PTM202 stimulates significantly faster movement (restitution) of monolayers shown at 24 hours (bottom right photo) compared to medium alone (top right photo).

The restitution/cell migration assay was used to evaluate the effect of PTM202 on rate of closure of wounded AGS cell monolayers in vitro. FIG. 8 shows the distance migrated by leading edge of wounded monolayer as measured ($\mu$m) by microscopy at t=0 h and t=24 hours as illustrated by horizontal arrows. The composition PTM202 stimulates significantly faster movement (restitution) of monolayers shown at 24 hours (bottom right photo) compared to medium alone (top right photo).

Example 5C. Indomethacin Gastric Damage (In Vivo—Rats)

Rats are given either 2 ml saline (negative control) or various concentrations of colostrum in solution also containing 2% hydroxymethylpropylcellulose to reduce the rate of gastric emptying. Thirty minutes later all rats receive indomethacin (20 mg/kg subcutaneously) and are placed in Bollman type restraint cages to cause stress. Animals are killed three hours later and their stomachs removed and inflated with 4 ml of 10% formalin. The amount of damage in the stomachs are assessed macroscopically using a dissecting microscope and a square grid to calculate the total area of ulceration per stomach (mm2/stomach). Microscopic damage is assessed from stomachs embedded in wax and subsequent sections cut onto a microscope slide. Microscopic injury is graded with a score from 0 to 4 where: 0=no damage, 1=one small erosion (less than 0.5 mm), 2=two small or one large erosion (greater than 0.5 mm), 3=two or more large erosions, and 4=any area of ulceration extending to the muscularis mucosa.

Example 5D. Indomethacin Small Intestinal Damage (In Vivo—Mice)

Mice are put into groups and fed on a standard diet ad libitum. Some of the groups get drinking water supplemented with various concentrations of colostrum for six days. To induce small intestinal injury mice are given a single dose of indomethacin (85 mg/kg subcutaneously) 24 hours before the end of the study. To assess changes in proliferation, each animal also receives vincristine (1 mg/kg intraperitoneally), to induce metaphase arrest, two hours before the end of the study. Samples of the small intestine and colon (defined by their percentage length) are fixed in Carnoy's fluid. To determine intestinal proliferation per section of gut, arrested metaphases are counted. To assess villus damage, the villi are microdissected and height is determined.

Example 5E. DSS Colitis Model (In Vivo—Rats/Mice).

Animals are put into groups and fed on a standard diet ad libitum, some receive either saline or various concentrations of colostrum. Colitis is induced with 4% (wt./vol.) dextran sulphate sodium (DSS) in the drinking water ad libitum. Rats are weighed daily and visually inspected for signs of distress, diarrhoea and rectal bleeding. At the end of the relevant time period the colon is weighed and opened longitudinally for morphological studies. The length of the colon is measured and it is cut into five equal pieces expressed as percentage colonic length. To assess microscopic damage the sections of colon are given a total colitis score. This is derived from the sum of four subscores of (i) inflammation severity, (ii) inflammation extent, (iii) crypt damage, and (iv) percentage involvement. To assess myeloperoxidase activity a small section (representing 80-85% of the colon) is rapidly removed and snap frozen in liquid nitrogen for subsequent assay for myeloperoxidase (MPO) activity. Myeloperoxidase activity, used as a marker of neutrophilic infiltration, is extracted and the activity is measured using a standard method.

Example 5F. Chemotherapy Induced Mucositis (In Vivo—Rats/Mice)

Animals are put into groups and fed on a standard diet ad libitum, some receive either saline or various concentrations of colostrum in the drinking water for 6 days. Mucositis is induced by the administration of a standard chemotherapeutic agent, such a 5 Fluorouracil, at an appropriate dose for an appropriate number of days. Animals are weighed daily and visually inspected and scored for signs of distress, diarrhoea and rectal bleeding. At the end of the study period gastrointestinal samples are collected and damage is assessed by microscopically scoring the extent of the damage, assessing villus height and crypt depth.

Example 5G. Intestinal Permeability Model (In Vivo—Human)

To assess intestinal permeability subjects are asked to fast overnight, then empty their bladder before dinking a standardized sugar solution containing the sugars lactulose, mannitol, and rhamnose in a total of 450 ml water. Following this all urine is collected for 5 hours. Urine samples are analysed using high pressure liquid chromatography (HPLC) and detected using a pulsed amphometric detector. With this technique, sugars are oxidized on the gold electrode at the working potential (0.05 V), the current produced being a measure of the amount of sugar present in the sample. Results are expressed in two forms, one as simple area under the curve ratios as of lactulose and rhamnose, the second is as a ratio of percentage of ingested sugar excreted in the urine.

Example 6. PTM202 Reduces Diarrhea Symptoms, and Colon and Plasma TNF-$\alpha$ Cytokine Levels in Mouse Model of LPS-Induced Diarrhea Broad-spectrum compositions of the disclosure without additional active component were previously shown to reduce duration of diarrheal symptoms in undifferentiated pediatric diarrhea field trials in human subjects, as shown in WO 2012/071346, Starzl, examples 4A and 4B, which is incorporated herein by reference. However, effects on cytokines were not previously evaluated. An animal model of LPS-induced diarrhea was employed to determine effects on both gut repair and certain cytokine levels.

Inflammatory reactions can cause various clinical manifestations frequently associated with abnormal motility of the gastrointestinal tract, such as nausea, vomiting, ileus, or diarrhea. It has been reported that bacterial lipopolysaccharide (LPS) could induce various alterations in gastrointestinal function. Intestinal motility, secretion and integrity of the mucosa are important barrier functions against the penetration of bacteria and endotoxins from the gut lumen to the blood stream. Impaired intestinal absorption is a major mechanism for diarrhea caused by endotoxin lipopolysaccharide (LPS) and is generally accompanied with damage to the intestine.

Infectious diarrhea is often caused by Gram-negative bacteria such as Escherichia coli. These organisms contain lipopolysaccharide (LPS).

An LPS-induced diarrhea animal model in C57BL/6 mice was utilized to evaluate effect of single doses of PTM202 on diarrhea score, and levels of plasma and tissue cytokines, TNF-α and IL-6, in mice. In previous studies, PTM202 at different doses showed significant reduction in diarrhea score in LPS-induced diarrhea model and significant reduction in colon tissue IL-6 levels, data not shown.

Animals: 10-12-week-old male C57BL/6 mice weighing 25-30 g, were acclimatized to the study area conditions for 3 days before dosing. The mice were provided ad libitum of standard pelleted food. Animals were dosed under fed condition. Mice were administered a single dose at 10 mL/kg dose volume orally of either vehicle (MILLI-Q® water) or PTM202. 3 h post treatment of test item, LPS was administered at a dose volume of 10 mL/kg by single intraperitoneal injection. Mice were divided in following treatment groups as shown in Table 3.

TABLE 3

Mouse treatment groups in LPS-induced diarrhea model.

| | Group |
|---|---|
| a | Naive, n = 8 |
| b | Vehicle (MiliQ water), 10 ml/kg, PO + LPS, 10 mg/kg, IP, n = 8 |
| c | PTM202, 50 mg/kg (−3 h), PO + LPS, 10 mg/kg, IP, n = 8 |
| d | PTM202, 100 mg/kg (−3 h), PO + LPS, 10 mg/kg, IP, n = 8 |
| e | PTM202, 200 mg/kg (−3 h), PO + LPS, 10 mg/kg, IP, n = 8 |
| f | PTM202, 500 mg/kg (−3 h), PO + LPS, 10 mg/kg, IP, n = 8 |
| g | PTM202, 1000 mg/kg (−3 h), PO + LPS, 10 mg/kg, IP, n = 8 |
| h | PTM202, 1500 mg/kg (−3 h), PO + LPS, 10 mg/kg, IP, n = 8 |
| i | PTM202, 3000 mg/kg (−3 h), PO + LPS, 10 mg/kg, IP, n = 8 |
| j | PTM202, 500 mg/kg (0 h), PO + LPS, 10 mg/kg, IP, n = 8 |
| k | Atropine, 100 mg/kg, PO + LPS, 10 mg/kg, IP, n = 8 |

Animals were first dosed with either vehicle or PTM202 or Atropine at 10 ml/kg dose volume as defined above. Then 3 hrs post treatment, animals were dosed by single intraperitoneal injection of LPS at 10 mg/kg dose.

Measurement of Diarrhea Score

After treatment with LPS, mice in each cage were placed on a filter paper couch. Filter paper was changed once an hour for 4 h. The frequency of diarrhea was determined by counting the number of feces deposits on the filter paper.

Blood samples were collected after 4 h for the measurement of plasma IL-6 (interleukin 6) and TNF-α (tumor necrosis factor alpha) levels. Small intestine and colon tissue samples were collected for the observation of morphologic changes by Histopathology and cytokines (IL-6 and TNF-α levels) level measurements.

Determination of IL-6 and TNF-α levels in colon tissue and plasma samples

Blood samples were collected at 4 h post dose and transferred to a labeled microfuge tube containing 200 mM $K_2EDTA$ (20 µL per mL of blood). The blood samples were kept on wet ice at all times immediately after collection and the plasma was separated by centrifugation at 5000 g for 5 minutes at 4±2° C. The plasma samples were separated within 1 h of scheduled time and stored below −60° C. until bioanalysis. The colon tissue samples were thawed and then homogenized in ice-cold Krebs solution containing NaCl 119 mM, KCl 5.4 mM, $CaCl_2$ 2.5 mM, $KH_2PO_4$ 0.6 mM, $MgSO_4$ 1.2 mM, $NaHCO_3$ 25 mM, and Glucose 11.7 mM on ice with polytron homogenizer at 15000 rpm. Samples were centrifuged at 36000×g for 15 min at 4° C. (Ultra centrifuge), and the supernatants frozen at −80° C. until assay. To estimate IL-6 and TNF-alpha from tissue supernatant, a double-antibody sandwich ELISA was performed according to the manufacturer's recommendations by R&D Systems (Minneapolis, USA). To estimate IL-6 and TNF-alpha from plasma samples, a double-antibody sandwich ELISA was performed according to the manufacturer's recommendations by R&D Systems (Minneapolis, USA).

Histopathological Examination of Colon and Small Intestine

Colon specimens were embedded in paraffin wax and sections measuring 5 mm were prepared. Colon sections were bathed in Ehrlich's haematoxylin for 5 min before being rinsed for 5 to 10 min in running water. The sections were subsequently dipped with tap water for 3 to 5 s in 70% alcohol containing 1% hydrochloric acid and then washed again for 5 to 10 min in running water. The slides were dipped in 1% eosin for 5 min and then placed under running water until the nuclei appeared blue. The sections were again dehydrated by the addition of serially concentrated alcohol (70%, 80%, 90%, and 100%). After H&E staining of the slide, the sections were histologically examined for each mouse as per following a) Severity of inflammation/leukocyte infiltration was assessed as: 0—none 1—slight, 2—moderate, 3—severe; b) Depth of inflammation/leukocyte infiltration was assessed as: 0—none 1—mucosal, 2—mucosal & Submucosal, 3—transmural; c) Crypt epithelial necrosis/ulceration was assessed as: 0—none, 1—basal one third damaged, 2—basal two third damaged, 3—only surface epithelium intact, 4—entire crypt and epithelium Lost; d) Multiplication factors based on the extent of tissue affected—Less than 25%—1, 26-50%—2, 51-75%—3, 76-100%—4. Histopathology index is sum of Severity of inflammation/leukocyte infiltration, Depth of inflammation/leukocyte infiltration and Crypt epithelial necrosis/ulceration.

Results are shown in shown in FIGS. 9A-B and FIGS. 10A-D.

Figure 9A:
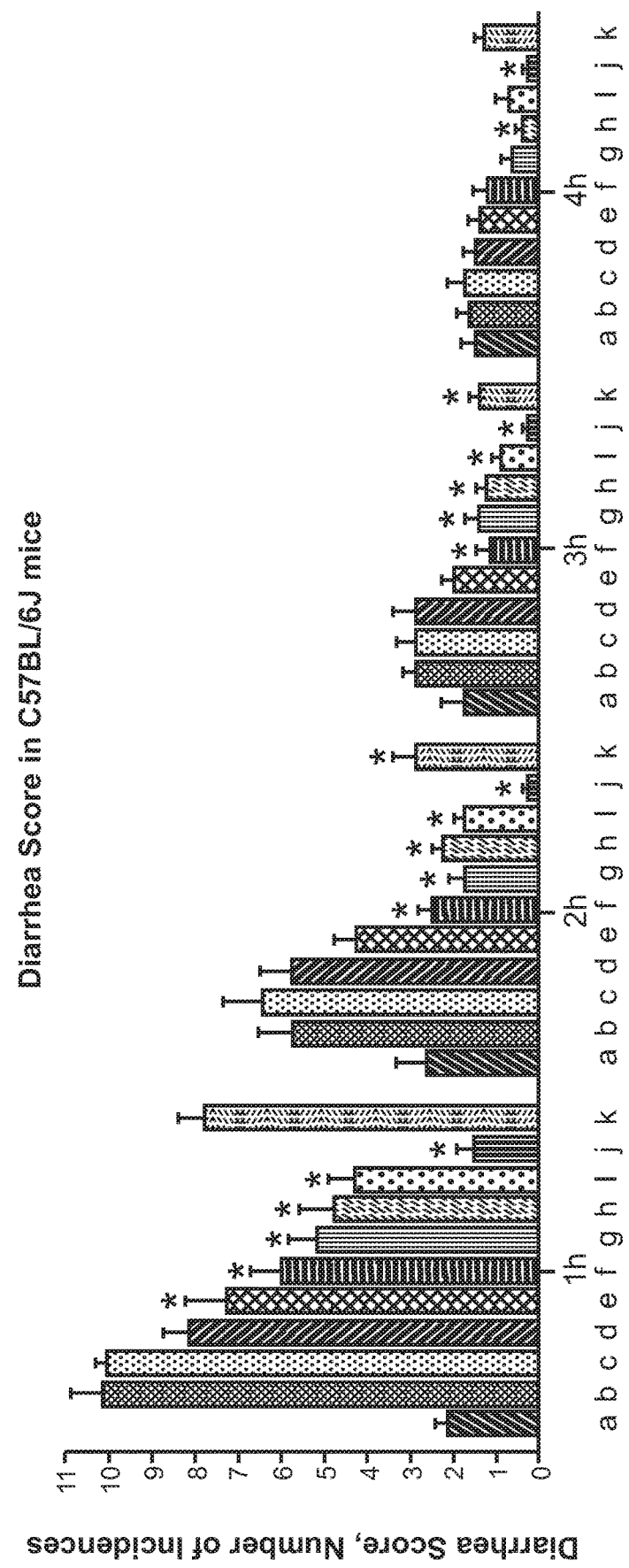
FIG. 9A shows a bar graph illustrating effect of PTM202 on LPS-induced diarrhea score in C57BL/6 mice over 4 hours. Mice were administered a single dose at 10 mL/kg dose volume orally of either vehicle (MTLLI-Q® water) or PTM202. 3 h post treatment of test item, LPS was administered at a dose volume of 10 mL/kg by single intraperitoneal injection. At 1 hour post LPS administration, PTM202 at 200 mg/kg to 3000 mg/kg oral doses—groups (e) to (i)—significantly reduced diarrhea score compared to vehicle group (b). At 1 hour, 2 hours, and 3 hours post LPS administration, PTM202 at 500 mg/kg to 3000 mg/kg oral doses—groups (f) to (i)—significantly reduced diarrhea score compared to vehicle group (b). Atropine (100 mg/kg) was used as a positive control (j). Data is shown as mean±SEM. * $P<0.05$ one way ANOVA followed by Dunnett's test.

FIG. 9A shows a bar graph illustrating effect of PTM202 on LPS-induced diarrhea score in C57BL/6 mice over 4 hours. Mice were administered a single dose at 10 mL/kg dose volume orally of either vehicle (MILLI-Q® water) or PTM202. 3 h post treatment of test item, LPS was administered at a dose volume of 10 mL/kg by single intraperitoneal injection. At 1 hour post LPS administration, PTM202 at 200 mg/kg to 3000 mg/kg oral doses—groups (e) to (i)—significantly reduced diarrhea score compared to vehicle group (b). At 1 hour, 2 hours, and 3 hours post LPS administration, PTM202 at 500 mg/kg to 3000 mg/kg oral doses—groups (f) to (i)—significantly reduced diarrhea score compared to vehicle group (b). Atropine (100 mg/kg) was used as a positive control (j). Data is shown as mean±SEM. * P<0.05 one way ANOVA followed by Dunnett's test.

Figure 9B:
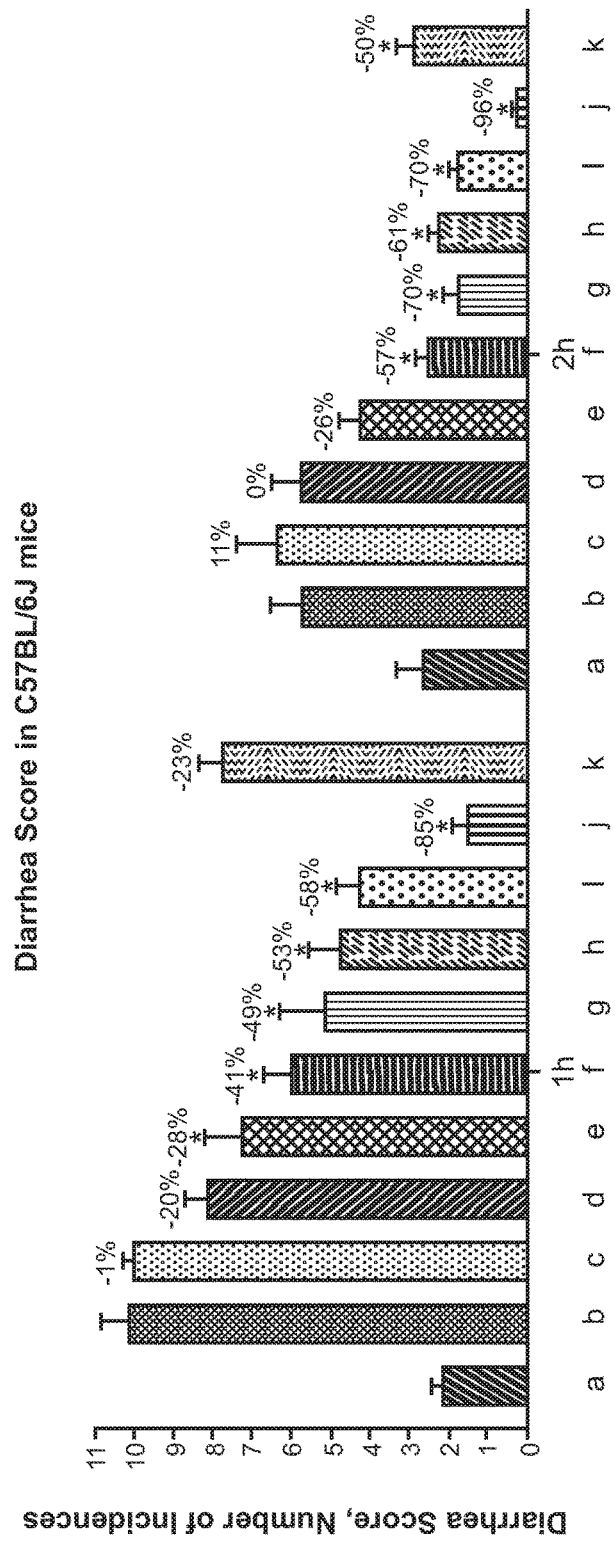
FIG. 9B shows a bar graph illustrating effect of PTM202 on LPS-induced diarrhea score in C57BL/6 mice over first two hours. Standard reference compound Atropine (j) significantly reduced LPS-induced diarrhea score by 85% and 96% respectively at 1 h and 2 h post LPS administration as compared to vehicle group. Data is shown as mean±SEM. * $P<0.05$ one way ANOVA followed by Dunnett's test.

FIG. 9B shows a bar graph illustrating effect of PTM202 on LPS induced-diarrhea score in C57BL/6 mice over first two hours. Standard reference compound Atropine (j) significantly reduced LPS induced-diarrhea score by 85% and 96% respectively at 1 h and 2 h post LPS administration as compared to vehicle group. Data is shown as mean±SEM. * P<0.05 one way ANOVA followed by Dunnett's test.

Figure 10A:
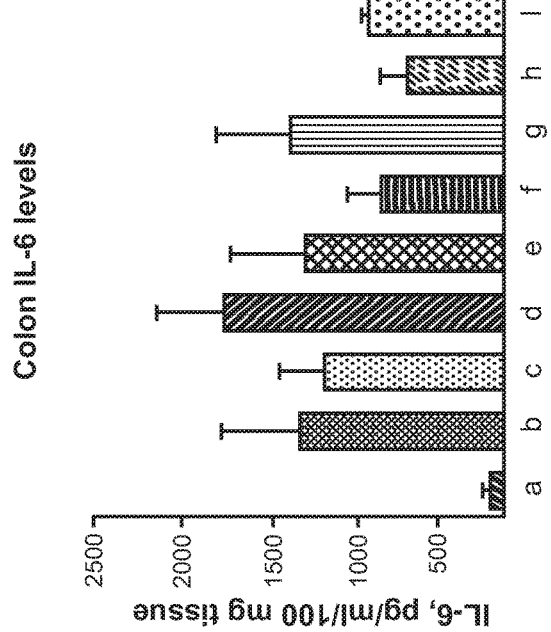
FIG. 10A shows a bar graph illustrating effect of PTM202 on LPS induced plasma IL-6 cytokine levels in mouse model at 4 h after LPS administration. Data is shown as mean SEM. Neither PTM202 nor atropine significantly affected plasma IL-6 levels compared to vehicle with LPS.

FIG. 10A shows a bar graph illustrating effect of PTM202 on LPS induced plasma IL-6 cytokine levels in mouse model at 4 h after LPS administration. Data is shown as mean SEM. Neither PTM202 nor atropine significantly affected plasma IL-6 levels compared to vehicle with LPS.

Figure 10B:
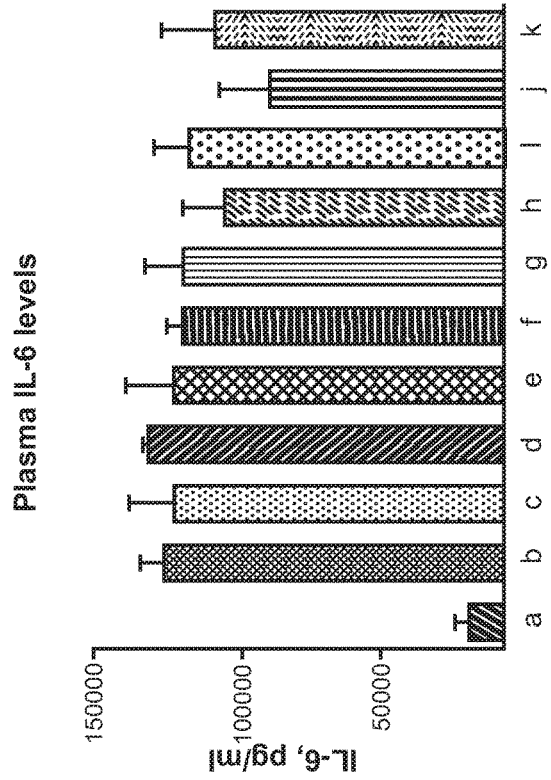
FIG. 10B shows a bar graph illustrating effect of PTM202 on LPS induced colon tissue IL-6 cytokine levels in mouse model at 4 h after LPS administration. Data is shown as mean SEM. High doses of PTM202 and atropine reduced colon IL-6 levels compared to vehicle with LPS, but data did not reach significance.

FIG. 10B shows a bar graph illustrating effect of PTM202 on LPS induced colon tissue IL-6 cytokine levels in mouse model at 4 h after LPS administration. Data is shown as mean SEM. High doses of PTM202 and atropine reduced colon IL-6 levels compared to vehicle with LPS, but data did not reach significance.

Figure 10C:
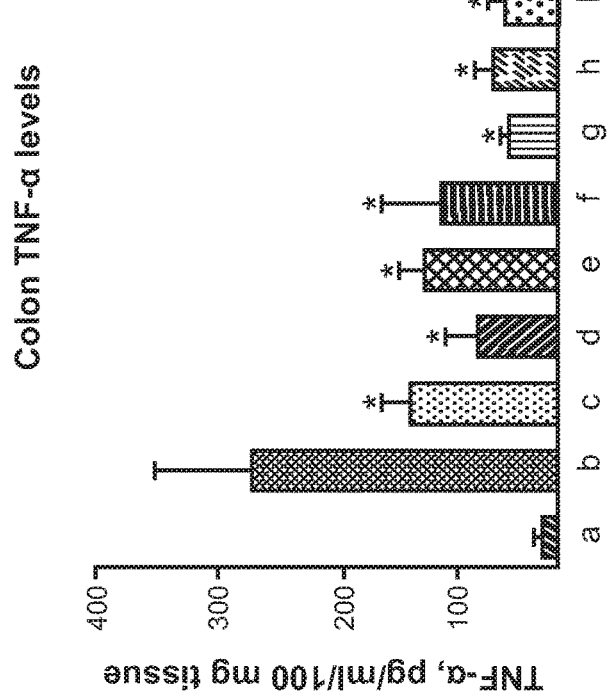
FIG. 10C shows a bar graph illustrating effect of PTM202 on LPS induced plasma TNF-α cytokine levels in mouse model at 4 h after LPS administration. PTM202 at doses 40 mg/kg-3000 mg/kg oral doses (c)-(i) and atropine (j) significantly reduced plasma TNF-α levels compared to vehicle with LPS. Data is shown as mean±SEM. * $P<0.05$ one way ANOVA followed by Dunnett's test.

FIG. 10C shows a bar graph illustrating effect of PTM202 on LPS induced plasma TNF-α cytokine levels in mouse model at 4 h after LPS administration. PTM202 at doses 40 mg/kg-3000 mg/kg oral doses (c)-(i) and atropine (j) significantly reduced plasma TNF-α levels compared to vehicle with LPS. Data is shown as mean±SEM. * P<0.05 one way ANOVA followed by Dunnett's test.

Figure 10D:
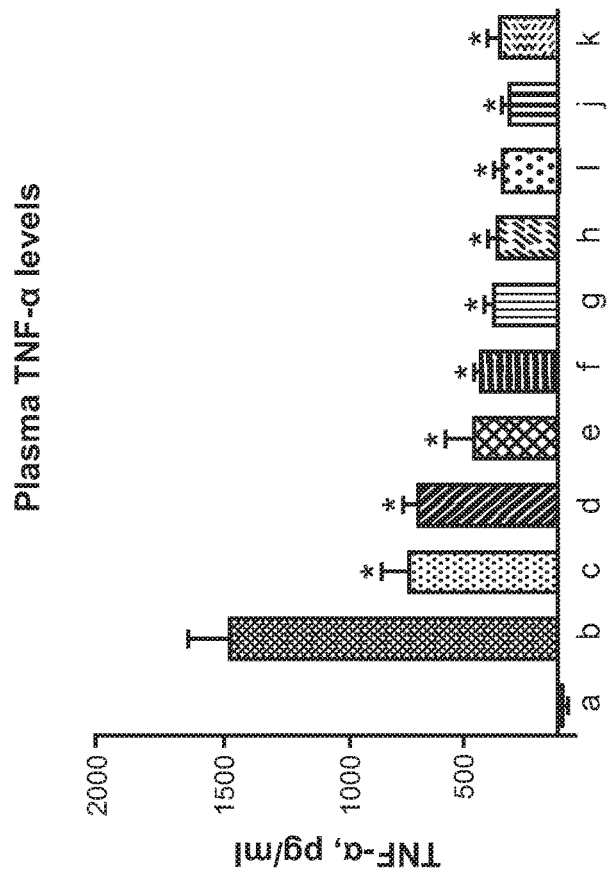
FIG. 10D shows a bar graph illustrating effect of PTM202 on LPS induced colon TNF-α cytokine levels in mouse model at 4 h after LPS administration. PTM202 at doses 40 mg/kg-3000 mg/kg oral doses (c)-(i) and atropine (j) significantly reduced colon TNF-α levels compared to vehicle with LPS. Data is shown as mean±SEM. * $P<0.05$ one way ANOVA followed by Dunnett's test.

FIG. 10D shows a bar graph illustrating effect of PTM202 on LPS induced colon TNF-α cytokine levels in mouse model at 4 h after LPS administration. PTM202 at doses 40 mg/kg-3000 mg/kg oral doses (c)-(i) and atropine (j) significantly reduced colon TNF-α levels compared to vehicle with LPS. Data is shown as mean±SEM. * P<0.05 one way ANOVA followed by Dunnett's test.

LPS administration at 10 mg/kg IP dose (b) led to significant increases in diarrhea score (80-90%) in C57BL/6 mice as compared to sentinel group (naïve)(a), as shown in FIG. 9B.

PTM202 at 200 mg/kg to 3000 mg/kg oral doses (e-i) significantly reduced diarrhea score compared to vehicle group (b) post LPS administration at 1 h, as shown in FIG. 9A and FIG. 9B.

PTM202 at 500 mg/kg oral dose (k) given at the time of LPS administration significantly reduced diarrhea score at 2 h and 3 h post LPS administration as compared to vehicle group (b), as shown in FIG. 9A.

Standard reference compound Atropine (k) significantly reduced LPS induced-diarrhea score by 85% and 96% respectively at 1 h and 2 h post LPS administration as compared to vehicle group, as shown in FIG. 9A and FIG. 9B.

Cytokine levels were measured from colon samples. PTM202 at 50 mg/kg to 3000 mg/kg oral doses (c-i) showed significant reduction in plasma and colon TNF-alpha levels compared to vehicle group (b) post LPS administration, as shown in FIG. 10C and FIG. 10D.

PTM202 at 50 mg/kg to 200 mg/kg oral doses (c-e) did not show significant changes in plasma and colon TL-6 levels compared to vehicle group (b) post LPS administration, as shown in FIG. 10A and FIG. 10B.

PTM202 at 500 mg/kg to 3000 mg/kg doses (f-i) reduced colon TL-6 levels (statistically not significant) post LPS administration as compared to vehicle group (b), as shown in FIG. 10B.

Histopathological analysis of small intestine and colon tissue were carried out. Intestinal segment was divided into three pieces to represent anterior, middle and posterior colon. Microscopic examination did not reveal any significant findings in any of the animal examined.

This example shows PTM202 without additional active agent was effective to significantly reduce diarrhea score in mouse model of LPS-induced diarrhea. In addition, PTM202 alone was effective to significantly reduce levels of plasma and colon TNF-alpha in mouse model of LPS-induced diarrhea compared to vehicle. A trend to reduced colon TL-6 was also exhibited.

Example 7. PTM202 Alleviates Symptoms of Crohn's Disease

A 19-year old Israeli female was diagnosed with Crohn's disease at age 18. She was being treated with oral mesalamine daily and rectal mesalamine as needed for episodic symptoms of diarrhea and abdominal pain. She was placed on a 25 g/day dose of PTM202 to prevent recurrent episodes and had immediate relief of episodes that allowed her to discontinue the rectal mesalamine. She has taken the product daily for a period of at least six months and has had no relapse.

Example 8. Pasteurised Chicken Egg Powder and Colostrum Powder Stimulates Gut Defence and Repair Processes Chicken eggs form an important dietary source of calories, protein, fats and minerals, and may be of interest to improve nutrition and growth in children suffering from stunting. Réhault-Godbert et al., Nutrients. 2019; 11:684; Stewart et al. *Am J Clin Nutr.* 2019 Aug. 6.

In addition to their nutritional value, eggs contain many proteins and peptides of potential therapeutic interest. These include antimicrobial and immunomodulatory factors such as lysozyme, avidin, ovalbumin, and ovomucoid, suggesting that egg may be a useful natural source of bioactives for clinical use. (Rehault-Godbert et al., *Nutrients.* 2019; Kovacs-Nolan et al., J Agric Food Chem. 53, 8421-8431.)

Until now, the major focus of identifying therapeutic opportunities originating from eggs relates to conferring passive immunity. For example, orally administered IgY isolated from hyperimmunised egg yolk has been shown to be helpful in the treatment of neonatal rotavirus enteritis (Wang et al., 2019 *Medicine (Baltimore)*. 98, e16100). The value of egg or its subcomponents for the prevention and treatment of gastrointestinal injury is, however, has been largely unexplored.

The gastrointestinal tract is constantly under attack from endogenous factors such as acid, bile and proteolytic enzymes, and exogenous ingested noxious agents, such as pathogenic microorganisms, aspirin or alcohol. In addition, the immune system plays an important protective role, but when uncontrolled, such as in inflammatory bowel disease, contributes to the breakdown in mucosal integrity. If a small area of injury is sustained, the healing process usually proceeds successfully via standard mechanisms. Surviving cells from the edge of the wound migrate over the denuded area to re-establish epithelial continuity. This process begins within a few minutes after injury and is termed "restitution". This is followed by increased proliferation and remodelling, which begins 24-48 h after the injury. Svanes et al., *Gastroenterology* 1982; 82: 1409-26.

In this example, experiments examined whether uncooked (pasteurised) or pre-heated (100° C. for 8 min) egg powder influenced pro-proliferative and migratory processes using in vitro models of gut repair. We then determined the distribution of activity between yolk and white, the importance of ovomucoid, ovalbumin, the EGF receptor and TGFβ in mediating these responses. We also compared the effect of administering egg alone or in combination with bovine colostrum as an additional source of natural growth factors and immune modulators. Previously, it was demonstrated that colostrum alone has beneficial effects on gut integrity and repair (Playford et al. *The American Journal of Clinical Nutrition* 2000; 72:5-14), and an egg and colostrum combination has been shown to be of benefit in the treatment of infectious diarrhoea. Gaensbauer et al *BMJ Glob Health.* 2017; 2:e000452. Bovine colostrum therefore also acted as a useful positive control. Having seen positive effects in vitro, in vivo studies were also employed to investigate the influence of egg and/or colostrum in proximal non-steroidal anti-inflammatory drug (NSAID)-induced small intestinal injury in mice and distal dextran sodium sulphate (DSS-induced colitis in rats) gut damage.

Materials & Methods

Chemicals & protein assays. Chemicals were purchased from Sigma (Poole, Dorset) unless otherwise stated. Protein assays used a standard Bicinchoninic Acid (BCA) assay.

Ethics. All animal experiments were approved by the Local Animals Ethics Committee and covered by the appropriate licenses under the Home Office Animals Procedures Acts, 1986.

Egg and colostrum samples. Pasteurized whole non-hyperimmune bovine colostrum powder, commercial pasteurized dried chicken whole immune egg powder, pasteurized dried immune egg yolk powder, pasteurized dried immune egg white powder, and a commercial form of combination of the two (DiaResQ®), which comprises 40% whole immune egg & 60% whole colostrum by weight, were each provided by Pantheryx, Inc. (Boulder, CO, USA). Fresh shell eggs were purchased from ASDA supermarket (UK), and tested as raw whole egg or separated into egg white and egg yolk. Fresh eggs were not pasteurized just broken and separated using a cup into yolk and white or whisked lightly together to get a mixture of the two. Cooked egg samples (8 min at 100° C.) were homogenised in PBS prior to use.

Cell lines. Caco-2 cells are derived from colorectal adenocarcinoma of a 72-year-old male (ATCC) and exhibits tight junctions and desmosomes between adjacent cells and grows as polarised monolayers. Fogh et al., *J Natl Cancer Inst* 1977; 59:221-6. AGS is derived from gastric adenocarcinoma of a 54-year-old female (ATCC), Barranco et al., *Cancer Res.* 1983; 43:1703-1709. RIE1 is a spontaneously immortalised rat intestinal epithelial cell line (ATCC). Blay et al., *Cell Biol Int Rep.* 1984; 8:551-60.

Proliferation Assays

Cell proliferation assays were performed as previously described, utilising ALAMARBLUE™ (Invitrogen, Paisley, UK), (Marchbank et al., *Am J Physiol Gastrointest Liver Physiol.* 2009; 296:G697-703) as per manufacturer's instructions. Briefly, cells were seeded at 2000 cells/well, grown in medium and 10% FCS in 96 well plates overnight. The following day, cells were washed with medium alone and incubated in medium alone (negative control), medium containing epidermal growth factor (EGF, 1 µg/ml, positive control) or egg and colostrum combination. BSA was added to additional wells as a further negative control. Data are expressed as % positive control where the rise in proliferation (increase in A570 above baseline) caused by 1p g/ml of EGF was defined as 100%.

Cell Migration Assays

Cell migration assays were performed using our previously published methods. Marchbank et al., *Am J Physiol Gastrointest Liver Physiol.* 2009; 296:G697-703. Briefly, confluent monolayers had standard wounds inflicted and serial photomicrographs taken. Twenty measurements per field were performed by placing a transparent grid over the photograph and measuring the distance moved from the original wound line. All results are expressed as mean (SEM) of four separate experiments.

Example 8A Study Series 1. In Vitro Studies

Distribution, heat sensitivity and signalling pathways of bioactivity within egg.

Whole powdered egg and colostrum (0.25-4 mg/ml) was added to cells and effect on proliferation and cell migration analysed. Additional studies compared "pure" yolk and egg white powder (1 mg powder/ml) along with separated yolk and white from fresh eggs (added at same protein concentration as equivalent powder) and also compared uncooked egg powder and whole fresh egg that had been heated to 100° C. for 8 minutes (samples placed in 50 ml falcon tube in waterbath, followed by homogenisation) prior to addition to cells.

Potential additive or synergistic responses of using egg and colostrum in combination was examined by comparing effects of adding (0.25-4 mg/ml) of egg or colostrum powder alone, or the 40:60 (egg:colostrum) combination. This 40:60 proportion was used to reproduce the product currently commercially available and used in trials of infectious diarrhoea. Gaensbauer et al. BMJ Glob Health. 2017; 2:e000452.

The importance of the EGFR and TGFβ in mediating proliferative and migratory effects was examined by adding whole egg powder (1 mg/ml, w/v) to cells in the presence and absence of tyrphostin (100 nM) and a TGFβ (100 g/ml) neutralising antibody (antibodies-online.com, Aachen, Germany). Additional samples examined the effect of pure ovomucoid (25-100 µg/ml) and ovalbumin (50-400 µg/ml) on proliferation and migration. To further examine the contribution of ovomucoid and ovalbumin in mediating the proliferative and migratory activity seen using whole egg powder, further wells had egg powder added (1 mg/ml) in the presence of anti-ovomucoid and ovalbumin antibodies (Generon, Slough, Berkshire, UK) at 1 µg/ml.

Size distribution of pro-proliferative components within the egg was determined by diluting whole egg powder in PBS followed by centrifugation through a series of size exclusion spin columns (Bio-Rad, Watford, UK) to separate fractions into >30 kDa, 10-30 kDa, 5-10 kDa and <5 kDa, followed by proliferation assays.

Example 8B Study 2. Mouse NSAID Small Intestinal Injury Model

Methods used were based on those described by us previously. Playford et al. *Clin Sci (Lond).* 2001; 100:627-33. C57BL/6 mice (Charles River, UK) were fed standard laboratory chow (Special Diet Services, Essex, UK) and allowed water ad libitum. Five groups of animals (n=6 per group) were used. Non-steroidal anti-inflammatory drug (NSAID) Indomethacin alone group received normal tap water throughout, the other 4 groups had colostrum, whole egg powder, whole cooked egg or the 40:60 combination (all at final dose of 20 mg/kg dose) added to the drinking water for 7 days. These doses of egg and colostrum were chosen based on efficacy of colostrum given alone as published previously. Playford et al. *Clin Sci (Lond)*. 2001; 100:627-33.

All animals received indomethacin (85 mg/kg sc.) 16 h before killing. A further group of animals did not receive indomethacin and were used as a normal control. The small intestine was dissected free and a 1 cm segment taken from the small intestine at 10% of small intestine length (duodenum). The segment was placed in Carnoy's solution at room temperature for 4 h and then stored in 70% alcohol until further assessment. Microdissected samples were assessed for villus height and width by tracing outline of villi using a precalibrated drawing tube. Twenty individual villi were assessed in each animal, and mean value from these 20 measurements used in the subsequent analysis of variance (ANOVA).

Example 8C. Study 3. Rat DSS Colitis Model

Male Sprague Dawley rats (225 to 250 g, n=8 per group; Charles River, UK) were housed in standard cages (five animals per cage) and fed standard laboratory chow (Special Diet Services, Essex, UK) and tap water ad libitum.

Methods used were as described previously (FitzGerald et al. (2004) Peptides. 25, 793-801). All rats received a 2 ml gavage daily for 9 days. Negative control group received no DSS and underwent daily gavage with bovine serum albumin (BSA) to determine baseline values. Positive control group received DSS and gavage with BSA. Other groups received DSS along with gavage of egg powder, colostrum, or the 40:60 combination (all at 20 mg/kg). Colitis was induced by adding 4% (w/v) DSS (molecular mass, 36 to 44 kDa; ICN, Aurora, OH) to the drinking water for 7 days, starting from day 3.

Mean DSS and food consumption were noted per cage each day. Rats were weighed daily and visually inspected for signs of distress, diarrhea, and rectal bleeding. The disease activity index (DAI, based on Cooper et al. *Lab Invest.* 1993; 69:238-249) was assessed every day after the induction of colitis. The DAI combines the scores of weight loss, stool consistency, and bleeding divided by 3. A cumulative score was then determined over the 7-day DSS treatment period. At the end of the study, animals were killed and colonic tissue collected and subsequently analysed for microscopic damage using the scoring system described by Williams and colleagues. Williams et al. *Gastroenterology* 2001; 120:925-37. The total histological colitis score is derived from the sum of the four subscores of i) inflammation severity, ii) inflammation extent, iii) crypt damage, and iv) percentage of involvement. Tissue was also analysed for myeloperoxidase (MPO) activity (used as a marker of neutrophilic infiltration) as described previously. Bradley et al. *J Invest Dermatol* 1982; 78:206-9.

Statistics

Dose response proliferation and cell migration studies were analysed using two-way analysis of variance (ANOVA), using dose and treatment as factors. Single dose proliferation and cell migration studies were analysed using one-way analysis of variance (ANOVA). In vivo studies were analysed using 2-way ANOVA with animal and treatment as factors. Where a significant effect was seen ($p<0.05$), individual comparisons between groups were performed based on the group means, residual, and degrees of freedom obtained from the ANOVA, a method equivalent to repeated measures analysis.

Results

Example 8A. Study Series 1. In Vitro Studies.

Distribution, heat sensitivity and signalling pathways of bioactivity within egg were studied.

Dose response curves showed optimal effect occurred at 1 mg of egg powder/ml (FIG. 11A) with higher doses beginning to affect cell viability. Cell migration studies showed similar results (data not shown). Subsequent studies on proliferation and migration therefore used 1 mg/ml concentration.

Figure 11B:
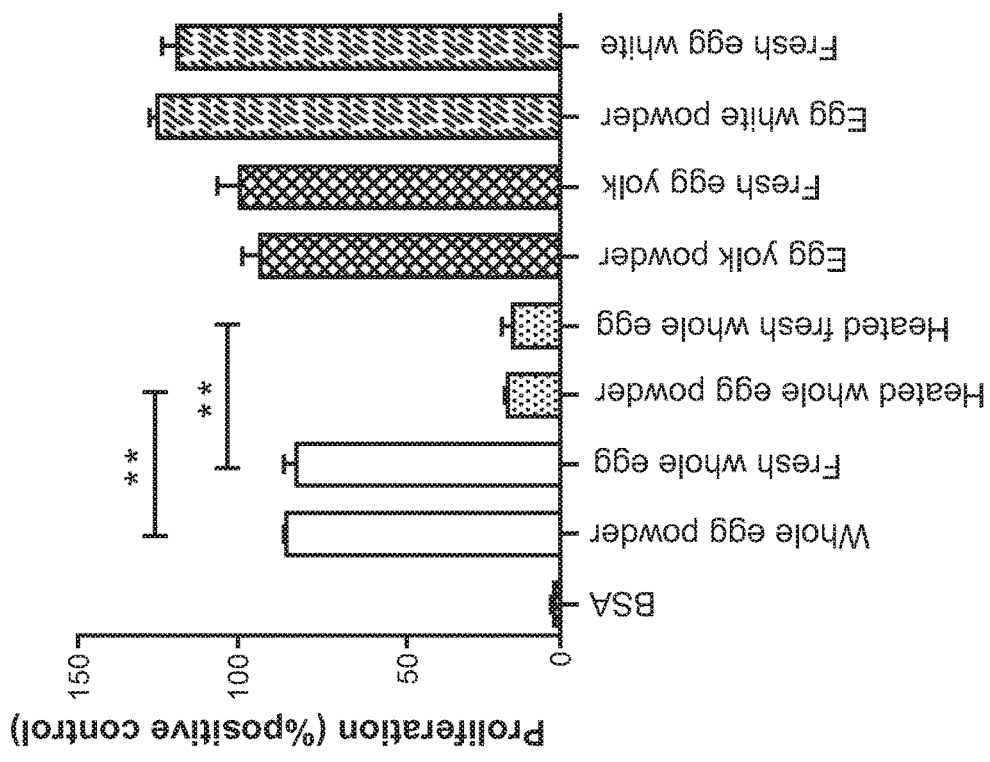
FIGS. 11A-D show in vitro bioactivity of egg and/or colostrum in AGS cells.

Pro-proliferative effects of whole egg, egg yolk and egg white were not significantly different between powdered or fresh egg at equivalent protein concentrations and activity was present in both the egg white and yolk (FIG. 11B). The proliferative activity was divided at a ratio of about 55%:45% between egg white and egg yolk when expressed in terms of activity per mg powder. Similar distribution between white and yolk was seen when analysing migratory activity (ratio 58%:42%, data not shown).

Subjecting egg powder or fresh egg to heat at 100° C. for 8 min caused a loss in bioactivity, reducing proliferative activity by 80% compared to non-heated equivalent sample ($p<0.01$, FIG. 11B).

Figure 11A:
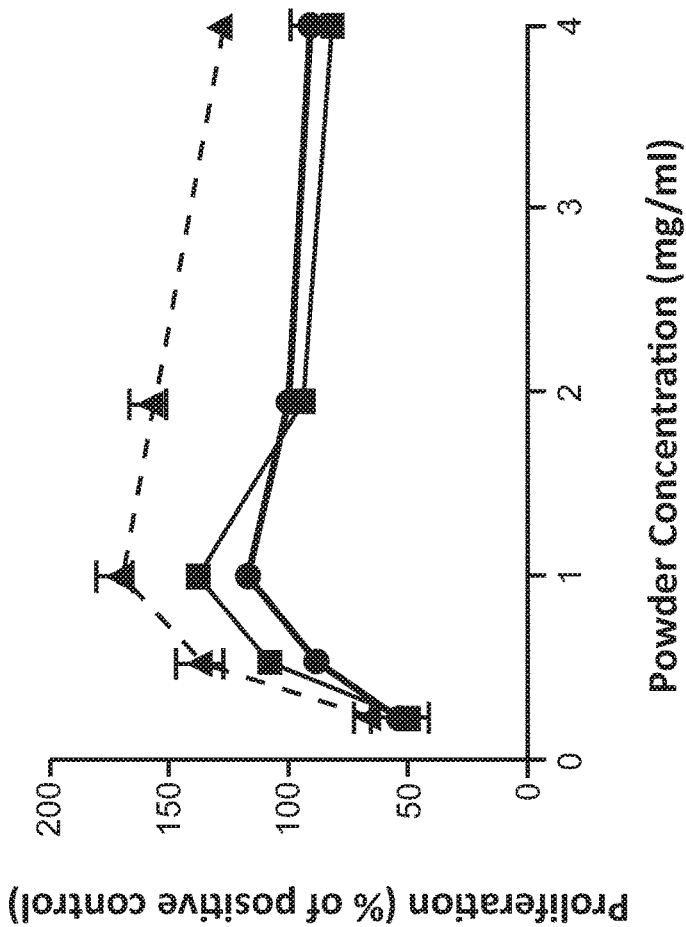

Changes in proliferation were assessed with results shown in FIG. 11A for cells incubated in 0.25-4 mg/ml of egg (■), bovine colostrum (●), or 40:60 combination (▲) of egg and colostrum. At all doses tested, synergistic responses were seen when the 40:60 egg and colostrum mixture was added, compared to adding egg or colostrum alone at the same final concentration (FIG. 11A). ANOVA effect of treatment $p<0.001$, effect of dose $p<0.001$, no interaction between dose and treatment $p>0.5$, showing synergy was seen at each dose tested. Similar results were seen following pro-migratory activity; results from optimum dose (1 mg/ml) showed colostrum alone 221.1+/−8.9 μm migrated/24 h, egg alone 266.1+/−9.1 μm migrated/24 h and the 40:60 combination 342.9+/−12.3 μm migrated/24 h, ($p<0.01$ vs colostrum or egg alone).

Figure 11D:
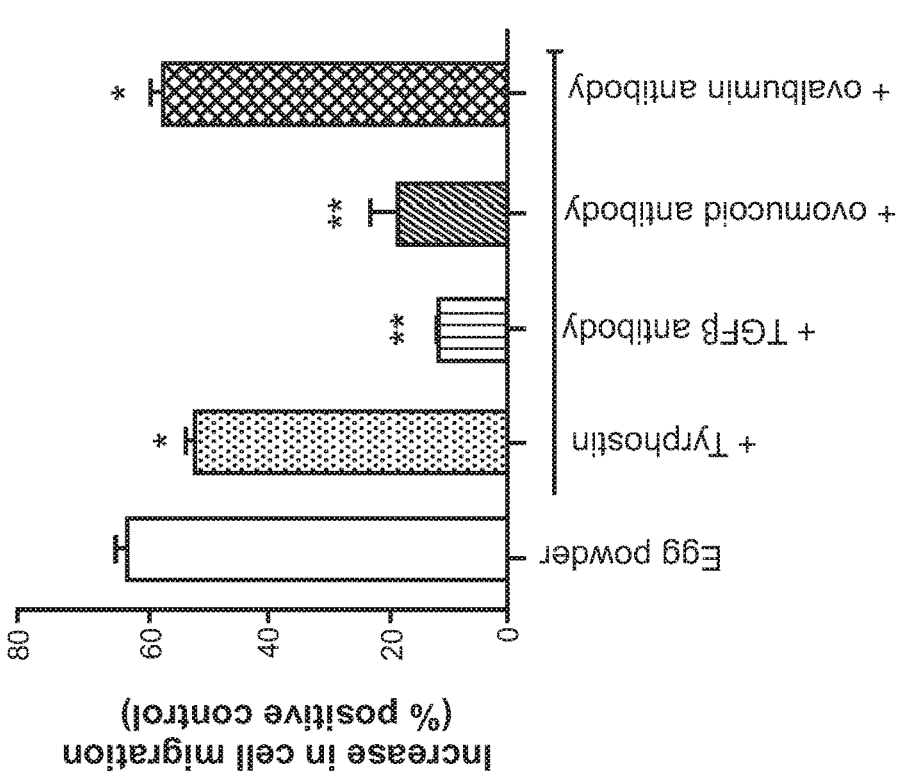

Addition of EGFR inhibitor tyrphostin reduced pro-proliferative activity of egg by 40% (FIG. 11C, $p<0.01$) whereas TGFβ neutralising antibody did not affect pro-proliferative effect. Pro-migratory activity of egg was reduced by 18% by tyrophostin (FIG. 11D, $p<0.01$) and addition of TGFβ neutralising antibody caused pro-migratory activity to fall by 81% (FIG. 11D, $p<0.01$).

Figure 11C:
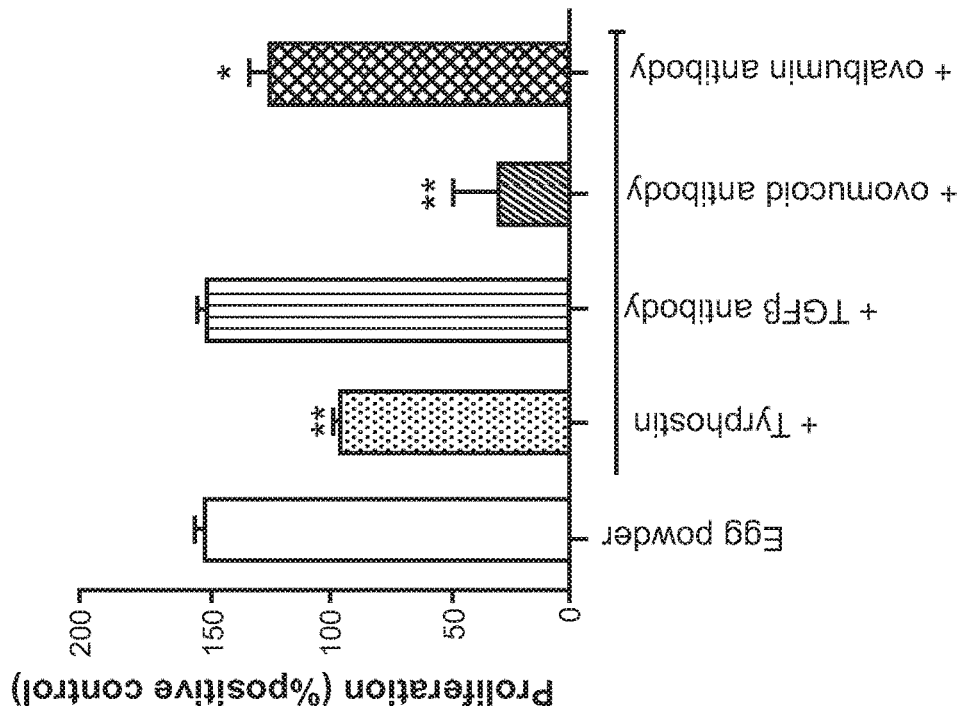
Figure 15B:
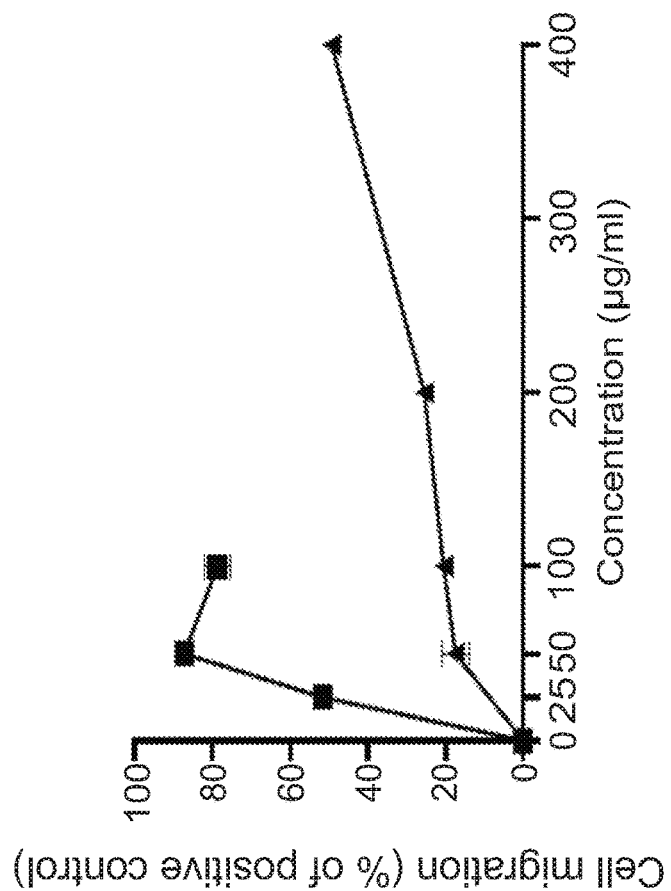
FIG. 15B shows cell migration (% of positive control) dose-response curves for purified ovomucoid (■), showed its peak effect at 50 µg/ml. Addition of purified ovalbumin (▲) to cells also showed a dose-response curve with increasing activity up to the highest dose.
Figure 15A:
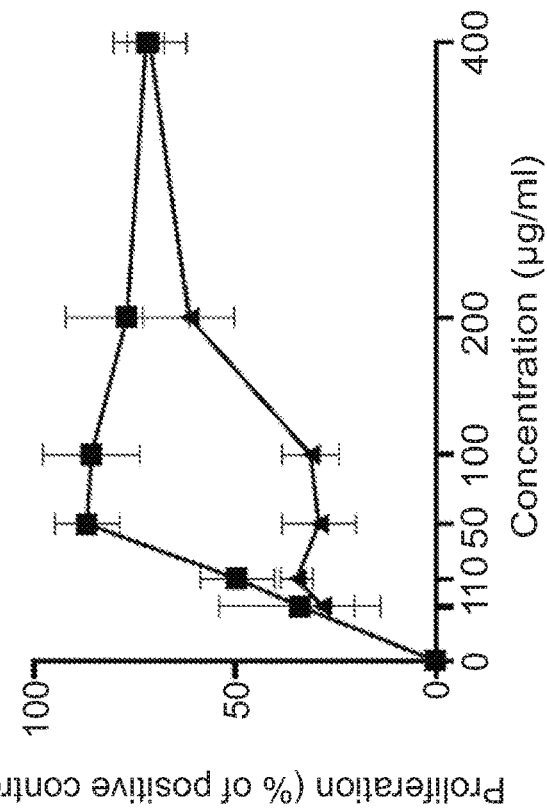
FIG. 15A shows cell proliferation (% of positive control) dose-response curves for purified ovomucoid (■), showed its peak effect at 50 µg/ml. Addition of purified ovalbumin (▲) to cells also showed a dose-response curve with increasing activity up to the highest dose.

Dose-response curves of purified ovomucoid showed its peak effect at 50 μg/ml (FIG. 15A, B). Addition of purified ovalbumin to cells also showed a dose-response curve with increasing activity up to the highest dose. Addition of ovomucoid antibody reduced proliferative activity of whole egg powder by 80% and migration by 69%, whereas ovalbumin antibody reduced proliferative activity by 27% and migration by 10% (FIGS. 11C & 11D).

Example 8B. Study 2. Mouse NSAID Duodenal Injury Model

Figure 12C:
FIG. 12A-F show effects of indomethacin alone or with egg and/or colostrum on villi in a mouse duodenal injury model.
Figure 12B:
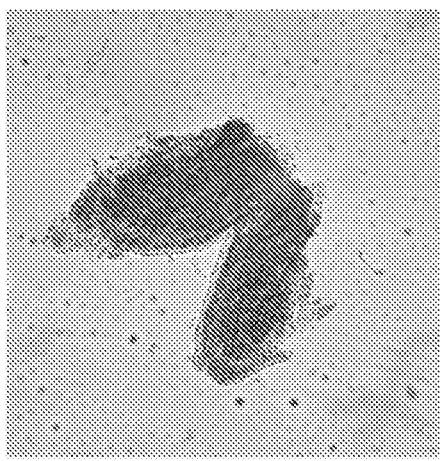
Figure 12A:
Figure 12E:
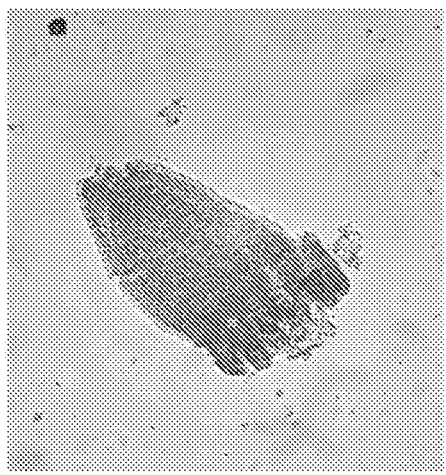
Figure 12D:

Morphological assessment showed NSAID caused marked shortening of villus length with some bulbous expansion (FIG. 12B), compared to non NSAID controls (FIG. 12A). The degree of injury appeared less severe in animals that received egg (FIG. 12C) alone or colostrum alone (not shown) with the greatest protection seen in animals that had received the 40:60 combination of egg:colostrum (FIG. 12D). Pre-heated whole egg powder had no effect on NSAID-induced injury (FIG. 12E).

Figure 12F:
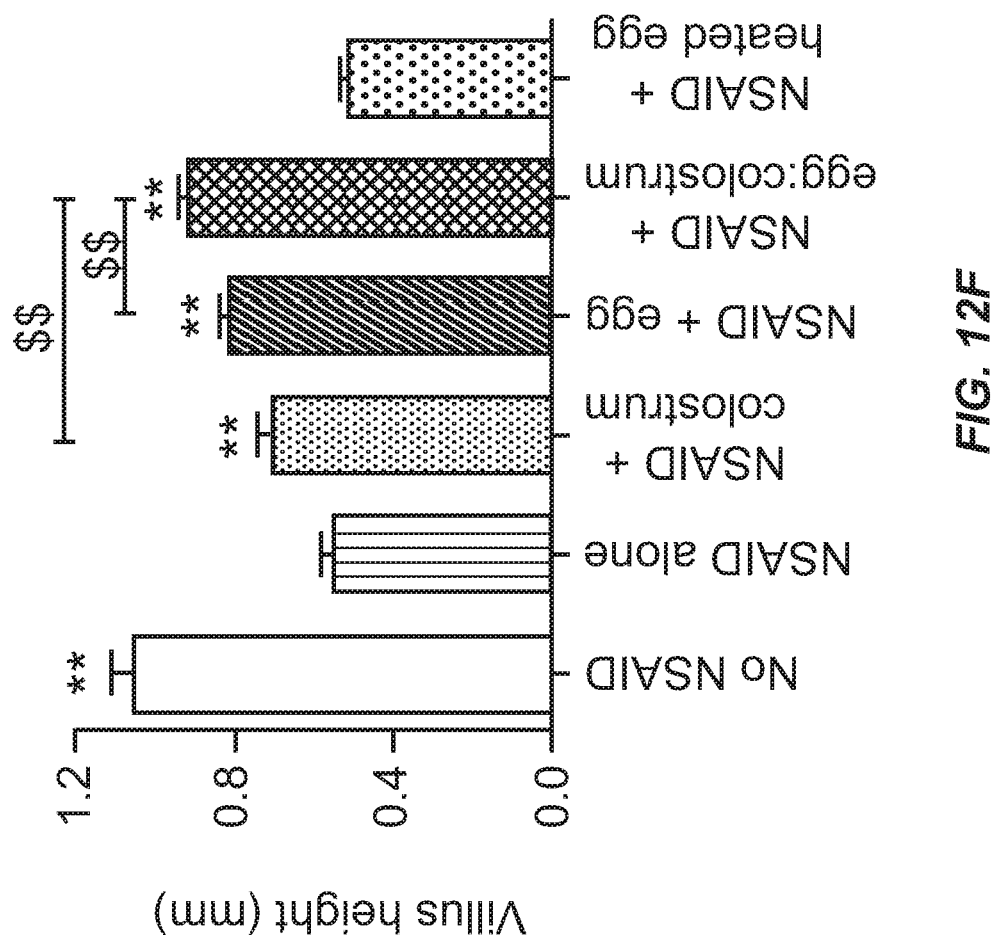

Formal histological measurement confirmed these findings (FIG. 12F). NSAID induced damage (shortening) was reduced by 29% in animals given colostrum alone, by 51% in animal given egg alone, and by 68% when the 40:60 combination of egg:colostrum was used (P<0.01 vs egg or colostrum given alone). Pre-heated whole egg powder was ineffective in truncating the villus shortening caused by NSAID.

Example 8C. Study 3. Rat DSS Colitis Model

Animals receiving DSS alone showed 46% reduction in weight gain over 7-day test period compared to animals who did not receive DSS (FIG. 13A). Administration of colostrum or egg to DSS-treated animals showed improved weight gain (both p<0.01 vs DSS alone) with greatest improvement seen in animals receiving 40:60 combination of egg:colostrum (p<0.01 vs egg or colostrum alone, FIG. 13A). Similar results were seen following cumulative DAI scores with best result seen in the 40:60 combination egg:colostrum group (DSS alone 4.42+/−0.52, DSS+colostrum 0.58+/−0.21, DSS+egg 1.21+/0.40, DSS+40:60 combination egg:colostrum 0.25+−0.12. Combination p<0.01 vs colostrum or egg alone).

Administration of DSS alone caused a 10-fold increase in MPO (marker of neutrophil infiltration) in colonic tissue (FIG. 13B). Co-administration of colostrum or egg alone significantly reduced MPO levels, with greatest reduction (62%) seen in animals that received the 40:60 egg:colostrum combination (p<0.01 vs egg or colostrum alone).

Figure 14A:
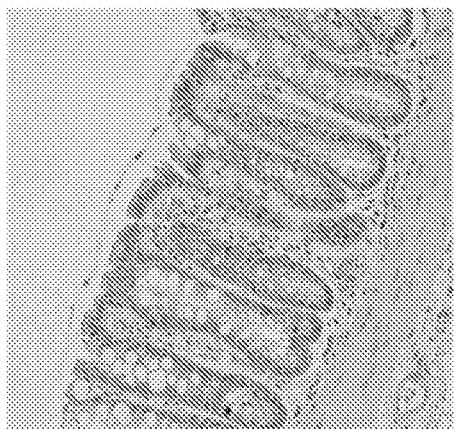
FIGS. 14A-F show colon morphology and colitis score in DSS-induced colitis rat model in same animals as in FIG. 13.
Figure 14B:
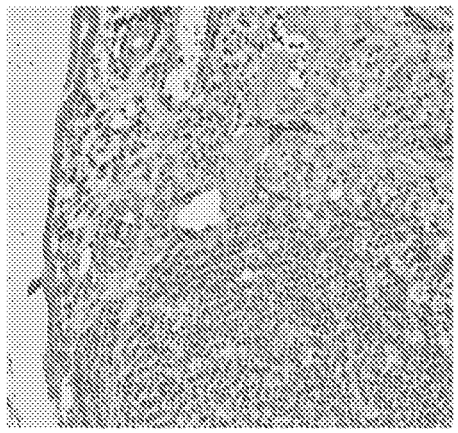
Figure 14C:
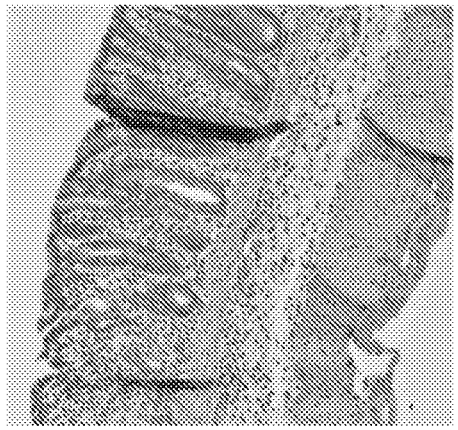
Figure 14D:
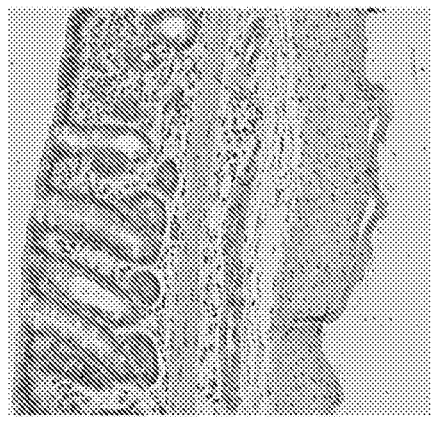
Figure 14E:
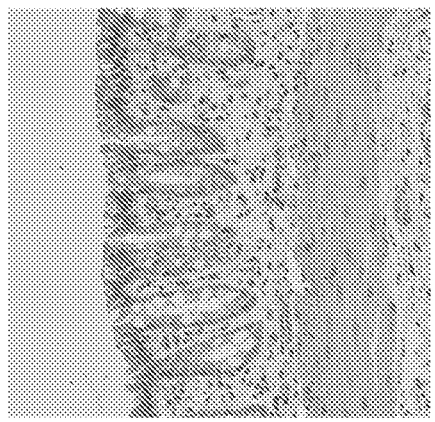

Morphology showed that compared to normal (no DSS) controls (FIG. 14A), administration of DSS alone caused virtually a complete loss of normal crypt structure with major infiltration of inflammatory cells (FIG. 14B). These changes were much less severe in animals that had also received colostrum (FIG. 14C) or egg (FIG. 14D) where the inflammatory infiltrate was less marked and crypt structure was maintained, although there was some degree of mucin depletion of goblet cells. Tissue from animals treated with DSS and the 40:60 egg and colostrum combination group had nearly normal morphology (FIG. 14E).

Figure 14F:
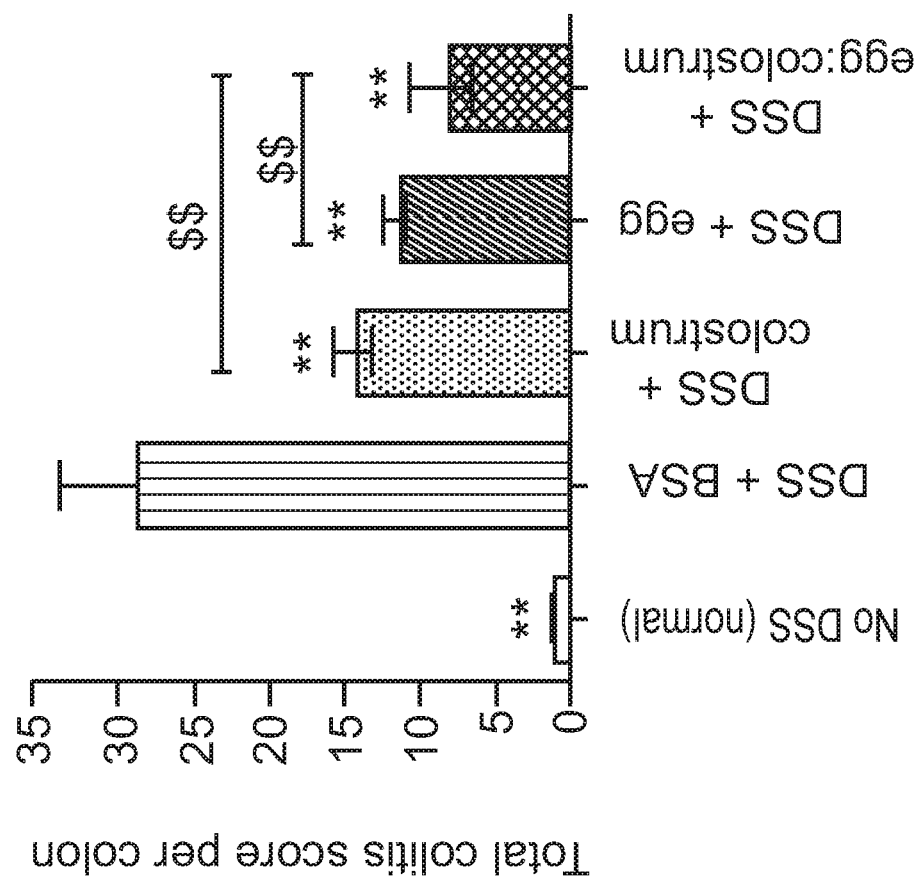

Formal histological scoring showed similar results with colostrum or egg alone significantly reducing tissue damage and greatest effect seen using 40:60 egg and colostrum combination (74% reduction in injury compared to DSS alone, P<0.01 vs using either egg or colostrum alone, FIG. 14F).

Well validated in vitro and in vivo models were used to investigate the value of pasteurised egg powder to reduce gastrointestinal damage. As demonstrated in present examples, promigratory and proliferative activity was present in egg yolk and white. Ovomucoid and ovalbumin both contributed to the biological effects seen. As provided herein, ovomucoid and ovalbumin have been shown to simulate cell migration and proliferation in dose-response studies using purified ovomucoid and ovalbumin. This has been confirmed by adding neutralizing antibodies to whole egg powder which markedly knocks down the proliferative and migratory activity of whole egg, demonsting a major role in mediating these effects.

Synergistic responses were found when egg was combined with bovine colostrum. These synergistic effects were also seen in models of NSAID-small intestinal injury and DSS induced colitis. Heating of the egg powder removed bioactivity.

Pro-proliferative and migratory bioactivity of egg was roughly equivalent in raw and pasteurised powdered form, showing that relevant egg bioactive molecules survived pasteurisation intact.

In conclusion, the present studies demonstrate that pasteurised raw egg powder contains bioactive compounds that stimulate protection and repair in a variety of in vitro and in vivo models of gut damage and that these reparative effects were enhanced synergistically when combined with bovine colostrum.

Example 9. EED Study in Malawi Infants

A prospective, randomized, double-blinded, controlled clinical trial in Malawian infants was performed to evaluate a composition comprising whole bovine colostrum and hyper immune egg powder (PTM1001) to determine if the composition could prevent or ameliorate symptoms of environmental enteric dysfunction including stunting.

Stunting means a child is too short for their age. Well-nourished children are more likely to stay in school longer, earn higher wages, and escape poverty.

A prospective, randomized, double-blinded, controlled clinical trial was performed to evaluate whether supplementary feeding with PTM1001 (4.3 immune egg powder+5.7 g bovine colostrum) (PTM) plus multiple micronutrient powder improves linear growth and reduces gut permeability in children 9-12 months of age when compared to a isoenergetic control composition comprising corn/soy blend (CSB) plus multiple micronutrient powder. 250 healthy infants in Malawi, recruited at 9 months of age, were individually randomised to intervention or control for 3 months.

Children were enrolled from two different village clusters in Malawi: Limera (Machinga distruct) and Masinjere (Nsanje district). Children were enrolled into the study at 9 months of age, finishing feeding at 12 months and complete the study at 16 months of age.

A total of 281 children were enrolled into the study (141 into the control group; 140 into the intervention group). A total of 18 children (14 in the control group; 4 in the intervention group) were withdrawn during the feeding period. A total of 263 children received food for 12 weeks and were included in the analysis.

At enrollment anthropometric measurements were taken, a demographic/health information collected, a dual sugar absorption test was given, and urine and fecal samples were collected.

Study subjects were given a 2-week (4-week after first month) supply of their randomly assigned study food (PTM+micronutrients or isoenergetic CSB+micronutrients) for a total of 12 weeks.

Caregivers of children enrolled were taught to prepare the foods by mixing the allotted amount and with the traditional maize porridge.

Anthropometric measurements, symptom, food frequency survey, and study food compliance survey, were performed at enrollment, and weeks 2, 4, 8, 12.

The dual sugar absorption test and fecal sample collection was conducted at enrollment and week 12.

Follow-up assessments were performed at 20 and 32 weeks including anthropometric measurements and symptom and food frequency surveys A total of 281 children were enrolled into the study (141 into the control group; 140 into the intervention group). A total of 18 children (14 in the control group; 4 in the intervention group) were withdrawn during the feeding period.

A total of 263 children received food for 12 weeks and were included in the analysis.

The primary outcome was change in length-for-age z-score from enrollment to 12 weeks post-enrollment. Secondary outcomes included change in dual sugar permeability (the lactulose-mannitol test) from baseline to end of the intervention (12 weeks after enrollment) and follow-up anthropometry and morbidity at 14 months and 16 months. Table 4 shows study activities for subjects by week of participation.

TABLE 4

Study Activities for subjects by week of participation

| | Week: 0 | 2 | 4 | 8 | 12 | 20 | 32 |
|---|---|---|---|---|---|---|---|
| | | | Child's Age: | | | | |
| | 9 months | | 10 mo | 11 mo | 12 mo | 14 mo | 16 mo |
| Screen for eligibility | X | | | | | | |
| Anthropomorphic measurements | X | X | X | X | X | X | X |
| Food frequency/diet diversity questions | X | X | X | X | X | X | X |
| Dual sugar permeability testing (lactulose:mannitol test) | X | | | | X | | |
| Stool Sample Collection | X | | | | X | | |
| Food distribution | X | X | X | X | | | |
| Supplement Adherence Questions | X | X | X | X | X | | |
| Health/clinical assessment | X | X | X | X | X | | |
| Follow-up Questions | | | | | | X | X |

Figure 16:
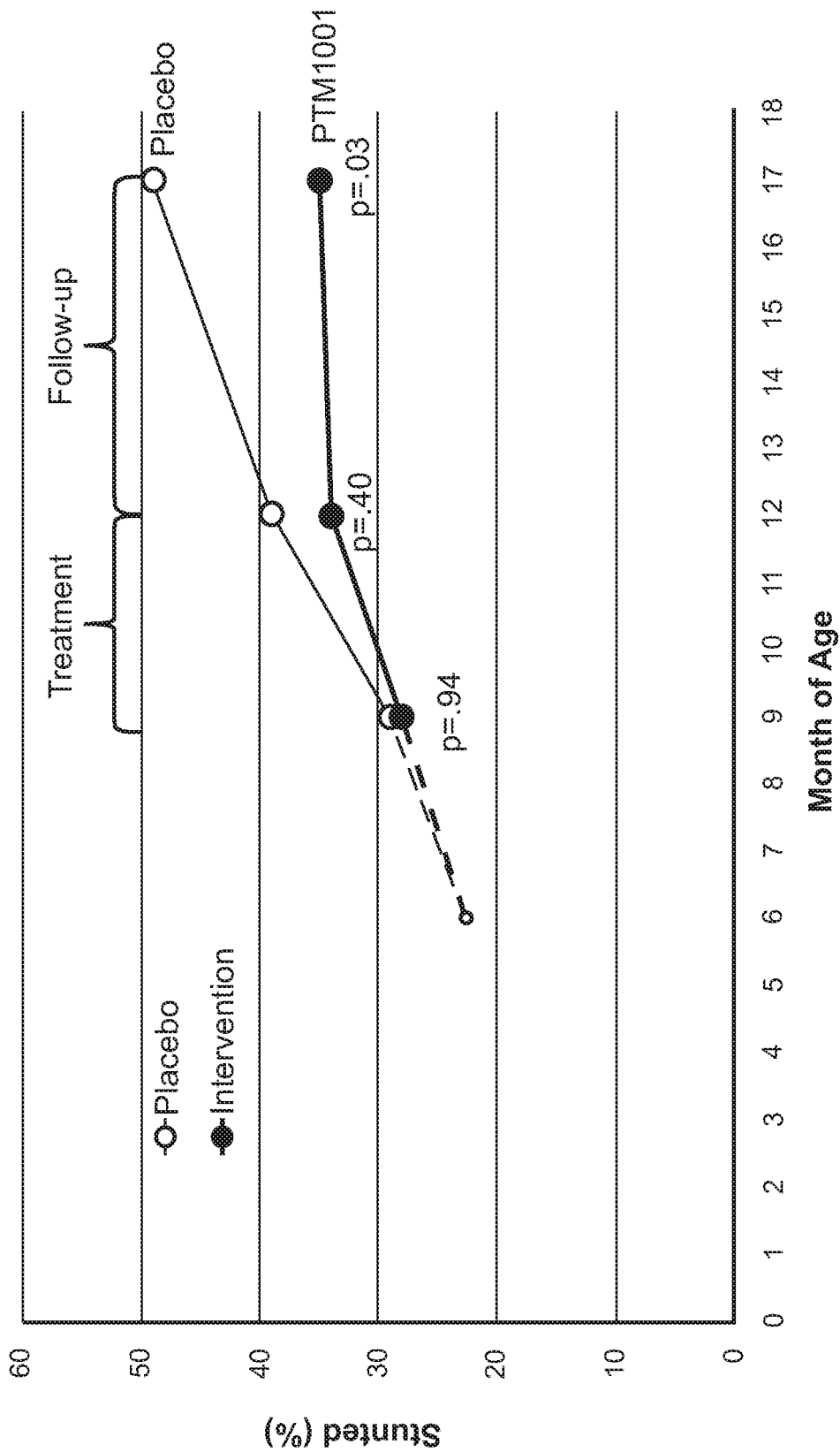
FIG. 16 shows a graph of a double, blind placebo control study of effect on stunting of test composition PTM1001 comprising immune egg and whole colostrum+micronutrients in Malawi children compared to an isoenergetic CSB+micronutrient placebo control. After feeding compositions for three months at ages 9 to 12 months, follow up anthropomorphic data was collected at 17 months of age showed significantly reduced stunting in children fed test composition compared to placebo control (p=0.03).
Figure 17:
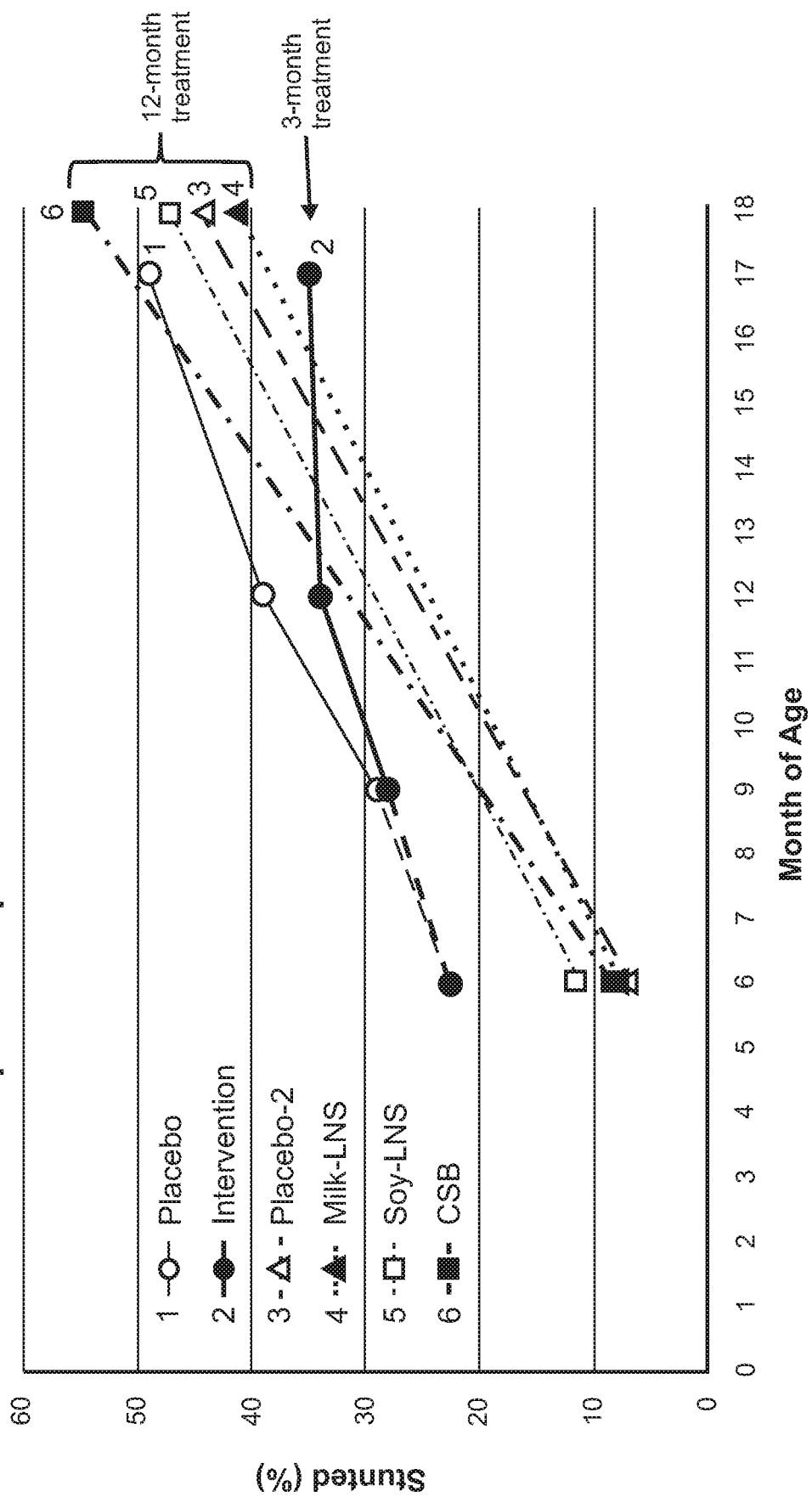
FIG. 17 shows the graph of a double, blind placebo control study of effect on stunting of test composition PTM1001 comprising immune egg and whole colostrum+micronutrients in Malawi children compared to an isoenergetic CSB+micronutrient placebo control, and compared to other prior studies in Malawi children. PTM test article was superior with respect to stunting prevention when compared to milk-LNS, soy-LNS, or CSB fed for 12 months.

Results on stunting are shown in FIGS. 16 and 17. As shown in FIG. 16, the children in the PTM Treatment group exhibited significantly reduced stunting during follow-up period when compared to children in Placebo Control Group. (p=0.03). FIG. 17 shows results compared to previous studies in Malawi using different test articles. Children fed PTM for three months between 9 and 12 months of age, exhibited significantly reduced stunting at 17 months of age compared to control, or when compared to other test articles milk-LNS, soy-LNS, or CSB, even after feeding for 12 months, as shown in FIG. 17. The effect of PTM on prevention (49%) was much greater than the effect on treatment (11%), suggesting an optimal impact on non-stunted but at-risk (i.e., younger) children.

Despite significant improvement in stunting rates, there was no absolute difference in Weight, Height, MUAC, LAZ, WHZ, or WAZ between the two study groups at the end of the study.

Growth after the intervention may suggest microbiome effects. It was planned to perform 16S ribosomal RNA analysis of stored samples. The 16S ribosomal RNA gene codes for the RNA component of the 30 s subunit of the bacterial ribosome. 16s rRNA gene sequencing is a common method targeting housekeeping genes to study bacterial phylogeny and genus/specis classitication.

Example 10. Partial Reversal of Pathogen-Induced Barrier Dysfunction

This example shows compositions of the disclosure have been shown to reduce bacterial translocation through an intestinal epithelial barrier and reduce pathogen-induced intestinal epithelial barrier dysregulation.

Current treatment for SIBO is with non-absorbable antibiotic+/−probiotic with variable results and with a need to repeat in many patients. The present inventors wondered if bovine colostrum, immune egg or a combination could affect this pathological process. These examples show the compositions stabilize the gut lining so as not to allow the bacteria to cross through the mucosa.

Many other disorders of the small intestine are characterized by increased permeability and impaired barrier function. For example, environmental enteropathy (EED) is emerging as an example of a small intestinal disorder induced by frequent, often co-existent, sub-clinical intestinal infections, with or without nutrient deficiencies. EED is associated with stunting and poor growth in young children throughout the developing world, with severe impaired responses to oral vaccines, and with reduced net absorption of micronutrients and some drugs. EED is characterized by chronic low-grade intestinal inflammation such as lymphocytic infiltration of the lamina propria and increased intraepithelial lymphocytes, increased translocation of bacteria across the intestinal mucosa, reduced epithelial surface area, and immaturity of the absorptive cells of the intestine.

There is also dysregulation of tight junctions (TJ) located at the apical margins of the lateral membranes of intestinal epithelial cells, which seal the intercellular space and define the boundary of the host versus the environment in the intestinal lumen. As this dysregulation appears, at least partly, to explain microbial translocation. It may also assist in understanding critical care sepsis, autoimmune and neurological disorders of the gut.

Method

A variety of microbes may be involved in SIBO and some of these were included in this study including streptococci, *Escherichia coli*, staphylococci, and *klebsiella*, as shown in Table 5.

TABLE 5

Bacterial strains

| | |
|---|---|
| 1. | *Escherichia coli* (*E.coli*; ATCC 25922-O6) |
| 2. | Enteropathogenic *E. coli* (EPEC; ICC481-O127:H6) |
| 3. | *Salmonella enteriditis* (Sal50-clinical strain) |
| 4. | *Staphylococcus aureus* (NCTC12981) |
| 5. | *Streptococcus pneumonia* (NCTC 1269. |
| 6. | *Klebsiella pneumoniae* (NCTC 9633) |
| 7. | *Enterococcus faecalis* (ATCC 29212) |
| 8. | *Proteus mirabilis* (NCTC 13376) |
| 9. | Non-pathogenic *Escherichia coli* K12 |

Bacterial colonies shown in Table 5 were stored on Luria-Bertani (LB) agar or on Columbia agar with horse blood (blood agar; Fisher Scientific, Loughborough, UK), with fresh colonies re-cultured weekly. Before each experiment, a single colony was cultured in LB broth and grown shaking overnight at 370 then the $OD_{600\ nm}$ measured.

Antimicrobial Activity Assay

The antibacterial effect of DiaResQ®, Skimmed Colostrum, Whole Colostrum, and Egg powder at concentrations 0.5, 1.0, 5 and 10 mg/ml were tested against each pathogen. Fresh bacterial colonies of the strains shown in Table 5 were grown overnight and the $OD_{600\ nm}$ measured. $1 \times 10^6$ colony forming units (CFU)/ml were incubated with each concentration of the compound. After 4 h and 24 h of incubation, the test samples were serially diluted in PBS and cultured on blood agar and MacConkey agar (Fisher Scientific, Loughborough, UK) and grown overnight at 37° C., followed by enumeration of the colonies formed.

Cell Culture

The human Caco-2 enterocyte cell line (passage 6-40) was obtained from the American Type Culture Collection (ATCC: HTB-37; Middlesex, UK) and grown as monolayers (VWR, Leicestershire, UK) at 37° C. in humidified 5% $CO_2$ in complete medium consisting of Dulbecco's Modified Essential Medium supplemented with 10% heat-inactivated fetal calf serum (FCS), 4 mM L-glutamine, 100 U/ml penicillin, 100 µg/ml streptomycin and 1% non-essential amino acids (Invitrogen Life Technologies, Paisley, UK). For membrane integrity and translocation investigations, trypsinised cells were seeded at a density of $1 \times 10^5$/well into 24 well plates holding polyethylene terephthalate (0.4 m) cell culture inserts (Transwell inserts, Millipore, Hertfordshire, UK) and grown until polarization (15-21 days). Formation and disruption of polarised monolayers (membrane integrity) were determined by regular measurement of transepithelial electrical resistance (TER) (Millicell-ERS; Millipore, Livingston, UK). Caco2 cell monolayers were considered polarised when TER readings reached 800-1000 ohms/cm$^2$.

In Vitro Bacterial Infections

Before infection commenced, monolayers were washed with PBS and overnight-cultured bacteria at $1 \times 10^6$ CFU/well were then added to the brush border face of the monolayer in 200 µl complete medium. Fresh 300 µl complete medium was also added to the well but outside the Transwell insert (basolateral compartment). Infections developed for 24 h without antibiotics at any stage.

Quantification of Transepithelial Resistance (TER) and Bacterial Translocation

Electrical resistance across the stratified epithelium was measured using a Millicell-ERS-2 instrument (Millipore, Bedford, UK) with tweezer-like electrodes. The value obtained from a blank insert (with culture medium only) was subtracted to give the net sample resistance, which was then multiplied by the membrane area to give the resistance in area-corrected units ($\Omega$/cm$^2$). TER was measured before and after 24 h. To observe bacterial translocation (BT), the medium from the basolateral compartment of the Transwell insert after infection was cultured for colony quantification for 24 h. The cultured agar plates were incubated for a total of 48 h to ensure any slow growing colonies were detected. The non-invasive bacteria *Escherichia coli* K12 (K12) were used in the in vitro model as a marker of BT during infection with pathogens that did not appear to translocate.

Data Analysis

One-way ANOVA with Kruskal-Wallis was used for antimicrobial data. The Mann-Whitney test was used to test the effect of the intervention on each pathogen. Statistical significance was established at $p<0.05$.

Results

Summary of Optimization

In preliminary experiments, overnight cultures of each bacterial strain were washed twice in PBS by centrifugation at 3000×g with the $OD_{600\ nm}$ values then established as shown in Table 6. Serial dilutions and culturing on both blood agar and MacConkey agar were also performed to determine corresponding CFU/ml and optimal nutrient requirements as shown in Table 6.

TABLE 6

$OD_{600nm}$ values and CFU/ml for Bacterial Stains in Overnight cultures

| Bacteria | OD600nm | CFU/ml |
|---|---|---|
| *Escherichia coli* (*E.coli*) | 3.4 | $3.2 \times 10^6$ |
| EPEC | 4.5 | $1.35 \times 10^6$ |
| *Salmonella enteriditis* | 3.8 | $1.72 \times 10^7$ |
| *Staphylococcus aureus* | 1.6 | $3.5 \times 10^7$ |
| *Streptococcus pneumonia* | 0.1 | $8 \times 10^5$ |
| *Klebsiella pneumoniae* | 2.2 | $1.5 \times 10^6$ |
| *Enterococcus faecalis* | 3.5 | $1.65 \times 10^7$ |
| *Proteus mirabilis* | 3.4 | $2.02 \times 10^7$ |
| Non-pathogenic *Escherichia coli* K12 | 3.4 | $3.2 \times 10^6$ |

The optimal concentration of pathogens used in both intestinal integrity (TER) and bacterial translocation experiments were established, as shown in Table 7.

TABLE 7

Optimal concentration of pathogens used in intestinal integrity (TER) and bacterial translocation experiments

| | |
|---|---|
| $1 \times 10^4$/well | |
| $1 \times 10^5$/well | |
| $1 \times 10^6$/well | This concentration was chosen as it produced consistent changes to the TER readings and gave good enumerable bacterial translocation results. |
| $1 \times 10^7$/well | |

Results:

The Test Compounds Did not Exhibit Antimicrobial Activity In Vitro

The antibacterial effect of DiaResQ®, Skimmed Colostrum, Colostrum and Egg powder at concentrations 0.5, 1.0, 5 and 10 mg/ml were tested in vitro against each pathogen $1 \times 10^6$ CFU/ml (n=6). All four compounds (at all four concentrations) did not show antimicrobial activity against the pathogens at either 4 h or 24 h incubation. No dose-dependent effect was observed in vitro at either 4 or 24 hours. (data not shown).

Selected Pathogens Induce Barrier Dysfunction in Caco2 Cell

Using an in vitro model, the epithelial barrier dysfunction was investigated in environmental enteropathy (EE) induced by the selected pathogens. All pathogens added to the apical sides of the intestinal monolayer reduced intestinal epithelial integrity by decreasing transepithelial electrical resistance (TER). *E. coli*, EPEC and *Salmonella enteriditis* induced a greater decrease of the TER than the other pathogens, *$p=0.02$, **$p=0.0022$ (n=6) as shown in FIG. 18.

Figure 19:
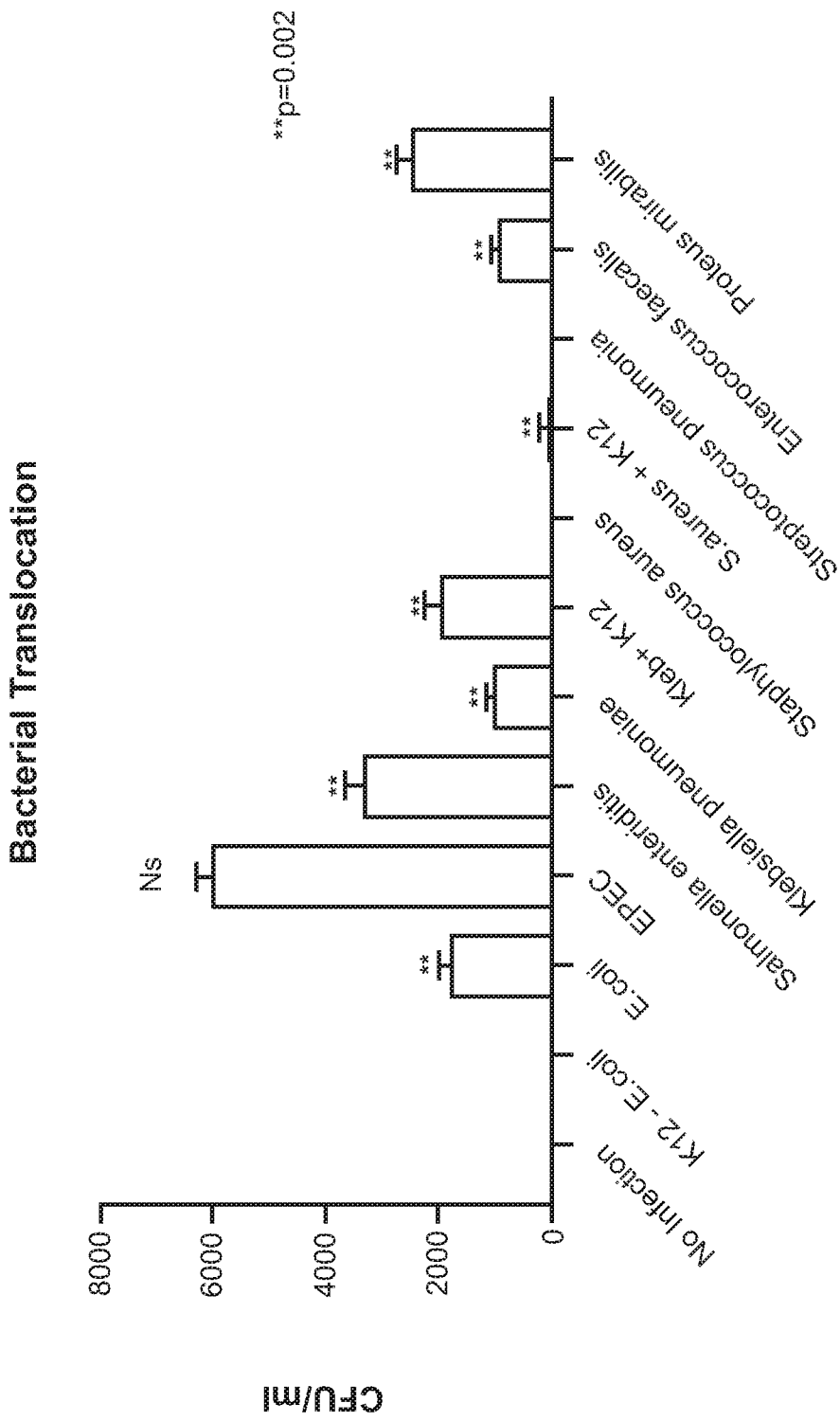
FIG. 19 shows a bar graph of an in vitro model of bacterial translocation across intestinal monolayer. Bacteria isolated and cultured from the basolateral compartment of the Transwell chamber, signified bacterial translocation (BT) had occurred across the epithelium. Consistent with observations of TER, there was no BT during incubation of *E. coli* K12 alone in the in vitro model, but this was induced by co-culture with *Staphylococcus aureus* and *Klebsiella pneumoniae*. ** p=0.002.

Bacteria isolated and cultured from the basolateral compartment of the Transwell chamber, signified bacterial translocation (BT) had occurred across the epithelium. Consistent with observations of TER, there was no BT during incubation of *E. coli* K12 alone in the in vitro model, but this was induced by co-culture with *Staphylococcus aureus* and *Klebsiella pneumonia*, as shown in FIG. 19.

Figure 18:
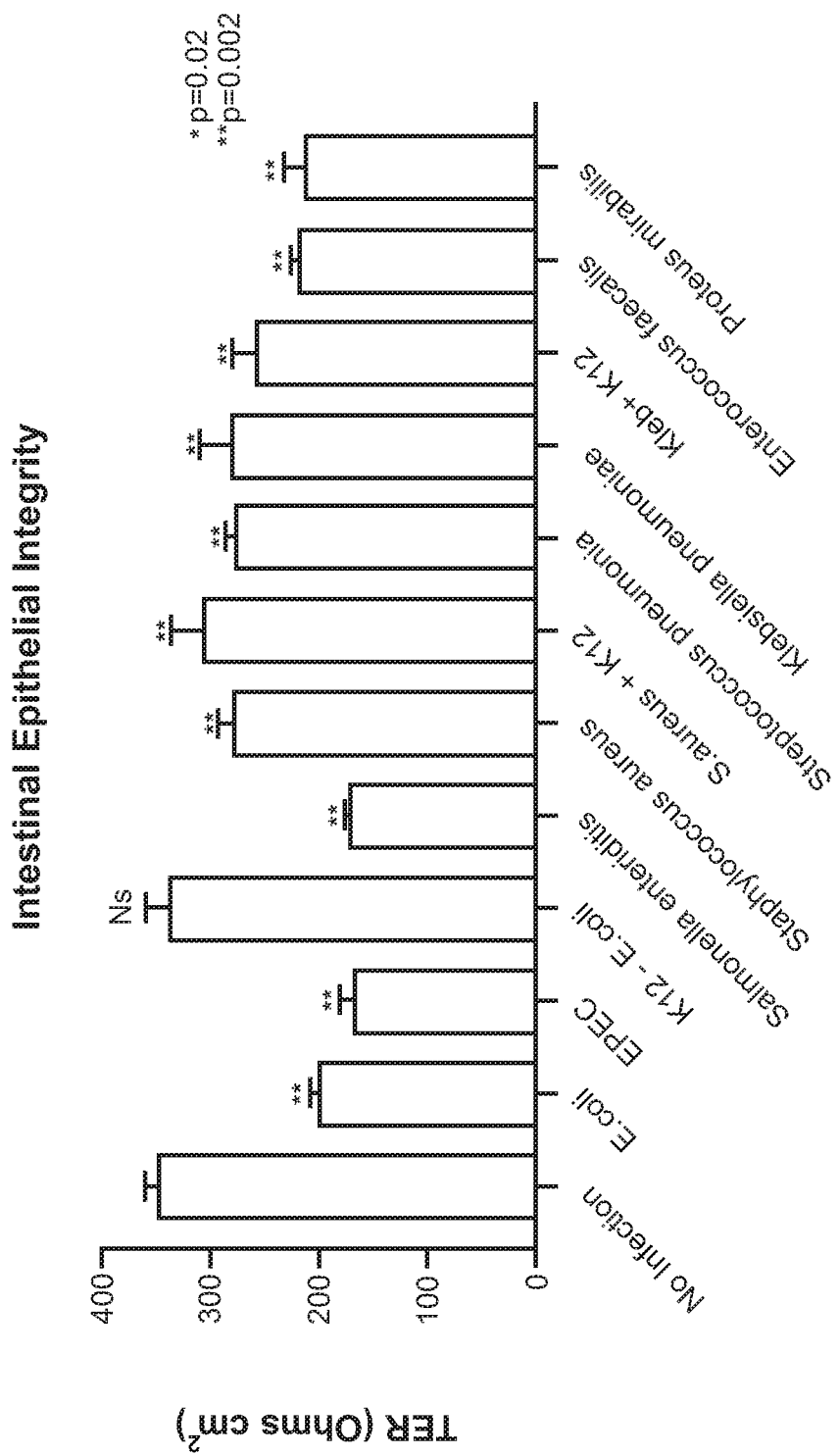
FIG. 18 shows a bar graph of an in vitro model of epithelial barrier dysfunction induced by selected pathogens in Caco2 cell monolayer. All pathogens added to the apical sides of the intestinal monolayer reduced intestinal epithelial integrity by decreasing TER. *E. coli*, EPEC and *Salmonella enteriditis* induced a greater decrease of the TER than the other pathogens. K12 is not a pathogen and was added as a negative control. *p=0.02, **p=0.002 (n=6).

Partial Reversal of Pathogen-Induced Barrier Dysfunction Using Contra-Pathogenicity Agents All pathogens except *E. coli*-K12 (which is a strain made non-pathogenic) induced intestinal epithelial barrier dysregulation (TER) in the in vitro model, as shown in FIG. 18. This was partially reversed by three products DiaResQ®, whole colostrum, and egg powder, as shown in FIGS. 20A-20K.

None of the four test compounds (at the concentrations: 0.5 or 1.0 mg/ml), when given alone, altered the intestinal epithelial integrity after 24 h.

Figure 20A:
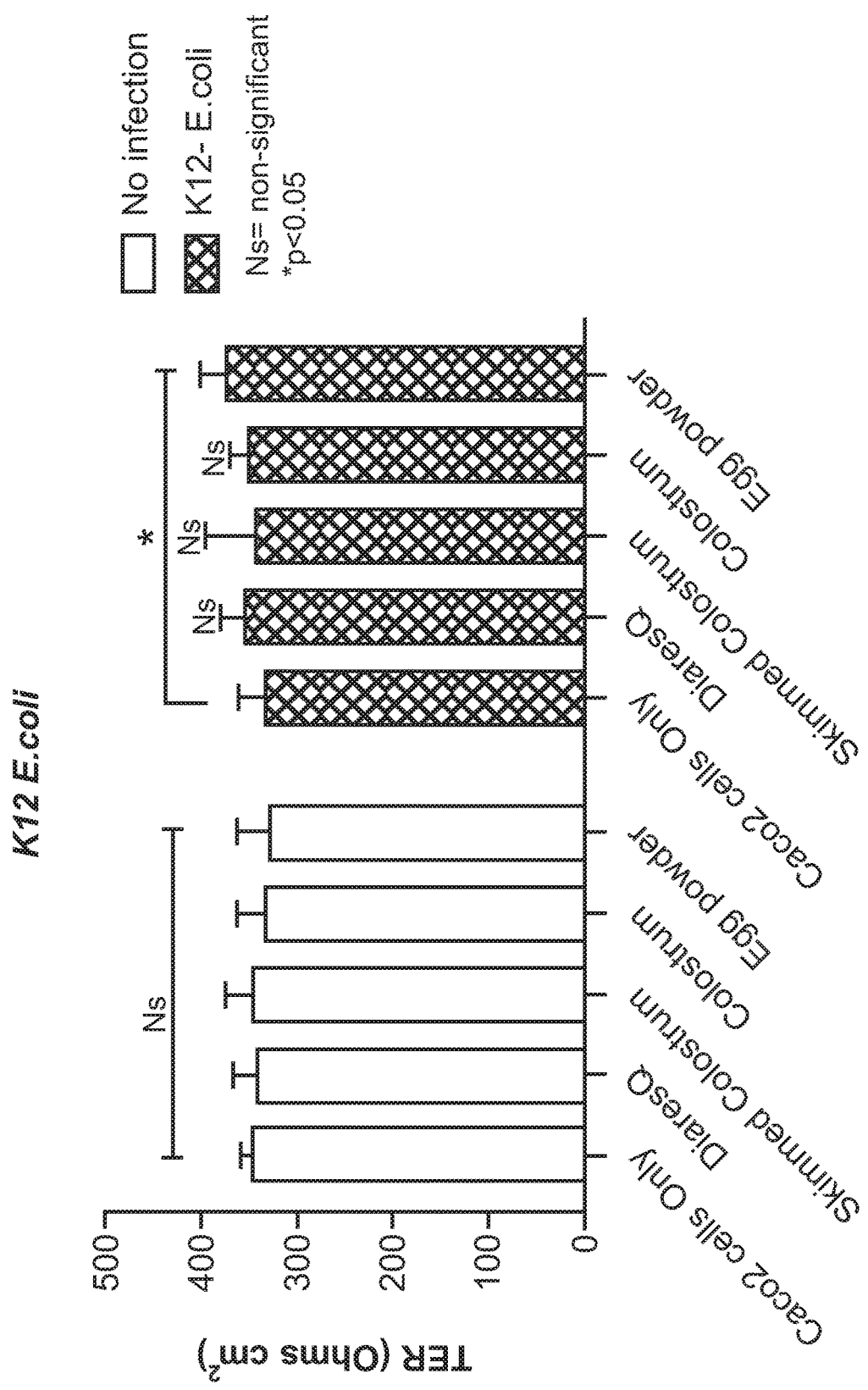
FIG. 20A-K show partial reversal of pathogen-induced barrier dysfunction using contra-pathogenicity agents at 1.0 mg/ml concentration co-cultured with pathogens at 24 hours. None of the four test compounds when given alone altered intestinal epithelial integrity after 24 h. NS– not significant, *p<0.05, ** p<0.005.
Figure 20B:
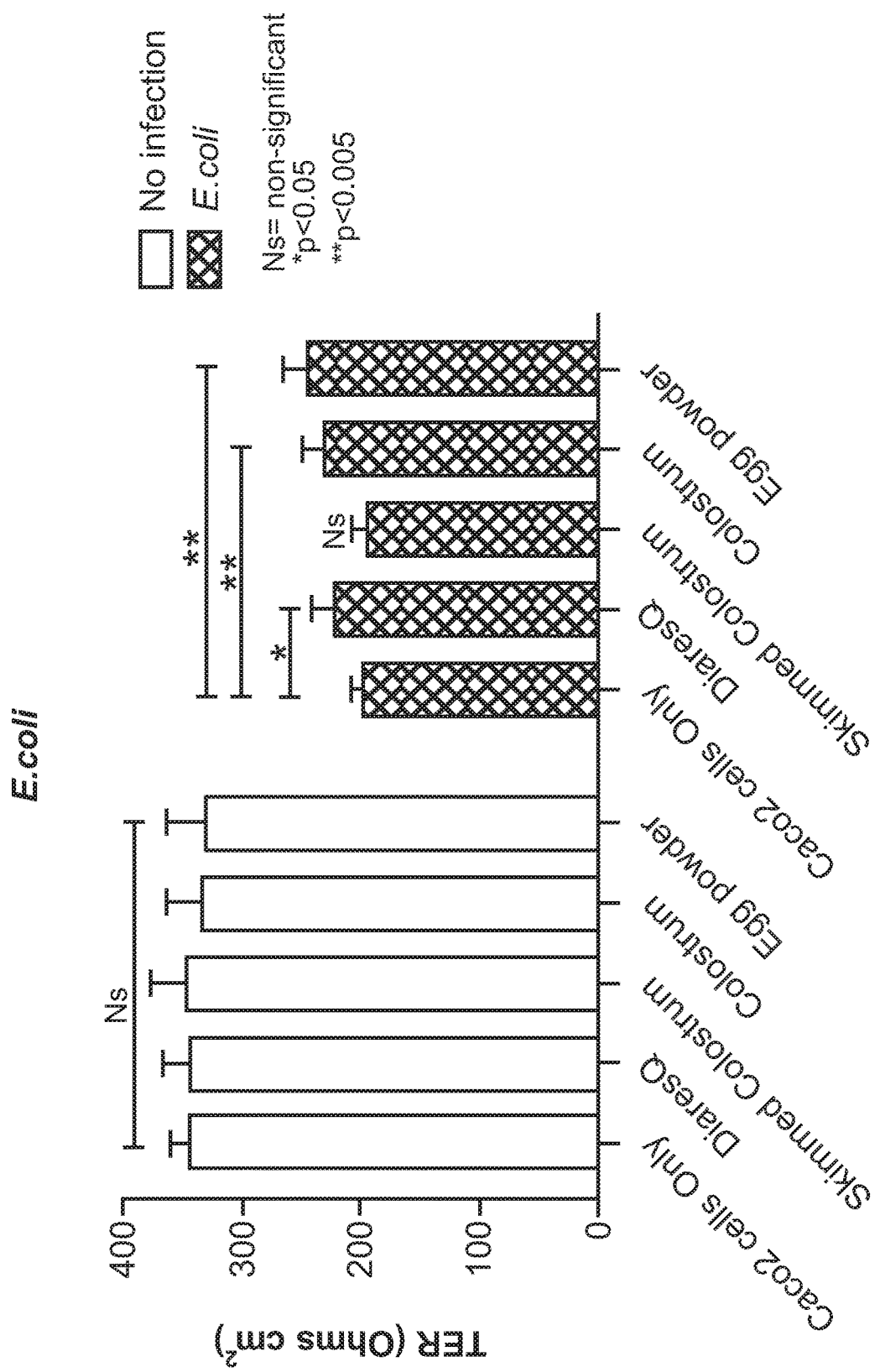
Figure 20C:
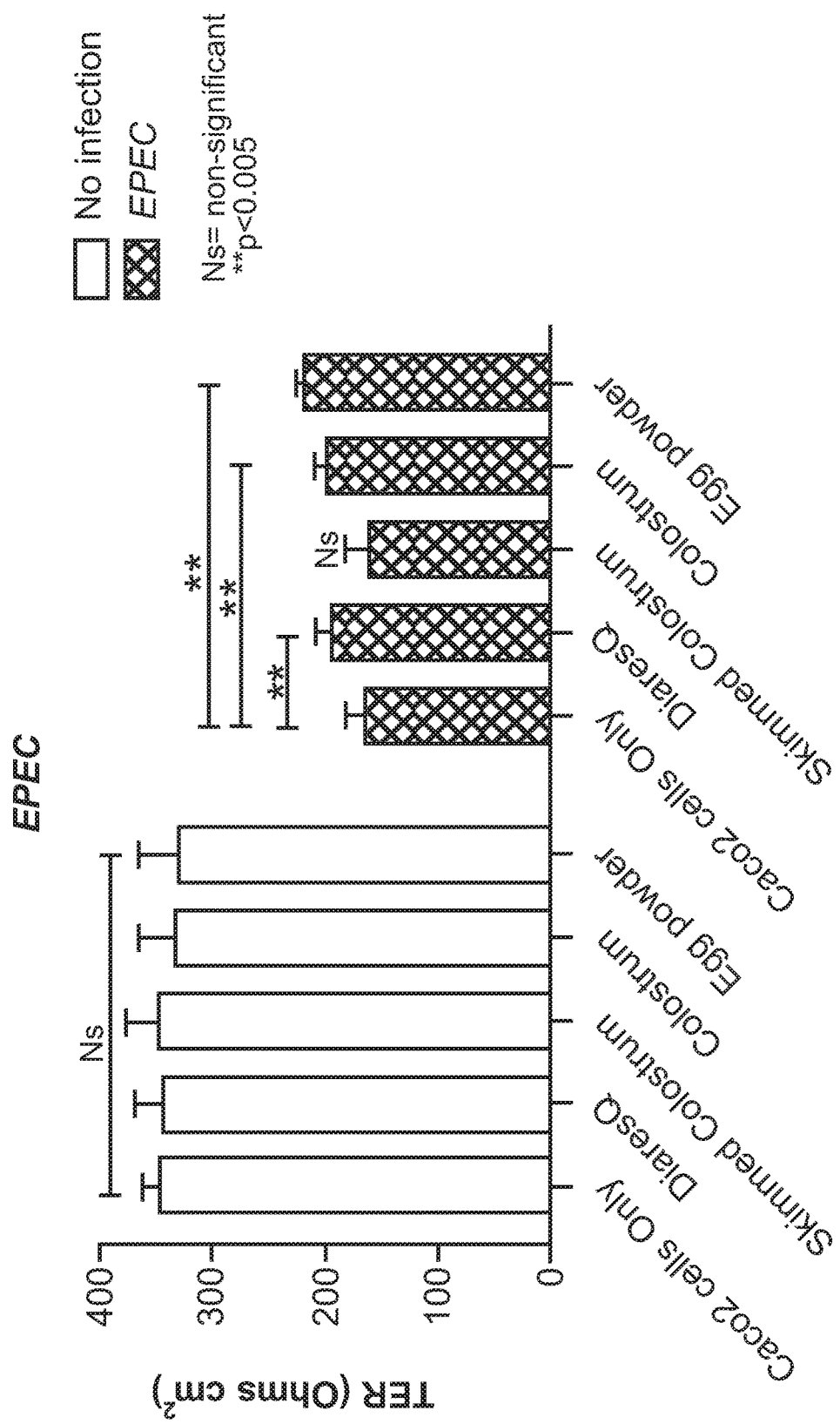
Figure 20D:
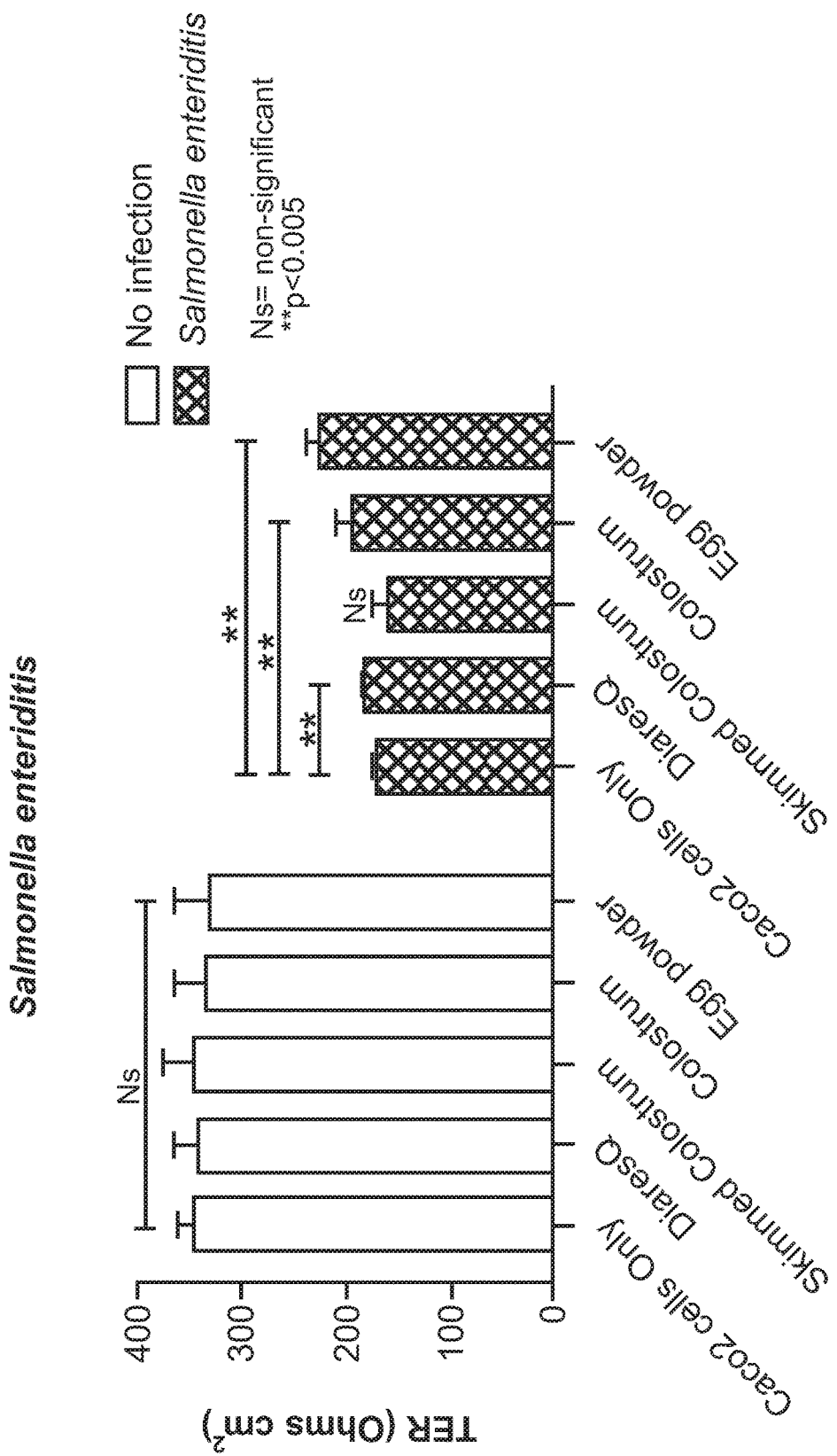
Figure 20E:
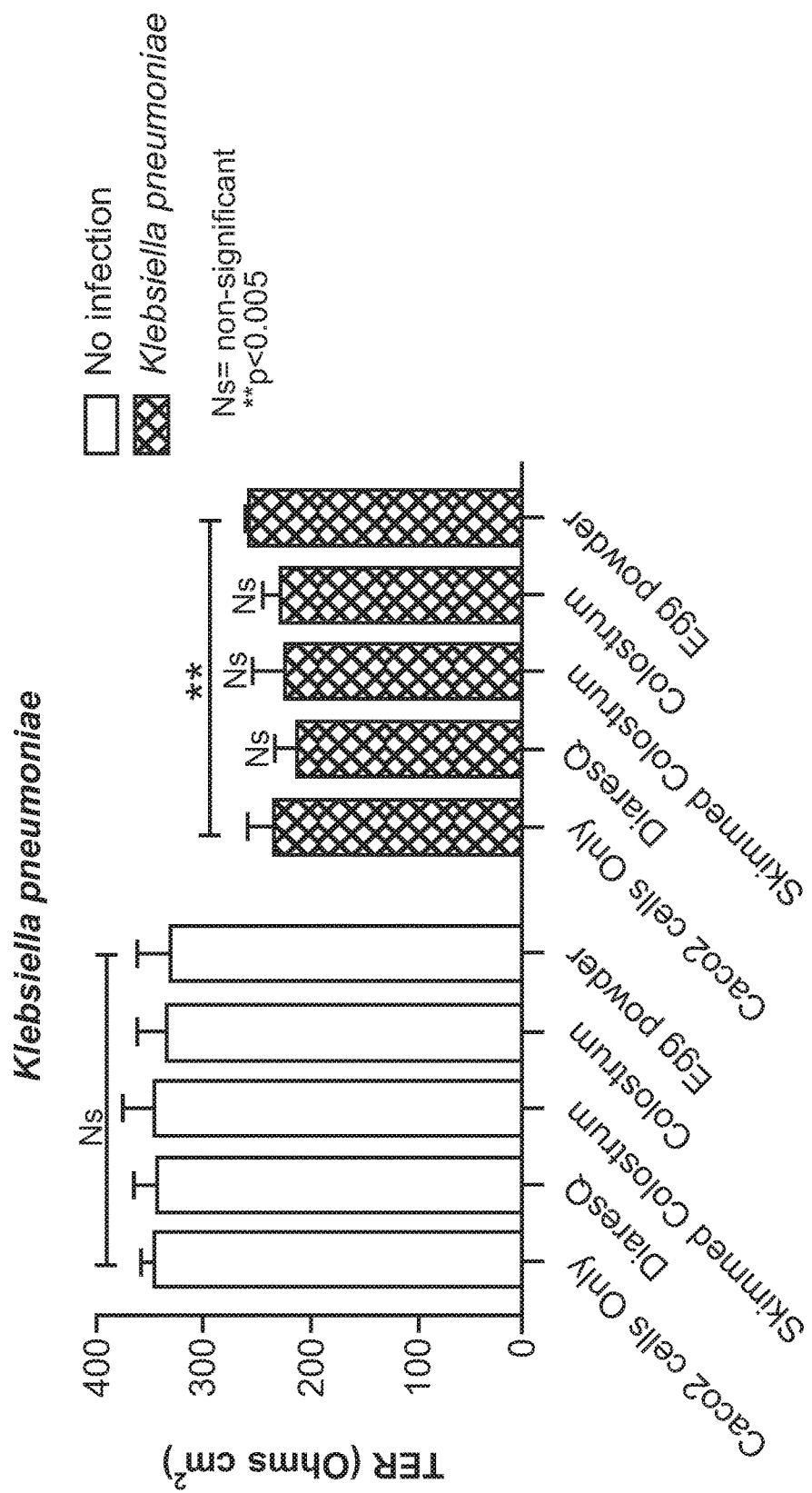
Figure 20F:
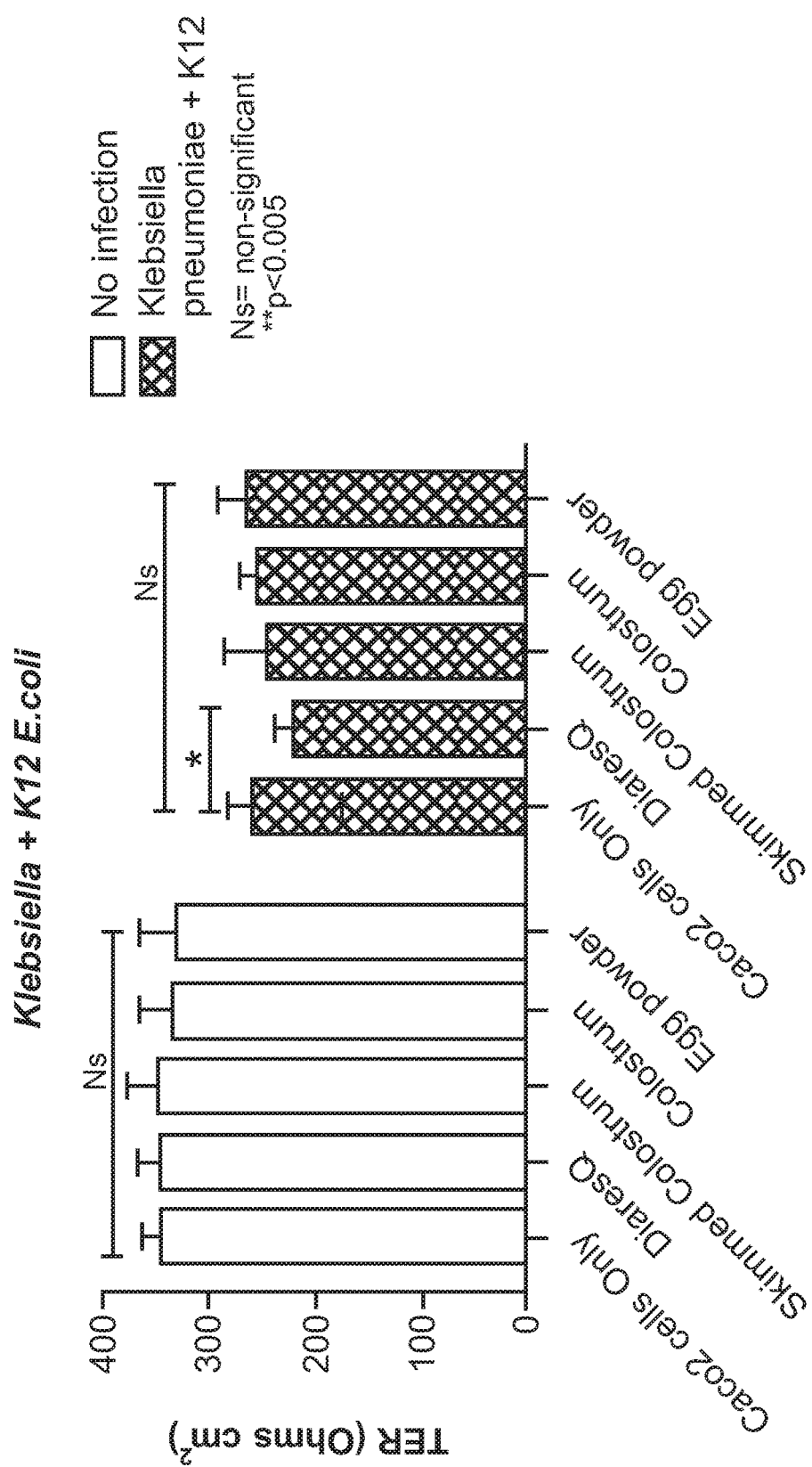
Figure 20G:
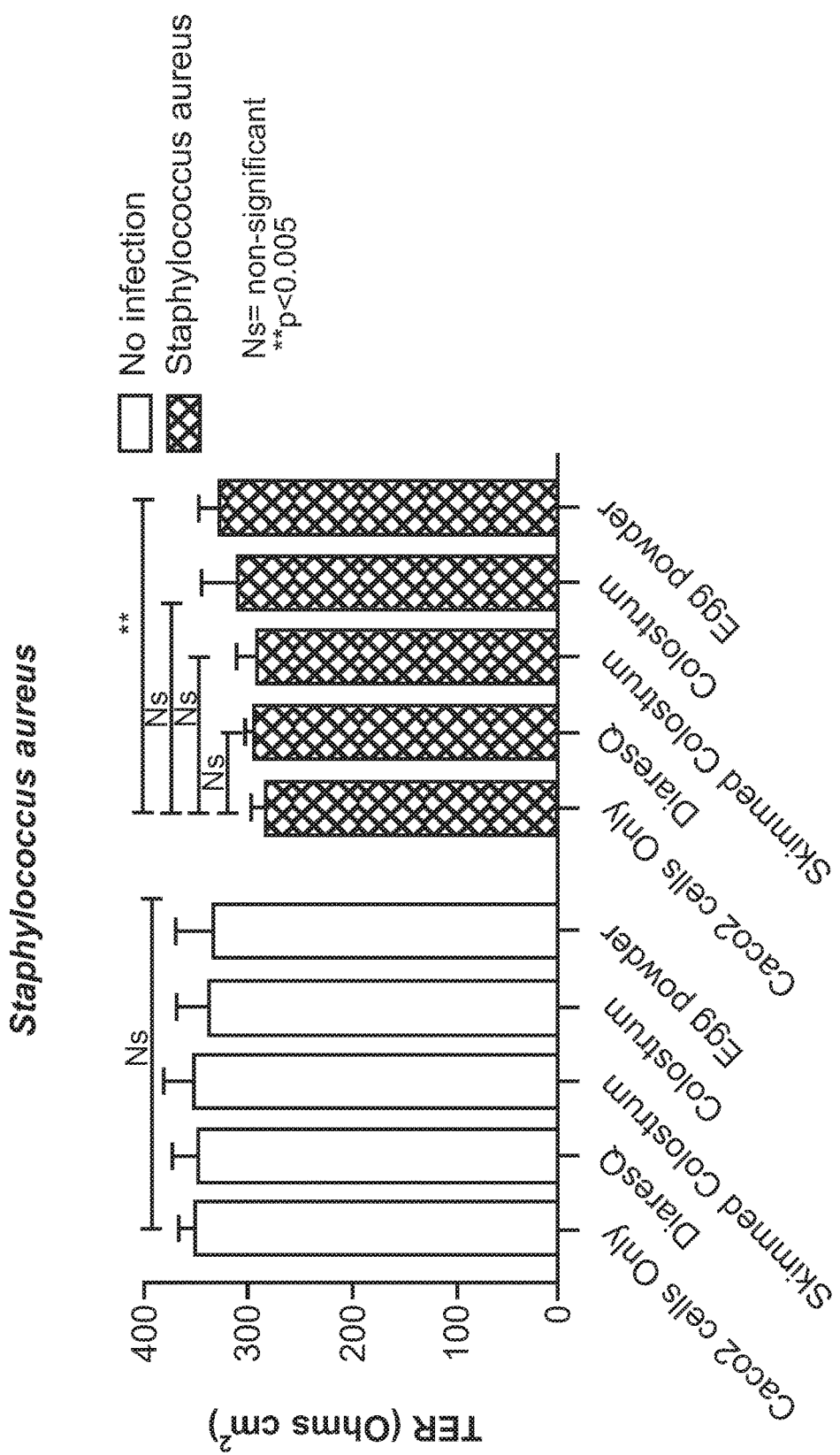
Figure 20H:
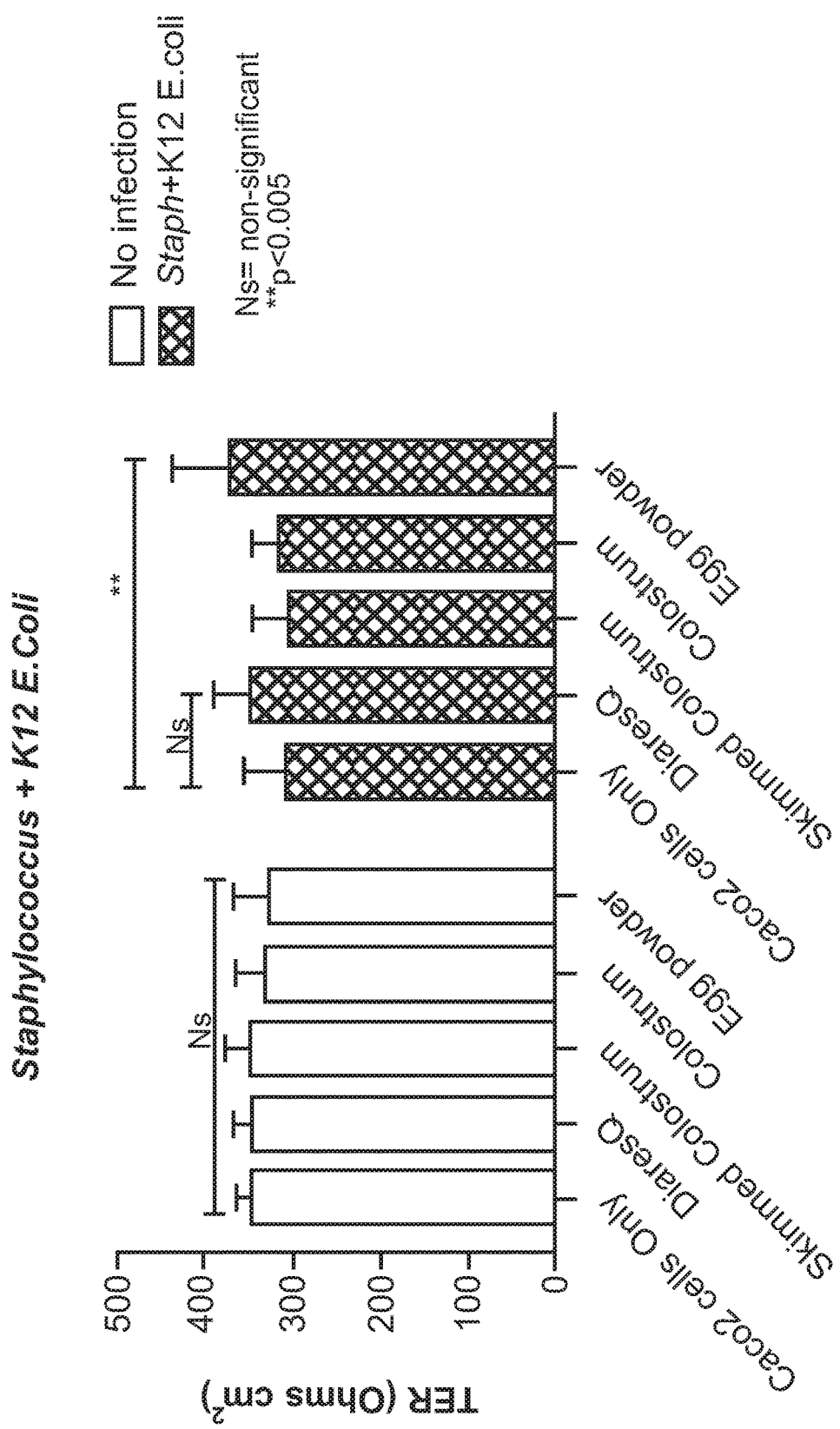
Figure 20I:
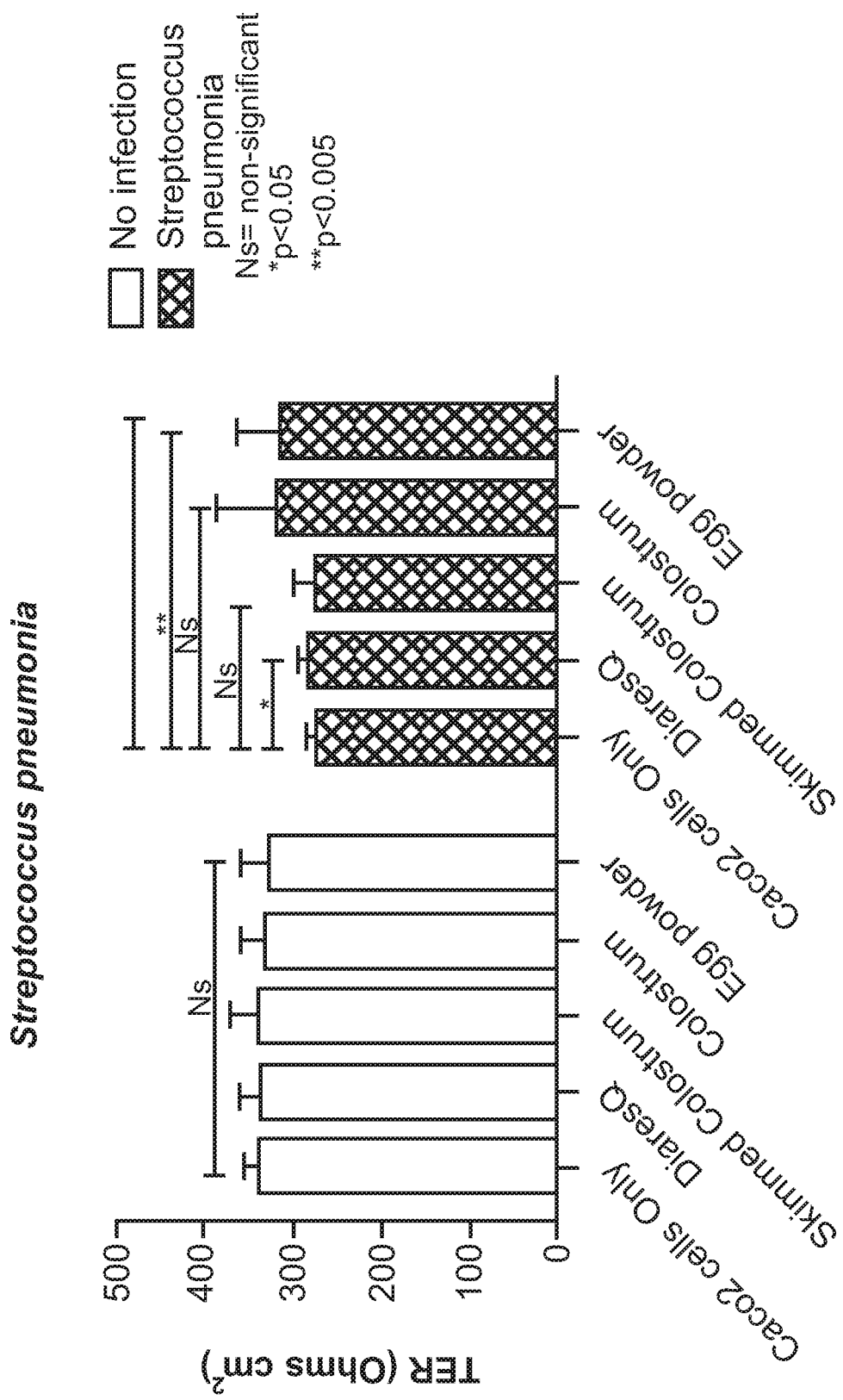
Figure 20J:
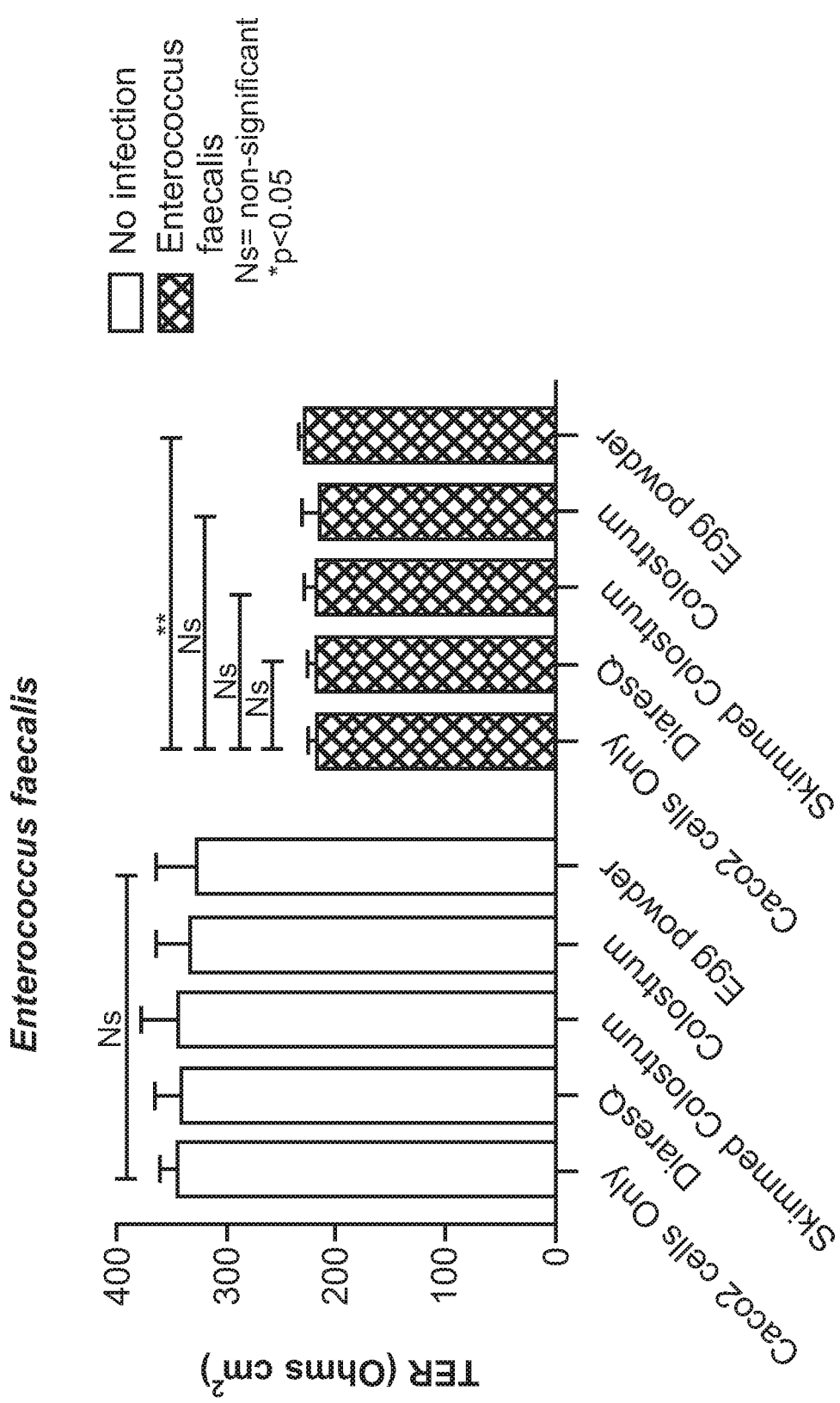
Figure 20K:
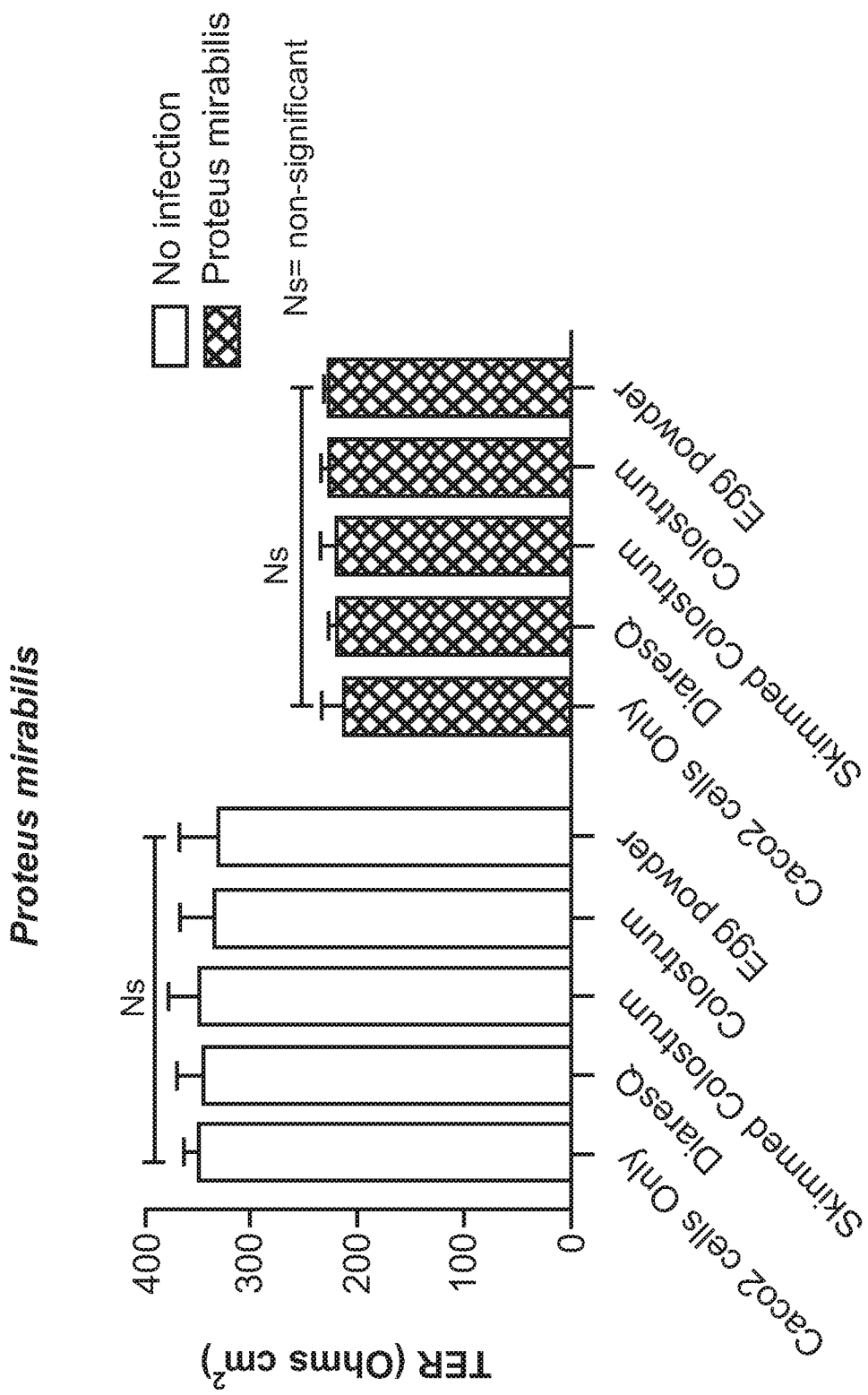

However, when co-incubated with the pathogens, DiaResQ®, egg powder, and whole colostrum and significantly improved TER values (n=6) compared to CaCo2 cells without treatment in the presence of *E. coli* (FIG. 20B), EPEC (FIG. 20C), and *Salmonella enteriditis* (FIG. 20D), showing the results of the compounds at 1.0 mg/ml concentration co-cultured with pathogens. DiaResQ® also significantly improved TER values (n=6) compared to CaCo2 cells without treatment in the presence of Staphylocossus+K12 *E. coli* (FIG. 20H, p<0.05). Skimmed Colostrum did not improved TER readings after infection.

Test Compositions Reduced Bacterial Translocation

The bacterial translocation CFU results correlated with TER results and showed reduced bacterial translocation when bacteria were co-cultured with DiaResQ®, colostrum and egg powder, as shown in FIGS. 21A-21K.

Figure 21D:
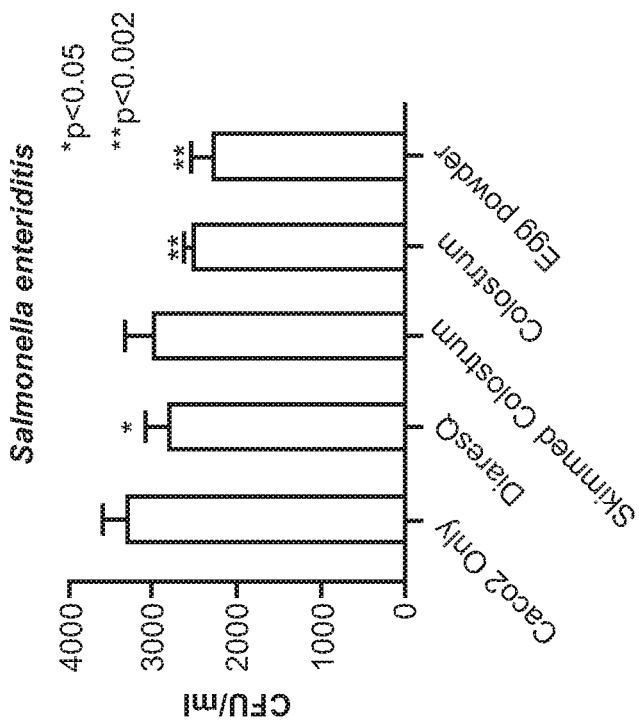
Figure 21C:
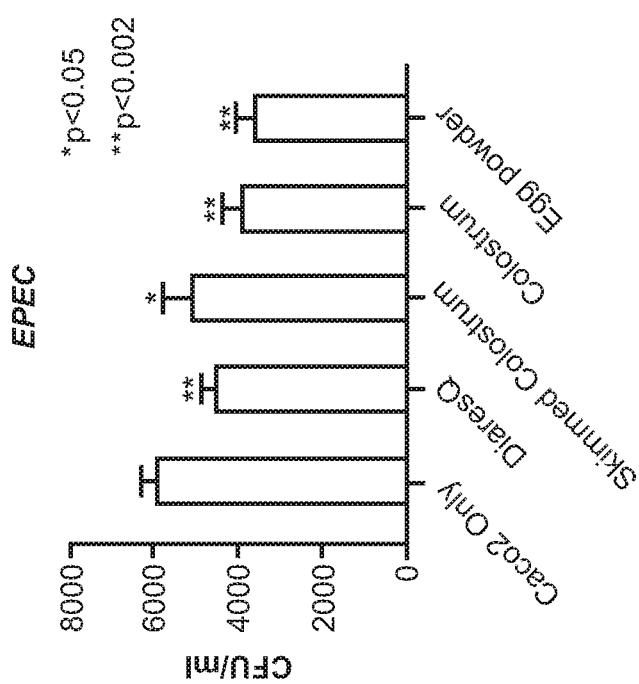
Figure 21F:
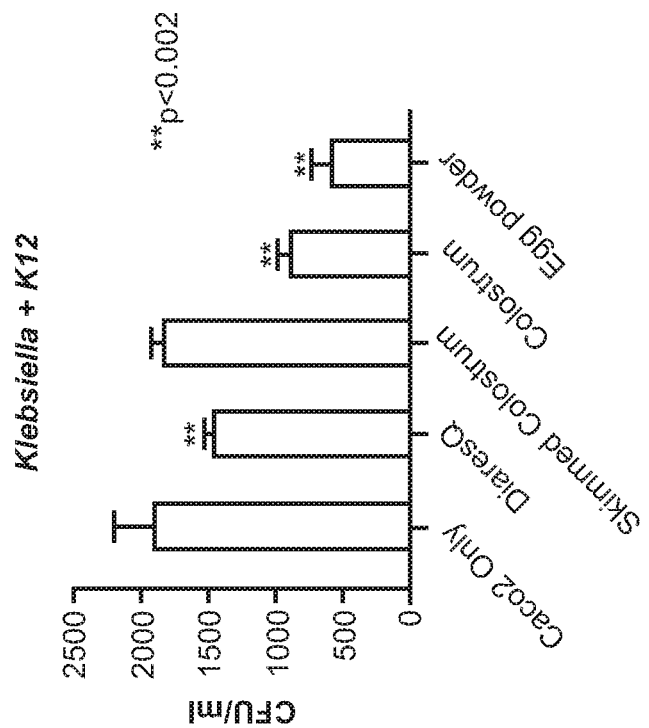
Figure 21E:
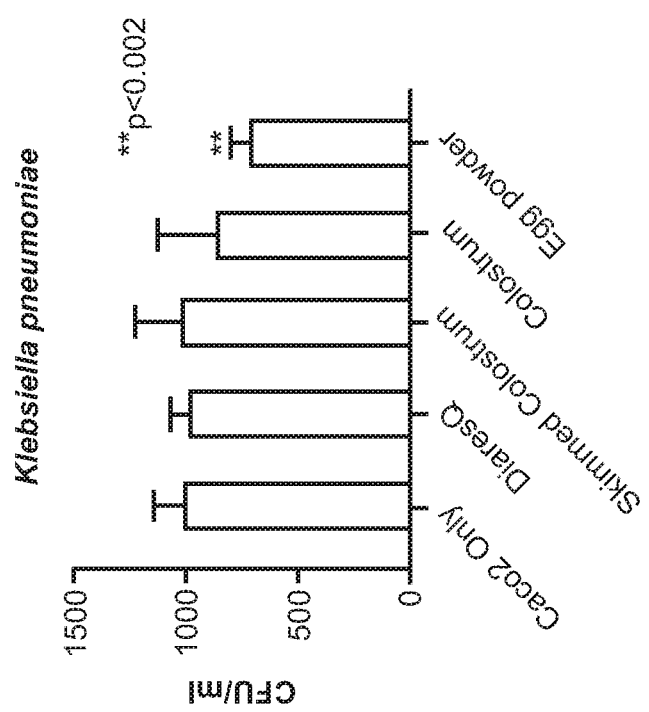
Figures 21G, 21H:
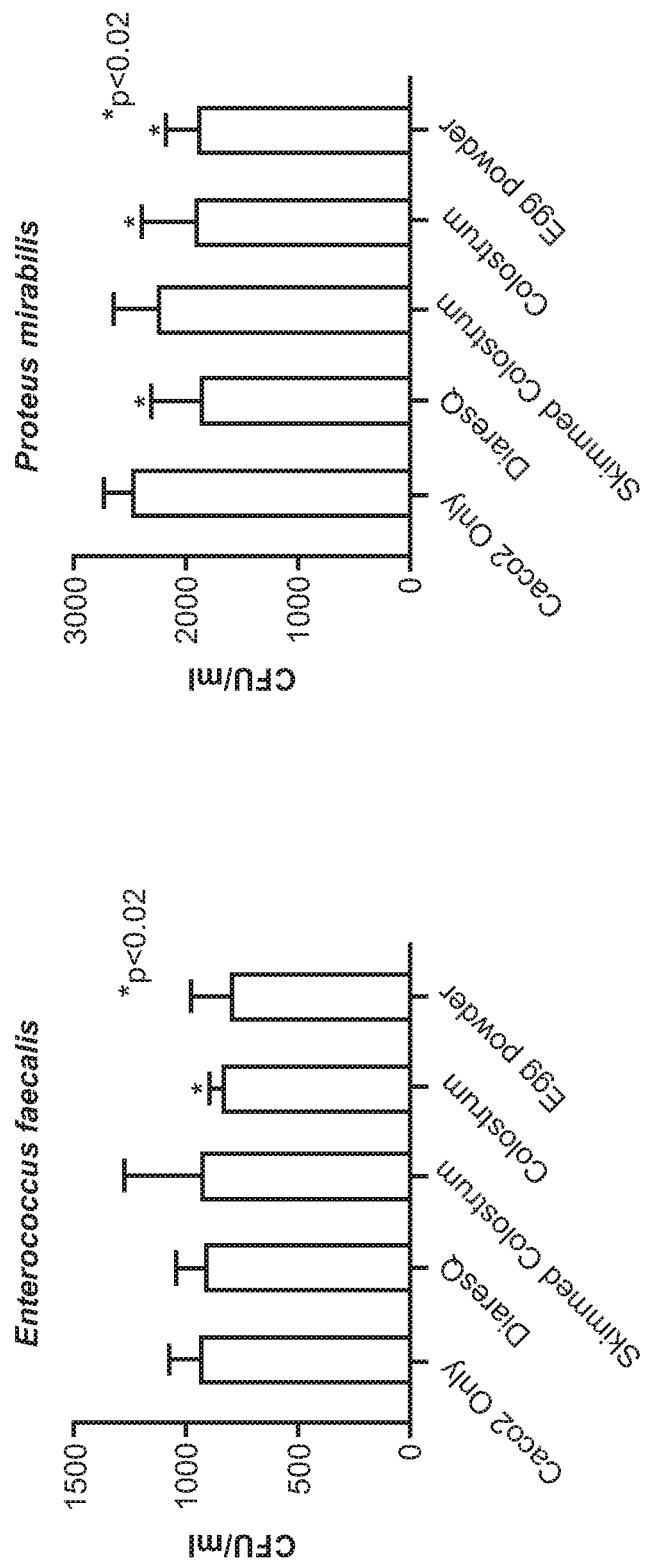
Figure 21J:
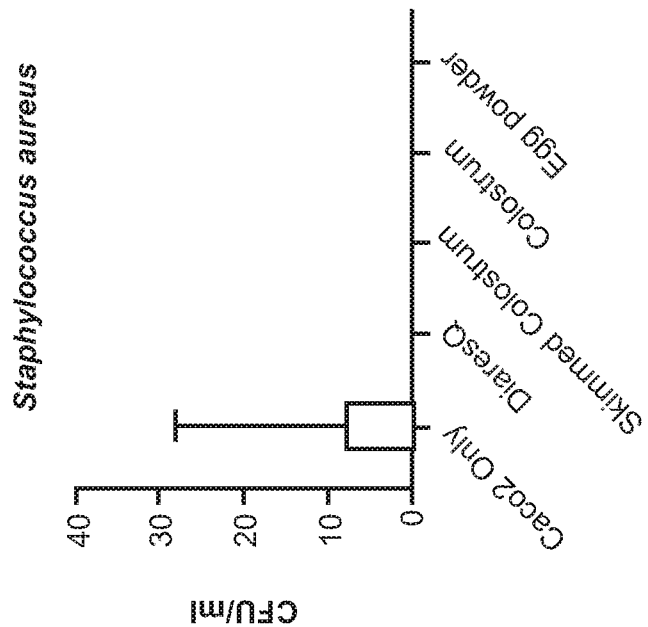
Figure 21I:
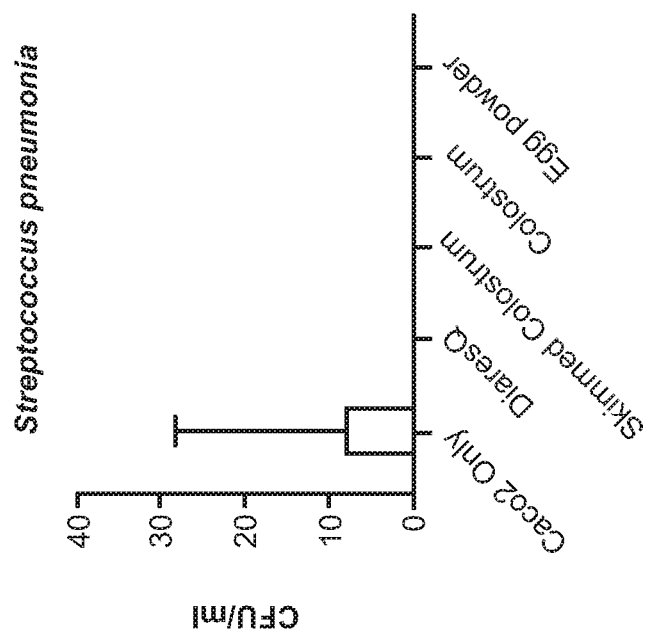
Figure 21K:
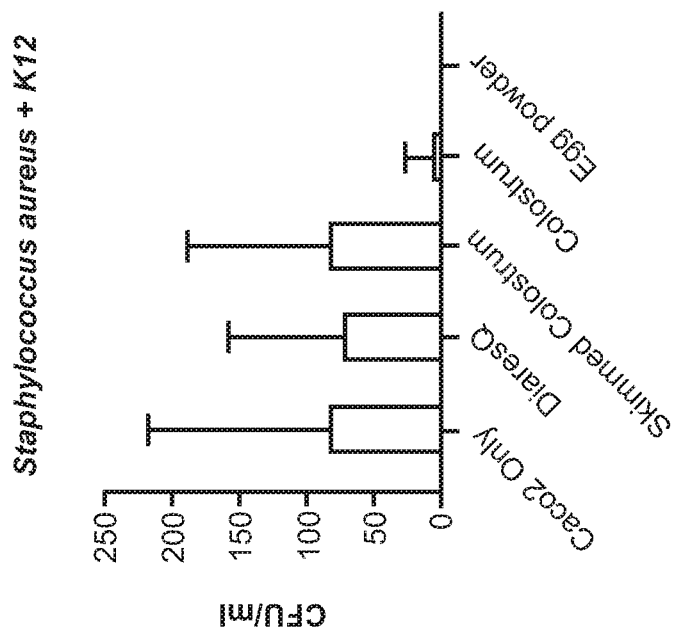

Specifically, three test products DiaResQ®, whole colostrum, and egg powder significantly decreased the intensity of bacterial translocation across the epithelial monolayer of classical *E. coli* (FIG. 21B), EPEC (FIG. 21C), *Salmonella* enteridis (FIG. 21D), *Klebsiella*+K12 *E. coli* (FIG. 21F, and *Proteus mirabilis* (FIG. 21H). Skimmed Colostrum was generally not effective to reduce bacterial translocation across the epithelial monolayer.

Although the invention has been described with reference to the above examples, it will be understood that modifications and variations are encompassed within the spirit and scope of the invention. Accordingly, the invention is limited only by the following claims.

We claim:

1. A method of treating small intestinal bacterial overgrowth (SIBO) in a subject in need thereof, the method comprising administering the subject an effective amount of a composition comprising:
   a) an egg antibody product comprising at least one specific avian antibody or antigen binding fragment thereof, and
   b) a bovine colostrum;
   wherein the administration results in treatment of the SIBO.

2. The method of claim 1, wherein the bovine colostrum is whole bovine colostrum.

3. The method of claim 1, wherein the egg antibody product is a whole immune egg.

4. The method of claim 3, wherein the whole immune egg is a pasteurized raw dried whole immune egg powder.

5. The method of claim 1, wherein the composition has a weight ratio of bovine colostrum to egg antibody product of about 10:1 to about 1:10, wherein the weight ratio is based on a dry weight equivalent.

6. The method of claim 1, wherein the method further comprises co-administering an effective amount of additional active agent.

7. The method of claim 1, wherein the composition further comprises an additional active agent.

8. The method of claim 1, wherein the subject is a non-neonate human.

9. The method of claim 1, wherein the effective amount of the composition comprises about 3 g to about 50 g of a combined weight of the egg antibody product and the bovine colostrum on a dry weight equivalent basis per dose.

10. The method of claim 1, wherein the specific avian antibodies or antigen binding fragments thereof, are specific for a pathogenic component from one, two, three, four, five, six, seven, or eight different pathogenic organisms.

11. The method of claim 1, wherein the at least one specific avian antibody or antigen binding fragment thereof binds to an antigenic region of a pathogenic component selected from the group consisting of a pathogenic organism, a pathogen-related toxin, a pathogen-related adhesion element, and combinations thereof.

12. The method of claim 11, wherein the pathogenic organism is selected from the group consisting of rotavirus, norovirus, calicivirus, enteric adenovirus, coronavirus, parvovirus, cytomegalovirus, astrovirus, herpes virus, *Acanthamoeba* spp., *Aeromonas* spp., *Alternaria* spp., *Ancylostoma* spp., *Ascaris* spp., *Aspergillus* spp., *Bacillus* spp., *Byssochlamys* spp., *Campylobacter* spp., *Candida* spp., *Chlamydia* spp., *Claviceps* spp., *Clostridium* spp., *Cryptosporidium* spp., *Cyclospora* spp., *E. coli*, *Entamoeba* spp., *Fusarium* spp., *Gardnerella* spp., *Giardia* spp., *Gibberella* spp., *Helicobacter* spp., *Klebsiella* spp., *Listeria* spp., *Mycoplasma* spp., *Necator* spp., *Neisseria* spp., *Penicillium* spp., *Plesiomonas* spp., *Salmonella* spp., *Shigella* spp., *Staphylococcus* spp., *Streptococcus* spp., *Taenia* spp., *Trichomonas* spp., *Vibrio* spp., *Yersinia* spp., *Bacteroides* spp., *Peptostreptococcus*, *Lactobacillus* spp., Enterobacterium and combinations thereof.

13. The method of claim 11, wherein the pathogenic organism is selected from the group consisting of *Aeromonas hydrophila*, *Ancylostoma caninum*, *Ancylostoma duodenale*, *Ascaris lumbricoides*, *Bacillus thuringiensis*, *Campylobacter jejuni*, *Candida albicans*, *Candida glabrata*, *Candida krusei*, *Candida parapsilosis*, *Candida tropicalis*, *Chlamydia trachomatis*, *Clostridium difficile*, *Clostridium perfringens*, typical EPEC strains, atypical EPEC (aEPEC) strains, *Helicobacter pylori*, *Listeria monocytogenes*, *Necator americanus*, *Neisseria gonorrhoeae*, *Plesiomonas shigelloides*, *Salmonella enterica* serovar *Typhi*, *Salmonella typhimurium*, *Salmonella enterica* serovar *Typhi*, *Shigella dysenteriae*, *Staphylococcus aureus*, *Taenia saginata*, *Taenia solium*, *Trichomonas vaginalis*, *Vibrio cholerae* O1, *Vibrio cholerae* O139, *Vibrio parahaemolyticus*, *Yersinia enterocolitica*, and combinations thereof.

14. The method of claim 11, wherein the pathogen-related toxin is selected from the group consisting of alpha toxin, *Alternaria* mycotoxin, *Aspergillus* mycotoxin, *Bacillus thuringiensis* delta endotoxin, *Byssochlamys* mycotoxin, *Campylobacter jejuni* enterotoxin, Cholera toxin, *Claviceps* mycotoxin, *Clostridium perfringens* enterotoxin, endotoxin from gram negative bacteria, *E. coli* heat stable enterotoxins LT and LT-II, *Fusarium* mycotoxin, *Gibberella* mycotoxin, *Penicillium* mycotoxin, perfringolysin 0 produced by *Clostridium perfringens* type C or type B, Shiga toxin, *Staphylococcus* enterotoxin B, and combinations thereof.

15. The method of claim 11, wherein the pathogen-related toxin is selected from the group consisting of an enterotoxin, endotoxin, exotoxin, and combinations thereof.

16. The method of claim 11, wherein the pathogen-related adhesion element is selected from the group consisting of *E. coli* K99 pili adherence factor, *E. coli* K88 pili adherence factor, *E. coli* 987P pili adherence factor, *E. coli* F41 pili adherence factor, *E. coli* F41 pili adherence factor, and combinations thereof.

17. The method of claim 11, wherein the pathogen-related adhesion element is selected from the group consisting of one or more adhesins, cadherins, cilia, fimbrillae, viral adhesin structures, and combinations thereof.

18. The method of claim 1, wherein the subject is treated and an expression of one or more biomarkers is decreased, wherein the one or more biomarkers are selected from the group consisting of fecal Reg IB, fecal MPO, serum sCD14, serum CRP, urine lactulose: mannitol (L:M) ratio, plasma IL-6, fecal IL-6, plasma TNF alpha, fecal TNF alpha, plasma IL-lRa, plasma IL-1sR1, and combinations thereof.

19. The method of claim 1, wherein the method further comprises administering one or more of vitamin A, vitamin D, vitamin E, vitamin B12, vitamin B6, riboflavin, niacin, pantothenic acid, thiamine, choline, folic acid, biotin, vitamin K, vitamin C, cobalt, copper, iron, manganese, iodine, calcium, magnesium, phosphorus, a zinc supplement, and selenium.

20. The method of claim 1, wherein the method further comprising administering one or more of about 100 pg to about 1000 pg vitamin A, about 15 mg to about 60 mg vitamin C, about 80 pg to about 600 pg folic acid, about 0.5 mg to about 18 mg iron, and zinc.

21. The method of claim 1, wherein the subject is treated and one or more changes are induced, wherein the one or more changes are selected from the group consisting of decreased enteric inflammation, change in intestinal microbiome, decreased blunting of intestinal villi, increased intestinal integrity, decreased ulceration, decreased leakage of intestinal contents, decreased systemic inflammation, increased weight-for-age (WAZ) z-score, increased height-for-age (HA Z) z-score, increased weight-for-height z-score (WHZ), increased mid-upper arm circumference (MU AC), change in antigen-specific antibody titer in the subject, reduction of diarrhea volume, reduction of diarrhea duration, reduction of abdominal pain, reduction of nausea, reduction of abdominal cramping, reduction of loss of bowel control or urgency of diarrhea symptoms; increase in physician-assessed well-being of the subject, decreased abnormal flattening of villi and inflammation of the lining of small intestine, decreased presence of inflammatory cells, and combinations thereof.

22. The method of claim 1, wherein a small intestinal bacterial overgrowth (SIBO) of the subject is measured using hydrogen breath testing.

23. The method of claim 22, wherein the SIBO of the subject is >12 ppm greater than a baseline or control measurement of SIBO after lactulose of the SIBO of the subject is >20 ppm greater than a baseline or control measurement of SIBO after a glucose challenge.

* * * * *